United States Patent
Dennis et al.

(10) Patent No.: US 8,679,490 B2
(45) Date of Patent: Mar. 25, 2014

(54) BINDING POLYPEPTIDES WITH DIVERSIFIED AND CONSENSUS VH/VL HYPERVARIABLE SEQUENCES

(75) Inventors: Mark S. Dennis, San Carlos, CA (US); Wei-Ching Liang, Foster City, CA (US); Yan Wu, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 11/557,466

(22) Filed: Nov. 7, 2006

(65) Prior Publication Data

US 2007/0160598 A1 Jul. 12, 2007

Related U.S. Application Data

(60) Provisional application No. 60/806,602, filed on Jul. 5, 2006, provisional application No. 60/734,092, filed on Nov. 7, 2005.

(51) Int. Cl.
| | | |
|---|---|---|
| *A61K 39/395* | (2006.01) | |
| *C07H 21/04* | (2006.01) | |
| *C07K 16/18* | (2006.01) | |
| *C07K 16/00* | (2006.01) | |
| *C12N 5/06* | (2006.01) | |
| *C12P 21/06* | (2006.01) | |
| *C07K 16/32* | (2006.01) | |

(52) U.S. Cl.
CPC ............ *C07K 16/005* (2013.01); *C07K 16/32* (2013.01); *C07K 2317/21* (2013.01); *C07K 2317/24* (2013.01); *C07K 2317/56* (2013.01)
USPC ................ 424/133.1; 435/69.1; 530/388.1; 536/23.53

(58) Field of Classification Search
CPC .. C07K 16/005; C07K 16/32; C07K 2317/21; C07K 2317/24
USPC ................ 424/133.1; 435/69.1; 530/388.1; 536/23.53
See application file for complete search history.

(56) References Cited

U.S. PATENT DOCUMENTS

| | | | |
|---|---|---|---|
| 3,773,919 A | 11/1973 | Boswell et al. | |
| 3,896,111 A | 7/1975 | Kupchan et al. | |
| 4,137,230 A | 1/1979 | Hashimoto et al. | |
| 4,151,042 A | 4/1979 | Higashide et al. | |
| 4,248,870 A | 2/1981 | Miyashita et al. | |
| 4,256,746 A | 3/1981 | Miyashita et al. | |
| 4,260,608 A | 4/1981 | Miyashita et al. | |
| 4,265,814 A | 5/1981 | Hashimoto et al. | |
| 4,294,757 A | 10/1981 | Asai | |
| 4,307,016 A | 12/1981 | Asai et al. | |
| 4,308,268 A | 12/1981 | Miyashita et al. | |
| 4,308,269 A | 12/1981 | Miyashita et al. | |
| 4,309,428 A | 1/1982 | Miyashita et al. | |
| 4,313,946 A | 2/1982 | Powell et al. | |
| 4,315,929 A | 2/1982 | Freedman et al. | |
| 4,317,821 A | 3/1982 | Miyashita et al. | |
| 4,322,348 A | 3/1982 | Asai et al. | |
| 4,331,598 A | 5/1982 | Hasegawa et al. | |
| RE30,985 E | 6/1982 | Cartaya | |
| 4,361,650 A | 11/1982 | Asai et al. | |
| 4,362,663 A | 12/1982 | Kida et al. | |
| 4,364,866 A | 12/1982 | Asai et al. | |
| 4,371,533 A | 2/1983 | Akimoto et al. | |
| 4,419,446 A | 12/1983 | Howley et al. | |
| 4,424,219 A | 1/1984 | Hashimoto et al. | |
| 4,450,254 A | 5/1984 | Isley et al. | |
| 4,560,655 A | 12/1985 | Baker | |
| 4,601,978 A | 7/1986 | Karin | |
| 4,657,866 A | 4/1987 | Kumar | |
| 4,670,393 A | 6/1987 | Seeburg | |
| 4,755,465 A | 7/1988 | Gray et al. | |
| 4,767,704 A | 8/1988 | Cleveland et al. | |
| 4,816,567 A | 3/1989 | Cabilly et al. | |
| 4,927,762 A | 5/1990 | Darfler | |
| 4,965,199 A | 10/1990 | Capon et al. | |
| 4,970,198 A | 11/1990 | Lee et al. | |
| 4,975,278 A | 12/1990 | Senter et al. | |
| 5,053,394 A | 10/1991 | Ellestad et al. | |
| 5,079,233 A | 1/1992 | Lee | |
| 5,122,469 A | 6/1992 | Mather et al. | |
| 5,208,020 A | 5/1993 | Chari et al. | |
| 5,223,409 A | 6/1993 | Ladner et al. | |
| 5,264,365 A | 11/1993 | Georgiou et al. | |
| 5,362,852 A | 11/1994 | Georghegan | |
| 5,403,484 A | 4/1995 | Ladner et al. | |
| 5,416,064 A | 5/1995 | Chari et al. | |
| 5,427,908 A | 6/1995 | Dower et al. | |

(Continued)

FOREIGN PATENT DOCUMENTS

| | | |
|---|---|---|
| EP | 0128733 A1 | 12/1984 |
| EP | 0230869 A2 | 8/1987 |

(Continued)

OTHER PUBLICATIONS

Paul, Fundamental Immunology, 3rd Edition, 1993, pp. 292-295.*
Pascalis et al. The Journal of Immunology (2002) 169, 3076-3084.*
Casset et al. (2003) BBRC 307, 198-205.*
Holm et al (2007) Mol. Immunol. 44: 1075-1084.*
Wu et al. J. Mol. Biol. (1999) 294, 151-162.*
Stedman's Medical on-line dictionary definition of "mutagenic".*
Biology Online definition of "mutagenic".*
Rudikoff et al (Proc. Natl. Acad. Sci. USA 1982 vol. 79: p. 1979.*
Lederman et al (Molecular Immunology 28:1171-1181, 1991).*
Li et al (Proc. Natl. Acad. Sci. USA 77:3211-3214, 1980).*
Rudikoff et al (Proc Natl Acad Sci USA 1982 vol. 79 p. 1979).*
MacCallum et al. (J. Mol. Biol. (1996) 262:732-745).*
De Pascalis et al. The Journal of Immunology (2002) 169, 3076-3084.*
Casset et al. ((2003) BBRC 307, 198-205).*
Vajdos et al. ((2002) J. Mol. Biol. 320, 415-428).*

(Continued)

*Primary Examiner* — Lynn Bristol
(74) *Attorney, Agent, or Firm* — Jones Day

(57) ABSTRACT

The invention provides variant hypervariable regions comprising selected amino acid sequence diversity. Libraries comprising a plurality of these polypeptides are also provided. In addition, methods of and compositions for generating and using these polypeptides and libraries are provided.

49 Claims, 13 Drawing Sheets

(56) References Cited

U.S. PATENT DOCUMENTS

| | | |
|---|---|---|
| 5,432,018 A | 7/1995 | Dower et al. |
| 5,498,530 A | 3/1996 | Schatz et al. |
| 5,500,362 A | 3/1996 | Robinson et al. |
| 5,508,192 A | 4/1996 | Georgiou et al. |
| 5,534,615 A | 7/1996 | Baker et al. |
| 5,565,332 A | 10/1996 | Hoogenboom et al. |
| 5,580,717 A | 12/1996 | Dower et al. |
| 5,580,723 A | 12/1996 | Wells et al. |
| 5,585,089 A | 12/1996 | Queen et al. |
| 5,591,828 A | 1/1997 | Bosslet et al. |
| 5,606,040 A | 2/1997 | Mcgahren et al. |
| 5,624,821 A | 4/1997 | Winter et al. |
| 5,639,635 A | 6/1997 | Joly et al. |
| 5,648,237 A | 7/1997 | Carter |
| 5,648,260 A | 7/1997 | Winter et al. |
| 5,658,727 A | 8/1997 | Barbas et al. |
| 5,667,780 A | 9/1997 | Ho et al. |
| 5,667,988 A | 9/1997 | Barbas et al. |
| 5,693,762 A | 12/1997 | Queen et al. |
| 5,702,892 A | 12/1997 | Mulligan-Kehoe |
| 5,712,374 A | 1/1998 | Kuntsmann et al. |
| 5,714,586 A | 2/1998 | Kunstmann et al. |
| 5,723,286 A | 3/1998 | Dower et al. |
| 5,723,323 A | 3/1998 | Kauffman et al. |
| 5,731,168 A | 3/1998 | Carter et al. |
| 5,733,743 A | 3/1998 | Johnson et al. |
| 5,739,116 A | 4/1998 | Hamann et al. |
| 5,739,277 A | 4/1998 | Presta et al. |
| 5,750,373 A | 5/1998 | Garrard et al. |
| 5,759,817 A | 6/1998 | Barbas |
| 5,763,192 A | 6/1998 | Kauffman et al. |
| 5,767,285 A | 6/1998 | Hamann et al. |
| 5,770,434 A | 6/1998 | Huse |
| 5,770,701 A | 6/1998 | Mcgahren et al. |
| 5,770,710 A | 6/1998 | Mcgahren et al. |
| 5,773,001 A | 6/1998 | Hamann et al. |
| 5,780,279 A | 7/1998 | Matthews et al. |
| 5,821,047 A | 10/1998 | Garrard et al. |
| 5,821,337 A | 10/1998 | Carter et al. |
| 5,834,250 A | 11/1998 | Wells et al. |
| 5,834,598 A | 11/1998 | Lowman et al. |
| 5,837,242 A | 11/1998 | Holliger et al. |
| 5,840,523 A | 11/1998 | Simmons et al. |
| 5,846,765 A | 12/1998 | Matthews et al. |
| 5,877,296 A | 3/1999 | Hamann et al. |
| 5,962,255 A | 10/1999 | Griffiths et al. |
| 5,965,371 A | 10/1999 | Marasco et al. |
| 5,969,108 A | 10/1999 | McCafferty et al. |
| 6,027,888 A | 2/2000 | Georgiou et al. |
| 6,037,454 A | 3/2000 | Jardieu et al. |
| 6,040,136 A | 3/2000 | Garrard et al. |
| 6,054,297 A | 4/2000 | Carter et al. |
| 6,057,098 A | 5/2000 | Buechler et al. |
| 6,083,715 A | 7/2000 | Georgiou et al. |
| 6,096,551 A | 8/2000 | Barbas et al. |
| 6,140,471 A | 10/2000 | Johnson et al. |
| 6,172,197 B1 | 1/2001 | McCafferty et al. |
| 6,190,908 B1 | 2/2001 | Kang |
| 6,248,516 B1 | 6/2001 | Winter et al. |
| 6,387,371 B1 | 5/2002 | Hudziak et al. |
| 6,627,196 B1 | 9/2003 | Baughman et al. |
| 6,696,245 B2 | 2/2004 | Winter et al. |
| 6,699,974 B2 | 3/2004 | Ono et al. |
| 6,846,634 B1 | 1/2005 | Tomlinson et al. |
| 2002/0081300 A1 | 6/2002 | McMichael |
| 2002/0082396 A1 | 6/2002 | Matsushima et al. |
| 2002/0086978 A1 | 7/2002 | Verhoeyen |
| 2003/0028009 A1 | 2/2003 | Huse |
| 2003/0091995 A1 | 5/2003 | Buechler et al. |
| 2003/0180714 A1 | 9/2003 | Sidhu et al. |
| 2004/0071696 A1 | 4/2004 | Adams et al. |
| 2004/0123343 A1 | 6/2004 | La Rosa et al. |
| 2004/0236078 A1 | 11/2004 | Carter et al. |
| 2005/0037420 A1 | 2/2005 | Zhang et al. |
| 2005/0069955 A1 | 3/2005 | Plaksin et al. |
| 2005/0079574 A1 | 4/2005 | Bond |
| 2005/0112698 A1* | 5/2005 | Neben et al. .................. 435/7.2 |
| 2005/0119455 A1 | 6/2005 | Fuh et al. |
| 2005/0266000 A1 | 12/2005 | Bond |
| 2006/0122377 A1* | 6/2006 | Dennis ...................... 530/387.3 |
| 2006/0292554 A1 | 12/2006 | Held et al. |
| 2007/0117126 A1 | 5/2007 | Sidhu et al. |
| 2007/0160598 A1 | 7/2007 | Dennis et al. |
| 2007/0202552 A1 | 8/2007 | Sidhu et al. |
| 2007/0237764 A1 | 10/2007 | Birtalan et al. |
| 2007/0292936 A1 | 12/2007 | Barthelemy et al. |
| 2008/0038717 A1 | 2/2008 | Garrard et al. |
| 2008/0213268 A1 | 9/2008 | Watts et al. |

FOREIGN PATENT DOCUMENTS

| | | |
|---|---|---|
| EP | 0266032 | 5/1988 |
| EP | 0288451 A2 | 10/1988 |
| EP | 0368684 | 5/1990 |
| EP | 0404097 A2 | 12/1990 |
| EP | 0425235 A2 | 5/1991 |
| EP | 0368684 B1 | 3/1994 |
| EP | 0628639 | 12/1994 |
| EP | 1391213 A1 | 2/2004 |
| WO | WO 87/00195 | 1/1987 |
| WO | WO 90/03430 | 4/1990 |
| WO | WO 90/04788 | 5/1990 |
| WO | WO 92/01047 | 1/1992 |
| WO | WO 92/03461 | 3/1992 |
| WO | 92/09690 | 6/1992 |
| WO | WO 92/20791 | 11/1992 |
| WO | WO 93/05072 | 3/1993 |
| WO | WO 93/06213 | 4/1993 |
| WO | WO 93/11161 | 6/1993 |
| WO | WO 93/11236 | 6/1993 |
| WO | WO 93/19172 | 9/1993 |
| WO | WO 93/21232 | 10/1993 |
| WO | WO 94/11026 | 5/1994 |
| WO | WO9409818 * | 5/1994 |
| WO | WO 94/29351 | 12/1994 |
| WO | WO 97/35196 | 9/1997 |
| WO | WO 98/15833 | 4/1998 |
| WO | WO 98/17797 | 4/1998 |
| WO | WO 98/35986 | 8/1998 |
| WO | WO 98/51793 | 11/1998 |
| WO | WO 99/06587 | 2/1999 |
| WO | WO 99/46284 | 9/1999 |
| WO | WO 99/51642 | 10/1999 |
| WO | WO9958570 * | 11/1999 |
| WO | 00/06717 | 2/2000 |
| WO | WO 00/24884 | 5/2000 |
| WO | WO 00/42072 | 7/2000 |
| WO | WO 00/77194 | 12/2000 |
| WO | WO 01/19861 | 3/2001 |
| WO | WO 01/27612 | 4/2001 |
| WO | 01/44463 A1 | 6/2001 |
| WO | WO 01/44463 A1 | 6/2001 |
| WO | WO 01/45746 | 6/2001 |
| WO | WO 01/70266 | 9/2001 |
| WO | WO 01/90190 A2 | 11/2001 |
| WO | WO 02/060919 | 8/2002 |
| WO | WO 02/061071 | 8/2002 |
| WO | WO 02/061071 A2 | 8/2002 |
| WO | WO 03/055979 | 7/2003 |
| WO | WO 03/089614 | 10/2003 |
| WO | 03/102157 A2 | 12/2003 |
| WO | WO 03/102157 | 12/2003 |
| WO | WO2004003019 * | 1/2004 |
| WO | WO 2004/003019 * | 6/2004 |
| WO | WO 2004/058821 A2 | 7/2004 |
| WO | 2004/065416 A2 | 8/2004 |
| WO | WO 2004/065416 | 8/2004 |
| WO | WO 2005/012359 | 2/2005 |
| WO | WO 2005/012531 | 2/2005 |
| WO | WO 2005/012531 A2 | 2/2005 |
| WO | WO2005019270 * | 3/2005 |
| WO | WO 2005023299 * | 3/2005 |
| WO | WO 2005056575 * | 6/2005 |
| WO | WO 2005/100399 | 10/2005 |

(56) References Cited

FOREIGN PATENT DOCUMENTS

| WO | 2005/118647 A2 | 12/2005 |
| --- | --- | --- |
| WO | WO2006050834 * | 5/2006 |
| WO | WO 2007/056441 | 5/2007 |
| WO | 2007/064919 A2 | 6/2007 |
| WO | 2007/094842 A2 | 8/2007 |
| WO | WO 2007/094842 | 8/2007 |
| WO | 2007/134050 A2 | 11/2007 |

OTHER PUBLICATIONS

Holm et al ((2007) Mol. Immunol. 44: 1075-1084).*
Chen et al. J. Mol. Bio. (1999) 293, 865-881.*
Wu et al. (J. Mol. Biol. (1999) 294, 151-162).*
Brummell et al. (Biochemistry 32:1180-1187 (1993)).*
Kobayashi et al. (Protein Engineering 12:879-844 (1999)).*
Burks et al. (PNAS 94:412-417 (1997)).*
Jang et al. (Molec. Immunol. 35:1207-1217 (1998)).*
Brorson et al. (J. Immunol. 163:6694-6701 (1999)).*
Coleman (Research in Immunol. 145:33-36 (1994)).*
Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Arndt, K. M., et al., "Factors Influencing the Dimer to Monomer Transition of an Antibody Single-Chain Fv Fragment" *Biochemistry* 37:12918-12926 (1998).
Barbas & Burton, "Selection and evolution of high-affinity human anti-viral antibodies" *Trends Biotech* 14:230-234 (1996).
Barbas III et al., "In Vitro Evolution of a Neutralizing Human Antibody to Human Immunodeficiency Virus Type 1 to Enhance Affinity and Broaden Strain Cross-Reactivity" *Proc. Natl. Acad. Sci. USA* 91(9):3809-3813 (Apr. 1994).
Bass et al., "Hormone Phage: An Enrichment Method for Variant Proteins with Altered Binding Properties" *Proteins: Structure, Function, and Genetics* 8(4):309-314 (1990).
Bond, C. J., et al., "Contributions of CDR3 to $V_HH$ Domain Stability and the Design of Monobody Scaffolds for Naive Antibody Libraries" *Journal of Molecular Biology* 332:643-655 (2003).
Braunagel, M. et al., "Construction of a semisynthetic antibody library using trinucleotide oligos" *Nucleic Acids Research* 25(22):4690-6491 (1997).
Carter et al., "Humanization of an Anti-p185$^{HER2}$ Antibody for Human Cancer Therapy" *Proc. Natl. Acad. Sci. USA* 89(10):4285-4289 (May 1992).
Chen et al., "Selection and Analysis of an Optimized Anti-VEGF Antibody: Crystal Structure of an Affinity-matured Fab in Complex with Antigen" *Journal of Molecular Biology* 293(4):865-881 (1999).
Clackson et al., "Making antibody fragments using phage display libraries" *Nature* 352:624-628 (Aug. 15, 1991).
Connolly, J., "Analytical Molecular Surface Calculation" *J. Appl. Cryst.* 16:548-558 (1983).
Conrath, Katja Els, et al., "Camel Single-domain Antibodies as Modular Building Units in Bispecific and Bivalent Antibody Constructs" *The Journal of Biological Chemistry* 276(10):7346-7350 (Mar. 9, 2001).
Cunningham and Wells, "High-Resolution Epitope Mapping of hGH-Receptor Interactions by Alanine-Scanning Mutagenesis" *Science* 244:1081-1085 (Jun. 2, 1989).
Dall'Acqua, W. et al., "Antibody Engineering" *Current Opinion in Structural Biology* 8:443-450 (1998).
Davis, B., et al. *Microbiology Including Immunology and Molecular Genetics Third Edition*, Hagerstown:Harper & Row pp. 237, 245-47, 374 (1980).
de Kruif et al., "Leucine Zipper Dimerized Bivalent and Bispecific scFv Antibodies from a Semi-synthetic Antibody Phage Display Library" *Journal of Biological Chemistry* 271(13):7630-7634 (Mar. 29, 1996).
de Kruif et al., "Selection and Application of Human Single Chain Fv Antibody Fragments from a Semi-synthetic Phage Antibody Display Library with Designed CDR3 Regions" *Journal of Molecular Biology* 248:97-105 (1995).
de Wildt et al., "Antibody arrays for high-throughput screening of antibody-antigen interactions" *Nat Biotechnol.* 18(9):989-994 (Sep. 2000).
Decanniere, K., et al., "A single-domain antibody fragment in complex with RNase A: non-canonical loop structures and nanomolar affinity using two CDR loops" *Structure* 7:361-370 (Apr. 1999).
Decanniere, K., et al., "Canonical Antigen-binding Loop Structures in Immunoglobulins: More Structures, More Canonical Classes?" *Journal of Molecular Biology* 300:83-91 (2000).
Decanniere, K., et al., "Degenerate Interfaces in Antigen-Antibody Complexes" *Journal of Molecular Biology* 313:473-478 (2001).
Deng et al.; "Selection of Antibody Single-chain Variable Fragments with Improved Carbohydrate Binding by Phage Display" *Journal of Biological Chemistry* 269:9533-9538 (1994).
Desmyter, A., et al., "Antigen Specificity and High Affinity Binding Provided by One Single Loop of a Camel Single-domain Antibody" *Journal of Biological Chemistry* 276(28):26285-26290 (Jul. 13, 2001).
Desmyter, A., et al., "Crystal structure of a camel single-domain $V_H$ antibody fragment in complex with lysozyme" *Nature Structural Biology* 3(9):803-811 (Sep. 1996).
Desmyter, A., et al., "Three Camelid VHH Domains in Complex with Porcine Pancreatic α-Amylase" *The Journal of Biological Chemistry* 277(26):23645-23650 (Jun. 28, 2002).
Distefano, M., et al., "Quantifying β-Sheet Stability by Phage Display" *J. Mol. Biol.* 322:179-188 (2002).
Dubaquie and Lowman, "Total Alanine-Scanning Mutagenesis of Insulin-Like Growth. Factor I (IGF-I) Identifies Differential Binding Epitopes for IGFBP-1 and IGFBP-3" *Biochemistry* 38(20):6386-6396 (1999).
Dumoulin, M., et al., "A camelid antibody fragment inhibits the formation of amyloid fibrils by human lysozyme" *Nature* 424:783-788 (Aug. 14, 2003).
Dumoulin, M., et al., "Single-domain antibody fragments with high conformational stability" *Protein Science* 11:500-515 (2002).
Eigenbrot et al., "X-Ray Structures of the Antigen-Binding Domains From Three Variants of Humanized Anti-p185$^{HER2}$ Antibody 4D5 and Comparison With Molecular Modeling" *J. Mol. Biol.* 229:969-995 (1993).
Engels et al., "Gene Synthesis" *Agnew. Chem. Int. Ed. Engl.* 28:716-734 (1989).
Ewert, S., et al., "Biophysical Properties of Camelid $V_{HH}$ Domains Compared to Those of Human $V_H3$ Domains" *Biochemistry* 41:3628-3636 (2002).
Ewert, S., et al., "Biophysical Properties of Human Antibody Variable Domains" *J. Mol. Biol.* 325:531-553 (2003).
Fellouse et al., "Molecular Recognition by a Binary Code" *Journal of Mol Biology* 348(5):1153-1162 (2005).
Fellouse et al., "Synthetic antibodies from a four-amino-acid code: A dominant role for tyrosine in antigen recognition" *Proceedings of the National Academy of Sciences* 101(34):12467-12472 (Aug. 24, 2004).
Ferrat, G., et al., "A peptide mimic of an antigenic loop of α-human chorionic gonadotropin hormone: solution structure and interaction with a llama $V_{HH}$ domain" *Biochemical Journal* 366:415-422 (2002).
Forsberg et al., "Identification of Framework Residues in a Secreted Recombinant Antibody Fragment That Control Production Level and Localization in *Escherichia coli*" *The Journal of Biological Chemistry* 272(19):12430-12436 (May 9, 1997).
Froehler et al., "Synthesis of DNA via Deoxynucleoside H-phosphonate Intermediates" *Nucleic Acids Research* 14(13):5399-5407 (1986).
Fuh et al., "Requirements for Binding and Signaling of the Kinase Domain Receptor for Vascular Endothelial Growth Factor." *J. Bio. Chem.* 273(18):11197-11204 (May 1, 1998).
Garrard and Henner, "Selection of an anti-IGF-1 Fab from a Fab phage library created by mutagenesis of multiple CDR loops" *Gene* 128(1):103-109 (Jun. 15, 1993).
Ghahroudi, M. Arbabi, et al., "Selection and identification of single domain antibody fragments from camel heavy-chain antibodies" *FEBS Letters* 414:521-526 (1997).
Glockshuber et al., "A Comparison of Strategies to Stabilize Immunoglobulin $F_v$-Fragments" *Biochemistry* 29:1362-1367 (1990).

(56) References Cited

OTHER PUBLICATIONS

Gregoret and Sauer, "Additivity of mutant effects assessed by binomial mutagenesis" *Proc. Natl. Acad. Sci. USA* 90:4246-4250 (1993).
Griffiths et al., "Isolation of High Affinity Human Antibodies Directly From Large Synthetic Repertoires" *EMBO Journal* 13:3245-3260 (1994).
Hamers-Casterman, C., et al., "Naturally occurring antibodies devoid of light chains" *Nature* 363:446-448 (Jun. 3, 1993).
Harmsen, M. et al., "Llama heavy-chain V regions consist of at least four distinct subfamilies revealing novel sequence features" *Molecular Immunology* 37:579-590 (2000).
Hawkins et al., "Selection of Phage Antibodies by Binding Affinity Mimicking Affinity Maturation" *J. Mol. Biol.* 226:889-896 (1992).
Holliger et al., ""Diabodies": Small Bivalent and Bispecific Antibody Fragments" *Proc. Natl. Acad. Sci. USA* 90:6444-6448 (Jul. 1993).
Honegger, A., et al., "Yet Another Numbering Scheme for Immunoglobulin Variable Domains: An Automatic Modeling and Analysis Tool" *J. Mol. Biol.* 309:657-670 (2001).
Hoogenboom and Winter, "By-passing immunisation. Human antibodies from synthetic repertoires of germline $V_H$ gene segments rearranged in vitro" *J. Mol. Biol.* 227(2):381-388 (Sep. 20, 1992).
Hoogenboom et al., "Antibody phage display technology and its applications" *Immunotechnology* 4:1-20 (1998).
Hoogenboom, "Designing and optimizing library selection strategies for generating high-affinity antibodies" *Trends in Biotechnology* 15(2):62-70 (Feb. 1997).
Hoogenboom, H., "Overview of antibody phage-display technology and its applications" *Methods Mol. Biol.* 178:1-37 (2002).
Jackson et al., "In vitro antibody maturation. Improvement of a high affinity, neutralizing antibody against IL-1 beta" *J. Immunol.* 154(7):3310-3319 (1995).
Jung, S., et al., "Selection for Improved Protein Stability by Phage Display" *J. Mol. Biol.* 294:163-180 (1999).
Knappik et al., "Fully Synthetic Human Combinatorial Antibody Libraries (HuCAL) Based on Modular Consensus Frameworks and CDRs Randomized with Trinucleotides" *Journal of Mol. Biol.* 296:57-86 (2000).
Kostelny et al., "Formation of a Bispecific Antibody by the Use of Leucine Zippers" *Journal of Immunology* 148(5):1547-1553 (Mar. 1, 1992).
Kunkel et al., "Rapid and Efficient Site-specific Mutagenesis Without Phenotypic Selection" *Methods in Enzymology* 154:367-382 (1987).
Ladner, R., et al., "Novel frameworks as a source of high-affinity ligands" *Curr. Opin. Biotechnol.* 12:406-410 (2001).
Lee et al., "High-affinity human antibodies from phage-displayed synthetic Fab libraries with a single framework scaffold" *J. Mol. Biol.* 340(5):1073-1093 (2004).
Lee et al., "The Interpretation of Protein Structures: Estimation of Static Accessibility" *J. Mol. Biol.* 55:379-400 (1971).
Liang et al., "Function Blocking Antibodies to Neuropilin-1 Generated from a Designed Human Synthetic Antibody Phage Library" *J. Mol. Biol.* 366:815-829 (Nov. 10, 2006).
Lowman and Wells, "Monovalent Phage Display: A Method for Selecting Variant Proteins from Random Libraries" *Methods: A Companion to Methods in Enzymology* 3:205-216 (Dec. 1991).
Lowman et al., "Selecting High-Affinity Binding Proteins by Monovalent Phage Display" *Biochemistry* 30(45):10832-10838 (1991).
Morrison, K. et al., "Combinatorial alanine-scanning" *Current Opinion in Chemical Biology* 5:302-307 (2001).
Muyldermans, S., "Single domain camel antibodies: current status" *Reviews in Molecular Biotechnology* 74(4):277-302 (2001).
Muyldermans, S., et al., "Sequence and structure of $V_H$ domain from naturally occurring camel heavy chain immunoglobulins lacking light chains" *Protein Eng.* 7(9):1129-1135 (1994).
Nieba, L., et al., "Disrupting the hydrophobic patches at the antibody variable/constant domain interface: improved in vivo folding and physical characterization of an engineered scFv fragment" *Protein Engineering* 10(4):435-444 (1997).

O'Neil and Hoess, "Phage display: protein engineering by directed evolution" *Current Opinion in Structural Biology* 5:443-449 (1995).
Pacios, L., "Variation of Surface Areas and Volumes in Distinct Molecular Surfaces of Biomolecules" *J. of Molecular Modeling* 1:46-53 (1995).
Pacios, L., et al., "ARVOMOL/CONTOUR: molecular surface areas and volumes on personal computers" *Computers Chem.* 18(4):377-385 (1994).
Pack and Pluckthun, "Miniantibodies: Use of Amphipathic Helices to Produce Functional, Flexibly Linked Dimeric Fv Fragments with High Avidity in *Escherichia coli*" *Biochemistry* 31(6):1579-1584 (Feb. 18, 1992).
Pluckthun, "Antibodies From *Escherichia coli*" *The Pharmacology of Monoclonal Antibodies: Handbook of Pharmacology*, Rosenberg and Moore, eds., Berlin:Springer-Verlag, Chapter 11, vol. 113:269-315 (1994).
Presta et al., "Humanization of an Anti-Vascular Endothelial Growth Factor Monoclonal Antibody for the Therapy of Solid Tumors and Other Disorders" *Cancer Research* 57(20):4593-4599 (Oct. 15, 1997).
Rader and Barbas III, "Phage display of combinatorial antibody libraries" *Current Opinion in Biotechnology* 8(4):503-508 (Aug. 1997).
Renisio, J., et al., "Solution Structure and Backbone Dynamics of an Antigen-Free Heavy Chain Variable Domain (VHH) from Llama" *Proteins: Struct., Funct., Genet.* 47:546-555 (2002).
Sheriff, S., et al., "Redefining the minimal antigen-binding fragment" *Nature Structural Biology* 3(9):733-736 (Sep. 1996).
Sidhu et al., "Phage Display for Selection of Novel Binding Peptides" *Methods Enzymology* 328:333-363 (2000).
Sidhu, "Phage display in pharmaceutical biotechnology" *Current Opinion in Biotechnology* 11(6):610-616 (2000).
Sidhu, S. et al., "High copy display of large proteins on phage for functional selections" *J. Mol. Biol.* 296(2):487-495 (2000).
Sidhu, S., et al., "Phage-displayed Antibody Libraries of Synthetic Heavy Chain Complementarity Determining Regions" *J. Mol. Biol.* 338:299-310 (2004).
Skerra and Pluckthun, "Assembly of a functional immunoglobulin $F_v$ fragment in *Escherichia coli*" *Science* 240:1038-1041 (1988).
Skerra, A., "Engineered protein scaffolds for molecular recognition" *J. Mol. Recognit.* 13:167-187 (2000).
Smith, "Filamentous fusion phage: novel expression vectors that display cloned antigens on the virion surface" *Science* 228(4705):1315-1317 (1985).
Spinelli et al., "The crystal structure of a llama heavy chain variable domain" *Nat. Struct. Biol.* 3(9):752-757 (Sep. 1996).
Spinelli, S., et al., "Lateral Recognition of a Dye Hapten by a Llama VHH Domain" *J. Mol. Biol.* 311:123-129 (2001).
Tanha, J., et al., "Optimal Design Features of Camelized Human Single-domain Antibody Libraries" *The Journal of Biological Chemistry* 276(27):24774-24780 (Jul. 6, 2001).
Tanha, J., et al., "Selection by phage display of llama conventional $V_H$ fragments with heavy chain antibody $V_H H$ properties" *Journal of Immunological Methods* 263:97-109 (2002).
Ulrich et al., "Expression studies of catalytic antibodies" *Proc. Natl. Acad. Sci. USA* 92(25):11907-11911 (Dec. 5, 1995).
Vajdos et al., "Comprehensive functional maps of the antigen-binding site of an anti-ErbB2 antibody obtained with shotgun scanning mutagenesis" *J Mol Biol.* 320(2):415-428 (Jul. 5, 2002).
van der Linden, R., et al., "Induction of immune responses and molecular cloning of the heavy chain antibody repertoire of Lama glama" *Journal of Immunological Methods* 240:185-195 (2000).
Vaughan et al., "Human Antibodies With Sub-nanomolar Affinities Isolated From a Large Non-immunized Phage Display Library" *Nature Biotechnology* 14:309-314 (Mar. 1996).
Vranken, W., et al., "Solution Structure of a Llama Single-Domain Antibody with Hydrophobic Residues Typical of the VH/VL Interface" *Biochemistry* 41:8570-8579 (2002).
Weiss et al., "Rapid mapping of protein functional epitopes by combinatorial alanine scanning" *Proc. Natl. Acad. Sci. USA* 97(16):8950-8954 (Aug. 1, 2000).
Wells and Lowman, "Rapid evolution of peptide and protein binding properties in vitro" *Curr. Opin. Biotechnol.* 3:355-362 (1992).

(56) References Cited

OTHER PUBLICATIONS

Wiesmann et al., "Crystal Structure at 1.7 A Resolution of VEGF in Complex with Domain 2 of the Flt-1 Receptor." *Cell* 91:695-704 (Nov. 28, 1997).
Wu et al., "Stepwise in vitro affinity maturation of Vitaxin, an $\alpha_v\beta_3$-specific humanized mAB" *Proc. Natl. Acad. Sci. USA* 95(11):6037-6042 (May 26, 1998).
Wu, T., et al., "Length distribution of CDRH3 in antibodies" *Proteins* 16:1-7 (1993).
Yelton et al., "Affinity Maturation of the BR96 Anti-Carcinoma Antibody by Codon-Based Mutagenesis" *The Journal of Immunology* 155:1994-2004 (1995).
Zapata et al., "Engineering Linear F(ab')$_2$ Fragments for Efficient Production in *Escherichia coli* and Enhanced Antiproliferative Activity" *Protein Engineering* 8(10):1057-1062 (1995).
Zhu et al., "Remodeling domain interfaces to enhance heterodimer formation" *Protein Science* 6(4):781-788 (Apr. 1997).
Bradbury et al., "Antibodies from phage anitbody libraries" *J Immunol Methods* 290(1-2):29-49 (Apr. 2004).
Chen et al., "Neuropilin-2, a novel member of the Neuropilin family, is a high affinity receptor for the Semaphorins Sema E and Sema IV but not Sema III" *Neuron* 19(3):547-559 (Sep. 1997).
Chothia et al., "Confirmations of immunoglobulin hypervariable regions" *Nature* 342(6252):877-883 (1989).
Feldhaus et al., "Yeast display of antibody fragments: a discovery and characterization platform" *J Immunol Methods* 290(1-2):69-80 (Apr. 2001).
Ferrara et al., "Angiogenisis as a therapeutic target" *Nature* 438(7070):967-974 (Dec. 15, 2005).
Ferrara et al., "Bevacizumab (Avastin), a humanized anti-VEGF monoclonal antibody for cancer therapy" *Biochem Biophys Res Commun* 333(2):328-335 (2005).
Ferrara, N., "VEGF as a therapeutic target in cancer" *Oncology* 69(Suppl 3):11-16 (Nov. 21, 2005).
Gallop et al., "Applications of combinatorial technologies to drug discovery. 1. background and peptide combinatorial libraries" *J Med Chem* 37(9):1233-1251 (1994).
Gu et al., "Characterization of Neuropilin-1 structural features that confer binding to Semaphorin 3A and vascular endothelial growth factor 165" *J Biol Chem* 277(20):18069-18076 (May 17, 2002).
He et al., "Neuropilin is a receptor for the axonal chemorepellent Semophorin III" *Cell* 90(4):739-751 (Aug. 22, 1997).
Hoogenboom, H.R., "Selecting and screening recombinant antibody libraries" *Nat Biotechnol.* 23(9):1105-1116 (Sep. 2005).
Jain et al., "Lessons from phase III clinical trials on anti-VEGF therapy for cancer" *Nat Clin Pract Oncol* 3(1):24-40 (Jan. 2006).
Kabat et al., "Unusual distributions of amino acids in complementarity-determining (hypervariable) segments of heavy and light chains of immunoglobulins and their possible roles in specificity of antibody-combining sites" *J Biol Chem* 252(19):6609-661 (Jan. 5, 1977).
Kawasaki et al., "A requirement for neuropilin-1 in embryonic vessel formation" *Development* 126(21):4895-4902 (Oct. 1999).
Kerbel et al., "Possible mechanisms of acquired resistance to anti-angiogenic drugs: Implications for the use of combination therapy approaches" *Cancer Metastasis Rev* 20(1-2):79-86 (2001).
Kitsukawa et al., "Neuropilin-Semaphorin III/D-mediated chemorepulsive signals play a crucial role in peripheral nerve projection in mice" *Neuron* 19(5):995-1005 (Nov. 1997).
Kohler et al., "Continuous cultures of fused cells secreting antibody of predifined specificity" *Nature* 256(5517):495-497 (1975).
Kolodkin et al., "Neuropilin is a Semaphorin III receptor" *Cell* 19(3):753-762 (Aug. 22, 1997).
Kunkel T.A.. et al., "Efficient site-directed mutagenisis using uracil-containing DNA" *Methods in Enzymology* 204:125-139 (1991).
Lee et al., "Bivalent antibody phage display mimics natural immunoglobulin" *J Immunol Methods.* 284(1-2):119-132 (Jan. 2004).
Liang et al., "Cross-species vascular endothelial growth factor (VEGF)-blocking antibodies completely inhibit the growth of human tumor xenografts and measure the contribution of stromal VEGF" *J Biol Chem* 281(2):951-961 (Jan. 13, 2006).
Lipovsek et al, "In-vitro protein evolution by ribosome display and mRNA display" *J Immunol Methods* 290(1-2):51-67 (Apr. 2004).
Mian et al., "Structure, function and properties of antibody binding sites" *J Mol Biol* 217(1):133-151 (1991).
Sheets et al., "Efficient construction of a large nonimmune phage antibody library: the production of high-affinity human single-chain antibodies to protein antigens" *Proc. Natl. Acad. Sci. USA* 95(11):6157-6162 (May 1998).
Soker et al., "Neuropilin-1 is expressed by endothelial and tumor cells as an isoform-specific receptor for vascular endothelial growth factor" *Cell* 92(6):735-745 (Mar. 20, 1998).
Xu et al., "Diversity in the CDR3 region of V(H) is sufficient for most antibody specificities" *Immunity* 13(1):37-45 (Jul. 2000).
de Haard et al., "A large non-immunized human fab fragment phage library that permits rapid isolation and kinetic analysis of high affinity antibodies" *J Biol Chem* 274(26):18218-18230 (Jun. 1999).
"Guidelines for the Management of Rheumatoid Arthritis," Arthritis & Rheumatism, 46(2):328-346 (2002).
Adams et al., "Generating improved single chain Fv molecules for tumor targeting," J. Immunol. Methods, 231(1-2):249-260 (Dec. 10, 1999).
Adey et al., "Preparation of Second Generation Phage Libraries," Phage Disp. Pept. Proteins, Academic Press, Inc., eds. Kays et al., 277-291 (1996).
Akanuma et al., "Combinatorial mutagenesis to restrict amino acid usage in an enzyme to a reduced set," Proc. Natl. Acad. Sci., 99(21):13549-13553 (2002).
Amit et al., "Three-Dimensional Structure of an Antigen-Antibody Complex at 2.8 A Resolution," Science, 233:747-753 (1986).
Arbabi et al., "Selection and identification of single domain antibody fragments from camel heavy-chain antibodies," FEBS Letter, 414:521-526 (1997).
Arie et al., "Chaperone function of FkpA, a heat shock prolyl isomerase, in the periplasm of *Escherichia coli*", Mol. Microbial., 39(1):199-210 (Jan. 2001).
Baca et al., "Antibody Humanization Using Monovalent Phage Display," J. Biol. Chem., 272(16):10678-10684 (1997).
Bachmann, "Derivations and Genotypes of Some Mutant Derivatives of *Escherichia coli* K-12," *Escherichia coli* and *Salmonella typhimurium*: Cellular and Molecular Biology. (Washington, DC: American Society for Microbiology.), Chapter 72, 2:1190-1219 (1987).
Baldwin et al., "Monoclonal Antibodies in Cancer Treatment," The Lancet, 1(8481):603-605 (Mar. 15, 1986).
Barbas III et al., "Selection and evolution of high-affinity human anti-viral antibodies," Trends Biotech., 14:230-234 (1996).
Bassing et al., "The Mechanism and Regulation of Chromosomal V(D)J Recombination," Cell, 109:S45-S55 (2002).
Bendig, "Humanization of Rodent Monoclonal Antibodies by CDR Grafting," Methods: A Companion to Methods in Enzymology, 8:83-93 (1995).
Bond et al., "A Structure-Based Database of Antibody Variable Domain Diversity," J. Mol. Biol., 348:699-709 (2005).
Bothmann et al., "The Periplasmic *Escherichia coil* Peptidylprolyl cis,trans-Isomerase FkpA," J. Biol. Chem. 275(22):17100-17105 (Jun. 2000).
Brown et al., "Tolerance of Arc repressor to multiple-alanine substitutions," Proc. Natl. Acad. Sci. USA, 96:1983-1988 (1999).
Bullock et al., "XL-1 Blue: a high efficiency plasmid transforming recA *Escherichia coli* strain with beta-galactosidase selection," BioTechniques, 5(4):376-378 (1987).
Cannata et al., "Simplifying amino acids alphabets by means of a branch and bound algorithm and substitution matrices," Bioinformatics, 18(8):1102-1108 (2002).
Carlsson et al., "Protein Thiolation and Reversible Protein-Protein Conjugation," Biochemical Journal 173:723-737 (1978).
Chan, "Folding Alphabets," Nat. Struct. Biol., 6(11):994-996 (1999).
Chang et al., "High-level secretion of human growth hormone by *Escherichia coli*," Gene, 55:189-196 (1987).

(56) References Cited

OTHER PUBLICATIONS

Chari et al., "Immunoconjugates Containing Novel Maytansinoids: Promising Anticancer Drugs," Cancer Research, 52:127-131 (Jan. 1992).
Chen et al., "Chaperone Activity of DsbC," J. Bio. Chem., 274(28):19601-19605 (Jul. 1999).
Chothia et al., "Canonical Structures for the Hypervariable Regions of Immunoglobulins," J. Mol. Biol., 196:901-917 (1987).
Chothia et al., "Structural Repertoire of the Human VH Segments," J. Mol. Biol., 227:799-817 (1992).
Clynes et al., "Fc Receptors Are Required in Passive and Active Immunity to Melanoma," Proc. Natl. Acad. Sci. USA, 95:652-656 (Jan. 1998).
Crea et al., "Chemical synthesis of genes for human insulin," Proc. Natl. Acad. Sci. USA, 75(12):5765-5769 (1978).
Culler, S. et al., "Cluster and information entropy patterns in immunoglobulin complementarity determining regions," BioSystems, 77:195-212 (2004).
Davidson et al., "Cooperatively folded proteins in random sequence libraries," Nat. Struct. Biol., 2(10):856-864 (1995).
Davies et al., "Interactions of Protein antigens with Antibodies," Proc. Natl. Sci. USA, 93:7-12 (1996).
Dennis et al., "Albumin Binding as a General Strategy for Improving the Pharmacokinetics of Proteins," J. Biol. Chern., 277(38):35035-35043 (2002).
Deshayes et al., "Rapid identification of small binding motifs with high-throughput phage display: discovery of peptidic antagonists of IGF-1 function," Chem. Biol., 9(4):495-505 (Apr. 2002).
Doronina et al., "Development of potent monoclonal antibody auristatin conjugates for cancer therapy." Nature Biotechnology, 21(7):778-784 (2003).
"Gemtuzumab Ozogamicin," Drug of the Future 25(7):686-692 (2000).
Duncan et al., "The binding site for Clq on IgG," Nature, 332:738-740 (Apr. 21, 1988).
Els Conrath et al., "Camel single-domain antibodies as modular building units in bispecific and bivalent antibody constructs," J. Biol. Chem., 276(10):7346-7350 (Mar. 9, 2001).
Enshell-Seijffers et al., "The rational design of a 'type 88' genetically stable peptide display vector in the filamentous bacteriophage fd," Nucleic Acids Research, 29(10):1-13 (2001).
Evan et al., "Isolation of Monoclonal Antibodies Specific for Human c-myc Proto-Oncogene Product," Mol. Cell. Biol., 5(12):3610-3616 (1985).
Ferrara et al., "Clinical applications of angiogenic growth factors and their inhibitors," Nature Medicine, 5(12):1359-1364 (1999).
Field et al., "Purification of a RAS-Responsive Adenylyl Cyclase Complex from *Saccharomyces cerevisiae* by Use of an Epitope Addition Method," Mol. Cell. Biol., 8(5):2159-2165 (1988).
Fraker et al., "Protein and cell membrane iodinations with a sparingly soluble chloroamide, 1,3,4,6-tetrachloro-3a,6a-diphrenylglycoluril," Biochem. Biophys. Res. Commun., 80(4):849-857 (1978).
Franklin et al., "Insights into ErbB signaling from the structure of the ErbB2-pertuzumab complex," Cancer Cell., 5(4):317-328 (2004).
Garrard et al., "Selection of an anti-IGF-1 Fab from a Fab phage library created by mutagenesis of multiple CDR loops," Gene, 128:103-109 (Jun. 15, 1993).
Gazzano-Santoro et al., "A non-radioactive complement-dependent cytotoxicity assay for anti-CD20 monoclonal antibody," J. Immunol. Methods, 202:163-171 (1997).
Geoghegan et al., "Site-Directed Conjugation of Nonpeptide Groups to Peptides and Proteins via Periodate Oxidation of a 2-Amino Alcohol. Application to Modification at N-Terminal Serine," Bioconjugate Chem., 3:138-146 (1992).
Ghetie et al., "Multiple Roles for the Major Histocompatibility Complex Class I-Related Receptor FcRn," Ann. Rev. Immunol., 18:739-766 (2000).
Glockshuber et al., "Mapping and Modification of an Antibody Hapten Binding Site: A Site-Directed Mutagenesis Study of McPC603," Biochemistry, 30(12):3049-3054 (1991).
Goeddel et al., "Direct expression in *Escherichia coli* of a DNA sequence coding for human growth hormone," Nature, 281:544-548 (1979).
Graham et al., "Characteristics of a Human Cell Line Transformed by DNA from Human Adenovirus Type 5," J. Gen Virol., 36:59-72 (1977).
Graille et al., "Crystal structure of a *Staphylococcus aureus* protein A domain complexed with the Fab fragment of a human IgM antibody: Structural basis for recognition of B-cell receptors and superantigen activity," PNAS, 97(10):5399-5404 (2000).
Gray et al., "*Pseudomonas aeruginosa* Secretes and Correctly Processes Human Growth Hormone," Biotechnology, 2:161-165 (1984).
Guss et al., "Structure of the 19G-binding regions of streptococcal protein G," EMBO J., 5(7): 1567-1575 (1986).
Ham et al, "Media and Growth Requirements," Meth. Enz., 58:44-93 (1979).
Hara et al., "Overproduction of penicillin-binding protein 7 suppresses thermosensitive growth defect at low osmolarity due to an spr mutation of *Escherichia coli*," Microb. Drug Resist., 2:63-72 (1996).
Harris, "Therapeutic Monoclonals," Biochem. Soc. Transactions, 23:1035-1038 (1995).
Heinz et al., "Folding and function of T4 lysozyme containing 10 consecutive alanincs illustrate the redundancy of information in an amino acid sequence," Proc. Natl. Acad. Sci. USA, 89:3751-3755 (1992).
Hinman et al., "Preparation and Characterization of Monoclonal Antibody Conjugates of the Calicheamicins: A Novel and Potent Family of Antitumor Antibiotics,", Cancer Research, 53:3336-3342 (1993).
Hinton et al., "Engineered Human IgG Antibodies with Longer Serum Half-lives in Primates," J. Biol. Chem., 279(8):6213-6216 (2004).
Hoet et al., "Generation of high-affinity human antibodies by combining donor-derived and synthetic complementarity-determining-region diversity," Nat Biotechnol., 23(3):344-348 (Mar. 2005).
Houck et al., "The Vascular Endothelial Growth Factor Family: Identification of a Fourth Molecular Species and Characterization of Alternative Splicing of RNA," Mol. Endocrin., 5:1806-1814 (1991).
Hufton et al., "Phage display of cDNA repertoires: the pVI display system and its applications for the selection of immunogenic ligands," J Immunol Methods, 231(1-2):39-51 (1999).
Hurle et al., "Protein engineering techniques for antibody humanization," Curr. Opin. Struct. Biol., 5:428-433 (1994).
Hymowitz et al., "Triggering cell death: the crystal structure of Apo2L/TRAIL in a complex with death receptor 5," Molecular Cell, 4(4):563-571 (Oct. 1999).
Jones et al., "Replacing the complementarity-determining regions in a human antibody with those from a mouse," Nature, 321:522-525 (1986).
Kabat et al., "Attempts to Locate Complementarity-Determining Residues in the Variable Positions of Light and Heavy Chain," Ann. NY Acad. Sci., 190:382-393 (1971).
Kabat, "Antibody Diversity Versus Antibody Complementarity" Pharmacological Reviews, 34(1):23-38 (1982).
Kamteker et al., "Protein Design by Binary Patterning of Polar and Nonpolar Amino Acids," Science, 262:1680-1685 (1993).
Kelley et al., "Antigen Binding Thermodynamics and Antiproliferative Effects of Chimeric and Humanized anti-p185$^{HER2}$ Antibody Fab Fragments," Biochemistry, 31(24):5434-5441 (1992).
Klagsbrun et al., "Regulators of Angiogenesis," Annu. Rev. Physiol., 53:217-239 (1991).
Klein et al., "I.29 lymphoma cells express a nonmutated $V_H$ gene before and after H chain switch," J. Immunol., 140(5):1676-1684 (Mar. 1, 1988).
Konthur et al., "Automation of page display for high throughput antibody development," Targets, 1(1):30-36 (Jul. 1, 2002).
Kyte et al., "A Simple Method for Displaying the Hydropathic Character of a Protein," J. Mol. Biol., 157:105-132 (1982).
Lazar et al., "Transforming Growth Factor (1.: Mutation of Aspartic Acid 47 and Leucine 48 Results in Different Biological Activities," Molecular & Cellular Biology, 8(3):1247-1252 (Mar. 1988).
Leung et al., "Vascular Endothelial Growth Factor is a Secreted Angiogenic Mitogen", Science, 246:1306-1309 (1989).

(56) References Cited

OTHER PUBLICATIONS

Lin et al., "Structure-function relationships in glucagon: properties of highly purified des-His[1]-, monoiodo-, and (des-Asn[28], Thr-[29])(homoserine lactone[27])-glucagon," Biochemistry 14(8):1559-1563 (1975).

Lindmark et al., "Binding of Immunoglobulins to Protein A and Immunoglobulin Levels in Mammalian Sera", J. Immunol. Meth., 62:1-13 (1983).

Liu et al., "Eradication of large colon tumor xenografts by targeted delivery of maytansinoids", Proc. Natl. Acad. Sci. USA, 93:8618-8623 (1996).

Lode et al., "Targeted therapy with a novel enediyne antibiotic calicheamicin theta(I)1 effectively suppresses growth and dissemination of liver metastases in a syngeneic model of murine neuroblastoma," Cancer Research, 58(14):2925-2928 (1998).

Mandler et al., "Immunoconjugates of geldanamycin and anti-HER2 monoclonal antibodies: antiproliferative activity on human breast carcinoma cell lines," Jour. of the Nat. Cancer Inst., 92(19):1573-1581 (Oct. 4, 2000).

Mandler et al., "Modifications in Synthesis Strategy Imprve the Yield and Efficacy of Geldanamycin-Herceptin Immunoconjugates", Bioconjugate Chem., 13:786-791 (2002).

Mandler et al., "Synthesis and evaluation of antiproliferative activity of a geldanamycin-Herceptin immunoconjugate," Bioorganic Med. Chem. Letters, 10(10):1025-1028 (May 15, 2000).

Marks et al., "By-passing Immunization Human Antibodies from V-gene Libraries Displayed on Phage," J. Mol. Biol., 222:581-597 (1991).

Marks et al., "By-Passing Immunization: Building High Affinity Human Antibodies by Chain Shuffling," Bio/Technology, 10:779-783 (1992).

Marsters et al., "Apo-3, a new member of the tumor necrosis factor receptor family, contains a death domain and activates apoptosis and NF-κB," Current Biology. 6(12):1669-1676, (Dec. 1, 1996).

Mather et al., "Culture of Testicular Cells in Hormone-Supplemented Serum-Free Medium," Annals N.Y. Acad. Sci., 383:44-68 (1982).

Mather, "Establishment and Characterization of Two Distinct Mouse Testicular Epithelial Cell Lines," Biol. Reprod., 23:243-252 (1980).

McCafferty, "Phage Display: Factors Affecting Panning Efficiency," Phage Display of Peptides and Proteins (Chapter 15), Academic Press, Inc., 261-276 (1996).

Monfardini et al., "Recombinant Antibodies in Bioactive Peptide Design," J. Biol. Chem., 270(12):6628-6638 (Mar. 12, 1995).

Moore et al., "Equivalent potency and pharmacokinetics of recombinant human growth hormones with or without an N-terminal methioninc," Endocrinology, 122(6):2920-2926 (1988).

Morea et al., "Conformations of the Third Hypervariable Region in the VH Domain of Immunoglobulins," J. Mol. Biol., 275:269-294 (1998).

Moritz et al., "A spacer region between the single chain antibody and the CD3 zeta-chain domain of chimeric T cell receptor components is required for efficient ligand binding and signaling activity," Gene Therapy, 2(8):539-546 (Oct. 1995).

Morrison et al., "Chimeric human antibody molecules: Mouse antigen-binding domains with human constant region domains," Proc. Natl. Acad. Sci. USA, 81:6851-6855 (1984).

Murphy et al., "Simplified amino acid alphabets for protein fold recognition and implications for folding," Prot. Eng., 13(3): 149-152 (2000).

Muyldennans et al., "Recognition of antigens by single-domain antibody fragments: the superfluous luxury of paired domains," TIBS, 26:230-235 (2001).

Nicolaou et al., "Calicheamicin Theta I1: A Rationally Designed Molecule with Extremely Potent and Selective DNA Cleaving Properties and Apoptosis Inducing Activity," Agnew Chem Intl. Ed. Engl., 33:183-186 (1994).

Nicoletti et al., "A rapid and simple method for measuring thymocyte apoptosis by propidium iodide staining and flow cytometry," J. Immunol. Methods, 139:271-279 (1991).

Niculescu-Duvaz et al., "Antibody-directed enzyme prodrug therapy (ADEPT): a review," Adv. Drg Del. Rev., 26:151-172 (1997).

Nieba et al., "Disrupting the hydrophobic patches at the antibody variable/constant domain interface: improved in vivo folding and physical characterization of an engineered scFv fragment," Protein Engineering, 10(4):435-444 (1997).

Paborsky et al., "Mammalian cell transient expression of tissue factor for the production of antigen," Protein Engineering, 3(6):547-553 (1990).

Padlan et al., "Identification of specificity-determining residues in antibodies," The FASEB Journal, 9:133-139 (1995).

Padlan, "Does Base Composition Help Predispose the Complementarity-Determining Regions of Antibodies to Hypermutation?" Molecular Immunology, 34(11):765-770 (1997).

Padlan, "Review—Anatomy of the Antibody Molecule," Molecular Immunology, 31(3):169-217 (1994).

Pereboev et al., "Phage Display of Adenovirus Type 5 Fiber Knob as a Tool for Specific Ligand Selection and Validation," Journal of Virology, 75(15):7107-7113 (2001).

Pini et al., "Design and use of a phage display library. Human antibodies with subnanomolar affinity against a marker of angiogenesis eluted from a two-dimensional gel," Journal of Biological Chemistry, 273(34):21769-21776 (1998).

Presta et al., "Humanization of an Antibody Directed Against IgE," J. Immunol., 151:2623-2632 (1993).

Presta, "Antibody Engineering," Curr. Opin. Struct. Biol., 2:593-596 (1992).

Proba et al., "Functional antibody single-chain fragments from the cytoplasm of *Escherichia coli*: influence of thioredoxin reductase (TrxB)," Gene, 159:203-207 (1995).

Radley et al., "Allosteric Switching by Mutually Exclusive Folding of Protein Domains," J. Mol. Biol., 332(3)529-758 (2003).

Ramm et al., "The Periplasmic *Escherichia coli* Peptidylprolyl cis,trans-Isomerase FkpA," J. Biol. Chem., 275:17106-17113 (2000).

Randen et al., "Complementarity-determining region 2 is implicated in the binding of staphylococcal protein A to human immunoglobulin $V_H$III variable regions," Eur. J. Immunol., 23:2682-2686 (1993).

Ravetch et al., "Fc Receptors," Annu. Rev. Immunol., 9:457-492 (1991).

Regan et al., "Characterization of a helical protein designed from first principles," Science, 241:976-978 (1988).

Reyes et al., "Expression of human β-interferon cDNA under the control of a thymidine kinase promoter from herpes simplex virus," Nature, 297:598-601 (1982).

Riddle et al., "Functional rapidly folding proteins from simplified amino acid sequences," Nat. Struct. Biol., 4(10):805-809 (1997).

Riechmann et al., "Reshaping human antibodies for therapy," Nature, 332:323-327 (1988).

RN 148222-13-3, Jun. 22, 1993 (ED).

Rondot et al., "A helper phage to improve single-chain antibody presentation in phage display," Nat. Biotechnology, 19:75-78 (2001).

Rowland et al., "Drug localisation and growth inhibition studies of vindesine-monoclonal anti-CEA conjugates in a human tumour xenograft," Cancer Immunol. Immunother., 21(3):183-187 (1986).

Saerens et al., "Identification of a universal VHH framework to graft non-canonical antigen-binding loops of camel single-domain antibodies," J. Mol. Biol., 352(3):597-607 (Sep. 2005).

Sato, "Molecular diagnosis of tumor angiogenesis and antiangiogenic cancer therapy," Int. J. Clin. Oncol., 8:200-206 (2003).

Schier et al., "Identification of functional and structural amino-acid residues by parsimonious mutagenesis," Gene, 169:147-155 (1996).

Schier et al.. "Isolation of high-affinity monomeric human anti-c-erbB-2 single chain Fv using affinity-driven selection." J. Mol. Biol. 255:28-43 (1996).

Schluter et al.. "The cell proliferation associated antigen of antibody Ki-67: a very large, ubiquitous nuclear protein with numerous repeated elements, representing a new kind of cell cycle-maintaining proteins," J. Cell Biol., 123(3):513-522 (Nov. 1993).

Schwartz et al., "A superactive insulin: (B10-Aspartic acid) insulin (human)," Proc. Natl. Acad. Sci. USA, 84:6408-6411 (Sep. 1987).

(56) References Cited

OTHER PUBLICATIONS

Shang et al., "Design of a "minimAl" homeodomain: The N-terminal arm modulates DNA binding affinity and stabilizes homeodomain structure," Proc. Natl. Acad. Sci. USA, 91:8373-8377 (1994).
Shields et al., "High Resolution Mapping of the Binding Site on Human IgG 1 for FcγRI, FcγRII, FcγIII, and FcRn and Design of IgG 1 Variants with Improved Binding to the FcγR," J. Biol. Chem., 276(9):6591-6604 (2001).
Sidhu et al., "Exploring protein-protein interactions with phage display," Chembiochem, 4(1):14-25 (Jan. 3, 2003).
Siebenlist et al., "*E. coli* RNA Polymerase Interacts Homologously with Two Different Promoters," Cell, 20:269-281 (1980).
Simmons et al., "Expression of full-length immunoglobulins in *Escherichia coli*: rapid and efficient production of aglycosylated antibodies," J. Immunol. Methods, 263:133-147 (2002).
Sims et al., "A Humanized CD18 Antibody Can Block Function without Cell Destruction," J. Immunol. 151(4):2296-2308 (1993).
Spinelli et al., "Camelid heavy-chain variable domains provide efficient combining sites to haptens," Biochemistry, 39:1217-1222 (2000).
Stella et al., "Prodrugs: A Chemical Approach to Targeted Drug Delivery," Directed Drug Delivery, Borchardt et al., (ed.), pp. 247-267, Humana Press (1985).
Stewart et al., "A Shannon Entropy Analysis of Immunoglobulin and T Cell Receptor," Mol. Immunol., 34(15):1067-1082 (1997).
Streit et al., "Angiogenesis, lymphangiogenesis, and melanoma metastasis," Oncogene, 22:3172-3179 (2003).
Supplementary Partial European Search Report for European Patent No. 03734379.5 dated Jul. 4, 2005.
Syrigos et al., "Antibody Directed Enzyme Prodrug Therapy (ADEPT): A Review of the Experimental and Clinical Considerations," Anticancer Research, 19:605-614 (1999).
Thompson et al., "Clustal W: improving the sensitivity of progressive multiple sequence alignment through sequence weighting, position specific gap penalties and weight matrix choice," Nucleic Acids Res., 22(22):4673-4680 (1994).
Tonegawa, "Somatic generation of antibody diversity," Nature, 302:575-581 (1983).
Tonini et al., "Molecular basis of angiogenesis and cancer," Oncogene, 22:6549-6556 (2003).
Urlaub et al., "Isolation of Chinese hamster cell mutants deficient in dihydrofolate reductase activity," Proc. Natl. Acad. Sci. USA, 77:4216-4220 (1980).
Vaswani et al., "Humanized antibodies as potential therapeutic drugs," Annals of Allergy, Asthma, & Immunology, 81:105-115 (1998).
Verhoeyen et al., "Reshaping Human Antibodies: Grafting an Antilysozyme Activity," Science, 239:1534-1536 (1988).
Vieira et al., "Production of Single-Stranded Plasmid DNA," Meth. Enzymol., 153:3-11 (1987).
Vitetta et al., "Redesigning Nature's Poisons to Create Anti-Tumor Reagents," Science, 238:1098-1104 (1987).
Wang et al., "A computational approach to simplifying the protein folding alphabet," Nat. Struct. Biol., 6(11):1033-1038 (1999).
Weiss et al., "Mutational analysis of the major coat protein of M13 identifies residues that control protein display," Protein Science, 9:647-654 (2000).
Wilman, "Prodrugs in Cancer Chemotherapy," Biochemical Society Transactions, 14:375-382, 615th Meeting Belfast (1986).
Wilson et al., "Receptor Revision of Immunoglobulin Heavy Chain Variable Region Genes in Normal Human B Lymphocytes," J. Exp. Med., 191(11):1881-1894 (2000).
Winter et al., "Making antibodies by phage display technology," Annu. Rev. Immunol., 12:433-455 (1994).
Wiseman et al., "Ibritumomab tiuxetan radioimmunotherapy for patients with relapsed or refractory non-Hodgkin lymphoma and mild thrombocytopenia: a phase II multicenter trial," Blood, 99(12):4336-4342 (2002).
Wiseman et al., "Phase I/II $^{90}$Y-Zevalin (yttrium-90 ibritumomab tiuxetan, IDEC-Y2B8) radioimmunotherapy dosimetry results in relapsed of refractory non-Hodgkin's lymphoma," Eur. J. Nucl. Med., 27(7):766-777 (2000).
Witzig et al., "Randomized Controlled Trial of Yttrium-90-Labeled Ibritumomab Tiuxetan Radioimmunotherapy Versus Rituximab Immunotherapy for Patients with Relapsed or Refractory Low-Grade, Follicular, or Transformed B-Cell Non-Hodgkin's Lymphoma," J. Clin. Oncol., 20(10):2453-2463 (2002).
Witzig et al., "Treatment with Ibritumomab Tiuxetan Radioimmunotherapy in Patients with Rituximab-Refractory Follicular Non-Hodgkin's Lymphoma," J. Clin. Oncol., 20(15):3262-3269 (2002).
Wong et al., "Expression of secreted insulin-like growth factor-1 in *Escherichia coli*," Gene, 68: 193-203 (1988).
Wu et al., "An Analysis of the Sequences of the Variable Regions of Bence Jones Proteins and Myeloma Light Chains and Their Implications for Antibody Complementarily," J. Exp. Med., 132:211-250 (1970).
Xiong et al., "Periodicity of polar and nonpolar amino acids is the major determinant of secondary structure in self-assembling oligomeric peptides," Proc. Natl. Acad Sci. USA, 92:6349-6353 (1995).
Yaniv, "Enhancing elements for activation of eukaryotic promoters," Nature, 297:17-18 (1982).
Yansura et al., "Nucleotide sequence selection for increased expression of heterologous genes in *Escherichia coli*," Methods: A Companion to Methods Enzymol. 4:151-158 (1992).
Zemlin et al, "Expressed Murine and Human CDR-H3 Intervals of Equal Length Exhibit distinct repertoires that differ in amino acid composition and predicted structures," J. Mol. Biol. 334:733-749 (2003).
Zoller et al., "Oligonucleotide-directed mutagenesis using M13-derived vectors: an efficient and general procedure for the production of point mutations in any fragment of DNA," Nucleic Acids Res., 10(20):6487-6500 (1982).
European Patent Office, European Search Report, dated May 8, 2012, in European No. EP 11 16 1038, pp. 1-9.
Knappik A et al: 'Fully synthetic human combinatorial antibody libraries (HuCAL) based on modular consensus frameworks and CDRs randomized with trinucleotides', Journal of Molecular Biology, London, GB, vol. 296, No. 1, Feb. 11, 2000, pp. 57-86, XP004461525, ISSN: 0022-2836.

* cited by examiner

FIG. 1A

Based on human antibody subgroup III in Kabat database

FIG._1B

| CDRs | Positions | Residues | Prevalence in natural human |
|---|---|---|---|
| CDR-L1 (SEQ ID NO: 75) | 28 | S | 33 |
| | 29 | I | 40 |
| | 30 | S | 55 |
| | 31 | S | 44 |
| | 32 | Y | 67 |
| | 33 | L | 94 |
| CDR-L2 (SEQ ID NO: 76) | 50 | G | 25 |
| | 51 | A | 79 |
| | 52 | S | 95 |
| | 53 | S | 36 |
| | 54 | R | 60 |
| | 55 | A | 45 |
| CDR-L3 (SEQ ID NO: 77) | 91 | Y | 54 |
| | 92 | Y | 23 |
| | 93 | S | 46 |
| | 94 | S | 24 |
| | 95 | P | 80 |
| | 96 | L | 22 |
| CDR-H1 (SEQ ID NO: 78) | 27 | F | 45 |
| | 28 | T | 54 |
| | 29 | F | 73 |
| | 30 | S | 68 |
| | 31 | S | 50 |
| | 32 | Y | 64 |
| | 33 | A | 22 |
| | 34 | M | 46 |
| | 35 | S | 34 |
| CDR-H2 (SEQ ID NO: 79) | 50 | R | 17 |
| | 51 | I | 84 |
| | 52 | S | 26 |
| | 52a | P | 29 |
| | 53 | S | 24 |
| | 54 | G | 37 |
| | 55 | G | 53 |
| | 56 | S | 28 |
| | 57 | T | 56 |
| | 58 | Y | 32 |

FIG._2

CDRL1: Consensus

CDRL2: Consensus

CDRL3: Hard randomized 91, 92, 93, 94, 96

| Kabat No. | 23 | 24 | 25 | 26 | 27 | 28 | 29 | 30 | 31 | 32 | 33 | 34 | 35 | |
|---|---|---|---|---|---|---|---|---|---|---|---|---|---|---|
| Consensus | TGC | CGT | GCC | AGT | CAG | AGC | ATC | TCC | AGC | TAC | CTG | GCC | TGG | SEQ ID NO: 99 |
|  | C | R | A | S | Q | S | I | S | S | Y | L | A | W | SEQ ID NO: 100 |

CDRL1 spans positions 24–34.

| Kabat No. | 47 | 48 | 49 | 50 | 51 | 52 | 53 | 54 | 55 | 56 | 57 | 58 | 59 | |
|---|---|---|---|---|---|---|---|---|---|---|---|---|---|---|
| Consensus | CTG | ATT | TAC | GGT | GCA | TCC | AGC | CGC | GCA | TCT | GGA | GTC | CCT | SEQ ID NO: 101 |
|  | L | I | Y | G | A | S | S | R | A | S | G | V | P | SEQ ID NO: 102 |

CDRL2 spans positions 50–56.

| Kabat No. | 87 | 88 | 89 | 90 | 91 | 92 | 93 | 94 | 95 | 96 | 97 | 98 | 99 | |
|---|---|---|---|---|---|---|---|---|---|---|---|---|---|---|
| Consensus | TAC | TGT | CAG | CAA | TAC | TAT | AGC | AGC | CCT | CTG | ACG | TTC | GGA | SEQ ID NO: 103 |
|  | Y | C | Q | Q | Y | Y | S | S | P | L | T | F | G | SEQ ID NO: 104 |
| Randomization | TAC | TGT | CAG | CAA | MGC | (567) | (6) | (678) | CCG | NTC | ACC | TTC | GGA | SEQ ID NO: 105 |
|  | Y | C | Q | Q | R/S | Y | S | Y | P | F | T | F | G | SEQ ID NO: 106 |
|  |  |  |  |  | TAT | S | 17 | S |  | I |  |  |  | SEQ ID NO: 107 |
|  |  |  |  |  | Y | 16 |  | 18 |  | L |  |  |  | SEQ ID NO: 108 |
|  |  |  |  |  |  |  |  |  |  | V |  |  |  | SEQ ID NO: 109 |

CDRL3 spans positions 89–97.

FIG._3

CDRH1: Hard randomized 27, 28, 30, 31, 32, 33, 34

CDRH2: Hard randomized 50, 52, 52a, 53, 54, 56, 58

CDRH3: Hard randomized 93, 95 ~ 100m, 102

[Figure showing CDRH1, CDRH2, and CDRH3 sequence randomization tables with Kabat numbering, consensus sequences, and randomization schemes. SEQ ID NOs referenced: 110–117 for CDRH1/CDRH2, and 118–121, 192, 193 for CDRH3.]

FIG. 4A

| | 5 | 6 | 7 | 8 | 5/6 | 5/7 | 5/8 | 5/6/7 | 5/6/8 | 5/7/8 | 5/6/7/8 | 6/7 | 6/8 | 6/7/8 |
|---|---|---|---|---|---|---|---|---|---|---|---|---|---|---|
| A | 2.5 | 2.5 | 2.5 | 5.0 | 2.5 | 2.5 | 3.8 | 2.5 | 3.3 | 3.3 | 3.1 | 2.5 | 3.8 | 3.3 |
| D | 2.5 | 2.5 | 2.5 | 5.0 | 2.5 | 2.5 | 3.8 | 2.5 | 3.3 | 3.3 | 3.1 | 2.5 | 3.8 | 3.3 |
| E | 2.5 | 2.5 | 2.5 | 5.0 | 2.5 | 2.5 | 3.8 | 2.5 | 3.3 | 3.3 | 3.1 | 2.5 | 3.8 | 3.3 |
| F | 2.5 | 2.5 | 2.5 | 5.0 | 2.5 | 2.5 | 3.8 | 2.5 | 3.3 | 3.3 | 3.1 | 2.5 | 3.8 | 3.3 |
| G | 52.5 | 2.5 | 2.5 | 5.0 | 27.5 | 27.5 | 28.8 | 19.2 | 20.0 | 20.0 | 15.6 | 2.5 | 3.8 | 3.3 |
| H | 2.5 | 2.5 | 2.5 | 5.0 | 2.5 | 2.5 | 3.8 | 2.5 | 3.3 | 3.3 | 3.1 | 2.5 | 3.8 | 3.3 |
| I | 2.5 | 2.5 | 2.5 | 5.0 | 2.5 | 2.5 | 3.8 | 2.5 | 3.3 | 3.3 | 3.1 | 2.5 | 3.8 | 3.3 |
| K | 2.5 | 2.5 | 2.5 | 5.0 | 2.5 | 2.5 | 3.8 | 2.5 | 3.3 | 3.3 | 3.1 | 2.5 | 3.8 | 3.3 |
| L | 2.5 | 2.5 | 2.5 | 5.0 | 2.5 | 2.5 | 3.8 | 2.5 | 3.3 | 3.3 | 3.1 | 2.5 | 3.8 | 3.3 |
| M | 2.5 | 2.5 | 2.5 | 5.0 | 2.5 | 2.5 | 3.8 | 2.5 | 3.3 | 3.3 | 3.1 | 2.5 | 3.8 | 3.3 |
| N | 2.5 | 2.5 | 2.5 | 5.0 | 2.5 | 2.5 | 3.8 | 2.5 | 3.3 | 3.3 | 3.1 | 2.5 | 3.8 | 3.3 |
| P | 2.5 | 2.5 | 2.5 | 5.0 | 2.5 | 2.5 | 3.8 | 2.5 | 3.3 | 3.3 | 3.1 | 2.5 | 3.8 | 3.3 |
| Q | 2.5 | 2.5 | 2.5 | 5.0 | 2.5 | 2.5 | 3.8 | 2.5 | 3.3 | 3.3 | 3.1 | 2.5 | 3.8 | 3.3 |
| R | 2.5 | 2.5 | 2.5 | 5.0 | 2.5 | 2.5 | 3.8 | 2.5 | 3.3 | 3.3 | 3.1 | 2.5 | 3.8 | 3.3 |
| S | 2.5 | 52.5 | 2.5 | 5.0 | 27.5 | 2.5 | 3.8 | 19.2 | 20.0 | 3.3 | 15.6 | 27.5 | 28.8 | 20.0 |
| T | 2.5 | 2.5 | 2.5 | 5.0 | 2.5 | 2.5 | 3.8 | 2.5 | 3.3 | 3.3 | 3.1 | 2.5 | 3.8 | 3.3 |
| V | 2.5 | 2.5 | 2.5 | 5.0 | 2.5 | 2.5 | 3.8 | 2.5 | 3.3 | 3.3 | 3.1 | 2.5 | 3.8 | 3.3 |
| W | 2.5 | 2.5 | 52.5 | 5.0 | 2.5 | 27.5 | 3.8 | 19.2 | 3.3 | 20.0 | 15.6 | 2.5 | 3.8 | 3.3 |
| Y | 2.5 | 2.5 | 2.5 | 5.0 | 2.5 | 2.5 | 3.8 | 2.5 | 3.3 | 3.3 | 3.1 | 27.5 | 3.8 | 20.0 |

FIG._4B

|   | X0 | X1 | X2 | X3 | X4 | X5 | X6 | X7 |
|---|---|---|---|---|---|---|---|---|
| A | 2.5 | 2.5 | 2.5 | 5.0 | 3.8 | 2.5 | 3.3 | 3.1 |
| D | 2.5 | 2.5 | 2.5 | 5.0 | 3.8 | 2.5 | 3.3 | 3.1 |
| E | 2.5 | 2.5 | 2.5 | 5.0 | 3.8 | 2.5 | 3.3 | 3.1 |
| F | 2.5 | 2.5 | 2.5 | 5.0 | 3.8 | 2.5 | 3.3 | 3.1 |
| G | 52.5 | 2.5 | 2.5 | 5.0 | 28.8 | 19.2 | 3.3 | 15.6 |
| H | 2.5 | 2.5 | 2.5 | 5.0 | 3.8 | 2.5 | 3.3 | 3.1 |
| I | 2.5 | 2.5 | 2.5 | 5.0 | 3.8 | 2.5 | 3.3 | 3.1 |
| K | 2.5 | 2.5 | 2.5 | 5.0 | 3.8 | 2.5 | 3.3 | 3.1 |
| L | 2.5 | 2.5 | 2.5 | 5.0 | 3.8 | 2.5 | 3.3 | 3.1 |
| M | 2.5 | 2.5 | 2.5 | 5.0 | 3.8 | 2.5 | 3.3 | 3.1 |
| N | 2.5 | 2.5 | 2.5 | 5.0 | 3.8 | 2.5 | 3.3 | 3.1 |
| P | 2.5 | 2.5 | 2.5 | 5.0 | 3.8 | 2.5 | 3.3 | 3.1 |
| Q | 2.5 | 2.5 | 2.5 | 5.0 | 3.8 | 2.5 | 3.3 | 3.1 |
| R | 2.5 | 2.5 | 2.5 | 5.0 | 3.8 | 2.5 | 3.3 | 3.1 |
| S | 2.5 | 52.5 | 2.5 | 5.0 | 3.8 | 19.2 | 20.0 | 15.6 |
| T | 2.5 | 2.5 | 2.5 | 5.0 | 3.8 | 2.5 | 3.3 | 3.1 |
| V | 2.5 | 2.5 | 2.5 | 5.0 | 3.8 | 2.5 | 3.3 | 3.1 |
| W | 2.5 | 2.5 | 2.5 | 5.0 | 3.8 | 2.5 | 3.3 | 3.1 |
| Y | 2.5 | 2.5 | 52.5 | 5.0 | 3.8 | 19.2 | 20.0 | 15.6 |

FIG. 4C

| CDRs | Positions | Codon | Design diversity | | | | | Natural diversity |
|---|---|---|---|---|---|---|---|---|
| | | | Residues encoded (%) | | | | | coverage (%) |
| | | | Y | G | S | others (-Cys) | | |
| CDR-L3 | Y91 | TAC | 100 | - | - | - | | 77 |
| | Y92 | MGC | - | - | - | R/S(50) | | 100 |
| | S93 | X5 | 19.2 | 19.2 | 19.2 | 2.5 | | 100 |
| | S94 | X1 | 2.5 | 2.5 | 52.5 | 2.5 | | 100 |
| | L96 | X6 | 20 | 3.3 | 20 | 3.3 | | 100 |
| | | NTC | - | - | - | F/I/L/V(25) | | 45 |
| CDR-H1 | F27 | TWC | 50 | - | - | F(50) | | 65 |
| | T28 | ASC | - | - | 50 | T(50) | | 90 |
| | S30 | ASC | - | - | 50 | T(50) | | 86 |
| | S31 | X1 | 2.5 | 2.5 | 52.5 | 2.5 | | 100 |
| | Y32 | X2 | 52.5 | 2.5 | 2.5 | 2.5 | | 100 |
| | A33 | X7 | 15.6 | 15.6 | 15.6 | 3.1 | | 100 |
| | M34 | ATS | - | - | - | M/I(50) | | 67 |
| CDR-H2 | R50 | X3 | 5 | 5 | 5 | 5 | | 100 |
| | S52 | X6 | 20 | 3.3 | 20 | 3.3 | | 100 |
| | P52a | CCT | - | - | - | P(100) | | 100 |
| | S53 | X7 | 15.6 | 15.6 | 15.6 | 3.1 | | 100 |
| | G54 | RRC | - | 15.6 | - | D/G/N(25) | | 81 |
| | S56 | DMT | 16.6 | - | 25 | A/D/N/T(16.6) | | 81 |
| | Y58 | DAC | 33.3 | - | 16.6 | D/N(33.3) | | 70 |
| CDR-H3 | 95 | X4 | 3.8 | 28.8 | 3.8 | 3.8 | | 100 |
| | 96 | X4 | 3.8 | 28.8 | 3.8 | 3.8 | | 100 |
| | 97~100k | (X7)4-15 | 15.6 | 15.6 | 15.6 | 3.1 | | >98 |
| | 100l | X7 | 15.6 | 15.6 | 15.6 | 3.1 | | 100 |
| | 100m | GBT | - | 33.3 | - | A/V(33.3) | | |
| | | TTC | - | - | - | F(100) | | 89 |
| | | ATG | - | - | - | M(100) | | |
| | 101 | GAT | - | - | - | D(100) | | 92 |
| | 102 | TAC | 100 | - | - | - | | 67 |
| | | GTC | - | - | - | V(100) | | |

FIG._5A

|   | | | -H1- | | -H2- |
|---|---|---|---|---|---|
| A | QVQLVQSGAEVKKPGASVKVSCKAS | GYTFT | -H1- | WVRQAPGQGLEWMG | -H2- |
| B | QVQLVQSGAEVKKPGASVKVSCKAS | | -H1- | WVRQAPGQGLEWM | -H2- |
| C | QVQLVQSGAEVKKPGASVKVSCKAS | | -H1- | WVRQAPGQGLEWM | -H2- |
| D | QVQLVQSGAEVKKPGASVKVSCKAS | | -H1- | WVRQAPGQGLEWM | -H2- |

II

| A | QVQLQESGPGLVKPSQTLSLTCTVS | GGSVS | -H1- | WIRQPPGKGLEWIG | -H2- |
|---|---|---|---|---|---|
| B | QVQLQESGPGLVKPSQTLSLTCTVS | | -H1- | WIRQPPGKGLEWI | -H2- |
| C | QVQLQESGPGLVKPSQTLSLTCTVS | | -H1- | WIRQPPGKGLEWI | -H2- |
| D | QVQLQESGPGLVKPSQTLSLTCTVS | | -H1- | WIRQPPGKGLEWI | -H2- |

III

| A | EVQLVESGGGLVQPGGSLRLSCAAS | GFTFS | -H1- | WVRQAPGKGLEWVS | -H2- |
|---|---|---|---|---|---|
| B | EVQLVESGGGLVQPGGSLRLSCAAS | | -H1- | WVRQAPGKGLEWV | -H2- |
| C | EVQLVESGGGLVQPGGSLRLSCAAS | | -H1- | WVRQAPGKGLEWV | -H2- |
| D | EVQLVESGGGLVQPGGSLRLSCAAS | | -H1- | WVRQAPGKGLEWV | -H2- |

Acceptor

| A | EVQLVESGGGLVQPGGSLRLSCAAS | GFNIK | -H1- | WVRQAPGKGLEWVS | -H2- |
|---|---|---|---|---|---|
| B | EVQLVESGGGLVQPGGSLRLSCAAS | | -H1- | WVRQAPGKGLEWV | -H2- |
| C | EVQLVESGGGLVQPGGSLRLSCAAS | | -H1- | WVRQAPGKGLEWV | -H2- |

Second Acceptor

| A | EVQLVESGGGLVQPGGSLRLSCAAS | GFNIK | -H1- | WVRQAPGKGLEWVS | -H2- |
|---|---|---|---|---|---|
| B | EVQLVESGGGLVQPGGSLRLSCAAS | | -H1- | WVRQAPGKGLEWV | -H2- |
| C | EVQLVESGGGLVQPGGSLRLSCAAS | | -H1- | WVRQAPGKGLEWV | -H2- |
| D | EVQLVESGGGLVQPGGSLRLSCAAS | | -H1- | WVRQAPGKGLEWV | -H2- |

FIG._5B

| | | | SEQ ID NOs |
|---|---|---|---|
| R V T I T A D T S T S T A Y M E L S S L R S E D T A V Y Y C A R | -H3- | W G Q G T L V T V S S | SEQ ID NOs.: 19; 122; 123; 124 |
| R V T I T A D T S T S T A Y M E L S S L R S E D T A V Y Y C A R | -H3- | W G Q G T L V T V S S | SEQ ID NOs.: 20; 125; 126; 127 |
| R V T I T A D T S T S T A Y M E L S S L R S E D T A V Y Y C A | -H3- | W G Q G T L V T V S S | SEQ ID NOs.: 21; 128; 129; 130 |
| R V T I T A D T S T S T A Y M E L S S L R S E D T A V Y Y C | -H3- | W G Q G T L V T V S S | SEQ ID NOs.: 22; 131; 132; 133 |
| R V T I S V D T S K N Q F S L K L S S V T A A D T A V Y Y C A R | -H3- | W G Q G T L V T V S S | SEQ ID NOs.: 23; 134; 135; 136 |
| R V T I S V D T S K N Q F S L K L S S V T A A D T A V Y Y C A R | -H3- | W G Q G T L V T V S S | SEQ ID NOs.: 24; 137; 138; 139 |
| R V T I S V D T S K N Q F S L K L S S V T A A D T A V Y Y C A | -H3- | W G Q G T L V T V S S | SEQ ID NOs.: 25; 140; 141; 142 |
| R V T I S V D T S K N Q F S L K L S S V T A A D T A V Y Y C | -H3- | W G Q G T L V T V S S | SEQ ID NOs.: 26; 143; 144; 145 |
| R F T I S R D N S K N T L Y L Q M N S L R A E D T A V Y Y C A R | -H3- | W G Q G T L V T V S S | SEQ ID NOs.: 27; 146; 147; 148 |
| R F T I S R D N S K N T L Y L Q M N S L R A E D T A V Y Y C A R | -H3- | W G Q G T L V T V S S | SEQ ID NOs.: 28; 149; 150; 151 |
| R F T I S R D N S K N T L Y L Q M N S L R A E D T A V Y Y C A | -H3- | W G Q G T L V T V S S | SEQ ID NOs.: 29; 152; 153; 154 |
| R F T I S R D N S K N T L Y L Q M N S L R A E D T A V Y Y C | -H3- | W G Q G T L V T V S S | SEQ ID NOs.: 30; 155; 156; 157 |
| R F T I S A D T S K N T A Y L Q M N S L R A E D T A V Y Y C A R | -H3- | W G Q G T L V T V S S | SEQ ID NOs.: 31; 158; 159; 160 |
| R F T I S A D T S K N T A Y L Q M N S L R A E D T A V Y Y C A R | -H3- | W G Q G T L V T V S S | SEQ ID NOs.: 32; 161; 162; 163 |
| R F T I S A D T S K N T A Y L Q M N S L R A E D T A V Y Y C A R | -H3- | W G Q G T L V T V S S | SEQ ID NOs.: 33; 164; 165; 166 |
| R F T I S A D T S K N T A Y L Q M N S L R A E D T A V Y Y C A R | -H3- | W G Q G T L V T V S S | SEQ ID NOs.: 34; 167; 168; 169 |
| R F T I S A D T S K N T A Y L Q M N S L R A E D T A V Y Y C A R | -H3- | W G Q G T L V T V S S | SEQ ID NOs.: 35; 170; 171; 172 |
| R F T I S A D T S K N T A Y L Q M N S L R A E D T A V Y Y C A | -H3- | W G Q G T L V T V S S | SEQ ID NOs.: 36; 173; 174; 175 |
| R F T I S A D T S K N T A Y L Q M N S L R A E D T A V Y Y C | -H3- | W G Q G T L V T V S S | SEQ ID NOs.: 37; 176; 177; 178 |

FIG. 6A

κv1  DIQMTQSPSSLSASVGDRVTITC -L1- WYQQKPGKAPKLLIY -L2- GVPSRFSGSGSGTDFTLTISSLQP

κv2  DIVMTQSPLSLPVTPGEPASISC -L1- WYLQKPGQSPQLLIY -L2- GVPDRFSGSGSGTDFTLKISRVEA

κv3  EIVLTQSPGTLSLSPGERATLSC -L1- WYQQKPGQAPRLLIY -L2- GIPDRFSGSGSGTDFTLTISRLEP

κv4  DIVMTQSPDSLAVSLGERATINC -L1- WYQQKPGQPPKLLIY -L2- GVPDRFSGSGSGTDFTLTISSLQA

FIG. 6B

E D F A T Y Y C -L3- F G Q G T K V E I K    SEQ ID NOs.: 38; 179; 180; 181

E D V G V Y Y C -L3- F G Q G T K V E I K    SEQ ID NOs.: 39; 182; 183; 184

E D F A V Y Y C -L3- F G Q G T K V E I K    SEQ ID NOs.: 40; 185; 186; 187

E D V A V Y Y C -L3- F G Q G T K V E I K    SEQ ID NOs.: 41; 188; 189; 190

FIG._7

Framework sequences of huMAb4D5-8 light chain

LC-FR1    $^1$Asp Ile Gln Met Thr Gln Ser Pro Ser Ser Leu Ser Ala Ser Val Gly Asp Arg Val Thr Ile Thr Cys$^{23}$ (SEQ ID NO: 42)

LC-FR2    $^{35}$Trp Tyr Gln Gln Lys Pro Gly Lys Ala Pro Lys Leu Leu Ile Tyr$^{49}$ (SEQ ID NO: 43)

LC-FR3    $^{57}$Gly Val Pro Ser Arg Phe Ser Gly Ser Arg Ser Gly Thr Asp Phe Thr Leu Thr Ile Ser Ser Leu Gln Pro Glu Asp Phe Ala Thr Tyr Tyr Cys$^{88}$ (SEQ ID NO: 44)

LC-FR4    $^{98}$Phe Gly Gln Gly Thr Lys Val Glu Ile Lys Arg Thr$^{109}$ (SEQ ID NO: 45)

Framework sequences of huMAb4D5-8 heavy chain

HC-FR1    $^1$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 46)

HC-FR2    $^{36}$Trp Val Arg Gln Ala Pro Gly Lys Gly Leu Glu Trp Val$^{48}$ (SEQ ID NO: 47)

HC-FR3    $^{66}$Arg Phe Thr Ile Ser Ala Asp Thr Ser Lys Asn Thr Ala Tyr Leu Gln Met Asn$^{83}$ Ser$^{83a}$ Leu$^{83b}$ Arg$^{83c}$ Ala Glu Asp Thr Ala Val Tyr Tyr Cys$^{92}$ (SEQ ID NO: 48)

HC-FR4    $^{103}$Trp Gly Gln Gly Thr Leu Val Thr Val Ser Ser$^{113}$ (SEQ ID NO: 49)

FIG._8

Framework sequences of huMAb4D5-8 light chain modified at position 66 (underlined)

LC-FR1  $^1$Asp Ile Gln Met Thr Gln Ser Pro Ser Leu Ser Ala Ser Val Gly Asp Arg Val Thr Ile Thr Cys$^{23}$ (SEQ ID NO: 50)

LC-FR2  $^{35}$Trp Tyr Gln Gln Lys Pro Gly Lys Ala Pro Lys Leu Leu Ile Tyr$^{49}$ (SEQ ID NO: 51)

LC-FR3  $^{57}$Gly Val Pro Ser Arg Phe Ser Gly Ser <u>Gly</u> Ser Gly Thr Asp Phe Thr Leu Thr Ile Ser Ser Leu Gln Pro Glu Asp Phe Ala Thr Tyr Tyr Cys$^{88}$ (SEQ ID NO: 52)

LC-FR4  $^{98}$Phe Gly Gln Gly Thr Lys Val Glu Ile Lys Arg Thr$^{109}$ (SEQ ID NO: 53)

Framework sequences of huMAb4D5-8 heavy chain modified at positions 71, 73 and 78 (underlined)

HC-FR1  $^1$Glu Val Gln Leu Val Glu Ser Gly Gly Gly Leu Val Gln Pro Gly Gly Ser Leu Arg Leu Ser Cys Ala Ala Ser$^{25}$ (SEQ ID NO: 54)

HC-FR2  $^{36}$Trp Val Arg Gln Ala Pro Gly Lys Gly Leu Glu Trp Val$^{48}$ (SEQ ID NO: 55)

HC-FR3  $^{66}$Arg Phe Thr Ile Ser Arg Asp Asp Ser Lys <u>Asn</u> Thr <u>Leu</u> Tyr Leu Gln Met Asn$^{83}$ Ser$^{83a}$ <u>Leu</u>$^{83b}$ Arg$^{83c}$ Ala Glu Asp Thr Ala Val Tyr Tyr Cys$^{92}$ (SEQ ID NO: 56)

HC-FR4  $^{103}$Trp Gly Gln Gly Thr Leu Val Thr Val Ser Ser$^{113}$ (SEQ ID NO: 57)

SEQUENCE LISTING

```
<160> NUMBER OF SEQ ID NOS: 193

<210> SEQ ID NO 1
<211> LENGTH: 4
<212> TYPE: PRT
<213> ORGANISM: Artificial sequence
<220> FEATURE:
<223> OTHER INFORMATION: Synthetic peptide

<400> SEQUENCE: 1

Ala Met Asp Val

<210> SEQ ID NO 2
<211> LENGTH: 4
<212> TYPE: PRT
<213> ORGANISM: Artificial sequence
<220> FEATURE:
<223> OTHER INFORMATION: Synthetic peptide

<400> SEQUENCE: 2

Gly Met Asp Val

<210> SEQ ID NO 3
<211> LENGTH: 35
<212> TYPE: PRT
<213> ORGANISM: Artificial sequence
<220> FEATURE:
<223> OTHER INFORMATION: Synthetic peptide

<400> SEQUENCE: 3

Gly Arg Met Lys Gln Leu Glu Asp Lys Val Glu Glu Leu Leu Ser
 1               5                  10                  15

Lys Asn Tyr His Leu Glu Asn Glu Val Ala Arg Leu Lys Lys Leu
                20                  25                  30

Val Gly Glu Arg Gly
                35

<210> SEQ ID NO 4
<211> LENGTH: 4
<212> TYPE: PRT
<213> ORGANISM: Artificial sequence
<220> FEATURE:
<223> OTHER INFORMATION: Synthetic peptide
```

```
<400> SEQUENCE: 4

Val Met Asp Val

<210> SEQ ID NO 5
<211> LENGTH: 4
<212> TYPE: PRT
<213> ORGANISM: Artificial sequence
<220> FEATURE:
<223> OTHER INFORMATION: Synthetic peptide

<400> SEQUENCE: 5

Tyr Phe Asp Tyr

<210> SEQ ID NO 6
<211> LENGTH: 4
<212> TYPE: PRT
<213> ORGANISM: Artificial sequence
<220> FEATURE:
<223> OTHER INFORMATION: Synthetic peptide

<400> SEQUENCE: 6

Gly Phe Asp Tyr

<210> SEQ ID NO 7
<211> LENGTH: 4
<212> TYPE: PRT
<213> ORGANISM: Artificial sequence
<220> FEATURE:
<223> OTHER INFORMATION: Synthetic peptide

<400> SEQUENCE: 7

Ser Phe Asp Tyr

<210> SEQ ID NO 8
<211> LENGTH: 4
<212> TYPE: PRT
<213> ORGANISM: Artificial sequence
<220> FEATURE:
<223> OTHER INFORMATION: Synthetic peptide

<400> SEQUENCE: 8

Ala Met Asp Tyr

<210> SEQ ID NO 9
<211> LENGTH: 21
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 1-19
<223> OTHER INFORMATION: Xaa = all amino acids but cysteine
<220> FEATURE:
<221> NAME/KEY: Misc-feature
<222> LOCATION: 21
<223> OTHER INFORMATION: Xaa = all amino acids but cysteine

<400> SEQUENCE: 9

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Asp Xaa
                 20

<210> SEQ ID NO 10
<211> LENGTH: 19
```

```
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 3, 10, 12
<223> OTHER INFORMATION: Xaa = all amino acids but cysteine
<220> FEATURE:
<221> NAME/KEY: Misc-feature
<222> LOCATION: 5-8
<223> OTHER INFORMATION: Xaa = all amino acids but cysteine

<400> SEQUENCE: 10

Val Ser Xaa Ile Xaa Xaa Xaa Xaa Gly Xaa Thr Xaa Tyr Ala Asp
 1               5                  10                  15

Ser Val Lys Gly

<210> SEQ ID NO 11
<211> LENGTH: 12
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 2-3, 5-9
<223> OTHER INFORMATION: Xaa = all amino acids but cysteine

<400> SEQUENCE: 11

Gly Xaa Xaa Phe Xaa Xaa Xaa Xaa Xaa Ser Trp Val
               5                  10

<210> SEQ ID NO 12
<211> LENGTH: 21
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 1-18
<223> OTHER INFORMATION: Xaa = G, Y, S, V, or A
<220> FEATURE:
<221> NAME/KEY: Misc-feature
<222> LOCATION: 19, 21
<223> OTHER INFORMATION: Xaa = all amino acids but cysteine

<400> SEQUENCE: 12

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Asp Xaa
                 20

<210> SEQ ID NO 13
<211> LENGTH: 21
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 1-18
<223> OTHER INFORMATION: Xaa = Y, G, or S
<220> FEATURE:
<221> NAME/KEY: Misc-feature
<222> LOCATION: 19, 21
<223> OTHER INFORMATION: Xaa = all amino acids but cysteine

<400> SEQUENCE: 13

Xaa Xaa Xaa Xaa Xaa Xaa Xaa Xaa Xaa Xaa Xaa Xaa Xaa Xaa Xaa
```

Xaa Xaa Xaa Xaa Asp Xaa
                20

<210> SEQ ID NO 14
<211> LENGTH: 21
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 1-2
<223> OTHER INFORMATION: Xaa = G
<220> FEATURE:
<221> NAME/KEY: Misc-feature
<222> LOCATION: 3-19
<223> OTHER INFORMATION: Xaa = all amino acids but cysteine
<220> FEATURE:
<221> NAME/KEY: Misc-feature
<222> LOCATION: 21
<223> OTHER INFORMATION: Xaa = all amino acids but cysteine

<400> SEQUENCE: 14

Gly Gly Xaa Xaa Xaa Xaa Xaa Xaa Xaa Xaa Xaa Xaa Xaa Xaa Xaa
 1               5                   10                  15

Xaa Xaa Xaa Xaa Asp Xaa
                20

<210> SEQ ID NO 15
<211> LENGTH: 21
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 1-17, 19, 21
<223> OTHER INFORMATION: Xaa = all amino acids but cysteine
<220> FEATURE:
<221> NAME/KEY: Misc-feature
<222> LOCATION: 18
<223> OTHER INFORMATION: Xaa = A, G, or V

<400> SEQUENCE: 15

Xaa Xaa Xaa Xaa Xaa Xaa Xaa Xaa Xaa Xaa Xaa Xaa Xaa Xaa Xaa
 1               5                   10                  15

Xaa Xaa Xaa Xaa Asp Xaa
                20

<210> SEQ ID NO 16
<211> LENGTH: 21
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 1-18, 21
<223> OTHER INFORMATION: Xaa = all amino acids but cysteine
<220> FEATURE:
<221> NAME/KEY: Misc-feature
<222> LOCATION: 19
<223> OTHER INFORMATION: Xaa = F or M

<400> SEQUENCE: 16

Xaa Xaa Xaa Xaa Xaa Xaa Xaa Xaa Xaa Xaa Xaa Xaa Xaa Xaa Xaa
 1               5                   10                  15

Xaa Xaa Xaa Xaa Asp Xaa
                20

```
<210> SEQ ID NO 17
<211> LENGTH: 21
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 1-19
<223> OTHER INFORMATION: Xaa = all amino acids but cysteine
<220> FEATURE:
<221> NAME/KEY: Misc-feature
<222> LOCATION: 21
<223> OTHER INFORMATION: Xaa = Y or V

<400> SEQUENCE: 17

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Asp Xaa
                20

<210> SEQ ID NO 18
<211> LENGTH: 22
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 1-6
<223> OTHER INFORMATION: Xaa = all amino acids but cysteine
<220> FEATURE:
<221> NAME/KEY: Misc-feature
<222> LOCATION: 7-19
<223> OTHER INFORMATION: Xaa = all amino acids but cysteine or is not
      present
<220> FEATURE:
<221> NAME/KEY: Misc-feature
<222> LOCATION: 20, 22
<223> OTHER INFORMATION: Xaa = all amino acids but cysteine

<400> SEQUENCE: 18

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Asp Xaa
                20

<210> SEQ ID NO 19
<211> LENGTH: 30
<212> TYPE: PRT
<213> ORGANISM: Homo sapiens

<400> SEQUENCE: 19

Gln Val Gln Leu Val Gln Ser Gly Ala Glu Val Lys Lys Pro Gly
 1               5                  10                  15

Ala Ser Val Lys Val Ser Cys Lys Ala Ser Gly Tyr Thr Phe Thr
                20                  25                  30

<210> SEQ ID NO 20
<211> LENGTH: 25
<212> TYPE: PRT
<213> ORGANISM: Homo sapiens

<400> SEQUENCE: 20

Gln Val Gln Leu Val Gln Ser Gly Ala Glu Val Lys Lys Pro Gly
 1               5                  10                  15

Ala Ser Val Lys Val Ser Cys Lys Ala Ser
                20                  25
```

<210> SEQ ID NO 21
<211> LENGTH: 25
<212> TYPE: PRT
<213> ORGANISM: Homo sapiens

<400> SEQUENCE: 21

Gln Val Gln Leu Val Gln Ser Gly Ala Glu Val Lys Lys Pro Gly
1               5                   10                  15

Ala Ser Val Lys Val Ser Cys Lys Ala Ser
            20                  25

<210> SEQ ID NO 22
<211> LENGTH: 25
<212> TYPE: PRT
<213> ORGANISM: Homo sapiens

<400> SEQUENCE: 22

Gln Val Gln Leu Val Gln Ser Gly Ala Glu Val Lys Lys Pro Gly
1               5                   10                  15

Ala Ser Val Lys Val Ser Cys Lys Ala Ser
            20                  25

<210> SEQ ID NO 23
<211> LENGTH: 30
<212> TYPE: PRT
<213> ORGANISM: Homo sapiens

<400> SEQUENCE: 23

Gln Val Gln Leu Gln Glu Ser Gly Pro Gly Leu Val Lys Pro Ser
1               5                   10                  15

Gln Thr Leu Ser Leu Thr Cys Thr Val Ser Gly Gly Ser Val Ser
            20                  25                  30

<210> SEQ ID NO 24
<211> LENGTH: 25
<212> TYPE: PRT
<213> ORGANISM: Homo sapiens

<400> SEQUENCE: 24

Gln Val Gln Leu Gln Glu Ser Gly Pro Gly Leu Val Lys Pro Ser
1               5                   10                  15

Gln Thr Leu Ser Leu Thr Cys Thr Val Ser
            20                  25

<210> SEQ ID NO 25
<211> LENGTH: 25
<212> TYPE: PRT
<213> ORGANISM: Homo sapiens

<400> SEQUENCE: 25

Gln Val Gln Leu Gln Glu Ser Gly Pro Gly Leu Val Lys Pro Ser
1               5                   10                  15

Gln Thr Leu Ser Leu Thr Cys Thr Val Ser
            20                  25

<210> SEQ ID NO 26
<211> LENGTH: 25
<212> TYPE: PRT
<213> ORGANISM: Homo sapiens

<400> SEQUENCE: 26

Gln Val Gln Leu Gln Glu Ser Gly Pro Gly Leu Val Lys Pro Ser
1               5                   10                  15

Gln Thr Leu Ser Leu Thr Cys Thr Val Ser
            20                  25

<210> SEQ ID NO 27
<211> LENGTH: 30
<212> TYPE: PRT
<213> ORGANISM: Homo sapiens

<400> SEQUENCE: 27

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Thr Phe Ser
            20                  25                  30

<210> SEQ ID NO 28
<211> LENGTH: 25
<212> TYPE: PRT
<213> ORGANISM: Homo sapiens

<400> SEQUENCE: 28

Glu Val Gln Leu Val Glu Ser Gly Gly Gly Leu Val Gln Pro Gly
1               5                   10                  15

Gly Ser Leu Arg Leu Ser Cys Ala Ala Ser
            20                  25

<210> SEQ ID NO 29
<211> LENGTH: 25
<212> TYPE: PRT
<213> ORGANISM: Homo sapiens

<400> SEQUENCE: 29

Glu Val Gln Leu Val Glu Ser Gly Gly Gly Leu Val Gln Pro Gly
1               5                   10                  15

Gly Ser Leu Arg Leu Ser Cys Ala Ala Ser
            20                  25

<210> SEQ ID NO 30
<211> LENGTH: 25
<212> TYPE: PRT
<213> ORGANISM: Homo sapiens

<400> SEQUENCE: 30

Glu Val Gln Leu Val Glu Ser Gly Gly Gly Leu Val Gln Pro Gly
1               5                   10                  15

Gly Ser Leu Arg Leu Ser Cys Ala Ala Ser
            20                  25

<210> SEQ ID NO 31
<211> LENGTH: 30
<212> TYPE: PRT
<213> ORGANISM: Homo sapiens

<400> SEQUENCE: 31

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Ile Lys
            20                  25                  30

<210> SEQ ID NO 32
<211> LENGTH: 25
<212> TYPE: PRT

<213> ORGANISM: Homo sapiens

<400> SEQUENCE: 32

Glu Val Gln Leu Val Glu Ser Gly Gly Gly Leu Val Gln Pro Gly
1               5                   10                  15

Gly Ser Leu Arg Leu Ser Cys Ala Ala Ser
            20                  25

<210> SEQ ID NO 33
<211> LENGTH: 25
<212> TYPE: PRT
<213> ORGANISM: Homo sapiens

<400> SEQUENCE: 33

Glu Val Gln Leu Val Glu Ser Gly Gly Gly Leu Val Gln Pro Gly
1               5                   10                  15

Gly Ser Leu Arg Leu Ser Cys Ala Ala Ser
            20                  25

<210> SEQ ID NO 34
<211> LENGTH: 30
<212> TYPE: PRT
<213> ORGANISM: Homo sapiens

<400> SEQUENCE: 34

Glu Val Gln Leu Val Glu Ser Gly Gly Gly Leu Val Gln Pro Gly
1               5                   10                  15

Gly Ser Leu Arg Leu Ser Cys Ala Ala Ser Gly Phe Asn Ile Lys
            20                  25                  30

<210> SEQ ID NO 35
<211> LENGTH: 25
<212> TYPE: PRT
<213> ORGANISM: Homo sapiens

<400> SEQUENCE: 35

Glu Val Gln Leu Val Glu Ser Gly Gly Gly Leu Val Gln Pro Gly
1               5                   10                  15

Gly Ser Leu Arg Leu Ser Cys Ala Ala Ser
            20                  25

<210> SEQ ID NO 36
<211> LENGTH: 25
<212> TYPE: PRT
<213> ORGANISM: Homo sapiens

<400> SEQUENCE: 36

Glu Val Gln Leu Val Glu Ser Gly Gly Gly Leu Val Gln Pro Gly
1               5                   10                  15

Gly Ser Leu Arg Leu Ser Cys Ala Ala Ser
            20                  25

<210> SEQ ID NO 37
<211> LENGTH: 25
<212> TYPE: PRT
<213> ORGANISM: Homo sapiens

<400> SEQUENCE: 37

Glu Val Gln Leu Val Glu Ser Gly Gly Gly Leu Val Gln Pro Gly
1               5                   10                  15

Gly Ser Leu Arg Leu Ser Cys Ala Ala Ser
            20                  25

```
<210> SEQ ID NO 38
<211> LENGTH: 23
<212> TYPE: PRT
<213> ORGANISM: Homo sapiens

<400> SEQUENCE: 38

Asp Ile Gln Met Thr Gln Ser Pro Ser Ser Leu Ser Ala Ser Val
 1               5                  10                  15

Gly Asp Arg Val Thr Ile Thr Cys
            20

<210> SEQ ID NO 39
<211> LENGTH: 23
<212> TYPE: PRT
<213> ORGANISM: Homo sapiens

<400> SEQUENCE: 39

Asp Ile Val Met Thr Gln Ser Pro Leu Ser Leu Pro Val Thr Pro
 1               5                  10                  15

Gly Glu Pro Ala Ser Ile Ser Cys
            20

<210> SEQ ID NO 40
<211> LENGTH: 23
<212> TYPE: PRT
<213> ORGANISM: Homo sapiens

<400> SEQUENCE: 40

Glu Ile Val Leu Thr Gln Ser Pro Gly Thr Leu Ser Leu Ser Pro
 1               5                  10                  15

Gly Glu Arg Ala Thr Leu Ser Cys
            20

<210> SEQ ID NO 41
<211> LENGTH: 23
<212> TYPE: PRT
<213> ORGANISM: Homo sapiens

<400> SEQUENCE: 41

Asp Ile Val Met Thr Gln Ser Pro Asp Ser Leu Ala Val Ser Leu
 1               5                  10                  15

Gly Glu Arg Ala Thr Ile Asn Cys
            20

<210> SEQ ID NO 42
<211> LENGTH: 23
<212> TYPE: PRT
<213> ORGANISM: Artificial sequence
<220> FEATURE:
<223> OTHER INFORMATION: Sequence is synthesized

<400> SEQUENCE: 42

Asp Ile Gln Met Thr Gln Ser Pro Ser Ser Leu Ser Ala Ser Val
 1               5                  10                  15

Gly Asp Arg Val Thr Ile Thr Cys
            20

<210> SEQ ID NO 43
<211> LENGTH: 15
<212> TYPE: PRT
<213> ORGANISM: Artificial sequence
<220> FEATURE:
<223> OTHER INFORMATION: Sequence is synthesized
```

-continued

```
<400> SEQUENCE: 43

Trp Tyr Gln Gln Lys Pro Gly Lys Ala Pro Lys Leu Leu Ile Tyr
1               5                   10                  15

<210> SEQ ID NO 44
<211> LENGTH: 32
<212> TYPE: PRT
<213> ORGANISM: Artificial sequence
<220> FEATURE:
<223> OTHER INFORMATION: Sequence is synthesized

<400> SEQUENCE: 44

Gly Val Pro Ser Arg Phe Ser Gly Ser Arg Ser Gly Thr Asp Phe
1               5                   10                  15

Thr Leu Thr Ile Ser Ser Leu Gln Pro Glu Asp Phe Ala Thr Tyr
                20                  25                  30

Tyr Cys

<210> SEQ ID NO 45
<211> LENGTH: 12
<212> TYPE: PRT
<213> ORGANISM: Artificial sequence
<220> FEATURE:
<223> OTHER INFORMATION: Sequence is synthesized

<400> SEQUENCE: 45

Phe Gly Gln Gly Thr Lys Val Glu Ile Lys Arg Thr
1               5                   10

<210> SEQ ID NO 46
<211> LENGTH: 25
<212> TYPE: PRT
<213> ORGANISM: Artificial sequence
<220> FEATURE:
<223> OTHER INFORMATION: Sequence is synthesized

<400> SEQUENCE: 46

Glu Val Gln Leu Val Glu Ser Gly Gly Gly Leu Val Gln Pro Gly
1               5                   10                  15

Gly Ser Leu Arg Leu Ser Cys Ala Ala Ser
                20                  25

<210> SEQ ID NO 47
<211> LENGTH: 13
<212> TYPE: PRT
<213> ORGANISM: Artificial sequence
<220> FEATURE:
<223> OTHER INFORMATION: Sequence is synthesized

<400> SEQUENCE: 47

Trp Val Arg Gln Ala Pro Gly Lys Gly Leu Glu Trp Val
1               5                   10

<210> SEQ ID NO 48
<211> LENGTH: 30
<212> TYPE: PRT
<213> ORGANISM: Artificial sequence
<220> FEATURE:
<223> OTHER INFORMATION: Sequence is synthesized

<400> SEQUENCE: 48

Arg Phe Thr Ile Ser Ala Asp Thr Ser Lys Asn Thr Ala Tyr Leu
1               5                   10                  15

Gln Met Asn Ser Leu Arg Ala Glu Asp Thr Ala Val Tyr Tyr Cys
                20                  25                  30
```

<210> SEQ ID NO 49
<211> LENGTH: 11
<212> TYPE: PRT
<213> ORGANISM: Artificial sequence
<220> FEATURE:
<223> OTHER INFORMATION: Sequence is synthesized

<400> SEQUENCE: 49

Trp Gly Gln Gly Thr Leu Val Thr Val Ser Ser
                 5                  10

<210> SEQ ID NO 50
<211> LENGTH: 23
<212> TYPE: PRT
<213> ORGANISM: Artificial sequence
<220> FEATURE:
<223> OTHER INFORMATION: Sequence is synthesized

<400> SEQUENCE: 50

Asp Ile Gln Met Thr Gln Ser Pro Ser Ser Leu Ser Ala Ser Val
  1               5                  10                  15

Gly Asp Arg Val Thr Ile Thr Cys
                 20

<210> SEQ ID NO 51
<211> LENGTH: 15
<212> TYPE: PRT
<213> ORGANISM: Artificial sequence
<220> FEATURE:
<223> OTHER INFORMATION: Sequence is synthesized

<400> SEQUENCE: 51

Trp Tyr Gln Gln Lys Pro Gly Lys Ala Pro Lys Leu Leu Ile Tyr
  1               5                  10                  15

<210> SEQ ID NO 52
<211> LENGTH: 32
<212> TYPE: PRT
<213> ORGANISM: Artificial sequence
<220> FEATURE:
<223> OTHER INFORMATION: Sequence is synthesized

<400> SEQUENCE: 52

Gly Val Pro Ser Arg Phe Ser Gly Ser Gly Ser Gly Thr Asp Phe
  1               5                  10                  15

Thr Leu Thr Ile Ser Ser Leu Gln Pro Glu Asp Phe Ala Thr Tyr
                 20                  25                  30

Tyr Cys

<210> SEQ ID NO 53
<211> LENGTH: 12
<212> TYPE: PRT
<213> ORGANISM: Artificial sequence
<220> FEATURE:
<223> OTHER INFORMATION: Sequence is synthesized

<400> SEQUENCE: 53

Phe Gly Gln Gly Thr Lys Val Glu Ile Lys Arg Thr
                 5                  10

<210> SEQ ID NO 54
<211> LENGTH: 25
<212> TYPE: PRT
<213> ORGANISM: Artificial sequence
<220> FEATURE:

<223> OTHER INFORMATION: Sequence is synthesized

<400> SEQUENCE: 54

Glu Val Gln Leu Val Glu Ser Gly Gly Gly Leu Val Gln Pro Gly
 1               5                  10                  15

Gly Ser Leu Arg Leu Ser Cys Ala Ala Ser
            20                  25

<210> SEQ ID NO 55
<211> LENGTH: 13
<212> TYPE: PRT
<213> ORGANISM: Artificial sequence
<220> FEATURE:
<223> OTHER INFORMATION: Sequence is synthesized

<400> SEQUENCE: 55

Trp Val Arg Gln Ala Pro Gly Lys Gly Leu Glu Trp Val
 1               5                  10

<210> SEQ ID NO 56
<211> LENGTH: 30
<212> TYPE: PRT
<213> ORGANISM: Artificial sequence
<220> FEATURE:
<223> OTHER INFORMATION: Sequence is synthesized

<400> SEQUENCE: 56

Arg Phe Thr Ile Ser Arg Asp Asn Ser Lys Asn Thr Leu Tyr Leu
 1               5                  10                  15

Gln Met Asn Ser Leu Arg Ala Glu Asp Thr Ala Val Tyr Tyr Cys
            20                  25                  30

<210> SEQ ID NO 57
<211> LENGTH: 11
<212> TYPE: PRT
<213> ORGANISM: Artificial sequence
<220> FEATURE:
<223> OTHER INFORMATION: Sequence is synthesized

<400> SEQUENCE: 57

Trp Gly Gln Gly Thr Leu Val Thr Val Ser Ser
 1               5                  10

<210> SEQ ID NO 58
<211> LENGTH: 12
<212> TYPE: PRT
<213> ORGANISM: Homo sapiens

<400> SEQUENCE: 58

Thr Cys Pro Pro Cys Pro Ala Pro Glu Leu Leu Gly
 1               5                  10

<210> SEQ ID NO 59
<211> LENGTH: 21
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 1-19
<223> OTHER INFORMATION: Xaa = all amino acids but cysteine
<220> FEATURE:
<221> NAME/KEY: Misc-feature
<222> LOCATION: 21
<223> OTHER INFORMATION: Xaa = all amino acids but cysteine

<400> SEQUENCE: 59

```
Xaa Xaa Xaa Xaa Xaa Xaa Xaa Xaa Xaa Xaa Xaa Xaa Xaa Xaa Xaa
 1               5                  10                  15

Xaa Xaa Xaa Xaa Asp Xaa
                20

<210> SEQ ID NO 60
<211> LENGTH: 22
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 1-2
<223> OTHER INFORMATION: Xaa = all amino acids but cysteine
<220> FEATURE:
<221> NAME/KEY: Misc-feature
<222> LOCATION: 3-19
<223> OTHER INFORMATION: Xaa = Y, G, S, A, or V
<220> FEATURE:
<221> NAME/KEY: Misc-feature
<222> LOCATION: 20, 22
<223> OTHER INFORMATION: Xaa = all amino acids but cysteine

<400> SEQUENCE: 60

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Asp Xaa
                20

<210> SEQ ID NO 61
<211> LENGTH: 22
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 1-2
<223> OTHER INFORMATION: Xaa = all amino acids but cysteine
<220> FEATURE:
<221> NAME/KEY: Misc-feature
<222> LOCATION: 3-19
<223> OTHER INFORMATION: Xaa = Y, G, or S
<220> FEATURE:
<221> NAME/KEY: Misc-feature
<222> LOCATION: 20, 22
<223> OTHER INFORMATION: Xaa = all amino acids but cysteine

<400> SEQUENCE: 61

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Asp Xaa
                20

<210> SEQ ID NO 62
<211> LENGTH: 22
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 1-18
<223> OTHER INFORMATION: Xaa = all amino acids but cysteine
<220> FEATURE:
<221> NAME/KEY: Misc-feature
<222> LOCATION: 19
<223> OTHER INFORMATION: Xaa = Y, G, or S
<220> FEATURE:
<221> NAME/KEY: Misc-feature
```

```
<222> LOCATION: 20, 22
<223> OTHER INFORMATION: Xaa = all amino acids but cysteine

<400> SEQUENCE: 62

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Asp Xaa
                20

<210> SEQ ID NO 63
<211> LENGTH: 22
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 1-18
<223> OTHER INFORMATION: Xaa = all amino acids but cysteine
<220> FEATURE:
<221> NAME/KEY: Misc-feature
<222> LOCATION: 19
<223> OTHER INFORMATION: Xaa = A, G, or V
<220> FEATURE:
<221> NAME/KEY: Misc-feature
<222> LOCATION: 20, 22
<223> OTHER INFORMATION: Xaa = all amino acids but cysteine

<400> SEQUENCE: 63

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Asp Xaa
                20

<210> SEQ ID NO 64
<211> LENGTH: 22
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 1-19
<223> OTHER INFORMATION: Xaa = all amino acids but cysteine
<220> FEATURE:
<221> NAME/KEY: Misc-feature
<222> LOCATION: 20
<223> OTHER INFORMATION: Xaa = F or M
<220> FEATURE:
<221> NAME/KEY: Misc-feature
<222> LOCATION: 22
<223> OTHER INFORMATION: Xaa = all amino acids but cysteine

<400> SEQUENCE: 64

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Asp Xaa
                20

<210> SEQ ID NO 65
<211> LENGTH: 22
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 1-20
<223> OTHER INFORMATION: Xaa = all amino acids but cysteine
<220> FEATURE:
<221> NAME/KEY: Misc-feature
```

```
<222> LOCATION: 22
<223> OTHER INFORMATION: Xaa = Y or V

<400> SEQUENCE: 65

Xaa Xaa Xaa Xaa Xaa Xaa Xaa Xaa Xaa Xaa Xaa Xaa Xaa Xaa Xaa
 1               5                  10                  15

Xaa Xaa Xaa Xaa Xaa Asp Xaa
                20

<210> SEQ ID NO 66
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 3-6
<223> OTHER INFORMATION: Xaa = all amino acids but cysteine
<220> FEATURE:
<221> NAME/KEY: Misc-feature
<222> LOCATION: 8
<223> OTHER INFORMATION: Xaa = all amino acids but cysteine

<400> SEQUENCE: 66

Gln Gln Xaa Xaa Xaa Xaa Pro Xaa Thr
                  5

<210> SEQ ID NO 67
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 3
<223> OTHER INFORMATION: Xaa = R, S, or Y
<220> FEATURE:
<221> NAME/KEY: Misc-feature
<222> LOCATION: 4-6
<223> OTHER INFORMATION: Xaa = all amino acids but cysteine
<220> FEATURE:
<221> NAME/KEY: Misc-feature
<222> LOCATION: 8
<223> OTHER INFORMATION: Xaa = all amino acids but cysteine

<400> SEQUENCE: 67

Gln Gln Xaa Xaa Xaa Xaa Pro Xaa Thr
                  5

<210> SEQ ID NO 68
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 3, 8
<223> OTHER INFORMATION: Xaa = all amino acids but cysteine
<220> FEATURE:
<221> NAME/KEY: Misc-feature
<222> LOCATION: 4
<223> OTHER INFORMATION: Xaa = Y, G, or S
<220> FEATURE:
<221> NAME/KEY: Misc-feature
<222> LOCATION: 5-6
<223> OTHER INFORMATION: Xaa = all amino acids but cysteine

<400> SEQUENCE: 68

Gln Gln Xaa Xaa Xaa Xaa Pro Xaa Thr
```

-continued

```
<210> SEQ ID NO 69
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 3, 5, 6, 8
<223> OTHER INFORMATION: Xaa = all amino acids but cysteine
<220> FEATURE:
<221> NAME/KEY: Misc-feature
<222> LOCATION: 4
<223> OTHER INFORMATION: Xaa = all amino acids but cysteine

<400> SEQUENCE: 69

Gln Gln Xaa Xaa Xaa Xaa Pro Xaa Thr
                 5

<210> SEQ ID NO 70
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 3, 4, 6, 8
<223> OTHER INFORMATION: Xaa = all amino acids but cysteine
<220> FEATURE:
<221> NAME/KEY: Misc-feature
<222> LOCATION: 5
<223> OTHER INFORMATION: Xaa = S

<400> SEQUENCE: 70

Gln Gln Xaa Xaa Xaa Xaa Pro Xaa Thr
                 5

<210> SEQ ID NO 71
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 3, 4, 6, 8
<223> OTHER INFORMATION: Xaa = all amino acids but cysteine
<220> FEATURE:
<221> NAME/KEY: Misc-feature
<222> LOCATION: 5
<223> OTHER INFORMATION: Xaa = all amino acids but cysteine

<400> SEQUENCE: 71

Gln Gln Xaa Xaa Xaa Xaa Pro Xaa Thr
                 5

<210> SEQ ID NO 72
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 3, 4, 5, 8
<223> OTHER INFORMATION: Xaa = all amino acids but cysteine
<220> FEATURE:
<221> NAME/KEY: Misc-feature
<222> LOCATION: 6
<223> OTHER INFORMATION: Xaa = Y or S
```

```
<400> SEQUENCE: 72

Gln Gln Xaa Xaa Xaa Xaa Pro Xaa Thr
                  5

<210> SEQ ID NO 73
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 3, 4, 5, 8
<223> OTHER INFORMATION: Xaa = all amino acids but cysteine
<220> FEATURE:
<221> NAME/KEY: Misc-feature
<222> LOCATION: 6
<223> OTHER INFORMATION: Xaa = all amino acids but cysteine

<400> SEQUENCE: 73

Gln Gln Xaa Xaa Xaa Xaa Pro Xaa Thr
                  5

<210> SEQ ID NO 74
<211> LENGTH: 9
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 3-6
<223> OTHER INFORMATION: Xaa = all amino acids but cysteine
<220> FEATURE:
<221> NAME/KEY: Misc-feature
<222> LOCATION: 8
<223> OTHER INFORMATION: Xaa = F, I, L, or V

<400> SEQUENCE: 74

Gln Gln Xaa Xaa Xaa Xaa Pro Xaa Thr
                  5

<210> SEQ ID NO 75
<211> LENGTH: 6
<212> TYPE: PRT
<213> ORGANISM: Artificial sequence
<220> FEATURE:
<223> OTHER INFORMATION: Synthetic peptide

<400> SEQUENCE: 75

Ser Ile Ser Ser Tyr Leu
                  5

<210> SEQ ID NO 76
<211> LENGTH: 6
<212> TYPE: PRT
<213> ORGANISM: Artificial sequence
<220> FEATURE:
<223> OTHER INFORMATION: Synthetic peptide

<400> SEQUENCE: 76

Gly Ala Ser Ser Arg Ala
                  5

<210> SEQ ID NO 77
<211> LENGTH: 6
<212> TYPE: PRT
<213> ORGANISM: Artificial sequence
<220> FEATURE:
```

<223> OTHER INFORMATION: Synthetic peptide

<400> SEQUENCE: 77

Tyr Tyr Ser Ser Pro Leu
                  5

<210> SEQ ID NO 78
<211> LENGTH: 9
<212> TYPE: PRT
<213> ORGANISM: Artificial sequence
<220> FEATURE:
<223> OTHER INFORMATION: Synthetic peptide

<400> SEQUENCE: 78

Phe Thr Phe Ser Ser Tyr Ala Met Ser
                  5

<210> SEQ ID NO 79
<211> LENGTH: 10
<212> TYPE: PRT
<213> ORGANISM: Artificial sequence
<220> FEATURE:
<223> OTHER INFORMATION: Synthetic peptide

<400> SEQUENCE: 79

Arg Ile Ser Pro Ser Gly Gly Ser Thr Tyr
                  5                  10

<210> SEQ ID NO 80
<211> LENGTH: 11
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 2-4
<223> OTHER INFORMATION: Xaa = a stop codon
<220> FEATURE:
<221> NAME/KEY: Misc-feature
<222> LOCATION: 7-8
<223> OTHER INFORMATION: Xaa = a stop codon

<400> SEQUENCE: 80

Trp Xaa Xaa Xaa Arg Pro Xaa Xaa Met Asp Tyr
                  5                  10

<210> SEQ ID NO 81
<211> LENGTH: 63
<212> TYPE: DNA
<213> ORGANISM: Artificial sequence
<220> FEATURE:
<223> OTHER INFORMATION: Sequence is synthesized

<400> SEQUENCE: 81
accatcacct gccgtgccag tcagagcatc tccagctacc tggcctggta            50
tcaacagaaa  cca                                                   63

<210> SEQ ID NO 82
<211> LENGTH: 21
<212> TYPE: PRT
<213> ORGANISM: Artificial sequence
<220> FEATURE:
<223> OTHER INFORMATION: Synthetic peptide

<400> SEQUENCE: 82

Thr Ile Thr Cys Arg Ala Ser Gln Ser Ile Ser Ser Tyr Leu Ala
1               5                   10                  15

```
Trp Tyr Gln Gln Lys Pro
            20

<210> SEQ ID NO 83
<211> LENGTH: 21
<212> TYPE: PRT
<213> ORGANISM: Artificial sequence
<220> FEATURE:
<223> OTHER INFORMATION: Sequence is synthesized

<400> SEQUENCE: 83

Thr Ile Thr Cys Arg Ala Ser Gln Asp Val Ser Thr Ala Val Ala
 1               5                  10                  15

Trp Tyr Gln Gln Lys Pro
            20

<210> SEQ ID NO 84
<211> LENGTH: 60
<212> TYPE: DNA
<213> ORGANISM: Artificial sequence
<220> FEATURE:
<223> OTHER INFORMATION: Sequence is synthesized

<400> SEQUENCE: 84
gctccgaagc ttctgattta cggtgcatcc agccgcgcat ctggagtccc         50
ttctcgcttc                                                     60

<210> SEQ ID NO 85
<211> LENGTH: 20
<212> TYPE: PRT
<213> ORGANISM: Artificial sequence
<220> FEATURE:
<223> OTHER INFORMATION: Synthetic peptide

<400> SEQUENCE: 85

Ala Pro Lys Leu Leu Ile Tyr Gly Ala Ser Ser Arg Ala Ser Gly
 1               5                  10                  15

Val Pro Ser Arg Phe
            20

<210> SEQ ID NO 86
<211> LENGTH: 20
<212> TYPE: PRT
<213> ORGANISM: Artificial sequence
<220> FEATURE:
<223> OTHER INFORMATION: Sequence is synthesized

<400> SEQUENCE: 86

Ala Pro Lys Leu Leu Ile Tyr Ser Ala Ser Phe Leu Tyr Ser Gly
 1               5                  10                  15

Val Pro Ser Arg Phe
            20

<210> SEQ ID NO 87
<211> LENGTH: 57
<212> TYPE: DNA
<213> ORGANISM: Artificial sequence
<220> FEATURE:
<223> OTHER INFORMATION: Sequence is synthesized

<400> SEQUENCE: 87
gcaacttatt actgtcagca atactatagc agccctctga cgttcggaca         50
gggtacc                                                        57
```

<210> SEQ ID NO 88
<211> LENGTH: 19
<212> TYPE: PRT
<213> ORGANISM: Artificial sequence
<220> FEATURE:
<223> OTHER INFORMATION: Synthetic peptide

<400> SEQUENCE: 88

Ala Thr Tyr Tyr Cys Gln Gln Tyr Tyr Ser Ser Pro Leu Thr Phe
 1               5                  10                  15

Gly Gln Gly Thr

<210> SEQ ID NO 89
<211> LENGTH: 19
<212> TYPE: PRT
<213> ORGANISM: Artificial sequence
<220> FEATURE:
<223> OTHER INFORMATION: Sequence is synthesized

<400> SEQUENCE: 89

Ala Thr Tyr Tyr Cys Gln Gln Ser Tyr Thr Thr Pro Pro Thr Phe
 1               5                  10                  15

Gly Gln Gly Thr

<210> SEQ ID NO 90
<211> LENGTH: 63
<212> TYPE: DNA
<213> ORGANISM: Artificial sequence
<220> FEATURE:
<223> OTHER INFORMATION: Sequence is synthesized

<400> SEQUENCE: 90
tcctgtgcag cttctggctt caccttcagc agctacgcta tgagctgggt            50
gcgtcaggcc  ccg                                                   63

<210> SEQ ID NO 91
<211> LENGTH: 21
<212> TYPE: PRT
<213> ORGANISM: Artificial sequence
<220> FEATURE:
<223> OTHER INFORMATION: Synthetic peptide

<400> SEQUENCE: 91

Ser Cys Ala Ala Ser Gly Phe Thr Phe Ser Ser Tyr Ala Met Ser
 1               5                  10                  15

Trp Val Arg Gln Ala Pro
                20

<210> SEQ ID NO 92
<211> LENGTH: 21
<212> TYPE: PRT
<213> ORGANISM: Artificial sequence
<220> FEATURE:
<223> OTHER INFORMATION: Sequence is synthesized
<220> FEATURE:
<221> NAME/KEY: Misc-feature
<222> LOCATION: 10, 13
<223> OTHER INFORMATION: Xaa = any amino acid

<400> SEQUENCE: 92

Ser Cys Ala Ala Ser Gly Phe Asn Ile Xaa Arg Pro Xaa Ile His
 1               5                  10                  15

Trp Val Arg Gln Ala Pro
                20

<210> SEQ ID NO 93
<211> LENGTH: 75
<212> TYPE: DNA
<213> ORGANISM: Artificial sequence
<220> FEATURE:
<223> OTHER INFORMATION: Sequence is synthesized

<400> SEQUENCE: 93
ggtaagggcc tggaatgggt tagcaggatt agccctagcg gcggtagcac        50
ttactatgcc gatagcgtca  agggc                                  75

<210> SEQ ID NO 94
<211> LENGTH: 25
<212> TYPE: PRT
<213> ORGANISM: Artificial sequence
<220> FEATURE:
<223> OTHER INFORMATION: Synthetic peptide

<400> SEQUENCE: 94

Gly Lys Gly Leu Glu Trp Val Ser Arg Ile Ser Pro Ser Gly Gly
 1               5                  10                  15

Ser Thr Tyr Tyr Ala Asp Ser Val Lys Gly
             20                  25

<210> SEQ ID NO 95
<211> LENGTH: 25
<212> TYPE: PRT
<213> ORGANISM: Artificial sequence
<220> FEATURE:
<223> OTHER INFORMATION: Sequence is synthesized
<220> FEATURE:
<221> NAME/KEY: Misc-feature
<222> LOCATION: 9, 11, 13, 14, 17
<223> OTHER INFORMATION: Xaa = any amino acid

<400> SEQUENCE: 95

Gly Lys Gly Leu Glu Trp Val Ala Xaa Ile Xaa Pro Xaa Xaa Arg
 1               5                  10                  15

Pro Xaa Thr Tyr Ala Asp Ser Val Lys Gly
             20                  25

<210> SEQ ID NO 96
<211> LENGTH: 75
<212> TYPE: DNA
<213> ORGANISM: Artificial sequence
<220> FEATURE:
<223> OTHER INFORMATION: Sequence is synthesized

<400> SEQUENCE: 96
gaggacactg ccgtctatta ttgtagccgc tggtaataat aaaggcctta        50
ataaatggac tactggggtc  aagga                                  75

<210> SEQ ID NO 97
<211> LENGTH: 25
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 12-14
<223> OTHER INFORMATION: Xaa = any amino acid
<220> FEATURE:
<221> NAME/KEY: Misc-feature
<222> LOCATION: 17-18
<223> OTHER INFORMATION: Xaa = any amino acid -continued

```
<400> SEQUENCE: 97

Glu Asp Thr Ala Val Tyr Tyr Cys Ser Arg Trp Xaa Xaa Xaa Arg
1               5                   10                  15

Pro Xaa Xaa Met Asp Tyr Trp Gly Gln Gly
            20                  25

<210> SEQ ID NO 98
<211> LENGTH: 25
<212> TYPE: PRT
<213> ORGANISM: Artificial sequence
<220> FEATURE:
<223> OTHER INFORMATION: Sequence is synthesized
<220> FEATURE:
<221> NAME/KEY: Misc-feature
<222> LOCATION: 12-14
<223> OTHER INFORMATION: Xaa = any amino acid
<220> FEATURE:
<221> NAME/KEY: Misc-feature
<222> LOCATION: 17-18
<223> OTHER INFORMATION: Xaa = any amino acid

<400> SEQUENCE: 98

Glu Asp Thr Ala Val Tyr Tyr Cys Ser Arg Trp Xaa Xaa Xaa Arg
1               5                   10                  15

Pro Xaa Xaa Met Asp Tyr Trp Gly Gln Gly
            20                  25

<210> SEQ ID NO 99
<211> LENGTH: 39
<212> TYPE: DNA
<213> ORGANISM: Artificial sequence
<220> FEATURE:
<223> OTHER INFORMATION: Sequence is synthesized

<400> SEQUENCE: 99
tgccgtgcca gtcagagcat ctccagctac ctggcctgg                              39

<210> SEQ ID NO 100
<211> LENGTH: 13
<212> TYPE: PRT
<213> ORGANISM: Artificial sequence
<220> FEATURE:
<223> OTHER INFORMATION: Synthetic peptide

<400> SEQUENCE: 100

Cys Arg Ala Ser Gln Ser Ile Ser Ser Tyr Leu Ala Trp
1               5                   10

<210> SEQ ID NO 101
<211> LENGTH: 39
<212> TYPE: DNA
<213> ORGANISM: Artificial sequence
<220> FEATURE:
<223> OTHER INFORMATION: Sequence is synthesized

<400> SEQUENCE: 101
ctgatttacg gtgcatccag ccgcgcatct ggagtccct                              39

<210> SEQ ID NO 102
<211> LENGTH: 13
<212> TYPE: PRT
<213> ORGANISM: Artificial sequence
<220> FEATURE:
<223> OTHER INFORMATION: Synthetic peptide

<400> SEQUENCE: 102

Leu Ile Tyr Gly Ala Ser Ser Arg Ala Ser Gly Val Pro
```

<210> SEQ ID NO 103
<211> LENGTH: 39
<212> TYPE: DNA
<213> ORGANISM: Artificial sequence
<220> FEATURE:
<223> OTHER INFORMATION: Sequence is synthesized

<400> SEQUENCE: 103
tactgtcagc aatactatag cagccctctg acgttcgga                          39

<210> SEQ ID NO 104
<211> LENGTH: 13
<212> TYPE: PRT
<213> ORGANISM: Artificial sequence
<220> FEATURE:
<223> OTHER INFORMATION: Synthetic peptide

<400> SEQUENCE: 104

Tyr Cys Gln Gln Tyr Tyr Ser Ser Pro Leu Thr Phe Gly
                 5                  10

<210> SEQ ID NO 105
<211> LENGTH: 37
<212> TYPE: DNA
<213> ORGANISM: Artificial sequence
<220> FEATURE:
<223> OTHER INFORMATION: Sequence is synthesized
<220> FEATURE:
<221> NAME/KEY: Modified base
<222> LOCATION: 16-22, 26
<223> OTHER INFORMATION: n = a, c, g, or t
<220> FEATURE:
<223> OTHER INFORMATION: See specification for description of
      substiutions

<400> SEQUENCE: 105
tactgtcagc aamgcnnnnn nnccgntcac cttcgga                            37

<210> SEQ ID NO 106
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 5
<223> OTHER INFORMATION: Xaa = R or S

<400> SEQUENCE: 106

Tyr Cys Gln Gln Xaa Tyr Ser Tyr Pro Phe Thr Phe Gly
                 5                  10

<210> SEQ ID NO 107
<211> LENGTH: 13
<212> TYPE: PRT
<213> ORGANISM: Artificial sequence
<220> FEATURE:
<223> OTHER INFORMATION: Synthetic peptide

<400> SEQUENCE: 107

Tyr Cys Gln Gln Tyr Gly Ser Ser Pro Ile Thr Phe Gly
                 5                  10

<210> SEQ ID NO 108
<211> LENGTH: 13
<212> TYPE: PRT

<213> ORGANISM: Artificial sequence
<220> FEATURE:
<223> OTHER INFORMATION: Synthetic peptide

<400> SEQUENCE: 108

Tyr Cys Gln Gln Tyr Ser Ser Ser Pro Leu Thr Phe Gly
                5                   10

<210> SEQ ID NO 109
<211> LENGTH: 13
<212> TYPE: PRT
<213> ORGANISM: Artificial sequence
<220> FEATURE:
<223> OTHER INFORMATION: Synthetic peptide

<400> SEQUENCE: 109

Tyr Cys Gln Gln Tyr Ser Ser Ser Pro Val Thr Phe Gly
                5                   10

<210> SEQ ID NO 110
<211> LENGTH: 42
<212> TYPE: DNA
<213> ORGANISM: Artificial sequence
<220> FEATURE:
<223> OTHER INFORMATION: Sequence is synthesized

<400> SEQUENCE: 110
gcttctggct tcaccttcag cagctacgct atgagctggg tg                           42

<210> SEQ ID NO 111
<211> LENGTH: 14
<212> TYPE: PRT
<213> ORGANISM: Artificial sequence
<220> FEATURE:
<223> OTHER INFORMATION: Synthetic peptide

<400> SEQUENCE: 111

Ala Ser Gly Phe Thr Phe Ser Ser Tyr Ala Met Ser Trp Val
                5                   10

<210> SEQ ID NO 112
<211> LENGTH: 39
<212> TYPE: DNA
<213> ORGANISM: Artificial sequence
<220> FEATURE:
<223> OTHER INFORMATION: Sequence is synthesized
<220> FEATURE:
<221> NAME/KEY: Modified base
<222> LOCATION: 22-27
<223> OTHER INFORMATION: n = a, c, g, or t
<220> FEATURE:
<223> OTHER INFORMATION: See specification for description of
      substiutions

<400> SEQUENCE: 112
gcttctggtt wcascttcas cnnnnnnats agctgggtg                              39

<210> SEQ ID NO 113
<211> LENGTH: 14
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 4
<223> OTHER INFORMATION: Xaa = F or Y
<220> FEATURE:
<221> NAME/KEY: Misc-feature
<222> LOCATION: 5, 7

```
<223> OTHER INFORMATION: Xaa = T or S
<220> FEATURE:
<221> NAME/KEY: Misc-feature
<222> LOCATION: 10
<223> OTHER INFORMATION: Xaa = Y, G, or S
<220> FEATURE:
<221> NAME/KEY: Misc-feature
<222> LOCATION: 11
<223> OTHER INFORMATION: Xaa = M or I

<400> SEQUENCE: 113

Ala Ser Gly Xaa Xaa Phe Xaa Ser Tyr Xaa Xaa Ser Trp Val
                 5               10

<210> SEQ ID NO 114
<211> LENGTH: 57
<212> TYPE: DNA
<213> ORGANISM: Artificial sequence
<220> FEATURE:
<223> OTHER INFORMATION: Sequence is synthesized

<400> SEQUENCE: 114
gttagcagga ttagccctag cggcggtagc acttactatg ccgatagcgt           50
caagggc                                                          57

<210> SEQ ID NO 115
<211> LENGTH: 19
<212> TYPE: PRT
<213> ORGANISM: Artificial sequence
<220> FEATURE:
<223> OTHER INFORMATION: Synthetic peptide

<400> SEQUENCE: 115

Val Ser Arg Ile Ser Pro Ser Gly Gly Ser Thr Tyr Tyr Ala Asp
 1               5                  10                  15

Ser Val Lys Gly

<210> SEQ ID NO 116
<211> LENGTH: 57
<212> TYPE: DNA
<213> ORGANISM: Artificial sequence
<220> FEATURE:
<223> OTHER INFORMATION: Sequence is synthesized
<220> FEATURE:
<221> NAME/KEY: Modified base
<222> LOCATION: 7
<223> OTHER INFORMATION: n = a, c, g, or t
<220> FEATURE:
<221> NAME/KEY: Modified base
<222> LOCATION: 11-21
<223> OTHER INFORMATION: n = a, c, g, or t
<220> FEATURE:
<223> OTHER INFORMATION: See specification for description of
      substiutions

<400> SEQUENCE: 116
gttagcnatt nnnnnnnnnn nrrcggtdmt actdactatg ccgatagcgt           50
caagggc                                                          57

<210> SEQ ID NO 117
<211> LENGTH: 19
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 5
<223> OTHER INFORMATION: Xaa = Y or S
```

```
<220> FEATURE:
<221> NAME/KEY: Misc-feature
<222> LOCATION: 6, 7
<223> OTHER INFORMATION: Xaa = Y, G, or S
<220> FEATURE:
<221> NAME/KEY: Misc-feature
<222> LOCATION: 8
<223> OTHER INFORMATION: Xaa = D, G, S, or N
<220> FEATURE:
<221> NAME/KEY: Misc-feature
<222> LOCATION: 10
<223> OTHER INFORMATION: Xaa = A, D, N, S, T, or Y
<220> FEATURE:
<221> NAME/KEY: Misc-feature
<222> LOCATION: 12
<223> OTHER INFORMATION: Xaa = D, N,or Y

<400> SEQUENCE: 117

Val Ser Arg Ile Xaa Xaa Xaa Xaa Gly Xaa Thr Xaa Tyr Ala Asp
 1               5                  10                  15

Ser Val Lys Gly

<210> SEQ ID NO 118
<211> LENGTH: 39
<212> TYPE: DNA
<213> ORGANISM: Artificial sequence
<220> FEATURE:
<223> OTHER INFORMATION: Sequence is synthesized

<400> SEQUENCE: 118
agccgctggt aataataaag gccttaataa  atggactac                              39

<210> SEQ ID NO 119
<211> LENGTH: 13
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 4-6
<223> OTHER INFORMATION: Xaa = any amino acid
<220> FEATURE:
<221> NAME/KEY: Misc-feature
<222> LOCATION: 9-10
<223> OTHER INFORMATION: Xaa = any amino acid

<400> SEQUENCE: 119

Ser Arg Trp Xaa Xaa Xaa Arg Pro Xaa Xaa Met Asp Tyr
                 5                  10

<210> SEQ ID NO 120
<211> LENGTH: 83
<212> TYPE: DNA
<213> ORGANISM: Artificial sequence
<220> FEATURE:
<223> OTHER INFORMATION: Sequence is synthesized
<220> FEATURE:
<221> NAME/KEY: Modified base
<222> LOCATION: 7-74
<223> OTHER INFORMATION: n = a, c, g or t
<220> FEATURE:
<223> OTHER INFORMATION: See specification for description of
      substiutions

<400> SEQUENCE: 120
gcgcgcnnnn nnnnnnnnnn nnnnnnnnnn nnnnnnnnnn nnnnnnnnnn                   50
nnnnnnnnnn nnnnnnnnnn nnnnttcgat  tac                                    83

<210> SEQ ID NO 121
```

```
<211> LENGTH: 82
<212> TYPE: DNA
<213> ORGANISM: Artificial sequence
<220> FEATURE:
<223> OTHER INFORMATION: Sequence is synthesized
<220> FEATURE:
<221> NAME/KEY: Modified base
<222> LOCATION: 7-70
<223> OTHER INFORMATION: n = a, c, g, or t
<220> FEATURE:
<223> OTHER INFORMATION: See specification for description of
      substiutions

<400> SEQUENCE: 121
agccgcnnnn nnnnnnnnnn nnnnnnnnnn nnnnnnnnnn nnnnnnnnnn        50
nnnnnnnnnn nnnnnnnnnn gbtatggatg tc                            82

<210> SEQ ID NO 122
<211> LENGTH: 14
<212> TYPE: PRT
<213> ORGANISM: Homo sapiens

<400> SEQUENCE: 122

Trp Val Arg Gln Ala Pro Gly Gln Gly Leu Glu Trp Met Gly
 1               5                  10

<210> SEQ ID NO 123
<211> LENGTH: 32
<212> TYPE: PRT
<213> ORGANISM: Homo sapiens

<400> SEQUENCE: 123

Arg Val Thr Ile Thr Ala Asp Thr Ser Thr Ser Thr Ala Tyr Met
 1               5                  10                  15

Glu Leu Ser Ser Leu Arg Ser Glu Asp Thr Ala Val Tyr Tyr Cys
                20                  25                  30

Ala Arg

<210> SEQ ID NO 124
<211> LENGTH: 11
<212> TYPE: PRT
<213> ORGANISM: Homo sapiens

<400> SEQUENCE: 124

Trp Gly Gln Gly Thr Leu Val Thr Val Ser Ser
 1               5                  10

<210> SEQ ID NO 125
<211> LENGTH: 13
<212> TYPE: PRT
<213> ORGANISM: Homo sapiens

<400> SEQUENCE: 125

Trp Val Arg Gln Ala Pro Gly Gln Gly Leu Glu Trp Met
 1               5                  10

<210> SEQ ID NO 126
<211> LENGTH: 32
<212> TYPE: PRT
<213> ORGANISM: Homo sapiens

<400> SEQUENCE: 126

Arg Val Thr Ile Thr Ala Asp Thr Ser Thr Ser Thr Ala Tyr Met
 1               5                  10                  15

Glu Leu Ser Ser Leu Arg Ser Glu Asp Thr Ala Val Tyr Tyr Cys
```

<210> SEQ ID NO 127
<211> LENGTH: 11
<212> TYPE: PRT
<213> ORGANISM: Homo sapiens

<400> SEQUENCE: 127

Trp Gly Gln Gly Thr Leu Val Thr Val Ser Ser
                5                   10

<210> SEQ ID NO 128
<211> LENGTH: 13
<212> TYPE: PRT
<213> ORGANISM: Homo sapiens

<400> SEQUENCE: 128

Trp Val Arg Gln Ala Pro Gly Gln Gly Leu Glu Trp Met
                5                   10

<210> SEQ ID NO 129
<211> LENGTH: 20
<212> TYPE: DNA
<213> ORGANISM: Artificial sequence
<220> FEATURE:
<223> OTHER INFORMATION: sequence is synthesized

<400> SEQUENCE: 129
ggtgcatcga tgcagggggg                                                   20

<210> SEQ ID NO 130
<211> LENGTH: 31
<212> TYPE: PRT
<213> ORGANISM: Homo sapiens

<400> SEQUENCE: 130

Arg Val Thr Ile Thr Ala Asp Thr Ser Thr Ser Thr Ala Tyr Met
1               5                   10                  15

Glu Leu Ser Ser Leu Arg Ser Glu Asp Thr Ala Val Tyr Tyr Cys
                20                  25                  30

Ala

<210> SEQ ID NO 131
<211> LENGTH: 11
<212> TYPE: PRT
<213> ORGANISM: Homo sapiens

<400> SEQUENCE: 131

Trp Gly Gln Gly Thr Leu Val Thr Val Ser Ser
                5                   10

<210> SEQ ID NO 132
<211> LENGTH: 13
<212> TYPE: PRT
<213> ORGANISM: Homo sapiens

<400> SEQUENCE: 132

Trp Val Arg Gln Ala Pro Gly Gln Gly Leu Glu Trp Met
                5                   10

<210> SEQ ID NO 133
<211> LENGTH: 30
<212> TYPE: PRT

<213> ORGANISM: Homo sapiens

<400> SEQUENCE: 133

Arg Val Thr Ile Thr Ala Asp Thr Ser Thr Ser Thr Ala Tyr Met
1               5                   10                  15

Glu Leu Ser Ser Leu Arg Ser Glu Asp Thr Ala Val Tyr Tyr Cys
            20                  25                  30

<210> SEQ ID NO 134
<211> LENGTH: 11
<212> TYPE: PRT
<213> ORGANISM: Homo sapiens

<400> SEQUENCE: 134

Trp Gly Gln Gly Thr Leu Val Thr Val Ser Ser
1               5                   10

<210> SEQ ID NO 135
<211> LENGTH: 14
<212> TYPE: PRT
<213> ORGANISM: Homo sapiens

<400> SEQUENCE: 135

Trp Ile Arg Gln Pro Pro Gly Lys Gly Leu Glu Trp Ile Gly
1               5                   10

<210> SEQ ID NO 136
<211> LENGTH: 32
<212> TYPE: PRT
<213> ORGANISM: Homo sapiens

<400> SEQUENCE: 136

Arg Val Thr Ile Ser Val Asp Thr Ser Lys Asn Gln Phe Ser Leu
1               5                   10                  15

Lys Leu Ser Ser Val Thr Ala Ala Asp Thr Ala Val Tyr Tyr Cys
            20                  25                  30

Ala Arg

<210> SEQ ID NO 137
<211> LENGTH: 11
<212> TYPE: PRT
<213> ORGANISM: Homo sapiens

<400> SEQUENCE: 137

Trp Gly Gln Gly Thr Leu Val Thr Val Ser Ser
1               5                   10

<210> SEQ ID NO 138
<211> LENGTH: 13
<212> TYPE: PRT
<213> ORGANISM: Homo sapiens

<400> SEQUENCE: 138

Trp Ile Arg Gln Pro Pro Gly Lys Gly Leu Glu Trp Ile
1               5                   10

<210> SEQ ID NO 139
<211> LENGTH: 32
<212> TYPE: PRT
<213> ORGANISM: Homo sapiens

<400> SEQUENCE: 139

Arg Val Thr Ile Ser Val Asp Thr Ser Lys Asn Gln Phe Ser Leu
1               5                   10                  15

-continued

Lys Leu Ser Ser Val Thr Ala Ala Asp Thr Ala Val Tyr Tyr Cys
            20                  25                  30

Ala Arg

<210> SEQ ID NO 140
<211> LENGTH: 11
<212> TYPE: PRT
<213> ORGANISM: Homo sapiens

<400> SEQUENCE: 140

Trp Gly Gln Gly Thr Leu Val Thr Val Ser Ser
                5                   10

<210> SEQ ID NO 141
<211> LENGTH: 13
<212> TYPE: PRT
<213> ORGANISM: Homo sapiens

<400> SEQUENCE: 141

Trp Ile Arg Gln Pro Pro Gly Lys Gly Leu Glu Trp Ile
                5                   10

<210> SEQ ID NO 142
<211> LENGTH: 31
<212> TYPE: PRT
<213> ORGANISM: Homo sapiens

<400> SEQUENCE: 142

Arg Val Thr Ile Ser Val Asp Thr Ser Lys Asn Gln Phe Ser Leu
 1               5                  10                  15

Lys Leu Ser Ser Val Thr Ala Ala Asp Thr Ala Val Tyr Tyr Cys
            20                  25                  30

Ala

<210> SEQ ID NO 143
<211> LENGTH: 11
<212> TYPE: PRT
<213> ORGANISM: Homo sapiens

<400> SEQUENCE: 143

Trp Gly Gln Gly Thr Leu Val Thr Val Ser Ser
                5                   10

<210> SEQ ID NO 144
<211> LENGTH: 13
<212> TYPE: PRT
<213> ORGANISM: Homo sapiens

<400> SEQUENCE: 144

Trp Ile Arg Gln Pro Pro Gly Lys Gly Leu Glu Trp Ile
                5                   10

<210> SEQ ID NO 145
<211> LENGTH: 30
<212> TYPE: PRT
<213> ORGANISM: Homo sapiens

<400> SEQUENCE: 145

Arg Val Thr Ile Ser Val Asp Thr Ser Lys Asn Gln Phe Ser Leu
 1               5                  10                  15

Lys Leu Ser Ser Val Thr Ala Ala Asp Thr Ala Val Tyr Tyr Cys
            20                  25                  30

```
<210> SEQ ID NO 146
<211> LENGTH: 11
<212> TYPE: PRT
<213> ORGANISM: Homo sapiens

<400> SEQUENCE: 146

Trp Gly Gln Gly Thr Leu Val Thr Val Ser Ser
                 5                  10

<210> SEQ ID NO 147
<211> LENGTH: 14
<212> TYPE: PRT
<213> ORGANISM: Homo sapiens

<400> SEQUENCE: 147

Trp Val Arg Gln Ala Pro Gly Lys Gly Leu Glu Trp Val Ser
                 5                  10

<210> SEQ ID NO 148
<211> LENGTH: 32
<212> TYPE: PRT
<213> ORGANISM: Homo sapiens

<400> SEQUENCE: 148

Arg Phe Thr Ile Ser Arg Asp Asn Ser Lys Asn Thr Leu Tyr Leu
  1               5                  10                  15

Gln Met Asn Ser Leu Arg Ala Glu Asp Thr Ala Val Tyr Tyr Cys
                 20                  25                  30

Ala Arg

<210> SEQ ID NO 149
<211> LENGTH: 11
<212> TYPE: PRT
<213> ORGANISM: Homo sapiens

<400> SEQUENCE: 149

Trp Gly Gln Gly Thr Leu Val Thr Val Ser Ser
                 5                  10

<210> SEQ ID NO 150
<211> LENGTH: 13
<212> TYPE: PRT
<213> ORGANISM: Homo sapiens

<400> SEQUENCE: 150

Trp Val Arg Gln Ala Pro Gly Lys Gly Leu Glu Trp Val
                 5                  10

<210> SEQ ID NO 151
<211> LENGTH: 32
<212> TYPE: PRT
<213> ORGANISM: Homo sapiens

<400> SEQUENCE: 151

Arg Phe Thr Ile Ser Arg Asp Asn Ser Lys Asn Thr Leu Tyr Leu
  1               5                  10                  15

Gln Met Asn Ser Leu Arg Ala Glu Asp Thr Ala Val Tyr Tyr Cys
                 20                  25                  30

Ala Arg

<210> SEQ ID NO 152
<211> LENGTH: 11
<212> TYPE: PRT
```

```
<213> ORGANISM: Homo sapiens

<400> SEQUENCE: 152

Trp Gly Gln Gly Thr Leu Val Thr Val Ser Ser
 1               5                  10

<210> SEQ ID NO 153
<211> LENGTH: 13
<212> TYPE: PRT
<213> ORGANISM: Homo sapiens

<400> SEQUENCE: 153

Trp Val Arg Gln Ala Pro Gly Lys Gly Leu Glu Trp Val
 1               5                  10

<210> SEQ ID NO 154
<211> LENGTH: 31
<212> TYPE: PRT
<213> ORGANISM: Homo sapiens

<400> SEQUENCE: 154

Arg Phe Thr Ile Ser Arg Asp Asn Ser Lys Asn Thr Leu Tyr Leu
 1               5                  10                  15

Gln Met Asn Ser Leu Arg Ala Glu Asp Thr Ala Val Tyr Tyr Cys
                20                  25                  30

Ala

<210> SEQ ID NO 155
<211> LENGTH: 11
<212> TYPE: PRT
<213> ORGANISM: Homo sapiens

<400> SEQUENCE: 155

Trp Gly Gln Gly Thr Leu Val Thr Val Ser Ser
 1               5                  10

<210> SEQ ID NO 156
<211> LENGTH: 13
<212> TYPE: PRT
<213> ORGANISM: Homo sapiens

<400> SEQUENCE: 156

Trp Val Arg Gln Ala Pro Gly Lys Gly Leu Glu Trp Val
 1               5                  10

<210> SEQ ID NO 157
<211> LENGTH: 30
<212> TYPE: PRT
<213> ORGANISM: Homo sapiens

<400> SEQUENCE: 157

Arg Phe Thr Ile Ser Arg Asp Asn Ser Lys Asn Thr Leu Tyr Leu
 1               5                  10                  15

Gln Met Asn Ser Leu Arg Ala Glu Asp Thr Ala Val Tyr Tyr Cys
                20                  25                  30

<210> SEQ ID NO 158
<211> LENGTH: 11
<212> TYPE: PRT
<213> ORGANISM: Homo sapiens

<400> SEQUENCE: 158

Trp Gly Gln Gly Thr Leu Val Thr Val Ser Ser
 1               5                  10
```

<210> SEQ ID NO 159
<211> LENGTH: 14
<212> TYPE: PRT
<213> ORGANISM: Homo sapiens

<400> SEQUENCE: 159

Trp Val Arg Gln Ala Pro Gly Lys Gly Leu Glu Trp Val Ser
1               5                   10

<210> SEQ ID NO 160
<211> LENGTH: 32
<212> TYPE: PRT
<213> ORGANISM: Homo sapiens

<400> SEQUENCE: 160

Arg Phe Thr Ile Ser Ala Asp Thr Ser Lys Asn Thr Ala Tyr Leu
1               5                   10                  15

Gln Met Asn Ser Leu Arg Ala Glu Asp Thr Ala Val Tyr Tyr Cys
                20                  25                  30

Ser Arg

<210> SEQ ID NO 161
<211> LENGTH: 11
<212> TYPE: PRT
<213> ORGANISM: Homo sapiens

<400> SEQUENCE: 161

Trp Gly Gln Gly Thr Leu Val Thr Val Ser Ser
1               5                   10

<210> SEQ ID NO 162
<211> LENGTH: 13
<212> TYPE: PRT
<213> ORGANISM: Homo sapiens

<400> SEQUENCE: 162

Trp Val Arg Gln Ala Pro Gly Lys Gly Leu Glu Trp Val
1               5                   10

<210> SEQ ID NO 163
<211> LENGTH: 32
<212> TYPE: PRT
<213> ORGANISM: Homo sapiens

<400> SEQUENCE: 163

Arg Phe Thr Ile Ser Ala Asp Thr Ser Lys Asn Thr Ala Tyr Leu
1               5                   10                  15

Gln Met Asn Ser Leu Arg Ala Glu Asp Thr Ala Val Tyr Tyr Cys
                20                  25                  30

Ser Arg

<210> SEQ ID NO 164
<211> LENGTH: 11
<212> TYPE: PRT
<213> ORGANISM: Homo sapiens

<400> SEQUENCE: 164

Trp Gly Gln Gly Thr Leu Val Thr Val Ser Ser
1               5                   10

<210> SEQ ID NO 165
<211> LENGTH: 13

```
<212> TYPE: PRT
<213> ORGANISM: Homo sapiens

<400> SEQUENCE: 165

Trp Val Arg Gln Ala Pro Gly Lys Gly Leu Glu Trp Val
                 5                  10

<210> SEQ ID NO 166
<211> LENGTH: 31
<212> TYPE: PRT
<213> ORGANISM: Homo sapiens

<400> SEQUENCE: 166

Arg Phe Thr Ile Ser Ala Asp Thr Ser Lys Asn Thr Ala Tyr Leu
 1               5                  10                  15

Gln Met Asn Ser Leu Arg Ala Glu Asp Thr Ala Val Tyr Tyr Cys
                20                  25                  30

Ser

<210> SEQ ID NO 167
<211> LENGTH: 11
<212> TYPE: PRT
<213> ORGANISM: Homo sapiens

<400> SEQUENCE: 167

Trp Gly Gln Gly Thr Leu Val Thr Val Ser Ser
                 5                  10

<210> SEQ ID NO 168
<211> LENGTH: 14
<212> TYPE: PRT
<213> ORGANISM: Homo sapiens

<400> SEQUENCE: 168

Trp Val Arg Gln Ala Pro Gly Lys Gly Leu Glu Trp Val Ser
                 5                  10

<210> SEQ ID NO 169
<211> LENGTH: 32
<212> TYPE: PRT
<213> ORGANISM: Homo sapiens

<400> SEQUENCE: 169

Arg Phe Thr Ile Ser Ala Asp Thr Ser Lys Asn Thr Ala Tyr Leu
 1               5                  10                  15

Gln Met Asn Ser Leu Arg Ala Glu Asp Thr Ala Val Tyr Tyr Cys
                20                  25                  30

Ala Arg

<210> SEQ ID NO 170
<211> LENGTH: 11
<212> TYPE: PRT
<213> ORGANISM: Homo sapiens

<400> SEQUENCE: 170

Trp Gly Gln Gly Thr Leu Val Thr Val Ser Ser
                 5                  10

<210> SEQ ID NO 171
<211> LENGTH: 13
<212> TYPE: PRT
<213> ORGANISM: Homo sapiens

<400> SEQUENCE: 171
```

```
Trp Val Arg Gln Ala Pro Gly Lys Gly Leu Glu Trp Val
                5                  10
```

<210> SEQ ID NO 172
<211> LENGTH: 32
<212> TYPE: PRT
<213> ORGANISM: Homo sapiens

<400> SEQUENCE: 172

```
Arg Phe Thr Ile Ser Ala Asp Thr Ser Lys Asn Thr Ala Tyr Leu
 1               5                  10                  15

Gln Met Asn Ser Leu Arg Ala Glu Asp Thr Ala Val Tyr Tyr Cys
                20                  25                  30

Ala Arg
```

<210> SEQ ID NO 173
<211> LENGTH: 11
<212> TYPE: PRT
<213> ORGANISM: Homo sapiens

<400> SEQUENCE: 173

```
Trp Gly Gln Gly Thr Leu Val Thr Val Ser Ser
                5                  10
```

<210> SEQ ID NO 174
<211> LENGTH: 13
<212> TYPE: PRT
<213> ORGANISM: Homo sapiens

<400> SEQUENCE: 174

```
Trp Val Arg Gln Ala Pro Gly Lys Gly Leu Glu Trp Val
                5                  10
```

<210> SEQ ID NO 175
<211> LENGTH: 31
<212> TYPE: PRT
<213> ORGANISM: Homo sapiens

<400> SEQUENCE: 175

```
Arg Phe Thr Ile Ser Ala Asp Thr Ser Lys Asn Thr Ala Tyr Leu
 1               5                  10                  15

Gln Met Asn Ser Leu Arg Ala Glu Asp Thr Ala Val Tyr Tyr Cys
                20                  25                  30

Ala
```

<210> SEQ ID NO 176
<211> LENGTH: 11
<212> TYPE: PRT
<213> ORGANISM: Homo sapiens

<400> SEQUENCE: 176

```
Trp Gly Gln Gly Thr Leu Val Thr Val Ser Ser
                5                  10
```

<210> SEQ ID NO 177
<211> LENGTH: 13
<212> TYPE: PRT
<213> ORGANISM: Homo sapiens

<400> SEQUENCE: 177

```
Trp Val Arg Gln Ala Pro Gly Lys Gly Leu Glu Trp Val
                5                  10
```

```
<210> SEQ ID NO 178
<211> LENGTH: 30
<212> TYPE: PRT
<213> ORGANISM: Homo sapiens

<400> SEQUENCE: 178

Arg Phe Thr Ile Ser Ala Asp Thr Ser Lys Asn Thr Ala Tyr Leu
 1               5                  10                  15
Gln Met Asn Ser Leu Arg Ala Glu Asp Thr Ala Val Tyr Tyr Cys
                20                  25                  30

<210> SEQ ID NO 179
<211> LENGTH: 11
<212> TYPE: PRT
<213> ORGANISM: Homo sapiens

<400> SEQUENCE: 179

Trp Gly Gln Gly Thr Leu Val Thr Val Ser Ser
 1               5                  10

<210> SEQ ID NO 180
<211> LENGTH: 15
<212> TYPE: PRT
<213> ORGANISM: Homo sapiens

<400> SEQUENCE: 180

Trp Tyr Gln Gln Lys Pro Gly Lys Ala Pro Lys Leu Leu Ile Tyr
 1               5                  10                  15

<210> SEQ ID NO 181
<211> LENGTH: 32
<212> TYPE: PRT
<213> ORGANISM: Homo sapiens

<400> SEQUENCE: 181

Gly Val Pro Ser Arg Phe Ser Gly Ser Gly Ser Gly Thr Asp Phe
 1               5                  10                  15
Thr Leu Thr Ile Ser Ser Leu Gln Pro Glu Asp Phe Ala Thr Tyr
                20                  25                  30
Tyr Cys

<210> SEQ ID NO 182
<211> LENGTH: 10
<212> TYPE: PRT
<213> ORGANISM: Homo sapiens

<400> SEQUENCE: 182

Phe Gly Gln Gly Thr Lys Val Glu Ile Lys
 1               5                  10

<210> SEQ ID NO 183
<211> LENGTH: 15
<212> TYPE: PRT
<213> ORGANISM: Homo sapiens

<400> SEQUENCE: 183

Trp Tyr Leu Gln Lys Pro Gly Gln Ser Pro Gln Leu Leu Ile Tyr
 1               5                  10                  15

<210> SEQ ID NO 184
<211> LENGTH: 32
<212> TYPE: PRT
<213> ORGANISM: Homo sapiens
```

```
<400> SEQUENCE: 184

Gly Val Pro Asp Arg Phe Ser Gly Ser Gly Ser Gly Thr Asp Phe
 1               5                  10                  15

Thr Leu Lys Ile Ser Arg Val Glu Ala Glu Asp Val Gly Val Tyr
                20                  25                  30

Tyr Cys

<210> SEQ ID NO 185
<211> LENGTH: 10
<212> TYPE: PRT
<213> ORGANISM: Homo sapiens

<400> SEQUENCE: 185

Phe Gly Gln Gly Thr Lys Val Glu Ile Lys
 1               5                  10

<210> SEQ ID NO 186
<211> LENGTH: 15
<212> TYPE: PRT
<213> ORGANISM: Homo sapiens

<400> SEQUENCE: 186

Trp Tyr Gln Gln Lys Pro Gly Gln Ala Pro Arg Leu Leu Ile Tyr
 1               5                  10                  15

<210> SEQ ID NO 187
<211> LENGTH: 32
<212> TYPE: PRT
<213> ORGANISM: Homo sapiens

<400> SEQUENCE: 187

Gly Ile Pro Asp Arg Phe Ser Gly Ser Gly Ser Gly Thr Asp Phe
 1               5                  10                  15

Thr Leu Thr Ile Ser Arg Leu Glu Pro Glu Asp Phe Ala Val Tyr
                20                  25                  30

Tyr Cys

<210> SEQ ID NO 188
<211> LENGTH: 10
<212> TYPE: PRT
<213> ORGANISM: Homo sapiens

<400> SEQUENCE: 188

Phe Gly Gln Gly Thr Lys Val Glu Ile Lys
 1               5                  10

<210> SEQ ID NO 189
<211> LENGTH: 15
<212> TYPE: PRT
<213> ORGANISM: Homo sapiens

<400> SEQUENCE: 189

Trp Tyr Gln Gln Lys Pro Gly Gln Pro Pro Lys Leu Leu Ile Tyr
 1               5                  10                  15

<210> SEQ ID NO 190
<211> LENGTH: 32
<212> TYPE: PRT
<213> ORGANISM: Homo sapiens

<400> SEQUENCE: 190

Gly Val Pro Asp Arg Phe Ser Gly Ser Gly Ser Gly Thr Asp Phe
 1               5                  10                  15
```

```
Thr Leu Thr Ile Ser Ser Leu Gln Ala Glu Asp Val Ala Val Tyr
             20                  25                  30

Tyr Cys

<210> SEQ ID NO 191
<211> LENGTH: 10
<212> TYPE: PRT
<213> ORGANISM: Homo sapiens

<400> SEQUENCE: 191

Phe Gly Gln Gly Thr Lys Val Glu Ile Lys
1               5                   10

<210> SEQ ID NO 192
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 5-20
<223> OTHER INFORMATION: Xaa = Y, G, or S

<400> SEQUENCE: 192

Ala Arg Gly Gly Xaa Xaa Xaa Xaa Xaa Xaa Xaa Xaa Xaa Xaa
1               5                   10                  15

Xaa Xaa Xaa Xaa Xaa Phe Asp Tyr
             20

<210> SEQ ID NO 193
<211> LENGTH: 23
<212> TYPE: PRT
<213> ORGANISM: Artificial sequence
<220> FEATURE:
<223> OTHER INFORMATION: Synthetic peptide
<220> FEATURE:
<221> NAME/KEY: Misc-feature
<222> LOCATION: 5-19
<223> OTHER INFORMATION: Xaa = Y, G, or S
<220> FEATURE:
<221> NAME/KEY: Misc-feature
<222> LOCATION: 20
<223> OTHER INFORMATION: Xaa = A, G, or V

<400> SEQUENCE: 193

Ser Arg Gly Gly Xaa Xaa Xaa Xaa Xaa Xaa Xaa Xaa Xaa Xaa
1               5                   10                  15

Xaa Xaa Xaa Xaa Xaa Met Asp Val
             20
```

BINDING POLYPEPTIDES WITH DIVERSIFIED AND CONSENSUS VH/VL HYPERVARIABLE SEQUENCES

RELATED APPLICATIONS

This application claims priority under 35 U.S.C. §119(e) to U.S. provisional application No. 60/734,092, filed Nov. 7, 2005, and to U.S. provisional application No. 60/806,602, filed Jul. 5, 2006, the contents of which are incorporated in their entirety herein by reference.

FIELD OF THE INVENTION

The invention generally relates to variant hypervariable regions of immunoglobulins that are either selectively diversified or comprise human consensus sequences, and libraries comprising a plurality of such immunoglobulin sequences. The invention also relates to fusion polypeptides comprising these variant hypervariable regions. The invention also relates to methods and compositions useful for identifying novel binding polypeptides that can be used therapeutically or as reagents.

BACKGROUND

Phage display technology has provided a powerful tool for generating and selecting novel proteins that bind to a ligand, such as an antigen. Using the techniques of phage display allows the generation of large libraries of protein variants that can be rapidly sorted for those sequences that bind to a target antigen with high affinity. Nucleic acids encoding variant polypeptides are fused to a nucleic acid sequence encoding a viral coat protein, such as the gene III protein or the gene VIII protein. Monovalent phage display systems where the nucleic acid sequence encoding the protein or polypeptide is fused to a nucleic acid sequence encoding a portion of the gene III protein have been developed. (Bass, S., *Proteins*, 8:309 (1990); Lowman and Wells, *Methods: A Companion to Methods in Enzymology*, 3:205 (1991)). In a monovalent phage display system, the gene fusion is expressed at low levels and wild type gene III proteins are also expressed so that infectivity of the particles is retained. Methods of generating peptide libraries and screening those libraries have been disclosed in many patents (e.g. U.S. Pat. No. 5,723,286, U.S. Pat. No. 5,432,018, U.S. Pat. No. 5,580,717, U.S. Pat. No. 5,427,908 and U.S. Pat. No. 5,498,530).

The demonstration of expression of peptides on the surface of filamentous phage and the expression of functional antibody fragments in the periplasm of *E. coli* was important in the development of antibody phage display libraries. (Smith et al., *Science* (1985), 228:1315; Skerra and Pluckthun, *Science* (1988), 240:1038). Libraries of antibodies or antigen binding polypeptides have been prepared in a number of ways including by altering a single gene by inserting random DNA sequences or by cloning a family of related genes. Methods for displaying antibodies or antigen binding fragments using phage display have been described in U.S. Pat. Nos. 5,750,373, 5,733,743, 5,837,242, 5,969,108, 6,172,197, 5,580,717, and 5,658,727. The library is then screened for expression of antibodies or antigen binding proteins with desired characteristics.

Phage display technology has several advantages over conventional hybridoma and recombinant methods for preparing antibodies with the desired characteristics. This technology allows the development of large libraries of antibodies with diverse sequences in less time and without the use of animals. Preparation of hybridomas or preparation of humanized antibodies can easily require several months of preparation. In addition, since no immunization is required, phage antibody libraries can be generated for antigens which are toxic or have low antigenicity (Hogenboom, *Immunotechniques* (1988), 4:1-20). Phage antibody libraries can also be used to generate and identify novel human antibodies.

Antibodies have become very useful as therapeutic agents for a wide variety of conditions. For example, humanized antibodies to HER-2, a tumor antigen, are useful in the diagnosis and treatment of cancer. Other antibodies, such as anti-INF-γ antibody, are useful in treating inflammatory conditions such as Crohn's disease. Phage display libraries have been used to generate human antibodies from immunized, non-immunized humans, germ line sequences, or naïve B cell Ig repertoires (Barbas & Burton, *Trends Biotech* (1996), 14:230; Griffiths et al., *EMBO J.* (1994), 13:3245; Vaughan et al., *Nat. Biotech.* (1996), 14:309; Winter E P 0368 684 B1). Naïve, or nonimmune, antigen binding libraries have been generated using a variety of lymphoidal tissues. Some of these libraries are commercially available, such as those developed by Cambridge Antibody Technology and Morphosys (Vaughan et al., *Nature Biotech* 14:309 (1996); Knappik et al., *J. Mol. Biol.* 296:57 (1999)). However, many of these libraries have limited diversity.

The ability to identify and isolate high affinity antibodies from a phage display library is important in isolating novel human antibodies for therapeutic use. Isolation of high affinity antibodies from a library is traditionally thought to be dependent, at least in part, on the size of the library, the efficiency of production in bacterial cells and the diversity of the library. See, e.g., Knappik et al., *J. Mol. Biol.* (1999), 296:57. The size of the library is decreased by inefficiency of production due to improper folding of the antibody or antigen binding protein and the presence of stop codons. Expression in bacterial cells can be inhibited if the antibody or antigen binding domain is not properly folded. Expression can be improved by mutating residues in turns at the surface of the variable/constant interface, or at selected CDR residues. (Deng et al., *J. Biol. Chem.* (1994), 269:9533, Ulrich et al., *PNAS* (1995), 92:11907-11911; Forsberg et al., *J. Biol. Chem.* (1997), 272:12430). The sequence of the framework region is a factor in providing for proper folding when antibody phage libraries are produced in bacterial cells.

Generating a diverse library of antibodies or antigen binding proteins is also important to isolation of high affinity antibodies. Libraries with diversification in limited CDRs have been generated using a variety of approaches. See, e.g., Tomlinson, *Nature Biotech.* (2000), 18:989-994. CDR-H3 regions are of interest in part because they often are found to participate in antigen binding. CDR-H3 regions on the heavy chain vary greatly in size, sequence and structural conformation.

Others have also generated diversity by randomizing CDR regions of the variable heavy and light chains using all 20 amino acids at each position. It was thought that using all 20 amino acids would result in a large diversity of sequences of variant antibodies and increase the chance of identifying novel antibodies. (Barbas, *PNAS* 91:3809 (1994); Yelton, D E, *J. Immunology*, 155:1994 (1995); Jackson, J. R., *J. Immunology*, 154:3310 (1995) and Hawkins, R E, *J. Mol. Biology*, 226:889 (1992)).

There have also been attempts to create diversity by restricting the group of amino acid substitutions in some CDRs to reflect the amino acid distribution in naturally occurring antibodies. See, Garrard & Henner, *Gene* (1993), 128:103; Knappik et al., *J. Mol. Biol* (1999), 296:57. However, these attempts have had varying success and have not been applied in a systematic and quantitative manner. Creating diversity in the CDR regions while minimizing the number of amino acid changes has been a challenge. Furthermore, in some instances, once a first library has been generated according to one set of criteria, it may be desirable to further enhance the diversity of the first library. However, this requires that the first library has sufficient diversity and yet remain sufficiently small in size such that further diversity can be introduced without substantially exceeding practical limitations such as yield, etc.

Some groups have reported theoretical and experimental analyses of the minimum number of amino acid repertoire that is needed for generating proteins. However, these analyses have generally been limited in scope and nature, and substantial skepticism and questions remain regarding the feasibility of generating polypeptides having complex functions using a restricted set of amino acid types. See, e.g., Riddle et al., *Nat. Struct. Biol.* (1997), 4(10):805-809; Shang et al., *Proc. Natl. Acad. Sci. USA* (1994), 91:8373-8377; Heinz et al., *Proc. Natl. Acad. Sci. USA* (1992), 89:3751-3755; Regan & Degrado, *Science* (1988), 241:976-978; Kamteker et al., *Science* (1993), 262:1680-1685; Wang & Wang, *Nat. Struct. Biol* (1999), 6(11):1033-1038; Xiong et al., *Proc. Natl. Acad. Sci. USA* (1995), 92:6349-6353; Heinz et al., *Proc. Natl. Acad. Sci. USA* (1992), 89:3751-3755; Cannata et al., *Bioinformatics* (2002), 18(8):1102-1108; Davidson et al., *Nat. Struct. Biol* (1995), 2(10):856-863; Murphy et al., *Prot. Eng.* (2000), 13(3):149-152; Brown & Sauer, *Proc. Natl. Acad. Sci. USA* (1999), 96:1983-1988; Akanuma et al., *Proc. Natl. Acad. Sci.* (2002), 99(21):13549-13553; Chan, *Nat. Struct. Biol* (1999), 6(11):994-996.

More recently, useful libraries with significantly improved diversities have been generated. See, e.g., Lee et al., J. Mol. Biol. (2000), 340:1073-1093. Interestingly, libraries resulting from mutation of select CDR positions with either two or four amino acids only have also shown interesting and useful characteristics. Fellouse et al., J. Mol. Biol. (2005); 348(5): 1153-62; Fellouse et al., Proc. Natl. Acad. Sci. USA. (2004), 101(34):12467-72.

It has also become apparent that there is a need for more libraries that cover a greater and different sequence diversity space compared to the libraries currently available. The invention described herein meets this need and provides other benefits.

DISCLOSURE OF THE INVENTION

The present invention provides efficient and selective methods of generating polypeptides comprising variant HVRs that comprise a combination of sequences with selected diversity and consensus sequences, wherein immunoglobulin polypeptides comprising such variant HVRs exhibit target antigen binding capability. Unlike conventional methods that are based on the proposition that adequate diversity of target binders can be generated only if a particular HVR/CDR(s), or all HVR/CDRs are diversified, and unlike conventional notions that adequate diversity is dependent upon the broadest range of amino acid substitutions (generally by substitution using all or most of the 20 amino acids), the invention provides methods capable of generating high quality target binders that are not necessarily dependent upon diversifying a particular HVR/CDR(s) or a particular number of HVR/CDRs of a reference polypeptide or source antibody. The invention is based, at least in part, on the surprising and unexpected finding that high quality and highly diverse libraries comprising functional polypeptides capable of binding target antigens can be generated by diversifying only a subset of the HVRs of an immunoglobulin polypeptide such as an antibody, while substituting the remaining HVRs with at least a portion of human consensus sequences for the corresponding HVRs. The diversified subset of HVRs are diversified in a selective manner, providing in most instances for a bias during the diversification process towards particular amino acids, thus increasing the likelihood that selected positions in the HVR are occupied by pre-determined amino acids, and furthermore resulting in a population of polypeptide binders whose composition is biased towards particular sequence combinations. Methods of the invention are rapid, convenient and flexible, based on using selective, biased codon sets that encode a selected number of amino acids at specific prevalence for some of these amino acids. The biased and less redundant sequence diversity, and thus generally smaller size of the populations (e.g., libraries) of polypeptides generated by methods of the invention allows for further diversification of these populations, and fuller coverage of the number of unique diversified sequences that are theoretically possible but that previously were limited by the practical limitations of recombination cloning techniques (e.g., limitation on number of bacterial transformants in the cloning process, etc.) Enhanced efficiency in generating functional diversified sequences also contributes to enhanced quality of libraries. These advantages are generally not provided by conventional methods. Candidate binder polypeptides generated by the invention possess high-quality target binding characteristics and have structural characteristics that provide for high yield of production in cell culture. The invention provides methods for generating these binder polypeptides, methods for using these polypeptides, and compositions comprising the same.

In one aspect, the invention provides fusion polypeptides comprising diversified HVR(s) and a heterologous polypeptide sequence (preferably that of at least a portion of a viral polypeptide), as single polypeptides and as a member of a plurality of unique individual polypeptides that are candidate binders to targets of interest. Compositions (such as libraries) comprising such polypeptides find use in a variety of applications, e.g., as pools of candidate immunoglobulin polypeptides (e.g., antibodies and antibody fragments) that bind to targets of interest. Such polypeptides may also be generated using non-immunoglobulin scaffolds (e.g., proteins, such as human growth hormone, etc.). The invention encompasses various aspects, including polynucleotides and polypeptides generated according to methods of the invention, and systems, kits and articles of manufacture for practicing methods of the invention, and/or using polypeptides/polynucleotides and/or compositions of the invention.

In one aspect, the invention provides a method of generating a polypeptide comprising at least one, two, three, four, five or all of variant HVRs selected from the group consisting of H1, H2, H3, L1, L2 and L3, wherein said polypeptide is capable of binding a target antigen of interest, said method comprising identifying at least one (or any number up to all) solvent accessible and highly diverse amino acid position in a reference HVR corresponding to the variant HVR; and (ii) varying the amino acid at the solvent accessible and high diverse position by generating variant copies of the HVR using a biased codon set (the definition of "biased codon set" as provided below).

Various aspects and embodiments of methods of the invention are useful for generating and/or using a pool comprising a plurality of polypeptides of the invention, in particular for selecting and identifying candidate binders to target antigens of interest. For example, the invention provides a method of generating a composition comprising a plurality of polypeptides, each polypeptide comprising at least one, two, three, four, five or all of variant HVRs selected from the group consisting of H1, H2, H3, L1, L2 and L3, wherein said polypeptide is capable of binding a target antigen of interest, said method comprising identifying at least one (or any number up to all) solvent accessible and highly diverse amino acid position in a reference HVR corresponding to the variant HVR; and (ii) varying the amino acid at the solvent accessible and high diverse position by generating variant copies of the HVR using a biased codon set; wherein a plurality of polypeptides are generated by amplifying a template polynucleotide with a set of oligonucleotides comprising highly biased degeneracy in the sequence encoding a variant amino acid, wherein said biased degeneracy reflects the biased codon sequences of the biased codon set.

In another example, the invention provides a method comprising: constructing an expression vector comprising a polynucleotide sequence which encodes a light chain, a heavy chain, or both the light chain and the heavy chain variable domains of a source antibody comprising at least one, two, three, four, five or all HVRs selected from the group consisting of HVR L1, L2, L3, H1, H2 and H3; and mutating at least one, two, three, four, five or all HVRs of the source antibody at least one (or any number up to all) solvent accessible and highly diverse amino acid position using a biased codon set.

In another example, the invention provides a method comprising: constructing a library of phage or phagemid particles displaying a plurality of polypeptides of the invention; contacting the library of particles with a target antigen under conditions suitable for binding of the particles to the target antigen; and separating the particles that bind from those that do not bind to the target antigen.

In any of the methods of the invention described herein, a solvent accessible and/or highly diverse amino acid position can be any that meet the criteria as described herein, in particular any combination of the positions as described herein, for example any combination of the positions described for the polypeptides of the invention (as described in greater detail herein). Suitable variant amino acids can be any that meet the criteria as described herein, for example variant amino acids in polypeptides of the invention as described in greater detail below.

Designing diversity in HVRs may involve designing diversity in the length and/or in sequence of the HVR. For example, HVRH3 may be diversified in length to be, e.g., 7 to 19 amino acids in length, and/or in its sequence, e.g. by varying highly diverse and/or solvent accessible positions with amino acids encoded by a biased codon set. In some embodiments, a portion of HVRH3 has a length ranging from 5 to 22, 7 to 20, 9 to 15, or 11 to 13 amino acids, and has a variant amino acid at one or more positions encoded by a biased codon set that encodes a biased set of amino acids. In some embodiments, the C terminal end has an amino acid sequence AM, MDY, FDY, MDV, AMDV (SEQ ID NO: 1), GMDV (SEQ ID NO: 2), VMDV (SEQ ID NO: 4), YFDY (SEQ ID NO: 5), GFDY (SEQ ID NO: 6), SFDY (SEQ ID NO: 7), or AMDY (SEQ ID NO: 8).

In some embodiments, polypeptides of the invention can be in a variety of forms as long as the target binding function of the polypeptides is retained. In some embodiments, a polypeptide of the invention is a fusion polypeptide (i.e., a fusion of two or more sequences from heterologous polypeptides). Polypeptides with diversified HVRs according to the invention can be prepared as fusion polypeptides to at least a portion of a viral coat protein, e.g., for use in phage display. Viral coat proteins that can be used for display of the polypeptides of the invention comprise protein p III, major coat protein pVIII, Soc (T4 phage), Hoc (T4 phage), gpD (lambda phage), pVI, or variants or fragments thereof. In some embodiments, the fusion polypeptide is fused to at least a portion of a viral coat protein, such as a viral coat protein selected from the group consisting of pIII, pVIII, Soc, Hoc, gpD, pVI, and variants or fragments thereof.

In some embodiments, in which the polypeptide with diversified HVRs is one or more antibody variable domains, the antibody variable domains can be displayed on the surface of the virus in a variety of formats including ScFv, Fab, Fab', scFv$_2$, F(ab')$_2$ and F(ab)$_2$. For display of the polypeptides in bivalent manner, the fusion protein preferably includes a dimerization domain. The dimerization domain can comprise a dimerization sequence and/or a sequence comprising one or more cysteine residues. The dimerization domain is preferably linked, directly or indirectly, to the C-terminal end of a heavy chain variable or constant domain (e.g., CH1). The structure of the dimerization domain can be varied depending on whether the antibody variable domain is produced as a fusion protein component with the viral coat protein component (without an amber stop codon after dimerization domain) or whether the antibody variable domain is produced predominantly without viral coat protein component (e.g. with an amber stop codon after dimerization domain). When the antibody variable domain is produced predominantly as a fusion protein with viral coat protein component, one or more disulfide bonds and/or a single dimerization sequence provides for bivalent display. For antibody variable domains predominantly produced without being fused to a viral coat protein component (e.g. with amber stop), it is preferable to have a dimerization domain comprising both a cysteine residue and a dimerization sequence.

In addition, optionally, a fusion polypeptide can comprise a tag that may be useful in purification, detection and/or screening such as FLAG, poly-his, gD tag, c-myc, fluorescence protein or B-galactosidase. In one embodiment, a fusion polypeptide comprises a light chain variable or constant domain fused to a polypeptide tag.

In another aspect of the invention, a polypeptide such as an antibody variable domain is obtained from a single source or template molecule. The source or template molecule is preferably selected or designed for characteristics such as good yield and stability when produced in prokaryotic or eukaryotic cell culture, and/or to accommodate HVRH3 regions of varying lengths. The sequence of the template molecule can be altered to improve folding and/or display of the variable domain when presented as a fusion protein with a phage coat protein component. For example, a source antibody may comprise framework sequences of huMAb4D5-8 as depicted in FIG. 7 or 8, with the template HVR sequences of the template comprising a human HVR consensus sequence. Framework sequences can also be any that can be combined with HVR sequences generated according to methods herein to obtain target polypeptide binding capability. For example, framework region residues can be modified or altered from the source or template molecule to improve or otherwise alter folding, yield, display or affinity of the antibody variable domain. In some embodiments, framework residues are selected to be modified from the source or template molecule when the amino acid in the framework position of the source molecule is different from the amino acid or amino acids commonly found at that position in naturally occurring antibodies or in a subgroup consensus sequence. The amino acids at those positions can be changed to the amino acids most commonly found in the naturally occurring antibodies or in a subgroup consensus sequence at that position. In one embodiment, framework residue 71 of the heavy chain may be R, V or A. In another example, framework residue 93 of the heavy chain may be S or A. In yet another example, framework residue 94 may be R, K or T or encoded by MRT. In yet another example, framework residue 49 in the heavy chain may be alanine or glycine. Framework residues in the light chain may also be changed. For example, the amino acid at position 66 may be arginine or glycine.

Methods of the invention are capable of generating a large variety of polypeptides comprising a diverse set of HVR sequences. For example, in one aspect, the invention provides:

(1) a polypeptide comprising an immunoglobulin heavy chain variable domain, wherein:
(i) HVR-H3 comprises an amino acid sequence:
X1-X2-X3-X4-X5-X6-X7-X8-X9-X10-X11-X12-X13-X14-X15-X16-X17-X18-X19-D-X20; (SEQ ID NO: 9)
wherein X1-X20 are naturally occurring amino acids other than cysteine, and X1 is position 95 according to the Kabat numbering system;
(ii) HVR-H2 comprises an amino acid sequence:
V-S-X1-I-X2-X3-X4-X5-G-X6-T-X7-Y-A-D-S-V-K-G; (SEQ ID NO: 10)
wherein X1-X7 are naturally occurring amino acids other than cysteine, and X1 is position 50 according to the Kabat numbering system;
(iii) HVR-H1 comprises an amino acid sequence:
G-X1-X2-F-X3-X4-X5-X6-X7-S-W-V; (SEQ ID NO: 11)
wherein X1-X7 are naturally occurring amino acids other than cysteine, wherein G is position 26 and X1 is position 27 according to the Kabat numbering system.

In one embodiment of (i), one or more of X1-X18 in HVR-H3 are G, Y, S, V or A (SEQ ID NO: 12). In one embodiment of (i), one or more of X1-X18 in HVR-H3 are Y, G or S (SEQ ID NO: 13). In one embodiment of (i), one or more of X1 and/or X2 in HVR-H3 is G (SEQ ID NO: 14). In one embodiment of (i), X18 is A, G or V (SEQ ID NO: 15). In one embodiment of (i), X19 in HVR-H3 is F or M (SEQ ID NO: 16). In one embodiment of (i), X20 in HVR-H3 is Y or V (SEQ ID NO: 17). In one embodiment, X1 in HVR-H3 is position 95 according to the Kabat numbering system.

In another aspect, the invention provides:

(2) a polypeptide comprising an immunoglobulin heavy chain variable domain, wherein:
(i) HVR-H3 comprises an amino acid sequence:
X1-X2-(X3)n-X4-D-X5 (SEQ ID NO: 18)
wherein X1-X5 are naturally occurring amino acids other than cysteine, and X1 is position 95 according to the Kabat numbering system, and n=a suitable number that would retain the functional activity of the HVR (e.g., n=4-17);
(ii) HVR-H2 comprises an amino acid sequence:
V-S-X1-I-X2-X3-X4-X5-G-X6-T-X7-Y-A-D-S-V-K-G; (SEQ ID NO: 10)
wherein X1-X7 are naturally occurring amino acids other than cysteine, and X1 is position 50 according to the Kabat numbering system;
(iii) HVR-H1 comprises an amino acid sequence:
G-X1-X2-F-X3-X4-X5-X6-X7-S-W-V; (SEQ ID NO: 11)
wherein X1-X7 are naturally occurring amino acids other than cysteine, wherein G is position 26 and X1 is position 27 according to the Kabat numbering system.

In one embodiment of (i), n=16 (SEQ ID NO: 59). In one embodiment of (i), X3 is Y, G, S, A or V (SEQ ID NO: 60). In one embodiment of (i), X3 is Y, G or S (SEQ ID NO: 61). In one embodiment of (i), the X3 residue immediately before X4 is Y, G or S (SEQ ID NO: 62). In one embodiment of (i), the X3 residue immediately before X4 is A, G or V (SEQ ID NO: 63). In one embodiment of (i), X4 is F or M (SEQ ID NO: 64). In one embodiment of (i), X5 is Y or V (SEQ ID NO: 65).

In another aspect, the invention provides:

(3) A polypeptide comprising an immunoglobulin heavy chain variable domain, wherein:
(i) HVR-H3 comprises an amino acid sequence:
X1-X2-X3-X4-X5-X6-X7-X8-X9-X10-X11-X12-X13-X14-X15-X16-X17-X18-X19-D-X20 (SEQ ID NO: 9);
wherein X1-X20 are naturally occurring amino acids other than cysteine, and X1 is position 95 according to the Kabat numbering system;
(ii) HVR-H1 comprises a first consensus hypervariable sequence or variant thereof comprising substitution at one or more positions compared to a corresponding consensus hypervariable sequence; and
(iii) HVR-H2 comprises a second consensus hypervariable sequence or variant thereof comprising substitution at one or more positions compared to a corresponding consensus hypervariable sequence.

In one embodiment of the polypeptide of any (3), the first consensus hypervariable sequence comprises a Kabat consensus CDR-H1 sequence. In one embodiment of the polypeptide of any (3), the second consensus hypervariable sequence comprises a Kabat consensus CDR-H2 sequence. Suitable CDR consensus sequences are well-established, publicly available and provided in the Kabat database (e.g., Kabat et al., *Sequences of Proteins of Immunological Interest*, 5th Ed. Public Health Service, National Institutes of Health, Bethesda, Md. (1991)). The subgroup III CDR-H1 and CDR-H2 consensus sequences are also set out in FIG. 1 and FIG. 3 (the lines indicated as "Consensus").

In one embodiment of the polypeptide of (3),
(a) HVR-H2 comprises a variant of the first consensus hypervariable sequence, wherein the variant comprises amino acid sequence:
V-S-X1-I-X2-X3-X4-X5-G-X6-T-X7-Y-A-D-S-V-K-G; (SEQ ID NO: 10)
wherein X1-X7 are any naturally occurring amino acids other than cysteine and the amino acid at the corresponding position in the first consensus hypervariable sequence, and X1 is position 50 according to the Kabat numbering system; and/or
(b) HVR-H1 comprises a variant of the second consensus hypervariable sequence, wherein the variant comprises amino acid sequence:
G-X1-X2-F-X3-X4-X5-X6-X7-S-W-V; (SEQ ID NO: 11)
wherein X1-X7 are any naturally occurring amino acids other than cysteine and the amino acid at the corresponding position in the second consensus hypervariable sequence, wherein G is position 26 and X1 is position 27 according to the Kabat numbering system.

In one aspect, the invention provides:

(4) A polypeptide comprising an immunoglobulin light chain variable domain, wherein:
(i) HVR-L3 comprises an amino acid sequence:
Q-Q-X1-X2-X3-X4-P-X5-T (SEQ ID NO: 66);
wherein X1-X5 are any naturally occurring amino acids other than cysteine, and X1 is position 91 according to the Kabat numbering system;
(ii) HVR-L1 comprises a first consensus hypervariable sequence or variant thereof comprising substitution at one or more positions compared to a corresponding consensus hypervariable sequence; and
(iii) HVR-L2 comprises a second consensus hypervariable sequence or variant thereof comprising substitution at one or more positions compared to a corresponding consensus hypervariable sequence.

In one embodiment of (i), X1 in HVR-L3 is R, S or Y (SEQ ID NO: 67). In one embodiment of (i), X1 in HVR-L3 is position 91 according to the Kabat numbering system. In one embodiment of (i), X2 in HVR-L3 is Y, G or S (SEQ ID NO: 68). In one embodiment of (i), X2 in HVR-L3 is any amino acid other than cysteine (SEQ ID NO: 69). In one embodiment of (i), X3 in HVR-L3 is S (SEQ ID NO: 70). In one embodiment of (i), X3 in HVR-L3 is any amino acid other than cysteine (SEQ ID NO: 71). In one embodiment of (i), X4 in HVR-L3 is Y or S (SEQ ID NO: 72). In one embodiment of (i), X4 in HVR-L3 is any amino acid other than cysteine (SEQ ID NO: 73). In one embodiment of (i), X5 in HVR-L3 is F, I, L or V (SEQ ID NO: 74).

In one aspect, the invention provides a combination of any of the immunoglobulin heavy chain variable domain as described herein (e.g., polypeptide (1), (2) or (3) above) and any light chain HVR-L3 as described herein (including, e.g., an immunoglobulin light chain variable domain as described herein, such as polypeptide (4) above).

In one embodiment of the polypeptide of (4), the first consensus hypervariable sequence comprises a Kabat consensus CDR-L1 sequence. In one embodiment of the polypeptide of (4), the second consensus hypervariable sequence comprises a Kabat consensus CDR-L2 sequence. Suitable CDR consensus sequences are well-established, publicly available and provided in the Kabat database (e.g., Kabat et al., *Sequences of Proteins of Immunological Interest*, 5th Ed. Public Health Service, National Institutes of Health, Bethesda, Md. (1991)). The subgroup III CDR-L1 and CDR-L2 consensus sequences are also set out in FIG. 1 and FIG. 2 (the lines indicated as "Consensus").

For clarity, where n is greater than 1 in HVR sequences described herein, in a single variant HVR, amino acid X can be any of the amino acids encoded by a particular codon set. For example, in a variant HVR-H3 sequence wherein X1 can be amino acid A, B, C or D, and n=4, the sequence of X1X1X1X1 (i.e., $(X1)_4$) in the variant HVR-H3 can be, for example, AAAA, BBBB, CCCC, DDDD, ABCD, ACBD, ADBC, ACBD, ADBC, or any combination of one or more of the four amino acids A, B, C, and D.

In one aspect, the invention provides a polypeptide comprising a variant HVR-H3 comprising a variant amino acid in at least one (or any number up to all) of positions 95, 96, 97, 98, 99, 100 and 100a, numbering of positions according to the Kabat system. Typically, the C terminal residues of HVR-H3 are kept constant as AM, MDY, FDY, MDV, AMDV (SEQ ID NO: 1), GMDV (SEQ ID NO: 2), VMDV (SEQ ID NO: 4), YFDY (SEQ ID NO: 5), GFDY (SEQ ID NO: 6), SFDY (SEQ ID NO: 7), or AMDY (SEQ ID NO: 8) (although some changes can be made as long as the desired polypeptide characteristics (such as target antigen binding) are substantially retained). In some embodiments, all positions between 100 and M in the MDY region comprise variant amino acids. In some embodiments, at least one position between 100 and M in the MDY region comprises a variant amino acid. In some embodiments, a polypeptide comprises a variant HVR-H3 comprising a variant amino acid in at least one of positions 95, 96, 97, 98, 99, 100, and at least one position between 100 and C-terminal sequence MDY. In some embodiments of these polypeptides, the variant HVR-H3 comprises an insertion of one or more residues/positions, wherein said one or more positions is varied with respect to the corresponding CDR consensus sequence. In some embodiments, said insertion comprises 1-15, 3-13, 5-11, or 7-9 residues/positions. In some embodiments, said insertion comprises at least 1, at least 3, at least 5, at least 7, at least 9, at least 11, at least 13 residues/positions. In some embodiments, said insertion comprises 15 or fewer, 13 or fewer, 11 or fewer, 9 or fewer, 7 or fewer, or 5 or fewer residues/positions.

In one aspect, the invention provides a polypeptide comprising a variant HVR-H2 comprising a variant amino acid in at least one (or any number up to all) of positions 50, 52 (and optionally 52a), 53, 54, 56 and 58, numbering of positions according to the Kabat system.

In one aspect, the invention provides a polypeptide comprising a variant HVR-H1 comprising a variant amino acid in at least one (or any number up to all) of positions 27, 28, 30, 31, 32, 33, and 34, numbering of positions according to the Kabat system.

In one aspect, the invention provides a polypeptide comprising a variant HVR-L3 comprising a variant amino acid in at least one (or any number up to all) of positions 91, 92, 93, 94 and 96, numbering of positions according to the Kabat system.

In one aspect, the invention provides a polypeptide comprising an HVR-L2 comprising a consensus HVR sequence. In one aspect, the invention provides a polypeptide comprising a variant HVR-L2 comprising a variant amino acid in at least one or both of positions 50 and 53, numbering of positions according to the Kabat system.

In one aspect, the invention provides a polypeptide comprising an HVR-L1 comprising a consensus HVR sequence. In one aspect, the invention provides a polypeptide comprising a variant HVR-L1 comprising a variant amino acid in at least one (or any number up to all) of positions 28, 29, 30, 31 and 32, numbering of positions according to the Kabat system.

In the preceding aspects, the variant HVRs are varied with respect to a corresponding consensus sequence, for example, consensus sequences for the corresponding HVR as described in the Kabat database (e.g., Kabat et al., *Sequences of Proteins of Immunological Interest*, 5th Ed. Public Health Service, National Institutes of Health, Bethesda, Md. (1991)).

In one aspect, a polypeptide of the invention comprises at least one, or both, of heavy chain and light chain antibody variable domains, wherein the antibody variable domain comprises one, two or three variant HVRs as described herein (e.g., as described in the foregoing).

In some embodiments, a polypeptide of the invention (in particular those comprising an antibody variable domain) further comprises an antibody framework sequence, for example, FR1, FR2, FR3 and/or FR4 for an antibody variable domain corresponding to the variant HVR, the FR sequences obtained from a single antibody template. In one embodiment, the FR sequences are obtained from a human antibody. In one embodiment, the FR sequences are obtained from a human consensus sequence (e.g., subgroup III consensus sequence). In one embodiment, the framework sequences comprise a modified consensus sequence as described herein (e.g., comprising modifications at position 49, 71, 93 and/or 94 in the heavy chain, and/or position 66 in the light chain). Exemplary framework sequences are depicted in FIGS. 5 & 6. In one embodiment, each of the FR has the sequence of antibody huMAb4D5-8, or a modified version thereof (FIGS. 7 & 8).

In one aspect, the invention provides methods of generating compositions comprising polypeptides and/or polynucleotides of the invention. Accordingly, in one aspect, the invention provides:

(1) A method of generating a composition comprising a plurality of polypeptides comprising:
  a) generating a plurality of polypeptides comprising:
    (i) HVR-H3 comprising an amino acid sequence:
      X1-X2-(X3)n-X4-D-X5; (SEQ ID NO: 18)

wherein X1-X5 are naturally occurring amino acids other than cysteine, and X1 is position 95 according to the Kabat numbering system, and n=a suitable number that would retain the functional activity of the HVR (e.g., n=4-17);
(ii) HVR-H2 comprising an amino acid sequence:
V-S-X1-I-X2-X3-X4-X5-G-X6-T-X7-Y-A-D-S-V-K-G; (SEQ ID NO: 10)
wherein X1-X7 are naturally occurring amino acids other than cysteine, and X1 is position 50 according to the Kabat numbering system;
(iii) HVR-H1 comprising an amino acid sequence: G-X1-X2-F-X3-X4-X5-X6-X7-S-W-V; (SEQ ID NO: 11)
wherein X1-X7 are naturally occurring amino acids other than cysteine, wherein G is position 26 and X1 is position 27 according to the Kabat numbering system.

(2) A method of generating a composition comprising a plurality of polypeptides comprising:
a) generating a plurality of polypeptides comprising:
(i) HVR-H3 comprises an amino acid sequence:
X1-X2-X3-X4-X5-X6-X7-X8-X9-X10-X11-X12-X13-X14-X15-X16-X17-X18-X19-D-X20; (SEQ ID NO: 9)
wherein X1-X20 are naturally occurring amino acids other than cysteine, and X1 is position 95 according to the Kabat numbering system;
(ii) HVR-H2 comprises an amino acid sequence:
V-S-X1-I-X2-X3-X4-X5-G-X6-T-X7-Y-A-D-S-V-K-G; (SEQ ID NO: 10)
wherein X1-X7 are naturally occurring amino acids other than cysteine, and X1 is position 50 according to the Kabat numbering system;
(iii) HVR-H1 comprises an amino acid sequence:
G-X1-X2-F-X3-X4-X5-X6-X7-S-W-V; (SEQ ID NO: 11)
wherein X1-X7 are naturally occurring amino acids other than cysteine, wherein G is position 26 and X1 is position 27 according to the Kabat numbering system.

(3) A method of generating a composition comprising a plurality of polypeptides comprising:
a) generating a plurality of polypeptides comprising:
(i) HVR-H3 comprises an amino acid sequence:
X1-X2-X3-X4-X5-X6-X7-X8-X9-X10-X11-X12-X13-X14-X15-X16-X17-X18-X19-D-X20; (SEQ ID NO: 9)
wherein X1-X20 are naturally occurring amino acids other than cysteine, and X1 is position 95 according to the Kabat numbering system;
(iv) HVR-H1 comprises a first consensus hypervariable sequence or variant thereof comprising substitution at one or more positions compared to a corresponding consensus hypervariable sequence; and
HVR-H2 comprises a second consensus hypervariable sequence or variant thereof comprising substitution at one or more positions compared to a corresponding consensus hypervariable sequence.

In one embodiment of method (3) above,
(a) HVR-H2 comprises a variant of the first consensus hypervariable sequence, wherein the variant comprises amino acid sequence:
V-S-X1-I-X2-X3-X4-X5-G-X6-T-X7-Y-A-D-S-V-K-G; (SEQ ID NO: 10)
wherein X1-X7 are any naturally occurring amino acids other than cysteine and the amino acid at the corresponding position in the first consensus hypervariable sequence, and X1 is position 50 according to the Kabat numbering system; and/or
(b) HVR-H1 comprises a variant of the second consensus hypervariable sequence,
wherein the variant comprises amino acid sequence:
G-X1-X2-F-X3-X4-X5-X6-X7-S-W-V; (SEQ ID NO: 11)
wherein X1-X7 are any naturally occurring amino acids other than cysteine and the amino acid at the corresponding position in the second consensus hypervariable sequence, wherein G is position 26 and X1 is position 27 according to the Kabat numbering system.

In one embodiment of method (1), (2) and (3), the method further comprises:
(b) generating a plurality of polypeptides comprising:
(i) HVR-L3 comprising an amino acid sequence:
Q-Q-X1-X2-X3-X4-P-X5-T; (SEQ ID NO: 66)
wherein X1-X5 are naturally occurring amino acids other than cysteine, and X1 is position 91 according to the Kabat numbering system;
(ii) HVR-L1 comprises a first consensus hypervariable sequence or variant thereof comprising substitution at one or more positions compared to a corresponding consensus hypervariable sequence; and
(iii) HVR-L2 comprises a second consensus hypervariable sequence or variant thereof comprising substitution at one or more positions compared to a corresponding consensus hypervariable sequence.

In one embodiment of the methods of (1), (2) and (3), the first consensus hypervariable sequence of HVR-L1 comprises a Kabat consensus CDR-L1 sequence. In one embodiment of the methods of (1), (2) and (3), the second consensus hypervariable sequence of HVR-L2 comprises a Kabat consensus CDR-L2 sequence. In one embodiment of the methods of (1), (2) and (3), the plurality of polypeptides are encoded by a plurality of polynucleotides. In one embodiment, the polynucleotides comprise non-redundant codons for each amino acid at each X position. In one embodiment, the non-redundant codons comprise trinucleotide codons.

In one embodiment of the methods of (1), (2) and (3), the generation of said plurality of polypeptides comprises mutagenizing a template/reference nucleic acid that encodes the respective HVR sequences at one or more X positions within said HVR sequences. In one embodiment, the template/reference nucleic acid comprises one or more stop codons in an HVR, and a mutagenic nucleic acid (e.g., an oligonucleotide) comprises one or more codons that encode amino acid(s) at the position(s) corresponding to the stop codon(s). In one embodiment, said plurality of polypeptides are encoded by mutagenic oligonucleotides comprising one or more codons that encode amino acid(s) at the position(s) corresponding to the stop codon(s) of the template/reference nucleic acid. In one embodiment, the HVR is HVR-H3. In one embodiment, only one HVR comprises the stop codon(s), wherein said HVR is HVR-H3.

In one embodiment of the methods of (1), (2) and (3), the probability of X1 and/or X2 of HVR-H3 being G is greater than any other individual amino acid. In one embodiment of the methods of (1), (2) and (3), the plurality of polynucleotides comprise (i) a first set of polynucleotides comprising a codon encoding G at X1 and/or X2 of HVR-H3, and (ii) a second set of polynucleotides comprising a codon encoding an amino acid other than G at X1 and/or X2 of HVR-H3, wherein the first set of polynucleotides is present at an amount greater than the amount of each subset of polynucleotides having the same HVR-H3 sequence within the second set of polynucleotides.

In one embodiment of the methods of (1), (2) and (3), at least about 20% (up to 29%) of the polynucleotides encoding HVR-H3 comprise a codon encoding G at X1 and/or X2. In one embodiment, no more than about 5% of the polynucleotides encoding HVR-H3 comprise a codon encoding any single amino acid other than G at X1 and/or X2. In one embodiment, the amount of polynucleotide comprising a codon encoding G at X1 and/or X2 of HVR-H3 in the plurality of polynucleotides is adjusted to provide a bias in favor of G at X1 and/or X2 of HVR-H3 of the plurality of polypeptides. In one embodiment, at least about 10% (up to 20%) of the polynucleotides encoding HVR-H3 comprise a codon encoding G, S or Y at X3. In one embodiment, no more than about 5% of the polynucleotides encoding HVR-H3 comprise a codon encoding any single amino acid other than G, S or Y at X3. In one embodiment, the amount of polynucleotide comprising a codon encoding G, S or Y at X3 of HVR-H3 in the plurality of polynucleotides is adjusted to provide a bias in favor of G, S and/or Y at X3 of HVR-H3 of the plurality of polypeptides.

In one embodiment of the methods of (1), (2) and (3), at least about 15% (up to 25%) of the polynucleotides encoding HVR-H2 comprise a codon encoding S or Y at X2. In one embodiment, no more than about 5% of the polynucleotides encoding HVR-H2 comprise a codon encoding any single amino acid other than S or Y at X2. In one embodiment, the amount of polynucleotide comprising a codon encoding S or Y at X2 of HVR-H2 in the plurality of polynucleotides is adjusted to provide a bias in favor of S and/or Y at X2 of HVR-H2 of the plurality of polypeptides. In one embodiment, at least about 10% (up to 20%) of the polynucleotides encoding HVR-H2 comprise a codon encoding G, S or Y at X3 and/or X4. In one embodiment, no more than about 5% of the polynucleotides encoding HVR-H2 comprise a codon encoding any single amino acid other than G, S or Y at X3 and/or X4. In one embodiment, the amount of polynucleotide comprising a codon encoding G, S or Y at X3 and/or X4 of HVR-H2 in the plurality of polynucleotides is adjusted to provide a bias in favor of G, S and/or Y at X3 and/or X4 of HVR-H2 of the plurality of polypeptides.

In one embodiment of the methods of (1), (2) and (3), at least about 50% (up to 60%) of the polynucleotides encoding HVR-H1 comprise a codon encoding S at X4. In one embodiment, no more than about 5% of the polynucleotides encoding HVR-H1 comprise a codon encoding any single amino acid other than S at X4. In one embodiment, the amount of polynucleotide comprising a codon encoding S at X4 of HVR-H1 in the plurality of polynucleotides is adjusted to provide a bias in favor of S at X4 of HVR-H1 of the plurality of polypeptides. In one embodiment, at least about 50% (up to 60%) of the polynucleotides encoding HVR-H1 comprise a codon encoding Y at X5. In one embodiment, no more than about 5% of the polynucleotides encoding HVR-H1 comprise a codon encoding any single amino acid other than Y at X5. In one embodiment, the amount of polynucleotide comprising a codon encoding Y at X5 of HVR-H1 in the plurality of polynucleotides is adjusted to provide a bias in favor of Y at X5 of HVR-H1 of the plurality of polypeptides. In one embodiment, at least about 10% (up to 20%) of the polynucleotides encoding HVR-H1 comprise a codon encoding G, S or Y at X6. In one embodiment, no more than about 5% of the polynucleotides encoding HVR-H1 comprise a codon encoding any single amino acid other than G, S or Y at X6. In one embodiment, the amount of polynucleotide comprising a codon encoding G, S or Y at X6 of HVR-H1 in the plurality of polynucleotides is adjusted to provide a bias in favor of G, S or Y at X6 of HVR-H1 of the plurality of polypeptides.

In one embodiment of the methods of (1), (2) and (3), at least about 15% (up to 25%) of the polynucleotides encoding HVR-L3 comprise a codon encoding G, S or Y at X2. In one embodiment, no more than about 5% of the polynucleotides encoding HVR-L3 comprise a codon encoding any single amino acid other than G, S or Y at X2. In one embodiment, the amount of polynucleotide comprising a codon encoding G, S or Y at X2 of HVR-L3 in the plurality of polynucleotides is adjusted to provide a bias in favor of G, S or Y at X2 of HVR-L3 of the plurality of polypeptides. In one embodiment, at least about 50% (up to 55%) of the polynucleotides encoding HVR-L3 comprise a codon encoding S at X3. In one embodiment, no more than about 5% of the polynucleotides encoding HVR-L3 comprise a codon encoding any single amino acid other than S at X3. In one embodiment, the amount of polynucleotide comprising a codon encoding S at X3 of HVR-L3 in the plurality of polynucleotides is adjusted to provide a bias in favor of S at X3 of HVR-L3 of the plurality of polypeptides. In one embodiment, at least about 15% (up to 25%) of the polynucleotides encoding HVR-L3 comprise a codon encoding S or Y at X4. In one embodiment, no more than about 5% of the polynucleotides encoding HVR-L3 comprise a codon encoding any single amino acid other than S or Y at X4. In one embodiment, the amount of polynucleotide comprising a codon encoding S or Y at X4 of HVR-L3 in the plurality of polynucleotides is adjusted to provide a bias in favor of S or Y at X4 of HVR-L3 of the plurality of polypeptides.

In one aspect, the invention provides compositions (e.g., plurality of polynucleotides, plurality of polypeptides, library of polynucleotides/polypeptides) produced by methods of the invention.

In some aspects, the invention provides a polypeptide comprising at least one, two, three, four, five or all of variant HVRs selected from the group consisting of HVR-L1, HVR-L2, HVR-L3, HVR-H1, HVR-H2 and HVR-H3, wherein the variant HVR is as described above.

In some embodiments, a polypeptide of the invention comprises a light chain and a heavy chain antibody variable domain, wherein the light chain variable domain comprises at least 1, 2 or 3 variant HVRs selected from the group consisting of HVR-L1, L2 and L3, and the heavy chain variable domain comprises at least 1, 2 or 3 variant HVRs selected from the group consisting of HVR-H1, H2 and H3.

In some embodiments, a polypeptide of the invention is an scFv. In some embodiments, it is a Fab fragment. In some embodiments, it is a F(ab)$_2$ or F(ab')$_2$. Accordingly, in some embodiments, a polypeptide of the invention further comprises a dimerization domain. In some embodiments, the dimerization domain is located between an antibody heavy chain or light chain variable domain and at least a portion of a viral coat protein. The dimerization domain can comprise a dimerization sequence, and/or sequence comprising one or more cysteine residues. The dimerization domain is preferably linked, directly or indirectly, to the C-terminal end of a heavy chain variable or constant domain. The structure of the dimerization domain can be varied depending on whether the antibody variable domain is produced as a fusion protein component with the viral coat protein component (without an amber stop codon after dimerization domain) or whether the antibody variable domain is produced predominantly without viral coat protein component (e.g. with an amber stop codon after dimerization domain). When the antibody variable domain is produced predominantly as a fusion protein with viral coat protein component, one or more disulfide bond and/or a single dimerization sequence provides for bivalent display. For antibody variable domains predominantly produced without being fused to a viral coat protein component (e.g. with amber stop), it is preferable, though not required, to have a dimerization domain comprising both a cysteine residue and a dimerization sequence. In some embodiments, heavy chains of the F(ab)$_2$ dimerize at a dimerization domain not including a hinge region. The dimerization domain may comprise a leucine zipper sequence (for example, a GCN4 sequence such as GRMKQLEDKVEELLSKNYHLENE-VARLKKLVGERG (SEQ ID NO: 3).

In some embodiments, a polypeptide of the invention further comprises a light chain constant domain fused to a light chain variable domain, which in some embodiments comprises at least one, two or three variant HVRs. In some embodiments of polypeptides of the invention, the polypeptide comprises a heavy chain constant domain fused to a heavy chain variable domain, which in some embodiments comprises at least one, two or three variant HVRs.

In some instances, it may be preferable to mutate a framework residue such that it is variant with respect to a reference polypeptide or source antibody. For example, framework residue 71 of the heavy chain may be amino acid R, V or A. In another example, framework residue 93 of the heavy chain may be amino acid S or A. In yet another example, framework residue 94 of the heavy chain may be amino acid R, K or T. In yet another example, framework residue 49 of the heavy chain may be amino acid A or G. Framework residues in the light chain may also be mutated. For example, framework residue 66 in the light chain may be amino acid R or G.

As described herein, a variant HVR refers to a HVR with a sequence variance as compared to the corresponding HVR of a single reference polypeptide/source antibody, for example wherein the reference/source antibody comprises HVRs comprising consensus CDR sequences (e.g., as provided in the Kabat database). Accordingly, the HVRs of a single polypeptide of the invention preferably correspond to the set of HVRs of a single reference polypeptide or source antibody. Polypeptides of the invention may comprise any one or combinations of variant HVRs. For example, a polypeptide of the invention may comprise a variant HVR-H1 and variant HVR-H2. A polypeptide of the invention may comprise a variant HVR-H1, variant HVR-H2 and variant HVR-H3. In another example, a polypeptide of the invention may comprise a variant HVR-H1, variant HVR-H2, variant HVR-H3 and variant HVR-L3. Any polypeptide of the invention may further comprise a variant HVR-L3. Any polypeptide of the invention may further comprise a variant HVR-H3.

In one embodiment, a polypeptide of the invention comprises one or more variant HVR sequences as depicted in FIGS. 2 and/or 3.

Polypeptides of the invention may be in a complex with one another. For example, the invention provides a polypeptide complex comprising two polypeptides, wherein each polypeptide is a polypeptide of the invention, and wherein one of said polypeptides comprises at least one, two or all of variant HVRs H1, H2 and H3, and the other polypeptide comprises a variant light chain HVR (e.g., HVR-L3). A polypeptide complex may comprise a first and a second polypeptide (wherein the first and second polypeptides are polypeptides of the invention), wherein the first polypeptide comprises at least one, two or three variant light chain HVRs, and the second polypeptide comprises at least one, two or three variant heavy chain HVRs. The invention also provides complexes of polypeptides that comprise the same variant HVR sequences. Complexing can be mediated by any suitable technique, including by dimerization/multimerization at a dimerization/multimerization domain such as those described herein or by covalent interactions (such as through a disulfide linkage) (which in some contexts is part of a dimerization domain, for example, a dimerization domain may contain a leucine zipper sequence and a cysteine).

In another aspect, the invention provides compositions comprising polypeptides and/or polynucleotides of the invention. For example, the invention provides a composition comprising a plurality of any of the polypeptides of the invention described herein. Said plurality may comprise polypeptides encoded by a plurality of polynucleotides generated using a set of oligonucleotides comprising degeneracy in the sequence encoding a variant amino acid, wherein said degeneracy is that of the multiple codon sequences of the codon set encoding the variant amino acid. A composition comprising a polynucleotide or polypeptide or library of the invention may be in the form of a kit or an article of manufacture (optionally packaged with instructions, buffers, etc.).

In one aspect, the invention provides a polynucleotide encoding a polypeptide of the invention as described herein. In another aspect, the invention provides a vector comprising a sequence encoding a polypeptide of the invention. The vector can be, for example, a replicable expression vector (e.g., the replicable expression vector can be M13, f1, fd, Pf3 phage or a derivative thereof, or a lambdoid phage, such as lambda, 21, phi80, phi81, 82, 424, 434, etc., or a derivative thereof). The vector can comprise a promoter region linked to the sequence encoding a polypeptide of the invention. The promoter can be any that is suitable for expression of the polypeptide, e.g., the lac Z promoter system, the alkaline phosphatase pho A promoter (Ap), the bacteriophage $l_{PL}$ promoter (a temperature sensitive promoter), the tac promoter, the tryptophan promoter, and the bacteriophage T7 promoter. Thus, the invention also provides a vector comprising a promoter selected from the group consisting of the foregoing promoter systems.

Polypeptides of the invention can be displayed in any suitable form in accordance with the need and desire of the practitioner. For example, a polypeptide of the invention can be displayed on a viral surface, e.g., a phage or phagemid viral particle. Accordingly, the invention provides viral particles comprising a polypeptide of the invention and/or polynucleotide encoding a polypeptide of the invention.

In one aspect, the invention provides a population comprising a plurality of polypeptide or polynucleotide of the invention, wherein each type of polypeptide or polynucleotide is a polypeptide or polynucleotide of the invention as described herein.

In some embodiments, polypeptides and/or polynucleotides are provided as a library, e.g., a library comprising a plurality of at least about $1 \times 10^4$, $1 \times 10^5$, $1 \times 10^6$, $1 \times 10^7$, $1 \times 10^8$ distinct polypeptide and/or polynucleotide sequences of the invention. In another aspect, the invention also provides a library comprising a plurality of the viruses or viral particles of the invention, each virus or virus particle displaying a polypeptide of the invention. A library of the invention may comprise viruses or viral particles displaying any number of distinct polypeptides (sequences), e.g., at least about $1 \times 10^4$, $1 \times 10^5$, $1 \times 10^6$, $1 \times 10^7$, $1 \times 10^8$ distinct polypeptides.

In another aspect, the invention provides host cells comprising a polynucleotide or vector comprising a sequence encoding a polypeptide of the invention.

In another aspect, the invention provides methods for selecting for high affinity binders to specific target antigens such as growth hormone, bovine growth hormone, ephrin (e.g., ephrinA2), neuropilin (e.g., neuropilin 1), stigma, insulin-like growth factors, human growth hormone including n-methionyl human growth hormone, parathyroid hormone, thyroxine, insulin, proinsulin, amylin, an apoptosis protein, relaxin, prorelaxin, glycoprotein hormones such as follicle stimulating hormone (FSH), leutinizing hormone (LH), hemapoietic growth factor, fibroblast growth factor, prolactin, placental lactogen, tumor necrosis factors, hepatocyte growth factor, hepatocyte growth factor receptor (c-met), mullerian inhibiting substance, mouse gonadotropin-associated polypeptide, inhibin, activin, vascular endothelial growth factors, integrin, nerve growth factors such as NGF-beta, insulin-like growth factor-I and -II, erythropoietin, osteoinductive factors, interferons, colony stimulating factors, interleukins, bone morphogenetic proteins, LIF, SCF, neutravidin, maltose binding protein, erbin GST, insulin, IgG, FLT-3 ligand, and kit-ligand.

The methods of the invention provide populations of polypeptides (e.g., libraries of polypeptides (e.g., antibody variable domains)) with one or more diversified HVR regions. These libraries are sorted (selected) and/or screened to identify high affinity binders to a target antigen. In one aspect, polypeptide binders from the library are selected for binding to target antigens, and for affinity. The polypeptide binders selected using one or more of these selection strategies may then be screened for affinity and/or for specificity (binding only to target antigen and not to non-target antigens).

In one aspect, a method of the invention comprises generating a plurality of polypeptides with one or more diversified HVRs, sorting the plurality of polypeptides for binders to a target antigen by contacting the plurality of polypeptides with a target antigen under conditions suitable for binding; separating the binders to the target antigen from those that do not bind; isolating the binders; and identifying the high affinity binders (or any binders having a desired binding affinity). The affinity of the binders that bind to the target antigen can be determined using a variety of techniques known in the art, e.g., competition ELISA such as described herein. Optionally, the polypeptides can be fused to a polypeptide tag, such as gD, poly his or FLAG, which can be used to sort binders in combination with sorting for the target antigen.

Another embodiment provides a method of isolating or selecting for an antibody variable domain that binds to a target antigen from a library of antibody variable domains, said method comprising: a) contacting a population comprising a plurality of polypeptides of the invention with an immobilized target antigen under conditions suitable for binding to isolate target antigen polypeptide binders; b) separating the polypeptide binders from nonbinders, and eluting the binders from the target antigen; c) optionally, repeating steps a-b at least once (in some embodiments, at least twice).

In some embodiments, a method may further comprise: d) incubating the polypeptide binders with a concentration of labelled target antigen in the range of 0.1 nM to 1000 nM under conditions suitable for binding to form a mixture; e) contacting the mixture with an immobilized agent that binds to the label on the target antigen; f) eluting the polypeptide binders from the labelled target antigen; g) optionally, repeating steps d) to f) at least once (in some embodiments, at least twice), using a successively lower concentration of labelled target antigen each time. Optionally, the method may comprise adding an excess of unlabelled target antigen to the mixture and incubating for a period of time sufficient to elute low affinity binders from the labelled target antigen.

Another aspect of the invention provides a method of isolating or selecting for high affinity binders (or binders having a desired binding affinity) to a target antigen. In one embodiment, said method comprises: a) contacting a population comprising a plurality of polypeptides of the invention with a target antigen, wherein the antigen is provided at a concentration in the range of about 0.1 nM to 1000 nM to isolate polypeptide binders to the target antigen; b) separating the polypeptide binders from the target antigen; c) optionally, repeating steps a-b at least once (in some embodiments, at least twice), each time with a successively lower concentration of target antigen to isolate polypeptide binders that bind to lowest concentration of target antigen; d) selecting the polypeptide binder that binds to the lowest concentration of the target antigen for high affinity (or any desired affinity) by incubating the polypeptide binders with several different dilutions of the target antigen and determining the IC50 of the polypeptide binder; and e) identifying a polypeptide binder that has a desired affinity for the target antigen. Said affinity can be, e.g., about 0.1 nM to 200 nM, 0.5 nM to 150 nM, 1 nM to 100 nM, 25 nM to 75 nM.

Another embodiment provides an assay for isolating or selecting polypeptide binders comprising (a) contacting a population comprising a plurality of polypeptides of the invention with a labelled target antigen, wherein the labeled target antigen is provided at a concentration in a range of 0.1 nM to 1000 nM, under conditions suitable for binding to form a complex of a polypeptide binder and the labelled target antigen; b) isolating the complexes and separating the polypeptide binder from the labelled target antigen; c) optionally, repeating steps a-b at least once, each time using a lower concentration of target antigen. Optionally, the method may further comprise contacting the complex of polypeptide binder and target antigen with an excess of unlabelled target antigen. In one embodiment, the steps of the method are repeated twice and the concentration of target in a first round of selection is in the range of about 100 nM to 250 nM, and, in a second round of selection (if performed) is in the range of about 25 nM to 100 nM, and in the third round of selection (if performed) is in the range of about 0.1 nM to 25 nM.

The invention also includes a method of screening a population comprising a plurality of polypeptides of the invention, said method comprising: a) incubating a first sample of the population of polypeptides with a target antigen under conditions suitable for binding of the polypeptides to the target antigen; b) subjecting a second sample of the population of polypeptides to a similar incubation but in the absence of the target antigen; (c) contacting each of the first and second sample with immobilized target antigen under conditions suitable for binding of the polypeptides to the immobilized target antigen; d) detecting amount of polypeptides bound to immobilized target antigen for each sample; e) determining affinity of a particular polypeptide for the target antigen by calculating the ratio of the amount of the particular polypeptide that is bound in the first sample over the amount of the particular polypeptide that is bound in the second sample.

The libraries generated as described herein may also be screened for binding to a specific target and for lack of binding to nontarget antigens. In one aspect, the invention provides a method of screening for a polypeptide, such as an antibody variable domain of the invention, that binds to a specific target antigen from a library of antibody variable domains, said method comprising: a) generating a population comprising a plurality of polypeptides of the invention; b) contacting the population of polypeptides with a target antigen under conditions suitable for binding; c) separating a binder polypeptide in the library from nonbinder polypeptides; d) identifying a target antigen-specific binder polypeptide by determining whether the binder polypeptide binds to a non-target antigen; and e) isolating a target antigen-specific binder polypeptide. In some embodiments, step (e) comprises eluting the binder polypeptide from the target antigen, and amplifying a replicable expression vector encoding said binder polypeptide.

Combinations of any of the sorting/selection methods described above may be combined with the screening methods. For example, in one embodiment, polypeptide binders are first selected for binding to an immobilized target antigen. Polypeptide binders that bind to the immobilized target antigen can then be screened for binding to the target antigen and for lack of binding to nontarget antigens. Polypeptide binders that bind specifically to the target antigen can be amplified as necessary. These polypeptide binders can be selected for higher affinity by contact with a concentration of a labelled target antigen to form a complex, wherein the concentration range of labelled target antigen is from about 0.1 nM to about 1000 nM, and the complexes are isolated by contact with an agent that binds to the label on the target antigen. A polypeptide binder can then be eluted from the labeled target antigen and optionally, the rounds of selection are repeated, each time a lower concentration of labelled target antigen is used. The binder polypeptides that can be isolated using this selection method can then be screened for high affinity using for example, a solution phase ELISA assay or other conventional methods known in the art. Populations of polypeptides of the invention used in methods of the invention can be provided in any form suitable for the selection/screening steps. For example, the polypeptides can be in free soluble form, attached to a matrix, or present at the surface of a viral particle such as phage or phagemid particle. In some embodiments of methods of the invention, the plurality of polypeptides are encoded by a plurality of replicable vectors provided in the form of a library. In selection/screening methods described herein, vectors encoding a binder polypeptide may be further amplified to provide sufficient quantities of the polypeptide for use in repetitions of the selection/screening steps (which, as indicated above, are optional in methods of the invention).

In one embodiment, the invention provides a method of selecting for a polypeptide that binds to a target antigen comprising:
  a) generating a composition comprising a plurality of polypeptides of the invention as described herein;
  b) selecting a polypeptide binder that binds to a target antigen from the composition;
  c) isolating the polypeptide binder from the nonbinders;
  d) identifying binders of the desired affinity from the isolated polypeptide binders.

In another embodiment, the invention provides a method of selecting for an antigen binding variable domain that binds to a target antigen from a library of antibody variable domains comprising:
  a) contacting the library of antibody variable domains of the invention (as described herein) with a target antigen;
  b) separating binders from nonbinders, and eluting the binders from the target antigen and incubating the binders in a solution with decreasing amounts of the target antigen in a concentration from about 0.1 nM to 1000 nM;
  c) selecting the binders that can bind to the lowest concentration of the target antigen and that have an affinity of about 0.1 nM to 200 nM.

In some embodiments, the concentration of target antigen is about 100 to 250 nM, or about 25 to 100 nM.

In one embodiment, the invention provides a method of selecting for a polypeptide that binds to a target antigen from a library of polypeptides comprising:
  a) isolating polypeptide binders to a target antigen by contacting a library comprising a plurality of polypeptides of the invention (as described herein) with an immobilized target antigen under conditions suitable for binding;
  b) separating the polypeptide binders in the library from nonbinders and eluting the binders from the target antigen to obtain a subpopulation enriched for the binders; and
  c) optionally, repeating steps a-b at least once (in some embodiments at least twice), each repetition using the subpopulation of binders obtained from the previous round of selection.

In some embodiments, methods of the invention further comprise the steps of:
  d) incubating the subpopulation of polypeptide binders with a concentration of labelled target antigen in the range of 0.1 nM to 1000 nM under conditions suitable for binding to form a mixture;
  e) contacting the mixture with an immobilized agent that binds to the label on the target antigen;
  f) detecting the polypeptide binders bound to labelled target antigens and eluting the polypeptide binders from the labelled target antigen;
  g) optionally, repeating steps d) to f) at least once (in some embodiments, at least twice), each repetition using the subpopulation of binders obtained from the previous round of selection and using a lower concentration of labelled target antigen than the previous round.

In some embodiments, these methods further comprise adding an excess of unlabelled target antigen to the mixture and incubating for a period of time sufficient to elute low affinity binders from the labelled target antigen.

In another embodiment, the invention provides a method of isolating high affinity binders to a target antigen comprising:
  a) contacting a library comprising a plurality of polypeptides of the invention (as described herein) with a target antigen in a concentration of at least about 0.1 nM to 1000 nM to isolate polypeptide binders to the target antigen;
  b) separating the polypeptide binders from the target antigen to obtain a subpopulation enriched for the polypeptide binders; and
  c) optionally, repeating steps a) and b) at least once (in some embodiments, at least twice), each repetition using the subpopulation of binders obtained from the previous round of selection and using a decreased concentration of target antigen than the previous round to isolate polypeptide binders that bind to lowest concentration of target antigen.

In one aspect, the invention provides an assay for selecting polypeptide binders from a library comprising a plurality of polypeptides of the invention (as described herein) comprising:
  a) contacting the library with a concentration of labelled target antigen in a concentration range of 0.1 nM to 1000 nM, under conditions suitable for binding to form a complex of a polypeptide binder and the labelled target antigen;
  b) isolating the complexes and separating the polypeptide binders from the labelled target antigen to obtain a subpopulation enriched for the binders;
  c) optionally, repeating steps a-b at least once (in some embodiments, at least twice), each time using the subpopulation of binders obtained from the previous round of selection and using a lower concentration of target antigen than the previous round.

In some embodiments, the method further comprises adding an excess of unlabelled target antigen to the complex of the polypeptide binder and target antigen. In some embodiments, the steps set forth above are repeated at least once (in some embodiments, at least twice) and the concentration of target in the first round of selection is about 100 nM to 250 nM, and in the second round of selection is about 25 nM to 100 nM, and in the third round of selection is about 0.1 nM to 25 nM.

In another aspect, the invention provides a method of screening a library comprising a plurality of polypeptides of the invention, said method comprising:
- a) incubating a first sample of the library with a concentration of a target antigen under conditions suitable for binding of the polypeptides to the target antigen;
- b) incubating a second sample of the library without a target antigen;
- c) contacting each of the first and second sample with immobilized target antigen under conditions suitable for binding of the polypeptide to the immobilized target antigen;
- d) detecting the polypeptide bound to immobilized target antigen for each sample;
- e) determining affinity of the polypeptide for the target antigen by calculating the ratio of the amounts of bound polypeptide from the first sample over the amount of bound polypeptide from the second sample.

In one embodiment, the invention provides a method comprising:
- (a) constructing an expression vector comprising a polynucleotide sequence which encodes a light chain variable domain, a heavy chain variable domain, or both, of a source antibody comprising at least one, two, three, four, five or all HVRs of the source antibody selected from the group consisting of HVR L1, L2, L3, H1, H2 and H3, wherein the HVRs comprise a CDR consensus sequence (such as the consensus sequences in the Kabat database); and
- b) mutating at least one, two, three, or four of the HVRs of the source antibody at least one solvent accessible and highly diverse amino acid position using a biased codon set to generate one or more of the polynucleotides/polypeptides of the invention as described herein.

Diagnostic and therapeutic uses for binder polypeptides of the invention are contemplated. In one diagnostic application, the invention provides a method for determining the presence of a protein of interest comprising exposing a sample suspected of containing the protein to a binder polypeptide of the invention and determining binding of the binder polypeptide to the sample. For this use, the invention provides a kit comprising the binder polypeptide and instructions for using the binder polypeptide to detect the protein.

The invention further provides: isolated nucleic acid encoding the binder polypeptide; a vector comprising the nucleic acid, optionally, operably linked to control sequences recognized by a host cell transformed with the vector; a host cell transformed with the vector; a process for producing the binder polypeptide comprising culturing this host cell so that the nucleic acid is expressed and, optionally, recovering the binder polypeptide from the host cell culture (e.g. from the host cell culture medium).

The invention also provides a composition comprising a binder polypeptide of the invention and a carrier (e.g., a pharmaceutically acceptable carrier) or diluent. This composition for therapeutic use is sterile and may be lyophilized. Also contemplated is the use of a binder polypeptide of this invention in the manufacture of a medicament for treating an indication described herein. The composition can further comprise a second therapeutic agent such as a chemotherapeutic agent, a cytotoxic agent or an anti-angiogenic agent.

The invention further provides a method for treating a mammal, comprising administering an effective amount of a binder polypeptide of the invention to the mammal. The mammal to be treated in the method may be a nonhuman mammal, e.g. a primate suitable for gathering preclinical data or a rodent (e.g., mouse or rat or rabbit). The nonhuman mammal may be healthy (e.g. in toxicology studies) or may be suffering from a disorder to be treated with the binder polypeptide of interest. In one embodiment, the mammal is suffering from or is at risk of developing abnormal angiogenesis (e.g., pathological angiogenesis). In one specific embodiment, the disorder is a cancer selected from the group consisting of colorectal cancer, renal cell carcinoma, ovarian cancer, lung cancer, non-small-cell lung cancer (NSCLC), bronchoalveolar carcinoma and pancreatic cancer. In another embodiment, the disorder is a disease caused by ocular neovascularisation, e.g., diabetic blindness, retinopathies, primarily diabetic retinopathy, age-induced macular degeneration and rubeosis. In another embodiment, the mammal to be treated is suffering from or is at risk of developing an edema (e.g., an edema associated with brain tumors, an edema associated with stroke, or a cerebral edema). In another embodiment, the mammal is suffering from or at risk of developing a disorder or illness selected from the group consisting of rheumatoid arthritis, inflammatory bowel disease, refractory ascites, psoriasis, sarcoidosis, arterial arteriosclerosis, sepsis, burns and pancreatitis. According to another embodiment, the mammal is suffering from or is at risk of developing a genitourinary illness selected from the group consisting of polycystic ovarian disease (POD), endometriosis and uterine fibroids. In one embodiment, the disorder is a disease caused by dysregulation of cell survival (e.g., abnormal amount of cell death), including but not limited to cancer, disorders of the immune system, disorders of the nervous system and disorders of the vascular system. The amount of binder polypeptide of the invention that is administered will be a therapeutically effective amount to treat the disorder. In dose escalation studies, a variety of doses of the binder polypeptide may be administered to the mammal. In another embodiment, a therapeutically effective amount of the binder polypeptide is administered to a human patient to treat a disorder in that patient. In one embodiment, binder polypeptides of this invention useful for treating inflammatory or immune diseases described herein (e.g., rheumatoid arthritis) are Fab or scFv antibodies. Accordingly, such binder polypeptides can be used in the manufacture of a medicament for treating an inflammatory or immune disease. A mammal that is suffering from or is at risk for developing a disorder or illness described herein can be treated by administering, a second therapeutic agent, simultaneously, sequentially or in combination with, a polypeptide (e.g., an antibody) of this invention. It should be understood that other therapeutic agents, in addition to the second therapeutic agent, can be administered to the mammal or used in the manufacture of a medicament for the desired indications.

These polypeptides can be used to understand the role of host stromal cell collaboration in the growth of implanted non-host tumors, such as in mouse models wherein human tumors have been implanted. These polypeptides can be used in methods of identifying human tumors that can escape therapeutic treatment by observing or monitoring the growth of the tumor implanted into a rodent or rabbit after treatment with a polypeptide of this invention. The polypeptides of this invention can also be used to study and evaluate combination therapies with a polypeptide of this invention and other therapeutic agents. The polypeptides of this invention can be used to study the role of a target molecule of interest in other diseases by administering the polypeptides to an animal suffering from the disease or a similar disease and determining whether one or more symptoms of the disease are alleviated.

For the sake of clarity, in the description herein, unless specifically or contextually indicated otherwise, all amino acid numberings are according to Kabat et al. (see further elaboration in "Definitions" below).

BRIEF DESCRIPTION OF THE FIGURES

FIG. 1 (A) illustrates consensus template sequences for a reference/source antibody, wherein the consensus sequences are based on human antibody subgroup III in the Kabat database. The lines labeled "Consensus" refer to the Kabat consensus sequences, and the lines labeled "h4D5 temp (V0350-4) refers to a huMAb4D5-8 antibody template. huMAb4D5-8 is also referred to as HERCEPTIN® (Genentech, Inc., South San Francisco, Calif., USA) (also referred to in U.S. Pat. No. 6,407,213 and Lee et al., J. Mol. Biol. (2004), 340(5):1073-93). (B) Consensus sequence of CDR-L1, CDR-L2, CDR-L3, CDR-H1 and CDR-H2 in the template of VH/VL library. Consensus CDR residues are determined by selecting the most prevalent amino acids existing in natural human antibodies. The prevalence (%) of each residue in human antibodies at a given position is shown, which is calculated from the alignment of approximately 1600 human light chain sequences and 3500 human heavy chain sequences in the Kabat database (34).

FIG. 2 illustrates diversities that can be generated in HVRs of the light chain. Numbers in parentheses in the line labeled "Randomization" refer to the designed diversities for randomization as illustrated in FIG. 4.

FIG. 3 illustrates diversities that can be generated in HVRs of the heavy chain. Numbers in parentheses in the lines labeled "Randomization" refer to the designed diversities for randomization as illustrated in FIG. 4. In some instances, degenerate codon sets are indicated for certain positions in the lines labeled "Randomization".

FIG. 4 (A) depicts designed diversities for randomization using various combinations of nucleotides (e.g., according to the trinucleotide scheme). The alphabets (A, D, E, F, etc.) refer to amino acid types (i.e., alanine, aspartic acid, etc.). 5: Gly (~50:50) plus remaining amino acids except Cys; 6: Ser (~50:50) plus remaining amino acids except Cys; 7: Tyr (~50:50) plus remaining amino acids except Cys; 8: all amino acids except Cys. (B) The percent of amino acid composition in each trinucleotide mixture [NOTE: The "X" designation for trinucleotide mixtures as depicted in FIG. 4 is separate and distinct from the "X" designation for particular HVR amino acid positions as used elsewhere in this specification]. X3: equal mixture of all 19 amino acids except Cys; X0: equal mixture of X3 and Gly; X1: equal mixture of X3 and Ser, X2: equal mixture of X3 and Tyr. Based on the above four trinucleotide mixtures, another four mixtures were generated. X4: (X0+X3)/2; X5: (X0+X1+X2)/3; X6: (X1+X2+X3)/3; X7: (X0+X1+X2+X3)/4. (C) Designed diversity of CDR-L3, CDR-H1, CDR-H2 and CDR-H3 for VH/VL library. CDR positions chosen for randomization in CDR-L3, CDR-H1, CDR-H2 and CDR-H3 are listed with consensus residues in the library template. Designed diversity is either a group of residues encoded by a tailored degenerate codon (italics) or 19 amino acids without cysteine encoded by mixtures of trinucleotides codon (bold text) so that the percentage of amino acid types encoded at each position was close to or higher than 50% of amino acid types found in the database. For particular positions, all 19 amino acids without cysteine are introduced using trinucleotides codon mixtures with different bias toward Tyr (Y), Gly (G) and Ser (S).

FIGS. 5 and 6 depict exemplary acceptor human consensus framework sequences for use in practicing the instant invention with sequence identifiers as follows:

Variable Heavy (VH) Consensus Frameworks (FIG. 5A, B)
human VH subgroup I consensus framework minus Kabat CDRs (SEQ ID NOs:19; 122-124)
human VH subgroup I consensus framework minus extended hypervariable regions (SEQ ID NOs:20-22; 125-139)
human VH subgroup II consensus framework minus Kabat CDRs (SEQ ID NOs:23; 134-136)
human VH subgroup II consensus framework minus extended hypervariable regions (SEQ ID NOs:24-26; 137-145)
human VH subgroup II consensus framework minus extended
human VH subgroup III consensus framework minus Kabat CDRs (SEQ ID NOs:27; 146-148)
human VH subgroup III consensus framework minus extended hypervariable regions (SEQ ID NOs:28-30; 149-157)
human VH acceptor framework minus Kabat CDRs (SEQ ID NOs:31; 158-160)
human VH acceptor framework minus extended hypervariable regions (SEQ ID NOs:32-33; 161-166)
human VH acceptor 2 framework minus Kabat CDRs (SEQ ID NOs:34; 167-169)
human VH acceptor 2 framework minus extended hypervariable regions (SEQ ID NOs:35-37; 170-178)
Variable Light (VL) Consensus Frameworks (FIG. 6A, B)
human VL kappa subgroup I consensus framework (SEQ ID NOs:38; 179-181)
human VL kappa subgroup II consensus framework (SEQ ID NOs:39; 182-184)
human VL kappa subgroup III consensus framework (SEQ ID NOs:40; 185-187)
human VL kappa subgroup IV consensus framework (SEQ ID NOs:41; 188-190)

FIG. 7 depicts framework region sequences of huMAb4D5-8 light and heavy chains. Numbers in superscript/bold indicate amino acid positions according to Kabat.

FIG. 8 depicts modified/variant framework region sequences of huMAb4D5-8 light and heavy chains. Numbers in superscript/bold indicate amino acid positions according to Kabat. Modified positions/amino acids are underlined.

MODES FOR CARRYING OUT THE INVENTION

The invention provides novel, unconventional, greatly simplified and flexible methods for diversifying HVR sequences (including antibody variable domain sequences) based on a source template sequence comprising HVR/CDR consensus sequences, and libraries comprising a multiplicity, generally a great multiplicity of diversified HVRs (including antibody variable domain sequences). Such libraries provide combinatorial libraries useful for, for example, selecting and/or screening for synthetic antibody clones with desirable activities such as binding affinities and avidities. These libraries are useful for identifying immunoglobulin polypeptide sequences that are capable of interacting with any of a wide variety of target antigens. For example, libraries comprising diversified immunoglobulin polypeptides of the invention expressed as phage displays are particularly useful for, and provide a high throughput, efficient and automatable systems of, selecting and/or screening for antigen binding molecules of interest. The methods of the invention are designed to provide high affinity binders to target antigens with minimal changes to a source or template molecule and provide for good production yields when the antibody or antigens binding fragments are produced in cell culture.

Methods and compositions of the invention provide numerous additional advantages. For example, relatively simple variant HVR sequences can be generated, using codon sets encoding a biased prevalence of amino acids, while retaining sufficient diversity of unique target binding sequences. The simplified nature of sequence populations generated according to the invention permits further diversification once a population, or sub-population thereof, has been identified to possess the desired characteristics.

DEFINITIONS

Amino acids are represented herein as either a single letter code or as the three letter code or both.

The term "affinity purification" means the purification of a molecule based on a specific attraction or binding of the molecule to a chemical or binding partner to form a combination or complex which allows the molecule to be separated from impurities while remaining bound or attracted to the partner moiety.

The term "antibody" is used in the broadest sense and specifically covers single monoclonal antibodies (including agonist and antagonist antibodies), antibody compositions with polyepitopic specificity, affinity matured antibodies, humanized antibodies, chimeric antibodies, as well as antigen binding fragments (e.g., Fab, F(ab')$_2$, scFv and Fv), so long as they exhibit the desired biological activity. In one embodiment, the term "antibody" also includes human antibodies.

The term "hypervariable region", "HVR", or "HV", when used herein refers to the regions of an antibody variable domain which are hypervariable in sequence and/or form structurally defined loops. Generally, antibodies comprise six hypervariable regions; three in the VH (H1, H2, H3), and three in the VL (L1, L2, L3). A number of hypervariable region delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). In some instances, and as used herein, HVR and CDR are terms that are used interchangeably. Chothia refers instead to the location of the structural loops (Chothia and Lesk *J. Mol. Biol.* 196:901-917 (1987)). The AbM hypervariable regions represent a compromise between the Kabat CDRs and Chothia structural loops, and are used by Oxford Molecular's AbM antibody modeling software. The "contact" hypervariable regions are based on an analysis of the available complex crystal structures. The residues from each of these hypervariable regions are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
| | | (Kabat Numbering) | | |
| H1 | H31-H35 | H26-H35 | H26-H32 | H30-H35 |
| | | (Chothia Numbering) | | |
| H2 | H50-H65 | H50-H58 | H53-H55 | H47-H58 |
| H3 | H95-H102 | H95-H102 | H96-H101 | H93-H101 |

Hypervariable regions may comprise "extended hypervariable regions" as follows: 24-36 or 24-34 (L1), 46-56 or 50-56 (L2) and 89-97 (L3) in the VL and 26-35 (H1), 50-65 or 49-65 (H2) and 93-102, 94-102 or 95-102 (H3) in the VH. The variable domain residues are numbered according to Kabat et al, supra for each of these definitions.

"Framework" or "FR" residues are those variable domain residues other than the hypervariable region residues as herein defined.

The term "variable domain residue numbering as in Kabat" or "amino acid position numbering as in Kabat", and variations thereof, refers to the numbering system used for heavy chain variable domains or light chain variable domains of the compilation of antibodies in Kabat et al., Sequences of Proteins of Immunological Interest, 5th Ed. Public Health Service, National Institutes of Health, Bethesda, Md. (1991). Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc according to Kabat) after heavy chain FR residue 82. The Kabat numbering of residues may be determined for a given antibody by alignment at regions of homology of the sequence of the antibody with a "standard" Kabat numbered sequence.

"Framework regions" (hereinafter FR) are those variable domain residues other than the HVR residues. Each variable domain typically has four FRs identified as FR1, FR2, FR3 and FR4. If the HVRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the HVRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the HVR comprises amino acids from both a CDR as defined by Kabat and those of a hypervariable loop, the FR residues can be adjusted accordingly. For example, when HVR-H1 includes amino acids H26-H35, the heavy chain FR1 residues are at positions 1-25 and the FR2 residues are at positions 36-49.

As used herein, "codon set" refers to a set of different nucleotide triplet sequences used to encode desired variant amino acids. A set of oligonucleotides can be synthesized, for example, by solid phase synthesis, including sequences that represent all possible combinations of nucleotide triplets provided by the codon set and that will encode the desired group of amino acids. A standard form of codon designation is that of the IUB code, which is known in the art and described herein. A codon set typically is represented by 3 capital letters in italics, e.g. NNK, NNS, XYZ, DVK and the like. Synthesis of oligonucleotides with selected nucleotide "degeneracy" at certain positions is well known in that art, for example the TRIM approach (Knappek et al.; J. Mol. Biol. (1999), 296: 57-86); Garrard & Henner, Gene (1993), 128:103). Such sets of oligonucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can, but does not necessarily, include restriction enzyme sites useful for, for example, cloning purposes.

The term "biased codon set", and variations thereof, as used herein refers to a codon set that encodes a predetermined number of amino acids, wherein there is bias of prevalence in the specific amino acid that is encoded. Such biased codon sets are used to achieve designed diversities for randomization at selected positions in an HVR in methods and compositions of the invention. One well-established method for achieving bias in encoding a desired amino acid among a predetermined number of amino acids encoded by a codon set is based on the use of trinucleotide codons. See, e.g., Knappik et al., J. Mol. Biol. (2000), 296:57-86. In one embodiment of the invention, biased codon sets are designed to not encode cysteine. Designed diversities and biased codon sets are exemplified in FIG. 4. For example, the biased codon set designated 5/6/7 encodes each of G, S and Y at a theoretical prevalence of about 19.2%, respectively, with the theoretical prevalence of the remaining 16 naturally occurring amino acid types (absent cysteine) being about 2.5%. This biased codon set is a combination of 3 biased codon sets: codon set 5, which encodes G at a theoretical prevalence of about 52.5%, and 2.5% for the remaining 16 naturally occurring amino acid types (absent cysteine); codon set 6, which encodes S at a theoretical prevalence of about 52.5%, and 2.5% for the remaining 16 naturally occurring amino acid types (absent cysteine); and codon set 7, which encodes Y at a theoretical prevalence of about 52.5%, and 2.5% for the remaining 16 naturally occurring amino acid types (absent cysteine). Determination of suitable biased codons, and the identification of specific amino acids encoded by a particular biased codon, is well known and would be evident to one skilled in the art. Determination of suitable amino acid sets to be used for diversification of a HVR sequence can be empirical and/or guided by criteria known in the art (e.g., inclusion of a combination of hydrophobic and hydrophilic amino acid types, etc.).

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the VH-VL dimer. Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

The "Fab" fragment contains a variable and constant domain of the light chain and a variable domain and the first constant domain (CH1) of the heavy chain. F(ab')$_2$ antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the $V_H$ and $V_L$ domains of antibody, wherein these domains are present in a single polypeptide chain. Generally the Fv polypeptide further comprises a polypeptide linker between the $V_H$ and $V_L$ domains, which enables the scFv to form the desired structure for antigen binding. For a review of scFv, see Pluckthun in *The Pharmacology of Monoclonal Antibodies*, Vol 113, Rosenburg and Moore eds. Springer-Verlag, New York, pp. 269-315 (1994).

The term "diabodies" refers to small antibody fragments with two antigen-binding sites, which fragments comprise a heavy chain variable domain (VH) connected to a light chain variable domain (VL) in the same polypeptide chain (VH and VL). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The expression "linear antibodies" refers to the antibodies described in Zapata et al., *Protein Eng.*, 8(10):1057-1062 (1995). Briefly, these antibodies comprise a pair of tandem Fd segments ($V_H$-$C_H$1-$V_H$-$C_H$1) which, together with complementary light chain polypeptides, form a pair of antigen binding regions. Linear antibodies can be bispecific or monospecific.

"Cell", "cell line", and "cell culture" are used interchangeably herein and such designations include all progeny of a cell or cell line. Thus, for example, terms like "transformants" and "transformed cells" include the primary subject cell and cultures derived therefrom without regard for the number of transfers. It is also understood that all progeny may not be precisely identical in DNA content, due to deliberate or inadvertent mutations. Mutant progeny that have the same function or biological activity as screened for in the originally transformed cell are included. Where distinct designations are intended, it will be clear from the context.

"Control sequences" when referring to expression means DNA sequences necessary for the expression of an operably linked coding sequence in a particular host organism. The control sequences that are suitable for prokaryotes, for example, include a promoter, optionally an operator sequence, a ribosome binding site, and possibly, other as yet poorly understood sequences. Eukaryotic cells are known to utilize promoters, polyadenylation signals, and enhancers.

The term "coat protein" means a protein, at least a portion of which is present on the surface of the virus particle. From a functional perspective, a coat protein is any protein which associates with a virus particle during the viral assembly process in a host cell, and remains associated with the assembled virus until it infects another host cell. The coat protein may be the major coat protein or may be a minor coat protein. A "major" coat protein is generally a coat protein which is present in the viral coat at preferably at least about 5, more preferably at least about 7, even more preferably at least about 10 copies of the protein or more. A major coat protein may be present in tens, hundreds or even thousands of copies per virion. An example of a major coat protein is the p8 protein of filamentous phage.

The "detection limit" for a chemical entity in a particular assay is the minimum concentration of that entity which can be detected above the background level for that assay. For example, in the phage ELISA, the "detection limit" for a particular phage displaying a particular antigen binding fragment is the phage concentration at which the particular phage produces an ELISA signal above that produced by a control phage not displaying the antigen binding fragment.

A "fusion protein" and a "fusion polypeptide" refers to a polypeptide having two portions covalently linked together, where each of the portions is a polypeptide having a different property. The property may be a biological property, such as activity in vitro or in vivo. The property may also be a simple chemical or physical property, such as binding to a target antigen, catalysis of a reaction, etc. The two portions may be linked directly by a single peptide bond or through a peptide linker containing one or more amino acid residues. Generally, the two portions and the linker will be in reading frame with each other. Preferably, the two portions of the polypeptide are obtained from heterologous or different polypeptides.

"Heterologous DNA" is any DNA that is introduced into a host cell. The DNA may be derived from a variety of sources including genomic DNA, cDNA, synthetic DNA and fusions or combinations of these. The DNA may include DNA from the same cell or cell type as the host or recipient cell or DNA from a different cell type, for example, from a mammal or plant. The DNA may, optionally, include marker or selection genes, for example, antibiotic resistance genes, temperature resistance genes, etc.

As used herein, "highly diverse position" refers to a position of an amino acid located in the variable regions of the light and heavy chains that have a number of different amino acid represented at the position when the amino acid sequences of known and/or naturally occurring antibodies or antigen binding fragments are compared. The highly diverse positions are typically in the CDR regions. In one aspect, the ability to determine highly diverse positions in known and/or naturally occurring antibodies is facilitated by the data provided by Kabat, Sequences of Proteins of Immunological Interest (National Institutes of Health, Bethesda, Md., 1987 and 1991). An Internet-based database located at http://immuno.bme.nwu.edu provides an extensive collection and alignment of human light and heavy chain sequences and facilitates determination of highly diverse positions in these sequences. According to the invention, an amino acid position is highly diverse if it has preferably from about 2 to about 11, preferably from about 4 to about 9, and preferably from about 5 to about 7 different possible amino acid residue variations at that position. In some embodiments, an amino acid position is highly diverse if it has preferably at least about 2, preferably at least about 4, preferably at least about 6, and preferably at least about 8 different possible amino acid residue variations at that position.

As used herein, "library" refers to a plurality of antibody or antibody fragment sequences (for example, polypeptides of the invention), or the nucleic acids that encode these sequences, the sequences being different in the combination of variant amino acids that are introduced into these sequences according to the methods of the invention.

"Ligation" is the process of forming phosphodiester bonds between two nucleic acid fragments. For ligation of the two fragments, the ends of the fragments must be compatible with each other. In some cases, the ends will be directly compatible after endonuclease digestion. However, it may be necessary first to convert the staggered ends commonly produced after endonuclease digestion to blunt ends to make them compatible for ligation. For blunting the ends, the DNA is treated in a suitable buffer for at least 15 minutes at 15° C. with about 10 units of the Klenow fragment of DNA polymerase I or T4 DNA polymerase in the presence of the four deoxyribonucleotide triphosphates. The DNA is then purified by phenol-chloroform extraction and ethanol precipitation or by silica purification. The DNA fragments that are to be ligated together are put in solution in about equimolar amounts. The solution will also contain ATP, ligase buffer, and a ligase such as T4 DNA ligase at about 10 units per 0.5 μg of DNA. If the DNA is to be ligated into a vector, the vector is first linearized by digestion with the appropriate restriction endonuclease(s). The linearized fragment is then treated with bacterial alkaline phosphatase or calf intestinal phosphatase to prevent self-ligation during the ligation step.

A "mutation" is a deletion, insertion, or substitution of a nucleotide(s) relative to a reference nucleotide sequence, such as a wild type sequence.

As used herein, "natural" or "naturally occurring" antibodies, refers to antibodies identified from a nonsynthetic source, for example, from a differentiated antigen-specific B cell obtained ex vivo, or its corresponding hybridoma cell line, or from antibodies obtained from the serum of an animal. These antibodies can include antibodies generated in any type of immune response, either natural or otherwise induced. Natural antibodies include the amino acid sequences, and the nucleotide sequences that constitute or encode these antibodies, for example, as identified in the Kabat database. As used herein, natural antibodies are different than "synthetic antibodies", synthetic antibodies referring to antibody sequences that have been changed from a source or template sequence, for example, by the replacement, deletion, or addition, of an amino acid, or more than one amino acid, at a certain position with a different amino acid, the different amino acid providing an antibody sequence different from the source antibody sequence.

"Operably linked" when referring to nucleic acids means that the nucleic acids are placed in a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous and, in the case of a secretory leader, contingent and in reading frame. However, enhancers do not have to be contiguous. Linking is accomplished by ligation at convenient restriction sites. If such sites do not exist, the synthetic oligonucleotide adapters or linkers are used in accord with conventional practice.

"Phage display" is a technique by which variant polypeptides are displayed as fusion proteins to at least a portion of coat protein on the surface of phage, e.g., filamentous phage, particles. A utility of phage display lies in the fact that large libraries of randomized protein variants can be rapidly and efficiently sorted for those sequences that bind to a target antigen with high affinity. Display of peptide and protein libraries on phage has been used for screening millions of polypeptides for ones with specific binding properties. Polyvalent phage display methods have been used for displaying small random peptides and small proteins through fusions to either gene III or gene VIII of filamentous phage. Wells and Lowman, *Curr. Opin. Struct. Biol.*, 3:355-362 (1992), and references cited therein. In monovalent phage display, a protein or peptide library is fused to a gene III or a portion thereof, and expressed at low levels in the presence of wild type gene III protein so that phage particles display one copy or none of the fusion proteins. Avidity effects are reduced relative to polyvalent phage so that sorting is on the basis of intrinsic ligand affinity, and phagemid vectors are used, which simplify DNA manipulations. Lowman and Wells, *Methods: A companion to Methods in Enzymology*, 3:205-0216 (1991).

A "phagemid" is a plasmid vector having a bacterial origin of replication, e.g., Co1E1, and a copy of an intergenic region of a bacteriophage. The phagemid may be used on any known bacteriophage, including filamentous bacteriophage and lambdoid bacteriophage. The plasmid will also generally contain a selectable marker for antibiotic resistance. Segments of DNA cloned into these vectors can be propagated as plasmids. When cells harboring these vectors are provided with all genes necessary for the production of phage particles, the mode of replication of the plasmid changes to rolling circle replication to generate copies of one strand of the plasmid DNA and package phage particles. The phagemid may form infectious or non-infectious phage particles. This term includes phagemids which contain a phage coat protein gene or fragment thereof linked to a heterologous polypeptide gene as a gene fusion such that the heterologous polypeptide is displayed on the surface of the phage particle.

The term "phage vector" means a double stranded replicative form of a bacteriophage containing a heterologous gene and capable of replication. The phage vector has a phage origin of replication allowing phage replication and phage particle formation. The phage is preferably a filamentous bacteriophage, such as an M13, f1, fd, Pf3 phage or a derivative thereof, or a lambdoid phage, such as lambda, 21, phi80, phi81, 82, 424, 434, etc., or a derivative thereof.

"Oligonucleotides" are short-length, single- or double-stranded polydeoxynucleotides that are chemically synthesized by known methods (such as phosphotriester, phosphite, or phosphoramidite chemistry, using solid-phase techniques such as described in EP 266,032 published 4 May 1988, or via deoxynucleoside H-phosphonate intermediates as described by Froeshler et al., *Nucl. Acids, Res.,* 14:5399-5407 (1986)). Further methods include the polymerase chain reaction defined below and other autoprimer methods and oligonucleotide syntheses on solid supports. All of these methods are described in Engels et al., *Agnew. Chem. Int. Ed. Engl.,* 28:716-734 (1989). These methods are used if the entire nucleic acid sequence of the gene is known, or the sequence of the nucleic acid complementary to the coding strand is available. Alternatively, if the target amino acid sequence is known, one may infer potential nucleic acid sequences using known and preferred coding residues for each amino acid residue. The oligonucleotides can be purified on polyacrylamide gels or molecular sizing columns or by precipitation.

DNA is "purified" when the DNA is separated from non-nucleic acid impurities. The impurities may be polar, non-polar, ionic, etc.

A "source antibody", as used herein, refers to an antibody or antigen binding fragment whose antigen binding sequence serves as the template sequence upon which diversification according to the criteria described herein is performed. An antigen binding sequence generally includes an antibody variable region, preferably at least one CDR, preferably including framework regions.

As used herein, "solvent accessible position" refers to a position of an amino acid residue in the variable regions of the heavy and light chains of a source antibody or antigen binding fragment that is determined, based on structure, ensemble of structures and/or modeled structure of the antibody or antigen binding fragment, as potentially available for solvent access and/or contact with a molecule, such as an antibody-specific antigen. These positions are typically found in the CDRs and on the exterior of the protein. The solvent accessible positions of an antibody or antigen binding fragment, as defined herein, can be determined using any of a number of algorithms known in the art. Preferably, solvent accessible positions are determined using coordinates from a 3-dimensional model of an antibody (or portion thereof, e.g., an antibody variable domain, or CDR segment(s)), preferably using a computer program such as the InsightII program (Accelrys, San Diego, Calif.). Solvent accessible positions can also be determined using algorithms known in the art (e.g., Lee and Richards, J. Mol. Biol. 55, 379 (1971) and Connolly, J. Appl. Cryst. 16, 548 (1983)). Determination of solvent accessible positions can be performed using software suitable for protein modeling and 3-dimensional structural information obtained from an antibody (or portion thereof). Software that can be utilized for these purposes includes SYBYL Biopolymer Module software (Tripos Associates). Generally and preferably, where an algorithm (program) requires a user input size parameter, the "size" of a probe which is used in the calculation is set at about 1.4 Angstrom or smaller in radius. In addition, determination of solvent accessible regions and area methods using software for personal computers has been described by Pacios ((1994) "ARVOMOL/CONTOUR: molecular surface areas and volumes on Personal Computers." *Comput. Chem.* 18(4): 377-386; and (1995). "Variations of Surface Areas and Volumes in Distinct Molecular Surfaces of Biomolecules." *J. Mol. Model.* 1: 46-53.)

A "transcription regulatory element" will contain one or more of the following components: an enhancer element, a promoter, an operator sequence, a repressor gene, and a transcription termination sequence. These components are well known in the art. U.S. Pat. No. 5,667,780.

A "transformant" is a cell which has taken up and maintained DNA as evidenced by the expression of a phenotype associated with the DNA (e.g., antibiotic resistance conferred by a protein encoded by the DNA).

"Transformation" means a process whereby a cell takes up DNA and becomes a "transformant". The DNA uptake may be permanent or transient.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues.

An "affinity matured" antibody is one with one or more alterations in one or more CDRs thereof which result in an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. *Bio/Technology* 10:779-783 (1992) describes affinity maturation by VH and VL domain shuffling. Random mutagenesis of CDR and/or framework residues is described by: Barbas et al. *Proc Nat. Acad. Sci, USA* 91:3809-3813 (1994); Schier et al. *Gene* 169:147-155 (1995); Yelton et al. *J. Immunol.* 155:1994-2004 (1995); Jackson et al., *J. Immunol.* 154(7):3310-9 (1995); and Hawkins et al, *J. Mol. Biol.* 226:889-896 (1992).

A "blocking" antibody or an "antagonist" antibody is one which inhibits or reduces biological activity of the antigen it bind. Preferred blocking antibodies or antagonist antibodies substantially or completely inhibit the biological activity of the antigen.

An "agonist antibody", as used herein, is an antibody which mimics at least one of the functional activities of a polypeptide of interest.

To increase the half-life of the antibodies or polypeptide containing the amino acid sequences of this invention, one can attach a salvage receptor binding epitope to the antibody (especially an antibody fragment), as described, e.g., in U.S. Pat. No. 5,739,277. For example, a nucleic acid molecule encoding the salvage receptor binding epitope can be linked in frame to a nucleic acid encoding a polypeptide sequence of this invention so that the fusion protein expressed by the engineered nucleic acid molecule comprises the salvage receptor binding epitope and a polypeptide sequence of this invention. As used herein, the term "salvage receptor binding epitope" refers to an epitope of the Fc region of an IgG molecule (e.g., IgG$_1$, IgG$_2$, IgG$_3$, or IgG$_4$) that is responsible for increasing the in vivo serum half-life of the IgG molecule (e.g., Ghetie, V et al., (2000) *Ann. Rev. Immunol* 18:739-766, Table 1). Antibodies with substitutions in an Fc region thereof and increased serum half-lives are also described in WO00/42072 (Presta, L.), WO 02/060919; Shields, R. L., et al., (2001) *JBC* 276(9):6591-6604; Hinton, P. R., (2004) *JBC* 279(8):6213-6216). In another embodiment, the serum half-life can also be increased, for example, by attaching other polypeptide sequences. For example, antibodies of this invention or other polypeptide containing the amino acid sequences of this invention can be attached to serum albumin or a portion of serum albumin that binds to the FcRn receptor or a serum albumin binding peptide so that serum albumin binds to the antibody or polypeptide, e.g., such polypeptide sequences are disclosed in WO01/45746. In one preferred embodiment, the serum albumin peptide to be attached comprises an amino acid sequence of DICLPRWGCLW. In another embodiment, the half-life of a Fab according to this invention is increased by these methods. See also, Dennis, M. S., et al., (2002) JBC 277(38):35035-35043 for serum albumin binding peptide sequences.

A "disorder" is any condition that would benefit from treatment with a substance/molecule or method of the invention. This includes chronic and acute disorders or diseases including those pathological conditions which predispose the mammal to the disorder in question. Non-limiting examples of disorders to be treated herein include malignant and benign tumors; non-leukemias and lymphoid malignancies; neuronal, glial, astrocytal, hypothalamic and other glandular, macrophagal, epithelial, stromal and blastocoelic disorders; and inflammatory, immunologic and other angiogenesis-related disorders.

The terms "cell proliferative disorder" and "proliferative disorder" refer to disorders that are associated with some degree of abnormal cell proliferation. In one embodiment, the cell proliferative disorder is cancer.

"Tumor", as used herein, refers to all neoplastic cell growth and proliferation, whether malignant or benign, and all precancerous and cancerous cells and tissues. The terms "cancer", "cancerous", "cell proliferative disorder", "proliferative disorder" and "tumor" are not mutually exclusive as referred to herein.

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia or lymphoid malignancies. More particular examples of such cancers include squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, multiple myeloma and B-cell lymphoma, brain, as well as head and neck cancer, and associated metastases.

Dysregulation of angiogenesis can lead to many disorders that can be treated by compositions and methods of the invention. These disorders include both non-neoplastic and neoplastic conditions. Neoplastics include but are not limited those described above. Non-neoplastic disorders include but are not limited to undesired or aberrant hypertrophy, arthritis, rheumatoid arthritis (RA), psoriasis, psoriatic plaques, sarcoidosis, atherosclerosis, atherosclerotic plaques, diabetic and other proliferative retinopathies including retinopathy of prematurity, retrolental fibroplasia, neovascular glaucoma, age-related macular degeneration, diabetic macular edema, corneal neovascularization, corneal graft neovascularization, corneal graft rejection, retinal/choroidal neovascularization, neovascularization of the angle (rubeosis), ocular neovascular disease, vascular restenosis, arteriovenous malformations (AVM), meningioma, hemangioma, angiofibroma, thyroid hyperplasias (including Grave's disease), corneal and other tissue transplantation, chronic inflammation, lung inflammation, acute lung injury/ARDS, sepsis, primary pulmonary hypertension, malignant pulmonary effusions, cerebral edema (e.g., associated with acute stroke/closed head injury/trauma), synovial inflammation, pannus formation in RA, myositis ossificans, hypertropic bone formation, osteoarthritis (OA), refractory ascites, polycystic ovarian disease, endometriosis, 3rd spacing of fluid diseases (pancreatitis, compartment syndrome, burns, bowel disease), uterine fibroids, premature labor, chronic inflammation such as IBD (Crohn's disease and ulcerative colitis), renal allograft rejection, inflammatory bowel disease, nephrotic syndrome, undesired or aberrant tissue mass growth (non-cancer), hemophilic joints, hypertrophic scars, inhibition of hair growth, Osler-Weber syndrome, pyogenic granuloma retrolental fibroplasias, scleroderma, trachoma, vascular adhesions, synovitis, dermatitis, preeclampsia, ascites, pericardial effusion (such as that associated with pericarditis), and pleural effusion.

As used herein, "treatment" refers to clinical intervention in an attempt to alter the natural course of the individual or cell being treated, and can be performed either for prophylaxis or during the course of clinical pathology. Desirable effects of treatment include preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or disorder.

An "effective amount" refers to an amount effective, at dosages and for periods of time necessary, to achieve the desired therapeutic or prophylactic result.

A "therapeutically effective amount" of a substance/molecule of the invention, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The term "cytotoxic agent" as used herein refers to a substance that inhibits or prevents the function of cells and/or causes destruction of cells. The term is intended to include radioactive isotopes (e.g., $At^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents e.g. methotrexate, adriamicin, vinca alkaloids (vincristine, vinblastine, etoposide), doxorubicin, melphalan, mitomycin C, chlorambucil, daunorubicin or other intercalating agents, enzymes and fragments thereof such as nucleolytic enzymes, antibiotics, and toxins such as small molecule toxins or enzymatically active toxins of bacterial, fungal, plant or animal origin, including fragments and/or variants thereof, and the various antitumor or anticancer agents disclosed below. Other cytotoxic agents are described below. A tumoricidal agent causes destruction of tumor cells.

A "chemotherapeutic agent" is a chemical compound useful in the treatment of cancer. Examples of chemotherapeutic agents include alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew, Chem Intl. Ed. Engl., 33: 183-186 (1994)); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2''-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., TAXOL® paclitaxel (Bristol-Myers Squibb Oncology, Princeton, N.J.), ABRAXANE™ Cremophor-free, albumin-engineered nanoparticle formulation of paclitaxel (American Pharmaceutical Partners, Schaumberg, Ill.), and TAXOTERE® doxetaxel (Rhône-Poulenc Rorer, Antony, France); chloranbucil; gemcitabine (GEMZAR®); 6-thioguanine; mercaptopurine; methotrexate; platinum analogs such as cis-platin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; capecitabine (XELODA®); pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), EVISTA® raloxifene, droloxifene, 4-hydroxytamoxifen, trioxifene, keoxifene, LY117018, onapristone, and FARESTON® toremifene; anti-progesterones; estrogen receptor down-regulators (ERDs); agents that function to suppress or shut down the ovaries, for example, leutinizing hormone-releasing hormone (LHRH) agonists such as LUPRON® and ELIGARD® leuprolide acetate, goserelin acetate, buserelin acetate and tripterelin; other anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole. In addition, such definition of chemotherapeutic agents includes bisphosphonates such as clodronate (for example, BONEFOS® or OSTAC®), DIDROCAL® etidronate, NE-58095, ZOMETA® zoledronic acid/zoledronate, FOSAMAX® alendronate, AREDIA® pamidronate, SKELID® tiludronate, or ACTONEL® risedronate; as well as troxacitabine (a 1,3-dioxolane nucleoside cytosine analog); antisense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; LURTOTECAN® topoisomerase 1 inhibitor; ABARELIX® rmRH; lapatinib ditosylate (an ErbB-2 and EGFR dual tyrosine kinase small-molecule inhibitor also known as GW572016); and pharmaceutically acceptable salts, acids or derivatives of any of the above.

A "growth inhibitory agent" when used herein refers to a compound or composition which inhibits growth of a cell whose growth is dependent upon activity of a target molecule of interest either in vitro or in vivo. Thus, the growth inhibitory agent may be one which significantly reduces the percentage of target molecule-dependent cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), taxanes, and topoisomerase II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The taxanes (paclitaxel and docetaxel) are anticancer drugs both derived from the yew tree. Docetaxel (TAXOTERE®, Rhone-Poulenc Rorer), derived from the European yew, is a semisynthetic analogue of paclitaxel (TAXOL®, Bristol-Myers Squibb). Paclitaxel and docetaxel promote the assembly of microtubules from tubulin dimers and stabilize microtubules by preventing depolymerization, which results in the inhibition of mitosis in cells.

"Doxorubicin" is an anthracycline antibiotic. The full chemical name of doxorubicin is (8S-cis)-10-[(3-amino-2,3, 6-trideoxy-α-L-lyxo-hexapyranosyl)oxy]-7,8,9,10-tetrahydro-6,8,11-trihydroxy-8-(hydroxyacetyl)-1-methoxy-5,12-naphthacenedione.

A "variant" or "mutant" of a starting or reference polypeptide (e.g., a source antibody or its variable domain(s)/CDR(s)), such as a fusion protein (polypeptide) or a heterologous polypeptide (heterologous to a phage), is a polypeptide that 1) has an amino acid sequence different from that of the starting or reference polypeptide and 2) was derived from the starting or reference polypeptide through either natural or artificial (manmade) mutagenesis. Such variants include, for example, deletions from, and/or insertions into and/or substitutions of, residues within the amino acid sequence of the polypeptide of interest. For example, a fusion polypeptide of the invention generated using an oligonucleotide comprising a biased codon set that encodes a sequence with a variant amino acid (with respect to the amino acid found at the corresponding position in a source antibody/antigen binding fragment) would be a variant polypeptide with respect to a source antibody and/or antigen binding fragment and/or CDR. Thus, a variant CDR refers to a CDR comprising a variant sequence with respect to a starting or reference polypeptide sequence (such as that of a source antibody and/or antigen binding fragment and/or CDR). A variant amino acid, in this context, refers to an amino acid different from the amino acid at the corresponding position in a starting or reference polypeptide sequence (such as that of a source antibody and/or antigen binding fragment and/or CDR). Any combination of deletion, insertion, and substitution may be made to arrive at the final variant or mutant construct, provided that the final construct possesses the desired functional characteristics. In some of the examples described herein, binder sequences contain point mutations such as deletions or additions. For example, a VEGF clone from the YADS library exhibits a missing Q in CDRL3 which was not the result of vector construction. In another example, the Q in position 89 of the 4D5 CDRL3 was intentionally deleted in the construction of the vector. The amino acid changes also may alter post-translational processes of the polypeptide, such as changing the number or position of glycosylation sites. Methods for generating amino acid sequence variants of polypeptides are described in U.S. Pat. No. 5,534,615, expressly incorporated herein by reference.

A "wild type" or "reference" sequence or the sequence of a "wild type" or "reference" protein/polypeptide, such as a coat protein, or a CDR or variable domain of a source antibody, maybe the reference sequence from which variant polypeptides are derived through the introduction of mutations. In general, the "wild type" sequence for a given protein is the sequence that is most common in nature. Similarly, a "wild type" gene sequence is the sequence for that gene which is most commonly found in nature. Mutations may be introduced into a "wild type" gene (and thus the protein it encodes) either through natural processes or through man induced means. The products of such processes are "variant" or "mutant" forms of the original "wild type" protein or gene.

A "plurality" of a substance, such as a polypeptide or polynucleotide of the invention, as used herein, generally refers to a collection of two or more types or kinds of the substance. There are two or more types or kinds of a substance if two or more of the substances differ from each other with respect to a particular characteristic, such as the variant amino acid found at a particular amino acid position. For example, there is a plurality of polypeptides of the invention if there are two or more polypeptides of the invention that are substantially the same, preferably identical, in sequence except for the sequence of a variant CDR or except for the variant amino acid at a particular solvent accessible and highly diverse amino acid position. In another example, there is a plurality of polynucleotides of the invention if there are two or more polynucleotides of the invention that are substantially the same, preferably identical, in sequence except for the sequence that encodes a variant CDR or except for the sequence that encodes a variant amino acid for a particular solvent accessible and highly diverse amino acid position.

The invention provides methods for generating and isolating novel target antigen binding polypeptides, such as antibodies or antigen binding fragments, that can have a high affinity for a selected antigen. A plurality of different binder polypeptides are prepared by mutating (diversifying) one or more selected amino acid positions in a source antibody light chain variable domain and/or heavy chain variable domain with selected (e.g., biased) codon sets to generate a library of with variant amino acids in at least one CDR sequence, wherein the number of types of variant amino acids is kept to a minimum (i.e., 10 or fewer, 8 or fewer, 6 or fewer, 4 or fewer, or only 2, but generally at least 2). The amino acid positions include those that are solvent accessible, for example as determined by analyzing the structure of a source antibody, and/or that are highly diverse among known and/or natural occurring immunoglobulin polypeptides. A further advantage afforded by the limited nature of diversification of the invention is that additional amino acid positions other than those that are highly diverse and/or solvent accessible can also be diversified in accordance with the need or desire of the practitioner; examples of these embodiments are described herein.

The amino acid positions that are solvent accessible and highly diverse are preferably those in the HVR regions of the antibody variable domains selected from the group consisting of HVR-L1, HVR-L2, HVR-L3, HVR-H1, HVR-H2, HVR-H3, and mixtures thereof. Amino acid positions are each mutated using a selected (e.g., biased) codon set encoding a predetermined number of amino acids. HVR sequences can also be diversified by varying the length, e.g., for HVR-H3, variant HVR-H3 regions can be generated that have different lengths and/or are randomized at selected positions using biased codon sets.

The diversity of the library of the polypeptides comprising variant HVRs is designed using selected codon sets that encode a predetermined number of amino acids with a biased prevalence of certain amino acid, such that a desired probability of a selected amino acid (and therefore a selected sequence diversity) is introduced into a HVR. The number of positions mutated in the HVR is minimized and the variant amino acids at each position are designed to include a limited number of amino acids. Preferably, a single antibody, including at least one HVR, is used as the source antibody. It is surprising that a library of antibody variable domains having diversity in sequences and size can be generated using a single source antibody as a template comprising consensus HVR sequences, and targeting diversity to particular positions using an unconventionally limited and biased number of amino acid substitutions.

Design of Diversity of Antibody Variable Domains

In one aspect of the invention, high quality libraries of antibody variable domains are generated. The libraries have biased diversity of different sequences of HVR sequences, e.g., diversity of the antibody variable domains. The libraries include high affinity binding antibody variable domains for one or more antigens, including, for example, neutravidin, an apoptosis protein (AP), maltose binding protein 2 (MBP2), erbin-GST, insulin, murine and human VEGF. The diversity in the library is designed by selecting amino acid positions that are solvent accessible and highly diverse in a single source antibody and mutating those positions in at least one HVR using biased codon sets.

One source antibody is an antibody comprising human consensus HVRs with framework sequences from the anti-HER2 antibody huMAb4D5-8 (see FIG. 7/8), but the methods for diversification can be applied to other source antibodies whose sequence is known. A source antibody can be a naturally occurring antibody, synthetic antibody, recombinant antibody, humanized antibody, germ line derived antibody, chimeric antibody, affinity matured antibody, or antigen binding fragment thereof. The antibodies can be obtained from a variety of mammalian species including humans, mice and rats. In some embodiments, a source antibody is an antibody that is obtained after one or more initial affinity screening rounds, but prior to an affinity maturation step(s). A source antibody may be selected or modified to provide for high yield and stability when produced in cell culture.

Antibody 4D5 is a humanized antibody specific for a cancer-associated antigen known as Her-2 (erbB2). The antibody includes variable domains having consensus framework regions; a few positions were reverted to mouse sequence during the process of increasing affinity of the humanized antibody. The sequence and crystal structure of humanized antibody 4D5 have been described in U.S. Pat. No. 6,054,297, Carter et al, PNAS 89:4285 (1992), the crystal structure is shown in J. Mol. Biol. 229:969 (1993).

A criterion for generating diversity in antibody variable domains is to mutate residues at positions that are solvent accessible (as defined above). These positions are typically found in the CDRs, and are typically on the exterior of the protein. Preferably, solvent accessible positions are determined using coordinates from a 3-dimensional model of an antibody, using a computer program such as the InsightII program (Accelrys, San Diego, Calif.). Solvent accessible positions can also be determined using algorithms known in the art (e.g., Lee and Richards, J. Mol. Biol. 55, 379 (1971) and Connolly, J. Appl. Cryst. 16, 548 (1983)). Determination of solvent accessible positions can be performed using software suitable for protein modeling and 3-dimensional structural information obtained from an antibody. Software that can be utilized for these purposes includes SYBYL Biopolymer Module software (Tripos Associates). Generally and preferably, where an algorithm (program) requires a user input size parameter, the "size" of a probe which is used in the calculation is set at about 1.4 Angstrom or smaller in radius. In addition, determination of solvent accessible regions and area methods using software for personal computers has been described by Pacios ((1994) "ARVOMOL/CONTOUR: molecular surface areas and volumes on Personal Computers", *Comput. Chem.* 18(4): 377-386; and "Variations of Surface Areas and Volumes in Distinct Molecular Surfaces of Biomolecules." *J. Mol. Model.* (1995), 1: 46-53).

In some instances, selection of solvent accessible residues is further refined by choosing solvent accessible residues that collectively form a minimum contiguous patch, for example when the reference polypeptide or source antibody is in its 3-D folded structure. For example, a compact (minimum) contiguous patch is formed by residues selected for CDRH1/H2/H3/L1/L2/L3 of humanized 4D5. A compact (minimum) contiguous patch may comprise only a subset (for example, 2-5 CDRs) of the full range of CDRs, for example, CDRH1/H2/H3/L3. Solvent accessible residues that do not contribute to formation of such a patch may optionally be excluded from diversification. Refinement of selection by this criterion permits the practitioner to minimize, as desired, the number of residues to be diversified. For example, residue 28 in H1 can optionally be excluded in diversification since it is on the edge of the patch. However, this selection criterion can also be used, where desired, to choose residues to be diversified that may not necessarily be deemed solvent accessible. For example, a residue that is not deemed solvent accessible, but forms a contiguous patch in the 3-D folded structure with other residues that are deemed solvent accessible may be selected for diversification. An example of this is CDRL1-29. Selection of such residues would be evident to one skilled in the art, and its appropriateness can also be determined empirically and according to the needs and desires of the skilled practitioner.

The solvent accessible positions identified from the crystal structure of humanized antibody 4D5 for each CDR are as follows (residue position according to Kabat):
  CDRL1: 28, 30, 31, 32
  CDRL2: 50, 53
  CDRL3: 91, 92, 93, 94, 96
  CDRH1: 28, 30, 31, 32, 33
  CDRH2: 50, 52, 52A, 53, 54, 55, 56, 57, 58.
In addition, in some embodiments, residue 29 of CDRL1 may also be selected based on its inclusion in a contiguous patch comprising other solvent accessible residues. All or a subset of the solvent accessible positions as set forth above may be diversified in methods and compositions of the invention. For example, in some embodiments, in HVR-H2, only positions 50, 52, 53, 54, 56 and 58 are diversified.

Another criterion for selecting positions to be mutated are those positions which show variability in amino acid sequence when the sequences of known and/or natural antibodies are compared. A highly diverse position refers to a position of an amino acid located in the variable regions of the light or heavy chains that have a number of different amino acids represented at the position when the amino acid sequences of known and/or natural antibodies/antigen binding fragments are compared. The highly diverse positions are preferably in the HVR regions. The positions of HVR-H3 are all considered highly diverse. According to the invention, amino acid residues are highly diverse if they have preferably from about 2 to about 11 (although the numbers can range as described herein) different possible amino acid residue variations at that position.

In one aspect, identification of highly diverse positions in known and/or naturally occurring antibodies is facilitated by the data provided by Kabat, Sequences of Proteins of Immunological Interest (National Institutes of Health, Bethesda, Md., 1987 and 1991). An Internet-based database located at http://immuno.bme.nwu.edu provides an extensive collection and alignment of human light and heavy chain sequences and facilitates determination of highly diverse positions in these sequences. The diversity at the solvent accessible positions of humanized antibody 4D5 in known and/or naturally occurring light and heavy chains is shown in FIGS. 22 and 23.

In one aspect of the invention, the highly diverse and solvent accessible residues in at least one, two, three, four, five or all of HVRs selected from the group consisting of HVR-L1, HVR-L2, HVR-L3, HVR-H1, HVR-H2, HVR-H3, and mixtures thereof are mutated (i.e., randomized using biased codon sets as described herein). For example, a population of polypeptides may be generated by diversifying at least one solvent accessible and/or highly diverse residue in HVR-L3 and HVR-H3 using biased codons. Accordingly, the invention provides for a large number of novel antibody sequences formed by replacing at least one solvent accessible and highly diverse position of at least one HVR of the source antibody variable domain with variant amino acids encoded by a biased codon. For example, a variant HVR or antibody variable domain can comprise a variant amino acid in one or more amino acid positions 28, 30, 31, 32 and/or 33 of HVR-H1; and/or in one or more amino acid positions 50, 52, 53, 54, 56 and/or 58 of CDRH2; and/or in one or more amino acid positions 28, 29, 30 and/or 31 of HVR-L1; and/or in one or more amino acid positions 50 and/or 53 in HVR-L2; and/or in one or more amino acid positions 91, 92, 93, 94 and/or 96 in HVR-L3. The variant amino acids at these positions can be encoded by biased codon sets, as described herein.

As discussed above, the variant amino acids are encoded by biased codon sets. A codon set is a set of different nucleotide triplet sequences which can be used to form a set of oligonucleotides used to encode the desired group of amino acids. A set of oligonucleotides can be synthesized, for example, by solid phase synthesis, containing sequences that represent all possible combinations of nucleotide triplets provided by the codon set and that will encode the desired group of amino acids. Synthesis of oligonucleotides with selected nucleotide "degeneracy" at certain positions is well known in that art. Such sets of nucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a variable domain nucleic acid template and also can include restriction enzyme sites for cloning purposes.

In one aspect, the selected repertoire of amino acids intended to occupy one or more of the solvent accessible and highly diverse positions in HVRs of humanized of a source antibody are determined (based on the desire of the practitioner, which can be based on any of a number of criteria, including specific amino acids desired for particular positions, specific amino acid(s) desired to be absent from a particular position, size of library desired, characteristic of antigen binders sought, etc.).

Heavy chain HVR-3s in known antibodies have diverse sequences, structural conformations, and lengths. HVR-H3s are often found in the middle of the antigen binding pocket and often participate in antigen contact. The design of HVR-H3 is thus preferably developed separately from that of the other HVRs because it can be difficult to predict the structural conformation of HVR-H3 and the amino acid diversity in this region is especially diverse in known antibodies. In accordance with the present invention, HVR-H3 is designed to generate diversity at specific positions within HVR-H3, e.g., positions 95, 96, 97, 98, 99, 100 and 100a (e.g., according to Kabat numbering). In some embodiments, diversity is also generated by varying HVR-H3 length using biased codon sets. Length diversity can be of any range determined empirically to be suitable for generating a population of polypeptides containing substantial proportions of antigen binding proteins. For example, polypeptides comprising variant HVR-H3 can be generated having the sequence $(X1)_n$-A-M, wherein X1 is an amino acid encoded by a biased codon set, and n is of various lengths, for example, n=3-20, 5-20, 7-20, 5-18 or 7-18. Other examples of possible n values are 5, 6, 7, 8, 9, 10, 11, 12, 13, 14, 15, 16, 17, 18, 19 and 20.

It is contemplated that the sequence diversity of libraries created by introduction of variant amino acids in a particular HVR, e.g., HVR-H3, can be increased by combining the variant HVR with other HVRs comprising variations in other regions of the antibody, specifically in other HVRs of either the light or heavy chain variable sequences. It is contemplated that the nucleic acid sequences that encode members of this set can be further diversified by introduction of other variant amino acids in the HVRs of either the light or heavy chain sequences, via biased codon sets. Thus, for example, in one embodiment, HVR-H3 sequences from fusion polypeptides that bind a target antigen can be combined with diversified HVR-L3, HVR-H1, or HVR-H2 sequences, or any combination of diversified HVRs.

It should be noted that in some instances framework residues may be varied relative to the sequence of a source antibody or antigen binding fragment, for example, to reflect a consensus sequence or to improve stability or display. For example, framework residues 49, 93, 94 or 71 in the heavy chain may be varied. Heavy chain framework residue 93 may be serine or alanine (which is the human consensus sequence amino acid at that position.) Heavy chain framework residue 94 may be changed to reflect framework consensus sequence from threonine to arginine or lysine. Another example of a framework residue that may be altered is heavy chain framework residue 71, which is R in about 1970 polypeptides, V in about 627 polypeptides and A in about 527 polypeptides, as found in the Kabat database. Heavy chain framework residue 49 may be alanine or glycine. In addition, optionally, the 3 N-terminal amino acids of the heavy chain variable domain can be removed. In the light chain, optionally, the arginine at amino acid position 66 can be changed to glycine.

In one aspect, the invention provides vector constructs for generating fusion polypeptides that bind with significant affinity to potential ligands. These constructs comprise a dimerizable domain that when present in a fusion polypeptide provides for increased tendency for heavy chains to dimerize to form dimers of Fab or Fab' antibody fragments/portions. These dimerization domains may include, e.g. a heavy chain hinge sequence (e.g., a sequence comprising TCPPCPA-PELLG (SEQ ID NO: 58) that may be present in the fusion polypeptide. Dimerization domains in fusion phage polypeptides bring two sets of fusion polypeptides (LC/HC-phage protein/fragment (such as pIII)) together, thus allowing formation of suitable linkages (such as interheavy chain disulfide bridges) between the two sets of fusion polypeptide. Vector constructs containing such dimerization domains can be used to achieve divalent display of antibody variable domains, for example the diversified fusion proteins described herein, on phage. Preferably, the intrinsic affinity of each monomeric antibody fragment (fusion polypeptide) is not significantly altered by fusion to the dimerization domain. Preferably, dimerization results in divalent phage display which provides increased avidity of phage binding, with significant decrease in off-rate, which can be determined by methods known in the art and as described herein. Dimerization domain-containing vectors of the invention may or may not also include an amber stop codon after the dimerization domain.

Dimerization can be varied to achieve different display characteristics. Dimerization domains can comprise a sequence comprising a cysteine residue, a hinge region from a full-length antibody, a dimerization sequence such as leucine zipper sequence or GCN4 zipper sequence or mixtures thereof. Dimerization sequences are known in the art, and include, for example, the GCN4 zipper sequence (GRMKQLEDKVEELLSKNYHLENE-VARLKKLVGERG) (SEQ ID NO: 3). The dimerization domain is preferably located at the C-terminal end of the heavy chain variable or constant domain sequence and/or between the heavy chain variable or constant domain sequence and any viral coat protein component sequence. An amber stop codon may also be present at or after the C-terminal end of the dimerization domain. In one embodiment, wherein an amber stop codon is present, the dimerization domain encodes at least one cysteine and a dimerizing sequence such as leucine zipper. In another embodiment, wherein no amber stop codon is present, the dimerization domain may comprise a single cysteine residue.

The polypeptides of the invention can also be fused to other types of polypeptides in order to provide for display of the variant polypeptides or to provide for purification, screening or sorting, and detection of the polypeptide. For embodiment involving phage display, the polypeptides of the invention are fused to all or a portion of a viral coat protein. Examples of viral coat protein include protein PIII, major coat protein, pVIII, Soc, Hoc, gpD, pVI and variants thereof. In addition, the variant polypeptides generated according to the methods of the invention can optionally be fused to a polypeptide marker or tag such as FLAG, polyhistidine, gD, c-myc, B-galactosidase and the like.

Methods of Generating Libraries of Randomized Variable Domains

A variety of methods are known in the art for generating phage display libraries from which an antibody of interest can be obtained. One method of generating antibodies of interest is through the use of a phage antibody library as described in Lee et al., J. Mol. Biol. (2004), 340(5):1073-93.

Methods of substituting an amino acid of choice into a template nucleic acid are well established in the art, some of which are described herein. For example, libraries can be created by targeting solvent accessible and/or highly diverse positions in at least one CDR region for amino acid substitution with variant amino acids using the Kunkel method. See, e.g., Kunkel et al., Methods Enzymol. (1987), 154:367-382. Generation of randomized sequences is also described below in the Examples.

The sequence of oligonucleotides includes one or more of the designed biased codon sets for different lengths of CDRH3 or for the solvent accessible and highly diverse positions in a CDR. A codon set is a set of different nucleotide triplet sequences used to encode desired variant amino acids. Codon sets can be represented using symbols to designate particular nucleotides or equimolar mixtures of nucleotides as shown below according to the IUB code. Typically, a codon set is represented by three capital letters e.g. KMT, TMT and the like.

IUB Codes
G Guanine
A Adenine
T Thymine
C Cytosine
R (A or G)
Y (C or T)
M (A or C)
K (G or T)
S (C or G)
W (A or T)
H (A or C or T)
B (C or G or T)
V (A or C or G)
D (A or G or T)
N (A or C or G or T)

For example, in the codon set TMT, T is the nucleotide thymine; and M can be A or C. This codon set can present multiple codons and can encode only a limited number of amino acids, namely tyrosine and serine.

Oligonucleotide or primer sets can be synthesized using standard methods. A set of oligonucleotides can be synthesized, for example, by solid phase synthesis, containing sequences that represent all possible combinations of nucleotide triplets provided by the biased codon set and that will encode the desired group of amino acids with the desired prevalence for selected amino acids. Synthesis of oligonucleotides with selected nucleotide "degeneracy" at certain positions is well known in that art. Such sets of oligonucleotides having certain codon sets can be synthesized using commercial nucleic acid synthesizers (available from, for example, Applied Biosystems, Foster City, Calif.), or can be obtained commercially (for example, from Life Technologies, Rockville, Md.). Therefore, a set of oligonucleotides synthesized having a particular codon set will typically include a plurality of oligonucleotides with different sequences, the differences established by the codon set within the overall sequence. Oligonucleotides, as used according to the invention, have sequences that allow for hybridization to a CDR (e.g., as contained within a variable domain) nucleic acid template and also can include restriction enzyme sites for cloning purposes.

In one method, nucleic acid sequences encoding variant amino acids can be created by oligonucleotide-mediated mutagenesis of a nucleic acid sequence encoding a source or template polypeptide such as the antibody variable domain of 4D5. This technique is well known in the art as described by Zoller et al. Nucleic Acids Res. 10:6487-6504 (1987). Briefly, nucleic acid sequences encoding variant amino acids are created by hybridizing an oligonucleotide set encoding the desired biased codon sets to a DNA template, where the template is the single-stranded form of the plasmid containing a variable region nucleic acid template sequence. After hybridization, DNA polymerase is used to synthesize an entire second complementary strand of the template that will thus incorporate the oligonucleotide primer, and will contain the biased codon sets as provided by the oligonucleotide set. Nucleic acids encoding other source or template molecules are known or can be readily determined.

Generally, oligonucleotides of at least 25 nucleotides in length are used. An optimal oligonucleotide will have at least 12 to 15 nucleotides that are completely complementary to the template on either side of the nucleotide(s) coding for the mutation(s). This ensures that the oligonucleotide will hybridize properly to the single-stranded DNA template molecule. The oligonucleotides are readily synthesized using techniques known in the art such as that described by Crea et al., *Proc. Natl. Acad. Sci. USA*, 75:5765 (1978).

The DNA template is generated by those vectors that are either derived from bacteriophage M13 vectors (the commercially available M13mp18 and M13mp19 vectors are suitable), or those vectors that contain a single-stranded phage origin of replication as described by Viera et al., *Meth. Enzymol.*, 153:3 (1987). Thus, the DNA that is to be mutated can be inserted into one of these vectors in order to generate single-stranded template. Production of the single-stranded template is described in sections 4.21-4.41 of Sambrook et al., above.

To alter the native DNA sequence, the oligonucleotide is hybridized to the single stranded template under suitable hybridization conditions. A DNA polymerizing enzyme, usually T7 DNA polymerase or the Klenow fragment of DNA polymerase I, is then added to synthesize the complementary strand of the template using the oligonucleotide as a primer for synthesis. A heteroduplex molecule is thus formed such that one strand of DNA encodes the mutated form of gene 1, and the other strand (the original template) encodes the native, unaltered sequence of gene 1. This heteroduplex molecule is then transformed into a suitable host cell, usually a prokaryote such as *E. coli* JM101. After growing the cells, they are plated onto agarose plates and screened using the oligonucleotide primer radiolabeled with a 32-Phosphate to identify the bacterial colonies that contain the mutated DNA.

The method described immediately above may be modified such that a homoduplex molecule is created wherein both strands of the plasmid contain the mutation(s). The modifications are as follows: The single stranded oligonucleotide is annealed to the single-stranded template as described above. A mixture of three deoxyribonucleotides, deoxyriboadenosine (dATP), deoxyriboguanosine (dGTP), and deoxyribothymidine (dTT), is combined with a modified thiodeoxyribocytosine called dCTP-(aS) (which can be obtained from Amersham). This mixture is added to the template-oligonucleotide complex. Upon addition of DNA polymerase to this mixture, a strand of DNA identical to the template except for the mutated bases is generated. In addition, this new strand of DNA will contain dCTP-(aS) instead of dCTP, which serves to protect it from restriction endonuclease digestion. After the template strand of the double-stranded heteroduplex is nicked with an appropriate restriction enzyme, the template strand can be digested with ExoIII nuclease or another appropriate nuclease past the region that contains the site(s) to be mutagenized. The reaction is then stopped to leave a molecule that is only partially single-stranded. A complete double-stranded DNA homoduplex is then formed using DNA polymerase in the presence of all four deoxyribonucleotide triphosphates, ATP, and DNA ligase. This homoduplex molecule can then be transformed into a suitable host cell.

As indicated previously the sequence of the oligonucleotide set is of sufficient length to hybridize to the template nucleic acid and may also, but does not necessarily, contain restriction sites. The DNA template can be generated by those vectors that are either derived from bacteriophage M13 vectors or vectors that contain a single-stranded phage origin of replication as described by Viera et al. ((1987) Meth. Enzymol., 153:3). Thus, the DNA that is to be mutated must be inserted into one of these vectors in order to generate single-stranded template. Production of the single-stranded template is described in sections 4.21-4.41 of Sambrook et al., supra.

According to another method, a library can be generated by providing upstream and downstream oligonucleotide sets, each set having a plurality of oligonucleotides with different sequences, the different sequences established by the codon sets provided within the sequence of the oligonucleotides. The upstream and downstream oligonucleotide sets, along with a variable domain template nucleic acid sequence, can be used in a polymerase chain reaction to generate a "library" of PCR products. The PCR products can be referred to as "nucleic acid cassettes", as they can be fused with other related or unrelated nucleic acid sequences, for example, viral coat protein components and dimerization domains, using established molecular biology techniques.

The sequence of the PCR primers includes one or more of the designed codon sets for the solvent accessible and highly diverse positions in a CDR region. As described above, a codon set is a set of different nucleotide triplet sequences used to encode desired variant amino acids.

Oligonucleotide sets can be used in a polymerase chain reaction using a variable region nucleic acid template sequence as the template to create nucleic acid cassettes. The variable region nucleic acid template sequence can be any portion of the light or heavy immunoglobulin chains containing the target nucleic acid sequences (i.e., nucleic acid sequences encoding amino acids targeted for substitution). The variable region nucleic acid template sequence is a portion of a double stranded DNA molecule having a first nucleic acid strand and complementary second nucleic acid strand. The variable region nucleic acid template sequence contains at least a portion of a variable domain and has at least one CDR. In some cases, the variable region nucleic acid template sequence contains more than one CDR. An upstream portion and a downstream portion of the variable region nucleic acid template sequence can be targeted for hybridization with members of an upstream oligonucleotide set and a downstream oligonucleotide set.

A first oligonucleotide of the upstream primer set can hybridize to the first nucleic acid strand and a second oligonucleotide of the downstream primer set can hybridize to the second nucleic acid strand. The oligonucleotide primers can include one or more codon sets and be designed to hybridize to a portion of the variable region nucleic acid template sequence. Use of these oligonucleotides can introduce two or more codon sets into the PCR product (i.e., the nucleic acid cassette) following PCR. The oligonucleotide primer that hybridizes to regions of the nucleic acid sequence encoding the antibody variable domain includes portions that encode CDR residues that are targeted for amino acid substitution.

The upstream and downstream oligonucleotide sets can also be synthesized to include restriction sites within the oligonucleotide sequence. These restriction sites can facilitate the insertion of the nucleic acid cassettes [i.e., PCR reaction products] into an expression vector having additional antibody sequences. Preferably, the restriction sites are designed to facilitate the cloning of the nucleic acid cassettes without introducing extraneous nucleic acid sequences or removing original CDR or framework nucleic acid sequences.

Nucleic acid cassettes can be cloned into any suitable vector for expression of a portion or the entire light or heavy chain sequence containing the targeted amino acid substitutions generated. According to methods detailed in the invention, the nucleic acid cassette is cloned into a vector allowing production of a portion or the entire light or heavy chain sequence fused to all or a portion of a viral coat protein (i.e., creating a fusion protein) and displayed on the surface of a particle or cell. While several types of vectors are available and may be used to practice this invention, phagemid vectors are the preferred vectors for use herein, as they may be constructed with relative ease, and can be readily amplified. Phagemid vectors generally contain a variety of components including promoters, signal sequences, phenotypic selection genes, origin of replication sites, and other necessary components as are known to those of ordinary skill in the art.

In another embodiment, wherein a particular variant amino acid combination is to be expressed, the nucleic acid cassette contains a sequence that is able to encode all or a portion of the heavy or light chain variable domain, and is able to encode the variant amino acid combinations. For production of antibodies containing these variant amino acids or combinations of variant amino acids, as in a library, the nucleic acid cassettes can be inserted into an expression vector containing additional antibody sequence, for example all or portions of the variable or constant domains of the light and heavy chain variable regions. These additional antibody sequences can also be fused to other nucleic acid sequences, such as sequences which encode viral coat protein components and therefore allow production of a fusion protein.

Vectors

One aspect of the invention includes a replicable expression vector comprising a nucleic acid sequence encoding a gene fusion, wherein the gene fusion encodes a fusion protein comprising a CDR-containing polypeptide (such as an antibody variable domain), or an antibody variable domain and a constant domain, fused to all or a portion of a viral coat protein. Also included is a library of diverse replicable expression vectors comprising a plurality of gene fusions encoding a plurality of different fusion proteins including a plurality of the fusion polypeptides generated with diverse sequences as described above. The vectors can include a variety of components and may be constructed to allow for movement of antibody variable domain between different vectors and/or to provide for display of the fusion proteins in different formats.

Examples of vectors include phage vectors and phagemid vectors (which is illustrated extensively herein, and described in greater detail above). A phage vector generally has a phage origin of replication allowing phage replication and phage particle formation. The phage is generally a filamentous bacteriophage, such as an M113, f1, fd, Pf3 phage or a derivative thereof, or a lambdoid phage, such as lambda, 21, phi80, phi81, 82, 424, 434, etc., or a derivative thereof.

Examples of viral coat proteins include infectivity protein PIII (sometimes also designated p3), major coat protein PVIII, Soc (T4), Hoc (T4), gpD (of bacteriophage lambda), minor bacteriophage coat protein 6 (pVI) (filamentous phage; *J Immunol Methods*. 1999 Dec. 10; 231(1-2):39-51), variants of the M13 bacteriophage major coat protein (P8) (*Protein Sci* 2000 April; 9(4):647-54). The fusion protein can be displayed on the surface of a phage and suitable phage systems include M13KO7 helper phage, M13R408, M13-VCS, and Phi X 174, pJuFo phage system (J Virol. 2001 August; 75(15):7107-13.v), hyperphage (*Nat Biotechnol*. 2001 January; 19(1):75-8). The preferred helper phage is M13KO7, and the preferred coat protein is the M13 Phage gene III coat protein. The preferred host is *E. coli*, and protease deficient strains of *E. coli*. Vectors, such as the fth1 vector (*Nucleic Acids Res*. 2001 May 15; 29(10):E50-0) can be useful for the expression of the fusion protein.

The expression vector also can have a secretory signal sequence fused to the DNA encoding a CDR-containing fusion polypeptide (e.g., each subunit of an antibody, or fragment thereof). This sequence is typically located immediately 5' to the gene encoding the fusion protein, and will thus be transcribed at the amino terminus of the fusion protein. However, in certain cases, the signal sequence has been demonstrated to be located at positions other than 5' to the gene encoding the protein to be secreted. This sequence targets the protein to which it is attached across the inner membrane of the bacterial cell. The DNA encoding the signal sequence may be obtained as a restriction endonuclease fragment from any gene encoding a protein that has a signal sequence. Suitable prokaryotic signal sequences may be obtained from genes encoding, for example, LamB or OmpF (Wong et al., *Gene*, 68:1931 (1983), MalE, PhoA and other genes. In one embodiment, a prokaryotic signal sequence for practicing this invention is the *E. coli* heat-stable enterotoxin II (STII) signal sequence as described by Chang et al., *Gene* 55:189 (1987), and/or malE.

As indicated above, a vector also typically includes a promoter to drive expression of the fusion polypeptide. Promoters most commonly used in prokaryotic vectors include the lac Z promoter system, the alkaline phosphatase pho A promoter (Ap), the bacteriophage $l_{PL}$ promoter (a temperature sensitive promoter), the tac promoter (a hybrid trp-lac promoter that is regulated by the lac repressor), the tryptophan promoter, and the bacteriophage T7 promoter. For general descriptions of promoters, see section 17 of Sambrook et al. supra. While these are the most commonly used promoters, other suitable microbial promoters may be used as well.

The vector can also include other nucleic acid sequences, for example, sequences encoding gD tags, c-Myc epitopes, poly-histidine tags, fluorescence proteins (e.g., GFP), or beta-galactosidase protein which can be useful for detection or purification of the fusion protein expressed on the surface of the phage or cell. Nucleic acid sequences encoding, for example, a gD tag, also provide for positive or negative selection of cells or virus expressing the fusion protein. In some embodiments, the gD tag is preferably fused to an antibody variable domain which is not fused to the viral coat protein component. Nucleic acid sequences encoding, for example, a polyhistidine tag, are useful for identifying fusion proteins including antibody variable domains that bind to a specific antigen using immunohistochemistry. Tags useful for detection of antigen binding can be fused to either an antibody variable domain not fused to a viral coat protein component or an antibody variable domain fused to a viral coat protein component.

Another useful component of the vectors used to practice this invention is phenotypic selection genes. Typical phenotypic selection genes are those encoding proteins that confer antibiotic resistance upon the host cell. By way of illustration, the ampicillin resistance gene (ampr), and the tetracycline resistance gene (tetr) are readily employed for this purpose.

The vector can also include nucleic acid sequences containing unique restriction sites and suppressible stop codons. The unique restriction sites are useful for moving antibody variable domains between different vectors and expression systems, especially useful for production of full-length antibodies or antigen binding fragments in cell cultures. The suppressible stop codons are useful to control the level of expression of the fusion protein and to facilitate purification of soluble antibody fragments. For example, an amber stop codon can be read as Gln in a supE host to enable phage display, while in a non-supE host it is read as a stop codon to produce soluble antibody fragments without fusion to phage coat proteins. These synthetic sequences can be fused to one or more antibody variable domains in the vector.

It is sometimes beneficial to use vector systems that allow the nucleic acid encoding an antibody sequence of interest, for example a CDR having variant amino acids, to be easily removed from the vector system and placed into another vector system. For example, appropriate restriction sites can be engineered in a vector system to facilitate the removal of the nucleic acid sequence encoding an antibody or antibody variable domain having variant amino acids. The restriction sequences are usually chosen to be unique in the vectors to facilitate efficient excision and ligation into new vectors. Antibodies or antibody variable domains can then be expressed from vectors without extraneous fusion sequences, such as viral coat proteins or other sequence tags.

Between nucleic acid encoding antibody variable or constant domain (gene 1) and the viral coat protein component (gene 2), DNA encoding a termination or stop codon may be inserted, such termination codons including UAG (amber), UAA (ocher) and UGA (opal). (*Microbiology*, Davis et al., Harper & Row, New York, 1980, pp. 237, 245-47 and 374). The termination or stop codon expressed in a wild type host cell results in the synthesis of the gene 1 protein product without the gene 2 protein attached. However, growth in a suppressor host cell results in the synthesis of detectable quantities of fused protein. Such suppressor host cells are well known and described, such as *E. coli* suppressor strain (Bullock et al., *BioTechniques* 5:376-379 (1987)). Any acceptable method may be used to place such a termination codon into the mRNA encoding the fusion polypeptide.

The suppressible codon may be inserted between the first gene encoding an antibody variable or constant domain, and a second gene encoding at least a portion of a phage coat protein. Alternatively, the suppressible termination codon may be inserted adjacent to the fusion site by replacing the last amino acid triplet in the antibody variable domain or the first amino acid in the phage coat protein. The suppressible termination codon may be located at or after the C-terminal end of a dimerization domain. When the plasmid containing the suppressible codon is grown in a suppressor host cell, it results in the detectable production of a fusion polypeptide containing the polypeptide and the coat protein. When the plasmid is grown in a non-suppressor host cell, the antibody variable domain is synthesized substantially without fusion to the phage coat protein due to termination at the inserted suppressible triplet UAG, UAA, or UGA. In the non-suppressor cell the antibody variable domain is synthesized and secreted from the host cell due to the absence of the fused phage coat protein which otherwise anchored it to the host membrane.

In some embodiments, the CDR being diversified (randomized) may have a stop codon engineered in the template sequence (referred to herein as a "stop template"). This feature provides for detection and selection of successfully diversified sequences based on successful repair of the stop codon(s) in the template sequence due to incorporation of the oligonucleotide(s) comprising the sequence(s) for the variant amino acids of interest. This feature is further illustrated in the Examples below.

The light and/or heavy chain antibody variable or constant domains can also be fused to an additional peptide sequence, the additional peptide sequence providing for the interaction of one or more fusion polypeptides on the surface of the viral particle or cell. These peptide sequences are herein referred to as "dimerization domains". Dimerization domains may comprise at least one or more of a dimerization sequence, or at least one sequence comprising a cysteine residue or both. Suitable dimerization sequences include those of proteins having amphipathic alpha helices in which hydrophobic residues are regularly spaced and allow the formation of a dimer by interaction of the hydrophobic residues of each protein; such proteins and portions of proteins include, for example, leucine zipper regions. Dimerization domains can also comprise one or more cysteine residues (e.g. as provided by inclusion of an antibody hinge sequence within the dimerization domain). The cysteine residues can provide for dimerization by formation of one or more disulfide bonds. In one embodiment, wherein a stop codon is present after the dimerization domain, the dimerization domain comprises at least one cysteine residue. The dimerization domains are preferably located between the antibody variable or constant domain and the viral coat protein component.

In some cases the vector encodes a single antibody-phage polypeptide in a single chain form containing, for example, both the heavy and light chain variable regions fused to a coat protein. In these cases the vector is considered to be "monocistronic", expressing one transcript under the control of a certain promoter. For example, a vector may utilize a promoter (such as the alkaline phosphatase (AP) or Tac promoter) to drive expression of a monocistronic sequence encoding VL and VH domains, with a linker peptide between the VL and VH domains. This cistronic sequence may be connected at the 5' end to a signal sequence (such as an *E. coli* malE or heat-stable enterotoxin II (STII) signal sequence) and at its 3' end to all or a portion of a viral coat protein (such as the bacteriophage pIII protein). The fusion polypeptide encoded by a vector of this embodiment is referred to herein as "ScFv-pIII". In some embodiments, a vector may further comprise a sequence encoding a dimerization domain (such as a leucine zipper) at its 3' end, between the second variable domain sequence (e.g., VH) and the viral coat protein sequence. Fusion polypeptides comprising the dimerization domain are capable of dimerizing to form a complex of two scFv polypeptides (referred to herein as "(ScFv)2-pIII)").

In other cases, the variable regions of the heavy and light chains can be expressed as separate polypeptides, the vector thus being "bicistronic", allowing the expression of separate transcripts. In these vectors, a suitable promoter, such as the Ptac or PhoA promoter, is used to drive expression of a bicistronic message. A first cistron encoding, for example, a light chain variable and constant domain, may be connected at the 5' end to a signal sequence, such as *E. coli* malE or heat-stable enterotoxin II (STII) signal sequence, and at the 3' end to a nucleic acid sequence encoding a tag sequence, such as gD tag. A second cistron, encoding, for example, a heavy chain variable domain and constant domain CH1, is connected at its 5' end to a signal sequence, such as *E. coli* malE or heat-stable enterotoxin II (STII) signal sequence, and at the 3' end to all or a portion of a viral coat protein.

In one embodiment of a vector which provides a bicistronic message and for display of F(ab')$_2$-pIII, a suitable promoter, such as Ptac or PhoA (AP) promoter, drives expression of a first cistron encoding a light chain variable and constant domain operably linked at 5' end to a signal sequence such as the *E. coli* malE or heat stable enteroxtoxin II (STII) signal sequence, and at the 3' end to a nucleic acid sequence encoding a tag sequence such as gD tag. The second cistron encodes, for example, a heavy chain variable and constant domain operatively linked at 5' end to a signal sequence such as *E. coli* malE or heat stable enterotoxin II (STII) signal sequence, and at 3' end has a dimerization domain comprising IgG hinge sequence and a leucine zipper sequence followed by at least a portion of viral coat protein.

Display of Fusion Polypeptides

Fusion polypeptides of a CDR-containing polypeptide (e.g., an antibody variable domain) can be displayed on the surface of a cell, virus, or phagemid particle in a variety of formats. These formats include single chain Fv fragment (scFv), F(ab) fragment and multivalent forms of these fragments. For example, multivalent forms include a dimer of ScFv, Fab, or F(ab'), herein referred to as (ScFv)$_2$, F(ab)$_2$ and F(ab')$_2$, respectively. The multivalent forms of display are advantageous in some contexts in part because they have more than one antigen binding site which generally results in the identification of lower affinity clones and also allows for more efficient sorting of rare clones during the selection process.

Methods for displaying fusion polypeptides comprising antibody fragments, on the surface of bacteriophage, are well known in the art, for example as described in patent publication number WO 92/01047 and herein. Other patent publications WO 92/20791; WO 93/06213; WO 93/11236 and WO 93/19172, describe related methods and are all herein incorporated by reference. Other publications have shown the identification of antibodies with artificially rearranged V gene repertoires against a variety of antigens displayed on the surface of phage (for example, H. R. Hoogenboom & G. Winter J. Mol. Biol. 227 381-388 1992; and as disclosed in WO 93/06213 and WO 93/11236).

When a vector is constructed for display in a scFv format, it includes nucleic acid sequences encoding an antibody variable light chain domain and an antibody variable heavy chain variable domain. Typically, the nucleic acid sequence encoding an antibody variable heavy chain domain is fused to a viral coat protein component. One or both of the antibody variable domains can have variant amino acids in at least one CDR region. The nucleic acid sequence encoding the antibody variable light chain is connected to the antibody variable heavy chain domain by a nucleic acid sequence encoding a peptide linker. The peptide linker typically contains about 5 to 15 amino acids. Optionally, other sequences encoding, for example, tags useful for purification or detection can be fused at the 3' end of either the nucleic acid sequence encoding the antibody variable light chain or antibody variable heavy chain domain or both.

When a vector is constructed for F(ab) display, it includes nucleic acid sequences encoding antibody variable domains and antibody constant domains. A nucleic acid encoding a variable light chain domain is fused to a nucleic acid sequence encoding a light chain constant domain. A nucleic acid sequence encoding an antibody heavy chain variable domain is fused to a nucleic acid sequence encoding a heavy chain constant CH1 domain. Typically, the nucleic acid sequence encoding the heavy chain variable and constant domains are fused to a nucleic acid sequence encoding all or part of a viral coat protein. One or both of the antibody variable light or heavy chain domains can have variant amino acids in at least one CDR. In some embodiments, the heavy chain variable and constant domains are expressed as a fusion with at least a portion of a viral coat protein, and the light chain variable and constant domains are expressed separately from the heavy chain viral coat fusion protein. The heavy and light chains associate with one another, which may be by covalent or non-covalent bonds. Optionally, other sequences encoding, for example, polypeptide tags useful for purification or detection, can be fused at the 3' end of either the nucleic acid sequence encoding the antibody light chain constant domain or antibody heavy chain constant domain or both.

In some embodiments, a bivalent moiety, for example, a F(ab)$_2$ dimer or F(ab')$_2$ dimer, is used for displaying antibody fragments with the variant amino acid substitutions on the surface of a particle. It has been found that F(ab')$_2$ dimers generally have the same affinity as F(ab) dimers in a solution phase antigen binding assay but the off rate for F(ab')$_2$ are reduced because of a higher avidity. Therefore, the bivalent format (for example, F(ab')$_2$) is a particularly useful format since it can allow for the identification of lower affinity clones and also allows more efficient sorting of rare clones during the selection process.

Introduction of Vectors into Host Cells

Vectors constructed as described in accordance with the invention are introduced into a host cell for amplification and/or expression. Vectors can be introduced into host cells using standard transformation methods including electroporation, calcium phosphate precipitation and the like. If the vector is an infectious particle such as a virus, the vector itself provides for entry into the host cell. Transfection of host cells containing a replicable expression vector which encodes the gene fusion and production of phage particles according to standard procedures provides phage particles in which the fusion protein is displayed on the surface of the phage particle.

Replicable expression vectors are introduced into host cells using a variety of methods. In one embodiment, vectors can be introduced into cells using electroporation as described in WO/00106717. Cells are grown in culture in standard culture broth, optionally for about 6-48 hours (or to OD$_{600}$=0.6-0.8) at about 37° C., and then the broth is centrifuged and the supernatant removed (e.g. decanted). Initial purification is preferably by resuspending the cell pellet in a buffer solution (e.g. 1.0 mM HEPES pH 7.4) followed by recentrifugation and removal of supernatant. The resulting cell pellet is resuspended in dilute glycerol (e.g. 5-20% v/v) and again recentrifuged to form a cell pellet and the supernatant removed. The final cell concentration is obtained by resuspending the cell pellet in water or dilute glycerol to the desired concentration.

A particularly preferred recipient cell is the electroporation competent *E. coli* strain of the present invention, which is *E. coli* strain SS320 (Sidhu et al., *Methods Enzymol.* (2000), 328:333-363). Strain SS320 was prepared by mating MC1061 cells with XL1-BLUE cells under conditions sufficient to transfer the fertility episome (F' plasmid) or XL1-BLUE into the MC1061 cells. Strain SS320 has been deposited with the American Type Culture Collection (ATCC), 10801 University Boulevard, Manassas, Va. USA, on Jun. 18, 1998 and assigned Deposit Accession No. 98795. Any F' episome which enables phage replication in the strain may be used in the invention. Suitable episomes are available from strains deposited with ATCC or are commercially available (CJ236, CSH18, DHF', JM101, JM103, JM105, JM107, JM109, JM110), KS1000, XL1-BLUE, 71-18 and others).

The use of higher DNA concentrations during electroporation (about 10×) increases the transformation efficiency and increases the amount of DNA transformed into the host cells. The use of high cell concentrations also increases the efficiency (about 10×). The larger amount of transferred DNA produces larger libraries having greater diversity and representing a greater number of unique members of a combinatorial library. Transformed cells are generally selected by growth on antibiotic containing medium.

Selection (Sorting) and Screening for Binders to Targets of Choice

Use of phage display for identifying target antigen binders, with its various permutations and variations in methodology, are well established in the art. One approach involves constructing a family of variant replicable vectors containing a transcription regulatory element operably linked to a gene fusion encoding a fusion polypeptide, transforming suitable host cells, culturing the transformed cells to form phage particles which display the fusion polypeptide on the surface of the phage particle, followed by a process that entails selection or sorting by contacting the recombinant phage particles with a target antigen so that at least a portion of the population of particles bind to the target with the objective to increase and enrich the subsets of the particles which bind from particles relative to particles that do not bind in the process of selection. The selected pool can be amplified by infecting host cells, such as fresh XL1-Blue cells, for another round of sorting on the same target with different or same stringency. The resulting pool of variants are then screened against the target antigens to identify novel high affinity binding proteins. These novel high affinity binding proteins can be useful as therapeutic agents as antagonists or agonists, and/or as diagnostic and research reagents.

Fusion polypeptides such as antibody variable domains comprising the variant amino acids can be expressed on the surface of a phage, phagemid particle or a cell and then selected and/or screened for the ability of members of the group of fusion polypeptides to bind a target antigen which is typically an antigen of interest. The processes of selection for binders to target can also be include sorting on a generic protein having affinity for antibody variable domains such as protein L or a tag specific antibody which binds to antibody or antibody fragments displayed on phage, which can be used to enrich for library members that display correctly folded antibody fragments (fusion polypeptides).

Target proteins, such as receptors, may be isolated from natural sources or prepared by recombinant methods by procedures known in the art. Target antigens can include a number of molecules of therapeutic interest.

A variety of strategies of selection (sorting) for affinity can be used. One example is a solid-support method or plate sorting or immobilized target sorting. Another example is a solution-binding method.

For the solid support method, the target protein may be attached to a suitable solid or semi solid matrix which are known in the art such as agarose beads, acrylamide beads, glass beads, cellulose, various acrylic copolymers, hydroxyalkyl methacrylate gels, polyacrylic and polymethacrylic copolymers, nylon, neutral and ionic carriers, and the like. Attachment of the target protein to the matrix may be accomplished by methods described in Methods in Enzymology, 44 (1976), or by other means known in the art.

After attachment of the target antigen to the matrix, the immobilized target is contacted with the library expressing the fusion polypeptides under conditions suitable for binding of at least a subset of the phage particle population with the immobilized target antigen. Normally, the conditions, including pH, ionic strength, temperature and the like will mimic physiological conditions. Bound particles ("binders") to the immobilized target are separated from those particles that do not bind to the target by washing. Wash conditions can be adjusted to result in removal of all but the high affinity binders. Binders may be dissociated from the immobilized target by a variety of methods. These methods include competitive dissociation using the wild-type ligand (e.g. excess target antigen), altering pH and/or ionic strength, and methods known in the art. Selection of binders typically involves elution from an affinity matrix with a suitable elution material such as acid like 0.1M HCl or ligand. Elution with increasing concentrations of ligand could elute displayed binding molecules of increasing affinity.

The binders can be isolated and then re-amplified in suitable host cells by infecting the cells with the viral particles that are binders (and helper phage if necessary, e.g. when viral particle is a phagemid particle) and the host cells are cultured under conditions suitable for amplification of the particles that display the desired fusion polypeptide. The phage particles are then collected and the selection process is repeated one or more times until binders of the target antigen are enriched in a way. any number of rounds of selection or sorting can be utilized. One of the selection or sorting procedures can involve isolating binders that bind to a generic affinity protein such as protein L or an antibody to a polypeptide tag present in a displayed polypeptide such as antibody to the gD protein or polyhistidine tag.

One aspect of the invention involves selection against libraries of the invention using a novel selection method which is termed "solution-binding method". The invention allows solution phase sorting with much improved efficiency over conventional solution sorting methods. The solution binding method may be used for finding original binders from a random library or finding improved binders from a library that was designated to improve affinity of a particular binding clone or group of clones. The method comprises contacting a plurality of polypeptides, such as those displayed on phage or phagemid particles (library), with a target antigen labelled or fused with a tag molecule. The tag could be biotin or other moieties for which specific binders are available. The stringency of the solution phase can be varied by using decreasing concentrations of labelled target antigen in the first solution binding phase. To further increase the stringency, the first solution binding phase can be followed by a second solution phase having high concentration of unlabelled target antigen after the initial binding with the labelled target in the first solution phase. Usually, 100 to 1000 fold of unlabelled target over labelled target is used in the second phase (if included). The length of time of incubation of the first solution phase can vary from a few minutes to one to two hours or longer to reach equilibrium. Using a shorter time for binding in this first phase may bias or select for binders that have fast on-rate. The length of time and temperature of incubation in second phase can be varied to increase the stringency. This provides for a selection bias for binders that have slow rate of coming off the target (off-rate). After contacting the plurality of polypeptides (displayed on the phage/phagemid particles) with a target antigen, the phage or phagemid particles that are bound to labelled targets are separated from phage that do not bind. The particle-target mixture from solution phase of binding is isolated by contacting it with the labelled target moiety and allowing for its binding to, a molecule that binds the labelled target moiety for a short period of time (e.g. 2-5 minutes). The initial concentration of the labelled target antigen can range from about 0.1 nM to about 1000 nM. The bound particles are eluted and can be propagated for next round of sorting. Multiple rounds of sorting are preferred using a lower concentration of labelled target antigen with each round of sorting.

For example, an initial sort or selection using about 100 to 250 nM labelled target antigen should be sufficient to capture a wide range of affinities, although this factor can be determined empirically and/or to suit the desire of the practitioner. In the second round of selection, about 25 to 100 nM of labelled target antigen may be used. In the third round of selection, about 0.1 to 25 nM of labeled target antigen may be used. For example, to improve the affinity of a 100 nM binder, it may be desirable to start with 20 nM and then progress to 5 and 1 nM labelled target, then, followed by even lower concentrations such as about 0.1 nM labelled target antigen.

The conventional solution sorting involves use of beads like streptavidin-coated beads, which is very cumbersome to use and often results in very low efficiency of phage binders recovery. The conventional solution sorting with beads takes much longer than 2-5 minutes and is less feasible to adapt to high throughput automation than the invention described above.

As described herein, combinations of solid support and solution sorting methods can be advantageously used to isolate binders having desired characteristics. After selection/sorting on target antigen for a few rounds, screening of individual clones from the selected pool generally is performed to identify specific binders with the desired properties/characteristics. Preferably, the process of screening is carried out by automated systems to allow for high-throughput screening of library candidates.

Two major screening methods are described below. However, other methods known in the art may also be used in the methods of the invention. The first screening method comprises a phage ELISA assay with immobilized target antigen, which provides for identification of a specific binding clone from a non-binding clone. Specificity can be determined by simultaneous assay of the clone on target coated well and BSA or other non-target protein coated wells. This assay is automatable for high throughput screening.

One embodiment provides a method of selecting for an antibody variable domain that binds to a specific target antigen from a library of antibody variable domain by generating a library of replicable expression vectors comprising a plurality of polypeptides; contacting the library with a target antigen and at least one nontarget antigen under conditions suitable for binding; separating the polypeptide binders in the library from the nonbinders; identifying the binders that bind to the target antigen and do not bind to the nontarget antigen; eluting the binders from the target antigen; and amplifying the replicable expression vectors comprising the polypeptide binder that bind to a specific antigen.

The second screening assay is an affinity screening assay that provides for screening for clones that have high affinity from clones that have low affinity in a high throughput manner. In the assay, each clone is assayed with and without first incubating with target antigen of certain concentration for a period of time (for e.g. 30-60 minutes) before application to target coated wells briefly (e.g.5-15 minutes). Then bound phage is measured by usual phage ELISA method, e.g. using anti-M13 HRP conjugates. The ratio of binding signal of the two wells, one well having been preincubated with target and the other well not preincubated with target antigen is an indication of affinity. The selection of the concentration of target for first incubation depends on the affinity range of interest. For example, if binders with affinity higher than 10 nM are desired, 100 nM of target in the first incubation is often used. Once binders are found from a particular round of sorting (selection), these clones can be screened with affinity screening assay to identify binders with higher affinity.

Combinations of any of the sorting/selection methods described above may be combined with the screening methods. For example, in one embodiment, polypeptide binders are first selected for binding to immobilized target antigen. Polypeptide binders that bind to the immobilized target antigen can then be amplified and screened for binding to the target antigen and for lack of binding to nontarget antigens. Polypeptide binders that bind specifically to the target antigen are amplified. These polypeptide binders can then selected for higher affinity by contact with a concentration of a labelled target antigen to form a complex, wherein the concentration ranges of labelled target antigen from about 0.1 nM to about 1000 nM, the complexes are isolated by contact with an agent that binds to the label on the target antigen. The polypeptide binders are then eluted from the labeled target antigen and optionally, the rounds of selection are repeated, each time a lower concentration of labelled target antigen is used. The high affinity polypeptide binders isolated using this selection method can then be screened for high affinity using a variety of methods known in the art, some of which are described herein.

These methods can provide for finding clones with high affinity without having to perform long and complex competition affinity assays on a large number of clones. The intensive aspect of doing complex assays of many clones often is a significant obstacle to finding best clones from a selection. This method is especially useful in affinity improvement efforts where multiple binders with similar affinity can be recovered from the selection process. Different clones may have very different efficiency of expression/display on phage or phagemid particles. Those clones more highly expressed have better chances being recovered. That is, the selection can be biased by the display or expression level of the variants. The solution-binding sorting method of the invention can improve the selection process for finding binders with high affinity. This method is an affinity screening assay that provides a significant advantage in screening for the best binders quickly and easily.

After binders are identified by binding to the target antigen, the nucleic acid can be extracted. Extracted DNA can then be used directly to transform *E. coli* host cells or alternatively, the encoding sequences can be amplified, for example using PCR with suitable primers, and sequenced by typical sequencing method. Variable domain DNA of the binders can be restriction enzyme digested and then inserted into a vector for protein expression.

Populations comprising polypeptides having HVR(s) with selected sequence diversity generated according to methods of the invention can be used to isolate binders against a variety of targets. These binders may comprise one or more variant HVRs comprising diverse sequences generated using biased codons. In some embodiments, a variant HVR is HVR-H3 comprising sequence diversity generated by amino acid substitution with biased codon sets and/or amino acid insertions resulting from varying HVR-H3 lengths. One or more variant HVRs may be combined. In some embodiments, only HVR-H3 is diversified. In other embodiments, two or more heavy chain HVRs, including HVR-H3, are variant. In other embodiments, one or more heavy chain HVRs, excluding HVR-H3, are variant. In some embodiments, at least one heavy chain and at least one light chain HVR are variant. In some embodiments, at least one, two, three, four, five or all of HVR-H1, H2, H3, L1, L2 and L3 are variant.

In some cases, it can be beneficial to combine one or more diversified light chain HVRs with novel binders isolated from a population of polypeptides comprising one or more diversified heavy chain CDRs. This process may be referred to as a 2-step process. An example of a 2-step process comprises first determining binders (generally lower affinity binders) within one or more libraries generated by randomizing one or more CDRs, wherein the CDRs randomized in each library are different or, where the same CDR is randomized, it is randomized to generate different sequences. Binders from a heavy chain library can then be randomized with CDR diversity in a light chain CDRs by, e.g. a mutagenesis technique such as that of Kunkel, or by cloning (cut-and-paste (e.g. by ligating different CDR sequences together)) the new light chain library into the existing heavy chain binders that has only a fixed light chain. The pool can then be further sorted against target to identify binders possessing increased affinity. For example, binders (for example, low affinity binders) obtained from sorting an H1/H2/H3 may be fused with library of an L1/L2/L3 diversity to replace its original fixed L1/L2/L3, wherein the new libraries are then further sorted against a target of interest to obtain another set of binders (for example, high affinity binders). Novel antibody sequences can be identified that display higher binding affinity to any of a variety of target antigens.

In some embodiments, libraries comprising polypeptides of the invention are subjected to a plurality of sorting rounds, wherein each sorting round comprises contacting the binders obtained from the previous round with a target antigen distinct from the target antigen(s) of the previous round(s). Preferably, but not necessarily, the target antigens are homologous in sequence, for example members of a family of related but distinct polypeptides, such as, but not limited to, cytokines (for example, alpha interferon subtypes).

Generation of Libraries Comprising Variant CDR-Containing Polypeptides

Libraries of variant CDR polypeptides can be generated by mutating the solvent accessible and/or highly diverse positions in at least one CDR of an antibody variable domain. Some or all of the CDRs can be mutated using the methods of the invention. In some embodiments, it may be preferable to generate diverse antibody libraries by mutating positions in CDRH1, CDRH2 and CDRH3 to form a single library or by mutating positions in CDRL3 and CDRH3 to form a single library or by mutating positions in CDRL3 and CDRH1, CDRH2 and CDRH3 to form a single library.

A library of antibody variable domains can be generated, for example, having mutations in the solvent accessible and/or highly diverse positions of CDRH1, CDRH2 and CDRH3. Another library can be generated having mutations in CDRL1, CDRL2 and CDRL3. These libraries can also be used in conjunction with each other to generate binders of desired affinities. For example, after one or more rounds of selection of heavy chain libraries for binding to a target antigen, a light chain library can be replaced into the population of heavy chain binders for further rounds of selection to increase the affinity of the binders.

In one embodiment, a library is created by substitution of original amino acids with a limited set of variant amino acids in the CDRH3 region of the variable region of the heavy chain sequence. According to the invention, this library can contain a plurality of antibody sequences, wherein the sequence diversity is primarily in the CDRH3 region of the heavy chain sequence.

In one aspect, the library is created in the context of the humanized antibody 4D5 sequence, or the sequence of the framework amino acids of the humanized antibody 4D5 sequence. Preferably, the library is created by substitution of at least residues 95-100a of the heavy chain with amino acids encoded by the TMT, KMT or WMT codon set, wherein the TMT, KMT or WMT codon set is used to encode a limited set of variant amino acids for every one of these positions. Examples of suitable oligonucleotide sequences include, but are not limited to, those listed in FIG. 2 and FIG. 9 and can be determined by one skilled in the art according to the criteria described herein.

In another embodiment, different CDRH3 designs are utilized to isolate high affinity binders and to isolate binders for a variety of epitopes. For diversity in CDRH3, multiple libraries can be constructed separately with different lengths of H3 and then combined to select for binders to target antigens. The range of lengths of CDRH3 generated in this library can be 3-20, 5-20, 7-20, 5-18 or 7-18 amino acids, although lengths different from this can also be generated. Diversity can also be generated in CDRH1 and CDRH2, as indicated above. In one embodiment of a library, diversity in H1 and H2 is generated utilizing the oligonucleotides illustrated in FIGS. 2 and 9. Other oligonucleotides with varying sequences can also be used. Oligonucleotides can be used singly or pooled in any of a variety of combinations depending on practical needs and desires of the practitioner. In some embodiments, randomized positions in heavy chain CDRs include those listed in FIG. 1.

Multiple libraries can be pooled and sorted using solid support selection and solution sorting methods as described herein. Multiple sorting strategies may be employed. For example, one variation involves sorting on target bound to a solid, followed by sorting for a tag that may be present on the fusion polypeptide (e.g. anti-gD tag) and followed by another sort on target bound to solid. Alternatively, the libraries can be sorted first on target bound to a solid surface, the eluted binders are then sorted using solution phase binding with decreasing concentrations of target antigen. Utilizing combinations of different sorting methods provides for minimization of selection of only highly expressed sequences and provides for selection of a number of different high affinity clones.

Of the binders isolated from the pooled libraries as described above, it has been discovered that in some instances affinity may be further improved by providing limited diversity in the light chain. Light chain diversity may be, but is not necessarily, generated in this embodiment as follows: in CDRL1, positions to be diversified include amino acid positions 28, 29, 30, 31, 32; in CDRL2, positions to be diversified include amino acid positions 50, 51, 53, 54, 55; in CDRL3, positions to be diversified include amino acid positions 91, 92, 93, 94, 95, 97.

High affinity binders isolated from the libraries of these embodiments are readily produced in bacterial and eukaryotic cell culture in high yield. The vectors can be designed to readily remove sequences such as gD tags, viral coat protein component sequence, and/or to add in constant region sequences to provide for production of full length antibodies or antigen binding fragments in high yield.

Any combination of codon sets and CDRs can be diversified according to methods of the invention.

Vectors Host Cells and Recombinant Methods

For recombinant production of an antibody polypeptide of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, preferred host cells are of either prokaryotic or eukaryotic (generally mammalian) origin.

Generating Antibodies Using Prokaryotic Host Cells:
Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli is typically transformed using pBR322, a plasmid derived from an E. coli species. pBR322 contains genes encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM.TM.-11 may be utilized in making a recombinant vector which can be used to transform susceptible host cells such as E. coli LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, Ipp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB⁻ strains) provide cytoplasm conditions that are favorable for disulfide bond formation, thereby permitting proper folding and assembly of expressed protein subunits. Proba and Pluckthun Gene, 159:203 (1995).

The present invention provides an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence, although silent changes in the nucleotide sequence are preferred. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) *METHODS: A Companion to Methods in Enzymol.* 4:151-158.

Preferably, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

Prokaryotic host cells suitable for expressing antibodies of the invention include Archaebacteria and Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium, Serratia marcescans, Klebsiella, Proteus, Shigella, Rhizobia, Vitreoscilla*, or *Paracoccus*. In one embodiment, gram-negative cells are used. In one embodiment, *E. coli* cells are used as hosts for the invention. Examples of *E. coli* strains include strain W3110 (Bachmann, *Cellular and Molecular Biology*, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kan$^R$ (U.S. Pat. No. 5,639,635). Other strains and derivatives thereof such as *E. coli* 294 (ATCC 31,446), *E. coli* B, *E. coli*$_\lambda$ 1776 (ATCC 31,537) and *E. coli* RV308 (ATCC 31,608) are also suitable. These examples are illustrative rather than limiting. Methods for constructing derivatives of any of the above-mentioned bacteria having defined genotypes are known in the art and described in, for example, Bass et al., *Proteins*, 8:309-314 (1990). It is generally necessary to select the appropriate bacteria taking into consideration replicability of the replicon in the cells of a bacterium. For example, *E. coli, Serratia*, or *Salmonella* species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. For *E. coli* growth, for example, the preferred temperature ranges from about 20° C. to about 39° C., more preferably from about 25° C. to about 37° C., even more preferably at about 30° C. The pH of the medium may be any pH ranging from about 5 to about 9, depending mainly on the host organism. For *E. coli*, the pH is preferably from about 6.8 to about 7.4, and more preferably about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. Preferably, the phosphate-limiting medium is the C.R.A.P medium (see, e.g., Simmons et al., *J. Immunol. Methods* (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, preferably about 1,000 to 100,000 liters of capacity. These fermentors use agitator impellers to distribute oxygen and nutrients, especially glucose (the preferred carbon/energy source). Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an $OD_{550}$ of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis, trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) *J Bio Chem* 274:19601-19605; Georgiou et al., U.S. Pat. No. 6,083,715; Georgiou et al., U.S. Pat. No. 6,027,888; Bothmann and Pluckthun (2000) *J. Biol. Chem.* 275:17100-17105; Ramm and Pluckthun (2000) *J. Biol. Chem.* 275:17106-17113; Arie et al. (2001) *Mol. Microbiol.* 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some *E. coli* protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, *E. coli* strains deficient for proteolytic enzymes and transformed with plasmids overexpressing one or more chaperone proteins are used as host cells in the expression system of the invention.

Antibody Purification

In one embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the invention. Protein A is a 41kD cell wall protein from *Staphylococcus aureas* which binds with a high affinity to the Fc region of antibodies. Lindmark et al (1983) *J. Immunol. Meth.* 62:1-13. The solid phase to which Protein A is immobilized is preferably a column comprising a glass or silica surface, more preferably a controlled pore glass column or a silicic acid column. In some applications, the column has been coated with a reagent, such as glycerol, in an attempt to prevent nonspecific adherence of contaminants.

As the first step of purification, the preparation derived from the cell culture as described above is applied onto the Protein A immobilized solid phase to allow specific binding of the antibody of interest to Protein A. The solid phase is then washed to remove contaminants non-specifically bound to the solid phase. Finally the antibody of interest is recovered from the solid phase by elution.

Generating Antibodies Using Eukaryotic Host Cells:

The vector components generally include, but are not limited to, one or more of the following: a signal sequence, an origin of replication, one or more marker genes, an enhancer element, a promoter, and a transcription termination sequence.

(i) Signal Sequence Component

A vector for use in a eukaryotic host cell may also contain a signal sequence or other polypeptide having a specific cleavage site at the N-terminus of the mature protein or polypeptide of interest. The heterologous signal sequence selected preferably is one that is recognized and processed (i.e., cleaved by a signal peptidase) by the host cell. In mammalian cell expression, mammalian signal sequences as well as viral secretory leaders, for example, the herpes simplex gD signal, are available.

The DNA for such precursor region is ligated in reading frame to DNA encoding the antibody.

(ii) Origin of Replication

Generally, an origin of replication component is not needed for mammalian expression vectors. For example, the SV40 origin may typically be used only because it contains the early promoter.

(iii) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, preferably primate metallothionein genes, adenosine deaminase, ornithine decarboxylase, etc.

For example, cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199.

(iv) Promoter Component

Expression and cloning vectors usually contain a promoter that is recognized by the host organism and is operably linked to the antibody polypeptide nucleic acid. Promoter sequences are known for eukaryotes. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Antibody polypeptide transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419, 446. A modification of this system is described in U.S. Pat. No. 4,601,978. See also Reyes et al, *Nature* 297:598-601 (1982) on expression of human β-interferon cDNA in mouse cells under the control of a thymidine kinase promoter from herpes simplex virus. Alternatively, the Rous Sarcoma Virus long terminal repeat can be used as the promoter.

(v) Enhancer Element Component

Transcription of DNA encoding the antibody polypeptide of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the cytomegalovirus early promoter enhancer, the polyoma enhancer on the late side of the replication origin, and adenovirus enhancers. See also Yaniv, *Nature* 297:17-18 (1982) on enhancing elements for activation of eukaryotic promoters. The enhancer may be spliced into the vector at a position 5' or 3' to the antibody polypeptide-encoding sequence, but is preferably located at a site 5' from the promoter.

(vi) Transcription Termination Component

Expression vectors used in eukaryotic host cells will typically also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

(vii) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al, *J. Gen Virol.* 36:59 (1977)); baby hamster kidney cells (BHK, ATCC CCL 10); Chinese hamster ovary cells/-DHFR (CHO, Urlaub et al., *Proc. Natl. Acad. Sci. USA* 77:4216 (1980)); mouse sertoli cells (TM4, Mather, *Biol. Reprod.* 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., *Annals N.Y. Acad. Sci.* 383:44-68 (1982)); MRC 5 cells; FS4 cells; and a human hepatoma line (Hep G2).

Host cells are transformed with the above-described expression or cloning vectors for antibody production and cultured in conventional nutrient media modified as appropriate for inducing promoters, selecting transformants, or amplifying the genes encoding the desired sequences.

(viii) Culturing the Host Cells

The host cells used to produce an antibody of this invention may be cultured in a variety of media. Commercially available media such as Ham's F10 (Sigma), Minimal Essential Medium ((MEM), (Sigma), RPMI-1640 (Sigma), and Dulbecco's Modified Eagle's Medium ((DMEM), Sigma) are suitable for culturing the host cells. In addition, any of the media described in Ham et al., *Meth. Enz.* 58:44 (1979), Barnes et al., *Anal. Biochem.* 102:255 (1980), U.S. Pat. No. 4,767,704; 4,657,866; 4,927,762; 4,560,655; or 5,122,469; WO 90/03430; WO 87/00195; or U.S. Pat. No. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other necessary supplements may also be included at appropriate concentrations that would be known to those skilled in the art. The culture conditions, such as temperature, pH, and the like, are those previously used with the host cell selected for expression, and will be apparent to the ordinarily skilled artisan.

(ix) Purification of Antibody

When using recombinant techniques, the antibody can be produced intracellularly, or directly secreted into the medium. If the antibody is produced intracellularly, as a first step, the particulate debris, either host cells or lysed fragments, are removed, for example, by centrifugation or ultrafiltration. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immunol. Meth.* 62:1-13 (1983)). Protein G is recommended for all mouse isotypes and for human γ3 (Guss et al., *EMBO J.* 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g., from about 0-0.25M salt).

Activity Assays

The antibodies of the present invention can be characterized for their physical/chemical properties and biological functions by various assays known in the art.

The purified immunoglobulins can be further characterized by a series of assays including, but not limited to, N-terminal sequencing, amino acid analysis, non-denaturing size exclusion high pressure liquid chromatography (HPLC), mass spectrometry, ion exchange chromatography and papain digestion.

In certain embodiments of the invention, the immunoglobulins produced herein are analyzed for their biological activity. In some embodiments, the immunoglobulins of the present invention are tested for their antigen binding activity. The antigen binding assays that are known in the art and can be used herein include without limitation any direct or competitive binding assays using techniques such as western blots, radioimmunoassays, ELISA (enzyme linked immnosorbent assay), "sandwich" immunoassays, immunoprecipitation assays, fluorescent immunoassays, and protein A immunoassays.

In one embodiment, the present invention contemplates an altered antibody that possesses some but not all effector functions, which make it a desired candidate for many applications in which the half life of the antibody in vivo is important yet certain effector functions (such as complement and ADCC) are unnecessary or deleterious. In certain embodiments, the Fc activities of the produced immunoglobulin are measured to ensure that only the desired properties are maintained. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol* 9:457-92 (1991). An example of an in vitro assay to assess ADCC activity of a molecule of interest is described in U.S. Pat. No. 5,500,362 or 5,821,337. Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al *PNAS (USA)* 95:652-656 (1998). C1q binding assays may also be carried out to confirm that the antibody is unable to bind C1q and hence lacks CDC activity. To assess complement activation, a CDC assay, e.g. as described in Gazzano-Santoro et al., *J. Immunol. Methods* 202:163 (1996), may be performed. FcRn binding and in vivo clearance/half life determinations can also be performed using methods known in the art, e.g. those described in the Examples section.

Humanized Antibodies

The present invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al (1986) *Nature* 321:522-525; Riechmann et al. (1988) *Nature* 332:323-327; Verhoeyen et al (1988) *Science* 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework for the humanized antibody (Sims et al (1993) *J. Immunol.* 151:2296; Chothia et al (1987) *J. Mol. Biol* 196:901. Another method uses a particular framework derived from the consensus sequence of all human antibodies of a particular subgroup of light or heavy chains. The same framework may be used for several different humanized antibodies (Carter et al (1992) *Proc. Natl. Acad. Sci. USA,* 89:4285; Presta et al (1993) *J. Immunol,* 151:2623.

It is further important that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

Antibody Variants

In one aspect, the invention provides antibody fragment comprising modifications in the interface of Fc polypeptides comprising the Fc region, wherein the modifications facilitate and/or promote heterodimerization. These modifications comprise introduction of a protuberance into a first Fc polypeptide and a cavity into a second Fc polypeptide, wherein the protuberance is positionable in the cavity so as to promote complexing of the first and second Fc polypeptides. Methods of generating antibodies with these modifications are known in the art, e.g., as described in U.S. Pat. No. 5,731,168.

In some embodiments, amino acid sequence modification(s) of the antibodies described herein are contemplated. For example, it may be desirable to improve the binding affinity and/or other biological properties of the antibody. Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) *Science*, 244: 1081-1085. Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in Table 2 under the heading of "preferred substitutions". If such substitutions result in a change in biological activity, then more substantial changes, denominated "exemplary substitutions" in the table below, or as further described below in reference to amino acid classes, may be introduced and the products screened.

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, in Biochemistry, second ed., pp. 73-75, Worth Publishers, New York (1975)):
(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:
 (1) hydrophobic: Norleucine, Met, Ala, Val, Leu, Ile;
 (2) neutral hydrophilic: Cys, Ser, Thr, Asn, Gln;
 (3) acidic: Asp, Glu;
 (4) basic: His, Lys, Arg;
 (5) residues that influence chain orientation: Gly, Pro;
 (6) aromatic: Trp, Tyr, Phe.

Non-conservative substitutions will entail exchanging a member of one of these classes for another class. Such substituted residues also may be introduced into the conservative substitution sites or, more preferably, into the remaining (non-conserved) sites.

One type of substitutional variant involves substituting one or more hypervariable region residues of a parent antibody (e.g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g. 6-7 sites) are mutated to generate all possible amino acid substitutions at each site. The antibodies thus generated are displayed from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of the immunoglobulin polypeptides of the invention, thereby generating a Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions including that of a hinge cysteine.

In accordance with this description and the teachings of the art, it is contemplated that in some embodiments, an antibody used in methods of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter *Nature* 322:738-40 (1988); U.S. Pat. No. 5,648,260; U.S. Pat. No. 5,624,821; and WO94/29351 concerning other examples of Fc region variants.

Immunoconjugates

The invention also pertains to immunoconjugates, or antibody-drug conjugates (ADC), comprising an antibody conjugated to a cytotoxic agent such as a chemotherapeutic agent, a drug, a growth inhibitory agent, a toxin (e.g., an enzymatically active toxin of bacterial, fungal, plant, or animal origin, or fragments thereof), or a radioactive isotope (i.e., a radioconjugate).

The use of antibody-drug conjugates for the local delivery of cytotoxic or cytostatic agents, i.e. drugs to kill or inhibit tumor cells in the treatment of cancer (Syrigos and Epenetos (1999) Anticancer Research 19:605-614; Niculescu-Duvaz and Springer (1997) Adv. Drg Del. Rev. 26:151-172; U.S. Pat. No. 4,975,278) theoretically allows targeted delivery of the drug moiety to tumors, and intracellular accumulation therein, where systemic administration of these unconjugated drug agents may result in unacceptable levels of toxicity to normal cells as well as the tumor cells sought to be eliminated (Baldwin et al., (1986) Lancet pp. (Mar. 15, 1986):603-05; Thorpe, (1985) "Antibody Carriers Of Cytotoxic Agents In Cancer Therapy: A Review," in Monoclonal Antibodies '84: Biological And Clinical Applications, A. Pinchera et al. (ed.s), pp. 475-506). Maximal efficacy with minimal toxicity is sought thereby. Both polyclonal antibodies and monoclonal antibodies have been reported as useful in these strategies (Rowland et al., (1986) Cancer Immunol. Immunother., 21:183-87). Drugs used in these methods include daunomycin, doxorubicin, methotrexate, and vindesine (Rowland et al., (1986) supra). Toxins used in antibody-toxin conjugates include bacterial toxins such as diphtheria toxin, plant toxins such as ricin, small molecule toxins such as geldanamycin (Mandler et al (2000) Jour. of the Nat. Cancer Inst. 92(19):1573-1581; Mandler et al (2000) Bioorganic & Med. Chem. Letters 10:1025-1028; Mandler et al (2002) Bioconjugate Chem. 13:786-791), maytansinoids (EP 1391213; Liu et al., (1996) Proc. Natl. Acad. Sci. USA 93:8618-8623), and calicheamicin (Lode et al (1998) Cancer Res. 58:2928; Hinman et al (1993) Cancer Res. 53:3336-3342). The toxins may effect their cytotoxic and cytostatic effects by mechanisms including tubulin binding, DNA binding, or topoisomerase inhibition. Some cytotoxic drugs tend to be inactive or less active when conjugated to large antibodies or protein receptor ligands.

ZEVALIN® (ibritumomab tiuxetan, Biogen/Idec) is an antibody-radioisotope conjugate composed of a murine IgG1 kappa monoclonal antibody directed against the CD20 antigen found on the surface of normal and malignant B lymphocytes and $^{111}$In or $^{90}$Y radioisotope bound by a thiourea linker-chelator (Wiseman et al (2000) Eur. Jour. Nucl. Med. 27(7):766-77; Wiseman et al (2002) Blood 99(12):4336-42; Witzig et al (2002) J. Clin. Oncol. 20(10):2453-63; Witzig et al (2002) J. Clin. Oncol. 20(15):3262-69). Although ZEVALIN has activity against B-cell non-Hodgkin's Lymphoma (NHL), administration results in severe and prolonged cytopenias in most patients. MYLOTARG™ (gemtuzumab ozogamicin, Wyeth Pharmaceuticals), an antibody drug conjugate composed of a huCD33 antibody linked to calicheamicin, was approved in 2000 for the treatment of acute myeloid leukemia by injection (Drugs of the Future (2000) 25(7):686; U.S. Pat. Nos. 4,970,198; 5,079,233; 5,585,089; 5,606,040; 5,693,762; 5,739,116; 5,767,285; 5,773,001). Cantuzumab mertansine (Immunogen, Inc.), an antibody drug conjugate composed of the huC242 antibody linked via the disulfide linker SPP to the maytansinoid drug moiety, DM1, is advancing into Phase II trials for the treatment of cancers that express CanAg, such as colon, pancreatic, gastric, and others. MLN-2704 (Millennium Pharm., BZL Biologics, Immunogen Inc.), an antibody drug conjugate composed of the anti-prostate specific membrane antigen (PSMA) monoclonal antibody linked to the maytansinoid drug moiety, DM1, is under development for the potential treatment of prostate tumors. The auristatin peptides, auristatin E (AE) and monomethylauristatin (MMAE), synthetic analogs of dolastatin, were conjugated to chimeric monoclonal antibodies cBR96 (specific to Lewis Y on carcinomas) and cAC10 (specific to CD30 on hematological malignancies) (Doronina et al (2003) Nature Biotechnology 21(7):778-784) and are under therapeutic development.

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}$Bi, $^{131}$I, $^{131}$In, $^{90}$Y, and $^{186}$Re. Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al, *Science,* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

Conjugates of an antibody and one or more small molecule toxins, such as a calicheamicin, maytansinoids, a trichothecene, and CC1065, and the derivatives of these toxins that have toxin activity, are also contemplated herein.

Maytansine and Maytansinoids

In one embodiment, an antibody (full length or fragments) of the invention is conjugated to one or more maytansinoid molecules.

Maytansinoids are mitototic inhibitors which act by inhibiting tubulin polymerization. Maytansine was first isolated from the east African shrub *Maytenus serrata* (U.S. Pat. No. 3,896,111). Subsequently, it was discovered that certain microbes also produce maytansinoids, such as maytansinol and C-3 maytansinol esters (U.S. Pat. No. 4,151,042). Synthetic maytansinol and derivatives and analogues thereof are disclosed, for example, in U.S. Pat. Nos. 4,137,230; 4,248,870; 4,256,746; 4,260,608; 4,265,814; 4,294,757; 4,307,016; 4,308,268; 4,308,269; 4,309,428; 4,313,946; 4,315,929; 4,317,821; 4,322,348; 4,331,598; 4,361,650; 4,364,866; 4,424,219; 4,450,254; 4,362,663; and 4,371,533, the disclosures of which are hereby expressly incorporated by reference.

Maytansinoid-Antibody Conjugates

In an attempt to improve their therapeutic index, maytansine and maytansinoids have been conjugated to antibodies specifically binding to tumor cell antigens. Immunoconjugates containing maytansinoids and their therapeutic use are disclosed, for example, in U.S. Pat. Nos. 5,208,020, 5,416,064 and European Patent EP 0 425 235 B1, the disclosures of which are hereby expressly incorporated by reference. Liu et al., *Proc. Natl. Acad. Sci. USA* 93:8618-8623 (1996) described immunoconjugates comprising a maytansinoid designated DM1 linked to the monoclonal antibody C242 directed against human colorectal cancer. The conjugate was found to be highly cytotoxic towards cultured colon cancer cells, and showed antitumor activity in an in vivo tumor growth assay. Chari et al., *Cancer Research* 52:127-131 (1992) describe immunoconjugates in which a maytansinoid was conjugated via a disulfide linker to the murine antibody A7 binding to an antigen on human colon cancer cell lines, or to another murine monoclonal antibody TA.1 that binds the HER-2/neu oncogene. The cytotoxicity of the TA.1-maytansonoid conjugate was tested in vitro on the human breast cancer cell line SK-BR-3, which expresses $3 \times 10^5$ HER-2 surface antigens per cell. The drug conjugate achieved a degree of cytotoxicity similar to the free maytansinoid drug, which could be increased by increasing the number of maytansinoid molecules per antibody molecule. The A7-maytansinoid conjugate showed low systemic cytotoxicity in mice.

Antibody-Maytansinoid Conjugates (Immunoconjugates)

Antibody-maytansinoid conjugates are prepared by chemically linking an antibody to a maytansinoid molecule without significantly diminishing the biological activity of either the antibody or the maytansinoid molecule. An average of 3-4 maytansinoid molecules conjugated per antibody molecule has shown efficacy in enhancing cytotoxicity of target cells without negatively affecting the function or solubility of the antibody, although even one molecule of toxin/antibody would be expected to enhance cytotoxicity over the use of naked antibody. Maytansinoids are well known in the art and can be synthesized by known techniques or isolated from natural sources. Suitable maytansinoids are disclosed, for example, in U.S. Pat. No. 5,208,020 and in the other patents and nonpatent publications referred to hereinabove. Preferred maytansinoids are maytansinol and maytansinol analogues modified in the aromatic ring or at other positions of the maytansinol molecule, such as various maytansinol esters.

There are many linking groups known in the art for making antibody-maytansinoid conjugates, including, for example, those disclosed in U.S. Pat. No. 5,208,020 or EP Patent 0 425 235 B1, and Chari et al., *Cancer Research* 52:127-131 (1992). The linking groups include disulfide groups, thioether groups, acid labile groups, photolabile groups, peptidase labile groups, or esterase labile groups, as disclosed in the above-identified patents, disulfide and thioether groups being preferred.

Conjugates of the antibody and maytansinoid may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). Particularly preferred coupling agents include N-succinimidyl-3-(2-pyridyldithio)propionate (SPDP) (Carlsson et al., *Biochem. J.* 173:723-737 [1978]) and N-succinimidyl-4-(2-pyridylthio)pentanoate (SPP) to provide for a disulfide linkage.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Calicheamicin

Another immunoconjugate of interest comprises an antibody conjugated to one or more calicheamicin molecules. The calicheamicin family of antibiotics are capable of producing double-stranded DNA breaks at sub-picomolar concentrations. For the preparation of conjugates of the calicheamicin family, see U.S. Pat. Nos. 5,712,374, 5,714,586, 5,739,116, 5,767,285, 5,770,701, 5,770,710, 5,773,001, 5,877,296 (all to American Cyanamid Company). Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$ (Hinman et al., *Cancer Research* 53:3336-3342 (1993), Lode et al., *Cancer Research* 58:2925-2928 (1998) and the aforementioned U.S. patents to American Cyanamid). Another anti-tumor drug that the antibody can be conjugated is QFA which is an antifolate. Both calicheamicin and QFA have intracellular sites of action and do not readily cross the plasma membrane. Therefore, cellular uptake of these agents through antibody mediated internalization greatly enhances their cytotoxic effects.

Other Cytotoxic Agents

Other antitumor agents that can be conjugated to the antibodies of the invention include BCNU, streptozoicin, vincristine and 5-fluorouracil, the family of agents known collectively LL-E33288 complex described in U.S. Pat. Nos. 5,053, 394, 5,770,710, as well as esperamicins (U.S. Pat. No. 5,877, 296).

Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin and the tricothecenes. See, for example, WO 93/21232 published Oct. 28, 1993.

The present invention further contemplates an immunoconjugate formed between an antibody and a compound with nucleolytic activity (e.g., a ribonuclease or a DNA endonuclease such as a deoxyribonuclease; DNase).

For selective destruction of the tumor, the antibody may comprise a highly radioactive atom. A variety of radioactive isotopes are available for the production of radioconjugated antibodies. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the conjugate is used for detection, it may comprise a radioactive atom for scintigraphic studies, for example $tc^{99m}$ or $I^{123}$, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

The radio—or other labels may be incorporated in the conjugate in known ways. For example, the peptide may be biosynthesized or may be synthesized by chemical amino acid synthesis using suitable amino acid precursors involving, for example, fluorine-19 in place of hydrogen. Labels such as $tc^{99m}$ or $I^{123}$, $Re^{186}$, $Re^{188}$ and $In^{111}$ can be attached via a cysteine residue in the peptide. Yttrium-90 can be attached via a lysine residue. The IODOGEN method (Fraker et al (1978) Biochem. Biophys. Res. Commun. 80: 49-57 can be used to incorporate iodine-123. "Monoclonal Antibodies in Immunoscintigraphy" (Chatal, CRC Press 1989) describes other methods in detail.

Conjugates of the antibody and cytotoxic agent may be made using a variety of bifunctional protein coupling agents such as N-succinimidyl-3-(2-pyridyldithio)propionate (SPDP), succinimidyl-4-(N-maleimidomethyl)cyclohexane-1-carboxylate, iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl)hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of the cytotoxic drug in the cell. For example, an acid-labile linker, peptidase-sensitive linker, photolabile linker, dimethyl linker or disulfide-containing linker (Chari et al., *Cancer Research* 52:127-131 (1992); U.S. Pat. No. 5,208, 020) may be used.

The compounds of the invention expressly contemplate, but are not limited to, ADC prepared with cross-linker reagents: BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A). See pages 467-498, 2003-2004 Applications Handbook and Catalog.

Preparation of Antibody Drug Conjugates

In the antibody drug conjugates (ADC) of the invention, an antibody (Ab) is conjugated to one or more drug moieties (D), e.g. about 1 to about 20 drug moieties per antibody, through a linker (L). The ADC of Formula I may be prepared by several routes, employing organic chemistry reactions, conditions, and reagents known to those skilled in the art, including: (1) reaction of a nucleophilic group of an antibody with a bivalent linker reagent, to form Ab-L, via a covalent bond, followed by reaction with a drug moiety D; and (2) reaction of a nucleophilic group of a drug moiety with a bivalent linker reagent, to form D-L, via a covalent bond, followed by reaction with the nucleophilic group of an antibody.

$$Ab\text{-}(L\text{-}D)_p \qquad \qquad I$$

Nucleophilic groups on antibodies include, but are not limited to: (i) N-terminal amine groups, (ii) side chain amine groups, e.g. lysine, (iii) side chain thiol groups, e.g. cysteine, and (iv) sugar hydroxyl or amino groups where the antibody is glycosylated. Amine, thiol, and hydroxyl groups are nucleophilic and capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups. Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol.

Antibody drug conjugates of the invention may also be produced by modification of the antibody to introduce electrophilic moieties, which can react with nucleophilic substituents on the linker reagent or drug. The sugars of glycosylated antibodies may be oxidized, e.g. with periodate oxidizing reagents, to form aldehyde or ketone groups which may react with the amine group of linker reagents or drug moieties. The resulting imine Schiff base groups may form a stable linkage, or may be reduced, e.g. by borohydride reagents to form stable amine linkages. In one embodiment, reaction of the carbohydrate portion of a glycosylated antibody with either galactose oxidase or sodium meta-periodate may yield carbonyl (aldehyde and ketone) groups in the protein that can react with appropriate groups on the drug (Hermanson, *Bioconjugate Techniques*). In another embodiment, proteins containing N-terminal serine or threonine residues can react with sodium meta-periodate, resulting in production of an aldehyde in place of the first amino acid (Geoghegan & Stroh, (1992) Bioconjugate Chem. 3:138-146; U.S. Pat. No. 5,362,852). Such aldehyde can be reacted with a drug moiety or linker nucleophile.

Likewise, nucleophilic groups on a drug moiety include, but are not limited to: amine, thiol, hydroxyl, hydrazide, oxime, hydrazine, thiosemicarbazone, hydrazine carboxylate, and arylhydrazide groups capable of reacting to form covalent bonds with electrophilic groups on linker moieties and linker reagents including: (i) active esters such as NHS esters, HOBt esters, haloformates, and acid halides; (ii) alkyl and benzyl halides such as haloacetamides; (iii) aldehydes, ketones, carboxyl, and maleimide groups.

Alternatively, a fusion protein comprising the antibody and cytotoxic agent may be made, e.g., by recombinant techniques or peptide synthesis. The length of DNA may comprise respective regions encoding the two portions of the conjugate either adjacent one another or separated by a region encoding a linker peptide which does not destroy the desired properties of the conjugate.

In yet another embodiment, the antibody may be conjugated to a "receptor" (such streptavidin) for utilization in tumor pre-targeting wherein the antibody-receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

Antibody Derivatives

The antibodies of the present invention can be further modified to contain additional nonproteinaceous moieties that are known in the art and readily available. Preferably, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly (n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymers are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

Pharmaceutical Formulations

Therapeutic formulations comprising an antibody of the invention are prepared for storage by mixing the antibody having the desired degree of purity with optional physiologically acceptable carriers, excipients or stabilizers (*Remington's Pharmaceutical Sciences* 16th edition, Osol, A. Ed. (1980)), in the form of aqueous solutions, lyophilized or other dried formulations. Acceptable carriers, excipients, or stabilizers are nontoxic to recipients at the dosages and concentrations employed, and include buffers such as phosphate, citrate, histidine and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. Such molecules are suitably present in combination in amounts that are effective for the purpose intended.

The active ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the immunoglobulin of the invention, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and $\gamma$ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods. When encapsulated immunoglobulins remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

Uses

An antibody of the present invention may be used in, for example, in vitro, ex vivo and in vivo therapeutic methods.

Antibodies of the invention can be used as an antagonist to partially or fully block the specific antigen activity in vitro, ex vivo and/or in vivo. Moreover, at least some of the antibodies of the invention can neutralize antigen activity from other species. Accordingly, the antibodies of the invention can be used to inhibit a specific antigen activity, e.g., in a cell culture containing the antigen, in human subjects or in other mammalian subjects having the antigen with which an antibody of the invention cross-reacts (e.g. chimpanzee, baboon, marmoset, cynomolgus and rhesus, pig or mouse). In one embodiment, the antibody of the invention can be used for inhibiting antigen activities by contacting the antibody with the antigen such that antigen activity is inhibited. Preferably, the antigen is a human protein molecule.

In one embodiment, an antibody of the invention can be used in a method for inhibiting an antigen in a subject suffering from a disorder in which the antigen activity is detrimental, comprising administering to the subject an antibody of the invention such that the antigen activity in the subject is inhibited. Preferably, the antigen is a human protein molecule and the subject is a human subject. Alternatively, the subject can be a mammal expressing the antigen with which an antibody of the invention binds. Still further the subject can be a mammal into which the antigen has been introduced (e.g., by administration of the antigen or by expression of an antigen transgene). An antibody of the invention can be administered to a human subject for therapeutic purposes. Moreover, an antibody of the invention can be administered to a non-human mammal expressing an antigen with which the immunoglobulin cross-reacts (e.g., a primate, pig or mouse) for veterinary purposes or as an animal model of human disease. Regarding the latter, such animal models may be useful for evaluating the therapeutic efficacy of antibodies of the invention (e.g., testing of dosages and time courses of administration). Blocking antibodies of the invention that are therapeutically useful include, for example but are not limited to, anti-HER2, anti-VEGF, anti-IgE, anti-CD11, anti-interferon, anti-interferon receptor, anti-hepatocyte growth factor (HGF), anti-c-met, and anti-tissue factor antibodies. The antibodies of the invention can be used to treat, inhibit, delay progression of, prevent/delay recurrence of, ameliorate, or prevent diseases, disorders or conditions associated with abnormal expression and/or activity of one or more antigen molecules, including but not limited to malignant and benign tumors; non-leukemias and lymphoid malignancies; neuronal, glial, astrocytal, hypothalamic and other glandular, macrophagal, epithelial, stromal and blastocoelic disorders; and inflammatory, angiogenic and immunologic disorders.

In one aspect, a blocking antibody of the invention is specific to a ligand antigen, and inhibits the antigen activity by blocking or interfering with the ligand-receptor interaction involving the ligand antigen, thereby inhibiting the corresponding signal pathway and other molecular or cellular events. The invention also features receptor-specific antibodies which do not necessarily prevent ligand binding but interfere with receptor activation, thereby inhibiting any responses that would normally be initiated by the ligand binding. The invention also encompasses antibodies that either preferably or exclusively bind to ligand-receptor complexes. An antibody of the invention can also act as an agonist of a particular antigen receptor, thereby potentiating, enhancing or activating either all or partial activities of the ligand-mediated receptor activation.

In certain embodiments, an immunoconjugate comprising an antibody conjugated with a cytotoxic agent is administered to the patient. In some embodiments, the immunoconjugate and/or antigen to which it is bound is/are internalized by the cell, resulting in increased therapeutic efficacy of the immunoconjugate in killing the target cell to which it binds. In one embodiment, the cytotoxic agent targets or interferes with nucleic acid in the target cell. Examples of such cytotoxic agents include any of the chemotherapeutic agents noted herein (such as a maytansinoid or a calicheamicin), a radioactive isotope, or a ribonuclease or a DNA endonuclease.

Antibodies of the invention can be used either alone or in combination with other compositions in a therapy. For instance, an antibody of the invention may be co-administered with another antibody, chemotherapeutic agent(s) (including cocktails of chemotherapeutic agents), other cytotoxic agent(s), anti-angiogenic agent(s), cytokines, and/or growth inhibitory agent(s). Where an antibody of the invention inhibits tumor growth, it may be particularly desirable to combine it with one or more other therapeutic agent(s) which also inhibits tumor growth. For instance, an antibody of the invention may be combined with an anti-VEGF antibody (e.g., AVASTIN) and/or anti-ErbB antibodies (e.g. HERCEPTIN® anti-HER2 antibody) in a treatment scheme, e.g. in treating any of the diseases described herein, including colorectal cancer, metastatic breast cancer and kidney cancer. Alternatively, or additionally, the patient may receive combined radiation therapy (e.g. external beam irradiation or therapy with a radioactive labeled agent, such as an antibody). Such combined therapies noted above include combined administration (where the two or more agents are included in the same or separate formulations), and separate administration, in which case, administration of the antibody of the invention can occur prior to, and/or following, administration of the adjunct therapy or therapies.

The antibody of the invention (and adjunct therapeutic agent) is/are administered by any suitable means, including parenteral, subcutaneous, intraperitoneal, intrapulmonary, and intranasal, and, if desired for local treatment, intralesional administration. Parenteral infusions include intramuscular, intravenous, intraarterial, intraperitoneal, or subcutaneous administration. In addition, the antibody is suitably administered by pulse infusion, particularly with declining doses of the antibody. Dosing can be by any suitable route, e.g. by injections, such as intravenous or subcutaneous injections, depending in part on whether the administration is brief or chronic.

The antibody composition of the invention will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibodies of the invention present in the formulation, the type of disorder or treatment, and other factors discussed above. These are generally used in the same dosages and with administration routes as used hereinbefore or about from 1 to 99% of the heretofore employed dosages.

For the prevention or treatment of disease, the appropriate dosage of an antibody of the invention (when used alone or in combination with other agents such as chemotherapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 μg/kg to 15 mg/kg (e.g. 0.1 mg/kg-10 mg/kg) of antibody is an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, etc. The containers may be formed from a variety of materials such as glass or plastic. The container holds a composition which is by itself or when combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice, such as cancer. Moreover, the article of manufacture may comprise (a) a first container with a composition contained therein, wherein the composition comprises an antibody of the invention; and (b) a second container with a composition contained therein, wherein the composition comprises a further cytotoxic agent. The article of manufacture in this embodiment of the invention may further comprise a package insert indicating that the first and second antibody compositions can be used to treat a particular condition, e.g. cancer. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

All publications (including patents and patent applications) cited herein are hereby incorporated in their entirety by reference.

EXAMPLES

The performance and quality of any library (e.g., phage displayed library), measured by the affinities and designed function of derived binder members (e.g., antibodies) of the library, is determined in large part by the library sizes, which is in turn limited by the efficiencies of the transformation of the library DNA into *Escherichia coli*. As a result, it has been observed that art libraries that have been successful sources of binder polypeptides with respect to many target antigens, have nevertheless not been successful for all target antigens despite extensive screening efforts. To address this lack of success, and based in part on new insights into the diversity of human antibodies, and success in reducing codon redundancy and increasing efficiency of mutagenesis, we have designed and engineered a novel and high-quality set of synthetic phage antibody libraries. These libraries, also referred to as VH/VL libraries, can be based on a single template sequence, for example that of humanized antibody 4D5-8, which is known to display well on phage surface, as well as being capable of being expressed as Fab (or other antibody fragment) or full length antibody (e.g., IgG). In one embodiment, the template HVRs were substituted with consensus sequences to avoid biasing binding characteristics of polypeptides toward particular antigens (e.g., antigens that share similarity with the target antigen of 4D5-8). Without being bound by theory, it is believed that the loops of HVR-H1, -H2, -H3 and -L3 are in close proximity, and are critical for antigen binding. Accordingly, in the libraries described herein, a subset of positions in HVR-H1, -H2, -H3 and -L3 (also referred to as CDR-H1, -H2, -H3 and -L3, respectively, hereinbelow) were chosen for diversification using criteria of high solvent exposure and/or especially high variability among natural antibody sequences. The design of the diversity was to mimic to the extent possible the natural diversity of human immunoglobulin. To improve the efficiency of mutagenesis (e.g., Kunkel mutagenesis) while minimizing background noise due to recovery of unmutagenized template sequences, stop codons were introduced in a limited number of HVRs, for example only in HVR-H3.

Materials and Methods

Materials

Enzymes and M13-KO7 helper phage were from New England Biolabs. *E. coli* XL-1 Blue was from Stratagene (La Jolla, Calif.). 96-well Maxisorp immunoplates were from NUNC (Roskilde, Denmark). Bovine serum albumin (BSA), Tween 20 and anti-human IgG-conjugated horseradish peroxidase (HRP) were from Sigma (St. Louis, Mo.). Neutravidin, casein, streptavidin conjugated HRP and Superblock were from Pierce (Rockford, Ill.). Anti-M13 conjugated HRP was from Amersham Pharmacia (Piscataway, N.J.). Tetramethylbenzidine (TMB) substrate was from Kirkegaard and Perry Laboratories (Gaithersburg, Md.). Carboxymethylated dextran biosensor chips (CM5), N-ethyl-N'-(3-dimethylaminopropyl)-carbodiimide hydrochloride (EDC), N-hydroxysuccinimide (NHS), and ethanolamine for BIAcore analysis were from BIAcore, Inc. (Piscataway, N.J.). Cell dissociation buffer and PE-Fab'$_2$ goat anti-human IgG, Fc specific antibody for flow cytometry was from Gibco (Gaithersburg, Md.) and ImmunoResearch Laboratories (West Grove, Pa.), respectively. Equimolar DNA degeneracies are represented in the IUB code (B=C/G/T, D=A/G/T, M=A/C, N=A/C/G/T, R=A/G, S=G/C, W=A/T). The trimer phosphoramidites (trinucleotide codon) reagents were from Glen Research (Sterling, Va.). Target antigens (hereinafter "TA") and oligonucleotides were generated according to standard molecular biology techniques (Genentech, Inc., South San Francisco, Calif.). VH/VL naïve library construction—The VH/VL naïve library template comprising consensus CDR-L1, -L2, -L3, -H1 and -H2 was generated using oligonucleotide-directed mutagenesis on phagemid pV0350-4 with stop codons on CDR-H3 and displaying bivalent on the surfaces of M13 bacteriophage particles (11). Phage-displayed libraries were constructed using Kunkel mutagenesis method as described (26), with a mixture of mutagenic oligonucleotides designed to introduce mutations at the designed sites in CDR-L3, H1, H2 and H3 and repair CDR-H3 stop codons. The mutagenesis reactions (~10 μg DNA) were electroporated into *E. coli* SS320 cells (~10$^{11}$ cells), as previously described (10).

Library Sorting and Screening to Identify Anti-TA Antibodies

Human and murine TA-coding sequences were cloned into mammalian expression vector, and expressed in CHO cells. Truncated forms of the TA were expressed in baculovirus. NUNC 96 well Maxisorp immunoplates were coated overnight at 4° C. with TA (10 ug/ml) and were blocked for 1 hr at room temperature (RT) with phage blocking buffer PBST (PBS and 1% BSA and 0.05% Tween 20). The antibody phage libraries were added to antigen plates and incubated overnight at RT. The following day antigen-coated plates were washed 10 times with PBT (PBS with 0.05% T-20), and bound phage were eluted with 50 mM HCl and 500 mM NaCl for 30 minutes and neutralized with equal volume of 1M Tris base pH7.5. Recovered phage was amplified in *E. coli* XL-1 Blue cells. During the subsequent selection rounds, incubation of antibody phage with the antigen-coated plates was reduced to 2-3 hours, and the stringency of plate washing was gradually increased (to 30× washes (2$^{nd}$ round), 40× washes (3$^{rd}$ round), and 40× washes plus 1 hr wash at RT (4th round). Eluted phage from the third and fourth rounds was titered on 2YT/carbenicillin/tetracycline agar plates to determine antigen specific enrichment.

Randomly-picked 96 clones selected from the 4$^{th}$ round were assayed using a high-throughput phage ELISA to check binding to TA, an anti-gD antibody, and two non-relevant proteins (BSA and a commercially available anti-IgE antibody). Only clones with specific binding to TA and anti-gD antibody were subjected to DNA sequence analysis of V$_L$ and V$_H$ region.

Binding Affinities, Specificity and Flow Cytometry Analysis of Anti-TA Antibodies Phage antibody IC$_{50}$ values were determined using competitive phage-binding ELISA as described (11). Competition curves were fit with a four-parameter non-linear regression curve-fitting program (Kaleidagraph, Synergy Software) to determine the IC$_{50}$ values which were calculated as the concentration of antigen in solution binding stage that inhibited 50% of the phage-displayed antibody from binding to immobilized antigen.

Clones of interest were then reformatted into IgGs by cloning V$_L$ and V$_H$ region of individual clones into LPG3 and LPG4 vector respectively (12), transiently expressed in mammalian cells, and purified with protein A columns. For binding affinity determinations of anti-TA IgGs, Surface Plasmon Resonance (SPR) measurement with a BIAcore™-3000 instrument was used. Anti-TA IgGs were coupled to activated CM5 biosensor chips to achieve approximately 500 response units (RU), followed by blocking un-reacted groups with 1M ethanolamine. For kinetic measurements, two-fold serial dilutions of TA (0.7 to 500 nM) were injected in PBST buffer at 25° C. with a flow rate of 30 μl/min. Association rates (k$_{on}$) and dissociation rates (k$_{off}$) were calculated using a simple one-to-one Langmuir binding model (BIAcore Evaluation Software version 3.2). The equilibrium dissociation constant (Kd) was calculated as the ratio k$_{off}$/k$_{on}$.

For binding specificity tests, 10 μg/ml of IgGs in PBST buffer was incubated with 2 μg/ml antigen-coated 96-well Maxisorp plates for at least 1 hr, and the plates were washed with PBT buffer. Bound antibodies were detected with anti-human antibody HRP conjugates, developed with TMB substrate for approximately 5 minutes, quenched with 1M H$_3$PO$_4$, and read spectrophotometrically at 450 nm.

For flow cytometry analysis, HUVEC cells were detached from the tissue culture flasks with cell dissociation buffer. Dissociated cells were washed in PBS and re-suspended in PBS containing 2% Fetal Bovine Serum (FACS buffer). Cells were incubated with 10 ug/ml anti-TA antibodies or control antibody (a commercially available anti-IgE antibody) in FACS buffer on ice for 30 minutes. Cells were then washed twice in PBS, and stained in FACS buffer with PE-Fab'$_2$ goat anti-human IgG, Fc specific antibody on ice for 30 minutes. Following two PBS washes, the cells were re-suspended in 200 μl FACS buffer and analyzed by flow cytometry (FACS caliber, Benton Dickenson, Mountain View, Calif.) using Cell-Quest software.

Blocking Function in Binding Assay

To evaluate anti-TA antibodies' ability to block the TA from binding its ligand, three-fold serial dilutions of antibodies were first incubated with 96-well Maxisorp plate coated TA (5 ug/ml) in PBST buffer for 1-2 hr, followed by adding biotinylated 1 nM ligand for 15 minutes. The amount of biotinylated ligand binding to TA was detected by streptavidin-HRP conjugates.

Affinity Maturation of Clone X of Anti-TA Antibody

To generate the library template for affinity maturation of clone X (one of the selected anti-TA antibody clones), the GCN4 leucine zipper of the parental phagemid was first removed using Kunkel mutagenesis to provide a monovalent display Fab format. A stop codon was incorporated in CDR-L3. A soft randomization strategy was used for affinity maturation, which introduced the mutation rate of approximately 50% at the selected positions by the mutagenic DNA synthesized with 70-10-10-10 (%) mixtures of bases favoring the wild type nucleotides (27). Three different libraries with combinations of CDR loops, L1/L2/L3, L3/H1/H2 and L3/H3 randomization, were generated through soft randomizing selected residues at positions 28-32 of CDR-L1; 50 and 53-55 of CDR-L2; 91, 92, 93, 94 and 96 of CDR-L3; 28-35 of CDR-H1; 50-58 of CDR-H2; and 95-100 of CDR-H3.

For selecting affinity-matured clones, phage libraries were subjected to plate sorting for the first round and followed by four rounds of solution phase sorting as previously described (11). At the first round of plate sorting, three libraries were added to TA-coated plate separately for 1 hr at 37° C. After that, four rounds of solution phase sorting were performed to enhance the efficiency of affinity-based selection with increasing stringency as follows: round 2 (5 nM biotinylated TA), round 3 (1 nM biotinylated TA), round 4 (0.5 nM biotinylated TA and 250 nM non-biotinylated TA competitor at 37° C. for 1 hr) and round 5 (0.5 nM biotinylated TA and 500 nM non-biotinylated TA competitor at 37° C. for 3 hr). During the selection process, the reaction without biotinylated TA was included and served as background phage binding for calculating the enrichment of each round of panning.

After five rounds of panning, a high-throughput single-point competitive phage ELISA was used to rapidly screen for high-affinity clones as described (10). Clones with low ratio of the absorbance at 450 nm in the presence of 5 nM TA to that in the absence of TA were chosen for further characterization.

Results

VH/VL Antibody Phage Libraries Design and Construction

The VH/VL library described here utilized the rhuMAb4D5-8-derived VL$_{kappa}$ and VH$_{subgroup\ III}$ framework, which has been shown to display well on bacteriophage, express well in E. coli, and which can rapidly be converted to a full length IgG that expresses well in mammalian cells (11, 12). The libraries were displayed on the phage surface as a bivalent Fab by being fused to the phage coat protein P3. This bivalent display was intended to increase the apparent binding affinities to immobilized antigens and help to improve the recovery of rare and/or low-affinity phage antibody clones.

To avoid potential biases inherited from the rhuMAB4D5-8-derived CDR sequences maintained in the light chain of the VH library, consensus kappa I CDR sequences were introduced into the template for the VH/VL library. Consensus CDR residues are determined by selecting the most prevalent amino acids existing in natural human antibodies. The stop codons, previously employed in the heavy chain of a "VH" library to ensure mutagenesis in all 3 CDRs (11), were similarly replaced with consensus subgroup III sequences for CDR-H1 and CDR-H2. The consensus CDR sequences represent the most prevalent amino acid in each position (FIG. 1B). CDR-H3 plays a dominant role in antigen recognition, thus several stop codons were placed in H3 to ensure functional antibody clones from the libraries were different from each other (28). The presence of human consensus CDR sequences was expected to allow partially mutated variants (not all targeted CDRs are changed) to be displayed and to remain potentially functional in binding. In this way the VH/VL design has the advantage of increasing the ratio of functional phage antibody clones in the library. The CDR sequences used were SISSYL (SEQ ID NO: 75) for CDR-L1 (positions 28-33), GASSRA (SEQ ID NO: 76) for CDR-L2 (positions 50-55), YYSSPL (SEQ ID NO: 77) for CDR-L3 (positions 91-96), FTFSSYAMS (SEQ ID NO: 78) for CDR-H1 (positions 27-35), and RISPSGGSTY (SEQ ID NO: 79) for CDR-H2 (positions 50-58), and WXXXRPXXMDY (SEQ ID NO: 80) for CDR-H3 (positions 95-102, X is a stop codon) as shown in FIG. 1B. The prevalence of each position in human antibodies is also shown in FIG. 1B.

Diversity in the VH/VL library was introduced into a subset of CDR positions based on their high solvent exposure and/or especially high variability among natural antibody sequences. Positions chosen for mutagenesis and the diversity that was introduced are shown in FIG. 4C. For example, in CDR-H1, position 27, 28, 30, 31, 32, 33 and 34 were chosen for diversification. For the VH/VL library design, degenerate oligo codons or trinucleotides were used to guide the diversity in each position so that the most prevalent amino acids would be represented. In CDR-H1 (position 30), serine represents about 50% of natural diversity, so a mixture of trinucleotides (X1) that have ca. 52% serine and 2.5% of each 19 amino acids except cysteine were used (FIG. 4B).

CDR-H3 and CDR-L3 form the center of the antigen-binding site and therefore show the highest frequency of antigen contacts in structurally known antibody-antigen complexes (29). Five residues in CDR-L3 (FIG. 4C) with the highest variability were randomized. Overall CDR-H3 is the most diverse in terms of length, sequence, and structure and is a key component of the diversity in natural antibodies (28, 30). Thus 12 sub-libraries were constructed with different CDR-H3 lengths varying from 9 to 20 amino acids. Combined, these sub-libraries cover approximately 90% of CDR-H3 length variation in natural antibodies. Oligonucleotides encoding CDR-H3 were synthesized using trinucleotide codons. This enabled us to easily delete cysteine (rare in CDR-H3), and to boost levels of glycine, tyrosine and serine, the most abundant residues in CDR-H3 (15). Codon X7, a trinucleotide mixture of about 15.6% each serine, tyrosine, and glycine, with 3.1% each of the remaining amino acids except cysteine, was used for each position in CDR-H3 (theoretical calculations for all trinucleotides mixture). Different combinations of trinucleotides were also used in selected positions of CDR-H1, H2, H3, and L3. As shown in FIG. 4C and FIG. 4B, Codons X1 to X6 have a high percentage of serine, tyrosine, or glycine. X1 has 52.5% of serine, X2 has 52.5% tyrosine, X3 has 10% tyrosine, glycine or serine, X4 has 28.8% glycine, X5 has 19.2% tyrosine, glycine or serine, and X6 has 20% tyrosine or serine. The VH/VL antibody phage library was estimated to have approximately $10^{10}$ variants displayed.

Selection of Antibodies that Bind to Both Human and Murine TA

The 12 VH/VL sub-libraries were individually panned against immobilized CHO cell expressed human TA-Fc protein for the first round of selection. Eluted phages from each sub-library were amplified and then combined for second round of selection. Since human TA (hTA)-Fc was used as the antigen, the pooled phage was pre-absorbed with excess irrelevant Fc fusion protein after the first round of panning to minimize the recovery of anti-Fc phage antibodies. After the fourth round of panning, 95 randomly picked phage clones were evaluated for the ability to specifically bind to TA. Ninety percent of clones were positive for hTA binding and 40% of positive clones bound both human and murine TA.

These phage clones were sequenced, 10 unique clones that bind to human and murine TA were chosen for further characterization. All bound to both human and murine TA with an $IC_{50}$ below 70 nM in the phage ELISA. Clone Y bound human and murine TA with $IC_{50}$'s of 0.5 and 3.4 nM, respectively. Sequences from the 10 clones reflect the VH/VL library design-variable CDR-H3 lengths, sequence diversity distributed throughout CDR-H1, H2 and L3, and some consensus CDR sequences from the library template. Clones Y and Z have changes in all 4 CDRs and also have the best binding affinities to both human and murine TA (Clone Y: IC50~3.4 nM & 0.48 nM to murine and human TA, respectively; Clone Z: IC50~9.9 nM & 2.7 nM to murine and human TA, respectively).

Domain-truncated variants of human TA were used to identify and select for phage antibodies that bound to domains of interest in the TA (data not shown).

Characterization of Selected Anti-TA IgG

Selected anti-TA clones were reformatted into full length human IgG1, expressed in CHO cells and purified for further characterization. The anti-TA phage antibodies Clone Y and Clone X bound specifically to human and murine TA and did not bind to human or murine form a another member from the same family as the TA, ErbB2-ECD or BSA. Each of the other eight-phage antibodies showed similar specificity (data not shown). By surface plasmon resonance, immobilized Clone Y and Clone X IgG did not interact with these antigens at concentrations up to 500 nM. However, both Clone Y and Clone X bound human TA with a Kd of 0.9 and 5 nM as well as murine TA with a Kd of 7.8 and 11 nM, respectively. Although these antibodies were selected using plate-immobilized antigen, FACS analysis demonstrated all purified IgGs also bound to cells which express TA endogenously.

The selected antibodies were also assessed for function blocking activity in biological assays. The results showed that these antibodies possessed the ability to block biological functions of the TA.

Affinity Maturation of Clone X

Clone X bound to both human and murine TA with a phage $IC_{50}$ of 5 and 11 nM, respectively, and completely blocked ligand binding to TA in vitro. To improve potency in vivo, this clone was affinity-matured using human TA-His. Three different CDR combinations, L1/L2/L3, L3/H1/H2 and L3/H3, were targeted for randomization using a 'soft randomization' strategy that maintains a wild-type sequence bias such that selected positions are mutated only 50 percent of the time (27). For affinity maturation, the monovalent Fab was displayed on phage rather than bi-valent Fab to reduce potential avidity during selection. Stop codons were introduced at CDR-L3 in each sub-library. Off-rate selection strategies (see Methods) were employed to improve the affinity of Clone X, since it already possessed a relatively high association rate constant. ($2.2 \times 10^5$), but the dissociation rate constant ($1.1 \times 10^{-3}$) was relatively fast.

In the first round of selection, all 3 CDR soft-randomized libraries were panned against immobilized hTA followed by subsequent rounds with a solution-phase sorting strategy to limit target concentration and enhance affinity-based selection. The concentration of biotinylated-hTA was gradually reduced from 5 to 0.5 nM and a 500-fold excess of non-biotinylated hTA was added to compete for fast off-rate binders. The mixture was also incubated at 37° C. for up to 2 hrs.

The L1/L2/L3 library showed significant enrichment following round 5. Ninety-six clones were randomly picked, sequenced and then affinities ranked. Twenty-three unique phage clones were selected and purified for further characterization. Most clones had improved affinity for hTA as determined by phage competition ELISA. Surprisingly, the affinity for mTA was also improved despite being omitted from the selection process, suggesting that the clones bound to a conserved epitope. Selected clones had 4 to 7 changes in the 3 light chain CDRs; positions 28 and 30 in CDR-L1 tended to be substituted with Tyrosine and Histidine, respectively, whereas positions 92, 93, and 96 in CDR-L3 were more diverse.

Clones with the highest affinity for both human and murine TA (Clone X-1, -2, -3, -4, -5 and -6) were reformatted and expressed as full-length antibodies. All 6 IgGs had improved affinity for hTA and maintained complete blocking of ligand binding (data not shown). Affinities for human and murine TA ranged from 0.4 to 1.8 nM. The dissociation rate constant of Clone X-6 was improved leading to an overall improvement in affinity of about 10-fold for both human and murine TA; no binding was observed to human or murine form of a member from the same family as TA. Clone X-6 also showed improved binding to cell surface TA.

Efficacy of Affinity Matured Anti-TA Antibodies in Migration and Tumor Growth Assays The affinity improved anti-TA antibodies were dramatically more effective than parental clone at antagonizing ligand-induced cell migration. Clone X-6 was also assessed for and shown to possess the ability to reduce tumor growth (including tumor growth in lung and colon carcinoma models.

Discussion

Synthetic and natural diversity libraries are an important source of antibodies. The VH/VL synthetic phage antibody library described here used a defined scaffold and introduced sequence diversity in a site-specific manner using synthetic DNA and site-directed mutagenesis. The performance of any antibody phage library, measured by the affinities and designed function of derived antibodies, is determined by the library size, which is in turn limited by the efficiency of transformation of the library DNA into *Escherichia coli*. To limit the diversity of the library design, we used sequences of natural antibodies to guide where and what kind of diversity should be introduced. The amino acid composition at many CDR positions is highly biased in the natural repertoire; for example, tyrosine is highly abundant in antigen-binding sites, accounting for about 10% of the total CDR composition and about 25% of antigen contacts (33). The oligonucleotide design in the VH/VL library (especially X1 to X7) was an attempt to reflect this bias, and this chemical diversity has enabled us to obtain certain functional antibodies that may be absent in the "VH" library (11). Unlike the "VH" library that incorporated diversity only in heavy chain CDR positions, this library design also included positions within CDR-L3 of the light chain and used pre-assembled trinucleotides during oligonucleotide synthesis to reduce the redundancy inherent in the genetic code. Furthermore, the VH/VL library used consensus CDR sequences in all but CDR-H3. A crystal structure of a Fab selected from this library showed the expected canonical conformation. This library has been challenged with several protein antigens and successfully yielded many functional phage antibodies with affinities in the range of 1-100 nM. Although the affinities of functional antibodies from "VH" or VH/VL library are similar, the chemical diversities of the two libraries are different, and thus they may work for different antigens. The VH/VL library is an excellent source for antibodies with good binding affinities and/or biological potency that are thus potentially useful for a variety of therapeutic applications.

PARTIAL LIST OF REFERENCES

1. Kohler, G., and Milstein, C. (1975) *Nature* 256(5517), 495-497
2. Smith, G. P. (1985) *Science* 228(4705), 1315-1317
3. Bradbury, A. R., and Marks, J. D. (2004) *J Immunol Methods* 290(1-2), 29-49
4. Lipovsek, D., and Pluckthun, A. (2004) *J Immunol Methods* 290(1-2), 51-67
5. Feldhaus, M. J., and Siegel, R. W. (2004) *J Immunol Methods* 290(1-2), 69-80
6. Hoogenboom, H. R. (2005) *Nat Biotechnol* 23(9), 1105-1116
7. Knappik, A., Ge, L., Honegger, A., Pack, P., Fischer, M., Wellnhofer, G., Hoess, A., Wolle, J., Pluckthun, A., and Virnekas, B. (2000) *J Mol Biol* 296(1), 57-86
8. Sheets, M. D., Amersdorfer, P., Finnern, R., Sargent, P., Lindquist, E., Schier, R., Hemingsen, G., Wong, C., Gerhart, J. C., and Marks, J. D. (1998) *Proc Natl Acad Sci USA* 95(11), 6157-6162
9. de Haard, H. J., van Neer, N., Reurs, A., Hufton, S. E., Roovers, R. C., Henderikx, P., de Bruine, A. P., Arends, J. W., and Hoogenboom, H. R. (1999) *J Biol Chem* 274(26), 18218-18230
10. Sidhu, S. S., L1, B., Chen, Y., Fellouse, F. A., Eigenbrot, C., and Fuh, G. (2004) *J Mol Biol* 338(2), 299-310
11. Lee, C. V., Liang, W. C., Dennis, M. S., Eigenbrot, C., Sidhu, S. S., and Fuh, G. (2004) *J Mol Biol* 340(5), 1073-1093
12. Carter, P., Presta, L., Gorman, C. M., Ridgway, J. B., Henner, D., Wong, W. L., Rowland, A. M., Kotts, C., Carver, M. E., and Shepard, H. M. (1992) *Proc Natl Acad Sci USA* 89(10), 4285-4289
13. Lee, C. V., Sidhu, S. S., and Fuh, G. (2004) *J Immunol Methods* 284(1-2), 119-132
14. Liang, W. C., Wu, X., Peale, F. V., Lee, C. V., Meng, Y. G., Gutierrez, J., Fu, L., Malik, A. K., Gerber, H. P., Ferrara, N., and Fuh, G. (2006) *J Biol Chem* 281(2), 951-961
15. Mian, I. S., Bradwell, A. R., and Olson, A. J. (1991) *J Mol Biol* 217(1), 133-151
16. He, Z., and Tessier-Lavigne, M. (1997) *Cell* 90(4), 739-751

17. Chen, H., Chedotal, A., He, Z., Goodman, C. S., and Tessier-Lavigne, M. (1997) *Neuron* 19(3), 547-559
18. Kolodkin, A. L., Levengood, D. V., Rowe, E. G., Tai, Y. T., Giger, R. J., and Ginty, D. D. (1997) *Cell* 90(4), 753-762
19. Soker, S., Takashima, S., Miao, H. Q., Neufeld, G., and Klagsbrun, M. (1998) *Cell* 92(6), 735-745
20. Kitsukawa, T., Shimizu, M., Sanbo, M., Hirata, T., Taniguchi, M., Bekku, Y., Yagi, T., and Fujisawa, H. (1997) *Neuron* 19(5), 995-1005
21. Kawasaki, T., Kitsukawa, T., Bekku, Y., Matsuda, Y., Sanbo, M., Yagi, T., and Fujisawa, H. (1999) *Development* 126(21), 4895-4902
22. Ferrara, N. (2005) *Oncology* 69 Suppl 3, 11-16
23. Ferrara, N., and Kerbel, R. S. (2005) *Nature* 438(7070), 967-974
24. Kerbel, R. S., Yu, J., Tran, J., Man, S., Viloria-Petit, A., Klement, G., Coomber, B. L., and Rak, J. (2001) *Cancer Metastasis Rev* 20(1-2), 79-86
25. Jain, R. K., Duda, D. G., Clark, J. W., and Loeffler, J. S. (2006) *Nat Clin Pract Oncol* 3(1), 24-40
26. Kunkel, T. A., Bebenek, K., and McClary, J. (1991) *Methods Enzymol* 204, 125-139
27. Gallop, M. A., Barrett, R. W., Dower, W. J., Fodor, S. P., and Gordon, E. M. (1994) *J Med Chem* 37(9), 1233-1251
28. Xu, J. L., and Davis, M. M. (2000) *Immunity* 13(1), 37-45
29. Chothia, C., Lesk, A. M., Tramontano, A., Levitt, M., Smith-Gill, S. J., Air, G., Sheriff, S., Padlan, E. A., Davies, D., Tulip, W. R., and et al. (1989) *Nature* 342(6252), 877-883
30. Wu, T. T., Johnson, G., and Kabat, E. A. (1993) *Proteins* 16(1), 1-7
31. Gu, C., Limberg, B. J., Whitaker, G. B., Perman, B., Leahy, D. J., Rosenbaum, J. S., Ginty, D. D., and Kolodkin, A. L. (2002) *J Biol Chem* 277(20), 18069-18076
32. Ferrara, N., Hillan, K. J., and Novotny, W. (2005) *Biochem Biophys Res Commun* 333(2), 328-335
33. Fellouse, F. A., Wiesmann, C., and Sidhu, S. S. (2004) *Proc Natl Acad Sci USA* 101(34), 12467-12472
34. Kabat, E. A., Wu, T. T., and Bilofsky, H. (1977) *J Biol Chem* 252(19), 6609-6616

---

We claim:

1. A phage display antibody fragment library comprising a plurality of at least about $1 \times 10^4$ distinct antibody fragments, or a plurality of polynucleotides encoding the plurality of at least about $1 \times 10^4$ distinct antibody fragments, wherein each antibody fragment comprises a heavy chain variable domain ($V_H$) and a light chain variable domain ($V_L$) from a source antibody, wherein $V_H$ comprises a variant hypervariable region 3 (HVR-H3) wherein:

(i) the variant HVR-H3 comprises an amino acid sequence:

X1-X2-(X3)n-X4-D-X5 (SEQ ID NO: 18)

wherein X1-X5 are naturally occurring amino acids other than cysteine, and X1 is position 95 according to the Kabat numbering system, and n=4-17; and at least one variant HVR selected from HVR-H2 and HVR-H1, wherein (ii) the variant HVR-H2 comprises an amino acid sequence:

V-S-X1-I-X2-X3-X4-X5-G-X6-T-X7-Y-A-D-S-V-K-G (SEQ ID NO: 10)

wherein X1-X7 are naturally occurring amino acids other than cysteine, and X1 is position 50 according to the Kabat numbering system; and (iii) the variant HVR-H1 comprises an amino acid sequence:

G-X1-X2-F-X3-X4-X5-X6-X7-S-W-V (SEQ ID NO: 11)

wherein X1-X7 are naturally occurring amino acids other than cysteine, wherein G is position 26 and X1 is position 27 according to the Kabat numbering system, wherein the distinct antibody fragments of the phage display antibody fragment library have amino acid diversity at position 99 or 100 of HVR-H3 and amino acid diversity at least at position 28, 30, 31, 32 or 33 of HVR-H1 or position 54 of HVR-H2, according to the Kabat numbering system, and wherein at least one of the distinct antibody fragments is capable of binding a target antigen of interest.

2. The library of claim 1, wherein the $V_L$ in each antibody fragment in the plurality of antibody fragments comprises HVR-L1, HVR-L2 and a variant HVR-L3 wherein the variant HVR-L3 comprises an amino acid sequence: Q-Q-X1-X2-X3-X4-P-X5-T (SEQ ID NO: 66)

wherein X1-X5 are any naturally occurring amino acids other than cysteine, and X1 is position 91 according to the Kabat numbering system;

HVR-L1 comprises a first consensus hypervariable sequence; and

HVR-L2 comprises a second consensus hypervariable sequence.

3. The library of claim 1, wherein the library comprises the plurality of polynucleotides encoding the plurality of the at least about $1 \times 10^4$ distinct antibody fragments.

4. The library of claim 3, wherein the polynucleotides comprise non-redundant codons for each amino acid at each X position.

5. The library of claim 4, wherein the non-redundant codons comprise trinucleotide codons.

6. The library of claim 1, wherein the probability of X1 and/or X2 of the variant HVR-H3 being G is greater than any other individual amino acid.

7. The library of claim 3, wherein the plurality of polynucleotides comprise (i) a first set of polynucleotides comprising a codon encoding G at X1 and/or X2 of the variant HVR-H3, and (ii) a second set of polynucleotides comprising a codon encoding an amino acid other than G at X1 and/or X2 of the variant HVR-H3, wherein the first set of polynucleotides is present at an amount greater than the amount of each subset of polynucleotides having the same variant HVR-H3 sequence within the second set of polynucleotides.

8. The library of claim 3, wherein 20% to 29% of the polynucleotides encoding the variant HVR-H3 comprise a codon encoding G at X1 and/or X2.

9. The library of claim 3, wherein no more than about 5% of the polynucleotides encoding the variant HVR-H3 comprise a codon encoding any single amino acid other than G at X1 and/or X2.

10. The library of claim 3, wherein the amount of polynucleotide comprising a codon encoding G at X1 and/or X2 of the variant HVR-H3 in the plurality of polynucleotides is adjusted to provide a bias in favor of G at X1 and/or X2 of the variant HVR-H3 of the plurality of distinct antibody fragments.

11. The library of claim 3, wherein 10% to 20% of the polynucleotides encoding the variant HVR-H3 comprise a codon encoding G, S or Y at X3.

12. The library of claim 3, wherein no more than about 5% of the polynucleotides encoding the variant HVR-H3 comprise a codon encoding any single amino acid other than G, S or Y at X3.

13. The library of claim 3, wherein the amount of polynucleotide comprising a codon encoding G, S or Y at X3 of the variant HVR-H3 in the plurality of polynucleotides is adjusted to provide a bias in favor of G, S and/or Y at X3 of the variant HVR-H3 of the plurality of distinct antibody fragments.

14. The library of claim 3, wherein 15% to 25% of the polynucleotides encoding the variant HVR-H2 comprise a codon encoding S or Y at X2.

15. The library of claim 3, wherein no more than about 5% of the polynucleotides encoding the variant HVR-H2 comprise a codon encoding any single amino acid other than S or Y at X2.

16. The library of claim 3, wherein the amount of polynucleotide comprising a codon encoding S or Y at X2 of the variant HVR-H2 in the plurality of polynucleotides is adjusted to provide a bias in favor of S and/or Y at X2 of the variant HVR-H2 of the plurality of distinct antibody fragments.

17. The library of claim 3, wherein 10% to 20% of the polynucleotides encoding the variant HVR-H2 comprise a codon encoding G, S or Y at X3 and/or X4.

18. The library of claim 3, wherein no more than about 5% of the polynucleotides encoding the variant HVR-H2 comprise a codon encoding any single amino acid other than G, S or Y at X3 and/or X4.

19. The library of claim 3, wherein the amount of polynucleotide comprising a codon encoding G, S or Y at X3 and/or X4 of the variant HVR-H2 in the plurality of polynucleotides is adjusted to provide a bias in favor of G, S and/or Y at X3 and/or X4 of the variant HVR-H2 of the plurality of distinct antibody fragments.

20. The library of claim 3, wherein 50% to 60% of the polynucleotides encoding the variant HVR-H1 comprise a codon encoding S at X4.

21. The library of claim 3, wherein no more than about 5% of the polynucleotides encoding the variant HVR-H1 comprise a codon encoding any single amino acid other than S at X4.

22. The library of claim 3, wherein the amount of polynucleotide comprising a codon encoding S at X4 of the variant HVR-H1 in the plurality of polynucleotides is adjusted to provide a bias in favor of S at X4 of the variant HVR-H1 of the plurality of distinct antibody fragments.

23. The library of claim 3, wherein 50% to 60% of the polynucleotides encoding the variant HVR-H1 comprise a codon encoding Y at X5.

24. The library of claim 3, wherein no more than about 5% of the polynucleotides encoding the variant HVR-H1 comprise a codon encoding any single amino acid other than Y at X5.

25. The library of claim 3, wherein the amount of polynucleotide comprising a codon encoding Y at X5 of the variant HVR-H1 in one plurality of polynucleotides is adjusted to provide a bias in favor of Y at X5 of the variant HVR-H1 of the plurality of distinct antibody fragments.

26. The library of claim 3, wherein 10% to 20% of the polynucleotides encoding the variant HVR-H1 comprise a codon encoding G, S or Y at X6.

27. The library of claim 3, wherein no more than about 5% of the polynucleotides encoding the variant HVR-H1 comprise a codon encoding any single amino acid other than G, S or Y at X6.

28. The library of claim 3, wherein the amount of polynucleotide comprising a codon encoding G, S or Y at X6 of the variant HVR-H1 in the plurality of polynucleotides is adjusted to provide a bias in favor of G, S or Y at X6 of the variant HVR-H1 of the plurality of distinct antibody fragments.

29. The library of claim 1, wherein the plurality of polypeptides is generated by mutagenizing a template nucleic acid that encodes the at least one respective variant HVR sequences at one or more X positions within the at least one variant HVR sequences.

30. The library of claim 29, wherein the template nucleic acid comprises one or more stop codons in the variant HVR-H3, and the plurality of polypeptides is encoded by oligonucleotides comprising one or more codons that encode amino acid(s) at the position(s) corresponding to the stop codon(s), wherein the oligonucleotides are mutagenized to replace the stop codon(s) with codons that encode amino acid(s).

31. The library of claim 30, wherein only the variant HVR-H3 comprises said stop codon(s).

32. The library of claim 2, wherein the first consensus hypervariable sequence comprises a Kabat consensus CDR-L1 sequence.

33. The library of claim 2, wherein the second consensus hypervariable sequence comprises a Kabat consensus CDR-L2 sequence.

34. The library of claim 2, wherein the first consensus hypervariable sequence and/or the second consensus hypervariable sequence comprises a substitution at one or more amino acid positions compared to the corresponding consensus hypervariable sequence.

35. The library of claim 2, wherein the library comprises the plurality of polynucleotides encoding the plurality of the at least about $1 \times 10^4$ distinct antibody fragments.

36. The library of claim 35, wherein 15% to 25% of the polynucleotides encoding the variant HVR-L3 comprise a codon encoding G, S or Y at X2.

37. The library of claim 35, wherein no more than about 5% of the polynucleotides encoding the variant HVR-L3 comprise a codon encoding any single amino acid other than G, S or Y at X2.

38. The library of claim 35, wherein the amount of polynucleotide comprising a codon encoding G, S or Y at X2 of the variant HVR-L3 in the plurality of polynucleotides is adjusted to provide a bias in favor of G, S or Y at X2 of the variant HVR-L3 of the plurality of distinct antibody fragments.

39. The library of claim 35, wherein 50% to 55% of the polynucleotides encoding the variant HVR-L3 comprise a codon encoding S at X3.

40. The library of claim 35, wherein no more than about 5% of the polynucleotides encoding the variant HVR-L3 comprise a codon encoding any single amino acid other than S at X3.

41. The library of claim 35, wherein the amount of polynucleotide comprising a codon encoding S at X3 of the variant HVR-L3 in the plurality of polynucleotides is adjusted to provide a bias in favor of S at X3 of the variant HVR-L3 of the plurality of distinct antibody fragments.

42. The library of claim 35, wherein 15% to 25% of the polynucleotides encoding the variant HVR-L3 comprise a codon encoding S or Y at X4.

43. The library of claim 35, wherein no more than about 5% of the polynucleotides encoding the variant HVR-L3 comprise a codon encoding any single amino acid other than S or Y at X4.

44. The library of claim 35, wherein the amount of polynucleotide comprising a codon encoding S or Y at X4 of the variant HVR-L3 in the plurality of polynucleotides is adjusted to provide a bias in favor of S or Y at X4 of the variant HVR-L3 of the plurality of distinct antibody fragments.

45. The library of claim 1 comprising a plurality of at least about $1 \times 10^5$ distinct antibody fragments.

46. The library of claim 1 comprising a plurality of at least about $1 \times 10^6$ distinct antibody fragments.

47. The library of claim 1 comprising a plurality of at least about $1 \times 10^7$ distinct antibody fragments.

48. The library of claim 1 comprising a plurality of at least about $1 \times 10^8$ distinct antibody fragments.

49. The phage display antibody fragment library of claim 1, wherein the source antibody is a 4D5 antibody.

* * * * *